US012565489B2

(12) United States Patent
Geist et al.

(10) Patent No.: US 12,565,489 B2
(45) Date of Patent: Mar. 3, 2026

(54) HETEROCYCLYL PYRIMIDINES AND TRIAZINES AS NOVEL FUNGICIDES

(71) Applicant: Bayer Aktiengesellschaft, Leverkusen (DE)

(72) Inventors: Julie Geist, Lyons (FR); Anthony Millet, Tignieu-jameyzieu (FR); Cyril Montagne, Lyons (FR); Lionel Nicolas, Lyons (FR); Tomoki Tsuchiya, Lyons (FR); Vincent Thomas, Lyons (FR)

(73) Assignee: BAYER AKTIENGESELLSCHAFT (DE)

( * ) Notice: Subject to any disclaimer, the term of this patent is extended or adjusted under 35 U.S.C. 154(b) by 571 days.

(21) Appl. No.: 18/008,116

(22) PCT Filed: Jun. 1, 2021

(86) PCT No.: PCT/EP2021/064684

§ 371 (c)(1),
(2) Date: Dec. 2, 2022

(87) PCT Pub. No.: WO2021/245087

PCT Pub. Date: Dec. 9, 2021

(65) Prior Publication Data

US 2023/0278994 A1 Sep. 7, 2023

(30) Foreign Application Priority Data

Jun. 4, 2020 (EP) .................................... 20178206

(51) Int. Cl.

| | |
|---|---|
| *C07D 413/04* | (2006.01) |
| *C07C 211/29* | (2006.01) |
| *C07C 233/11* | (2006.01) |
| *C07C 323/32* | (2006.01) |
| *C07D 239/34* | (2006.01) |
| *C07D 333/20* | (2006.01) |
| *C07D 403/04* | (2006.01) |
| *C07D 403/12* | (2006.01) |
| *C07D 405/12* | (2006.01) |
| *C07D 409/12* | (2006.01) |
| *C07D 413/14* | (2006.01) |

(52) U.S. Cl.

CPC .......... *C07D 413/04* (2013.01); *C07C 211/29* (2013.01); *C07C 233/11* (2013.01); *C07C 323/32* (2013.01); *C07D 239/34* (2013.01); *C07D 333/20* (2013.01); *C07D 403/04* (2013.01); *C07D 403/12* (2013.01); *C07D 405/12* (2013.01); *C07D 409/12* (2013.01); *C07D 413/14* (2013.01)

(58) Field of Classification Search

CPC .................................................... C07D 413/04

See application file for complete search history.

(56) References Cited

U.S. PATENT DOCUMENTS

| | | | |
|---|---|---|---|
| 6,090,831 | A | 7/2000 | Assmann et al. |
| 2008/0132522 | A1 | 6/2008 | Rheinheimer et al. |
| 2008/0176831 | A1 | 7/2008 | Schwögler et al. |
| 2023/0064576 | A1 | 3/2023 | Chen et al. |

FOREIGN PATENT DOCUMENTS

| | | | |
|---|---|---|---|
| EP | 3351533 | A1 | 7/2018 |
| WO | 2006119400 | A2 | 11/2006 |
| WO | 2020127780 | A1 | 6/2020 |

*Primary Examiner* — Golam M Shameem

(74) *Attorney, Agent, or Firm* — MORRISON & FOERSTER LLP

(57) ABSTRACT

The present disclosure relates to heterocyclyl pyrimidine and heterocyclyl triazine compounds, processes and intermediates for their preparation as well as the uses thereof for controlling phytopathogenic microorganisms, such as phytopathogenic fungi.

9 Claims, No Drawings

HETEROCYCLYL PYRIMIDINES AND TRIAZINES AS NOVEL FUNGICIDES

CROSS REFERENCE TO RELATED APPLICATIONS

This application is a national stage application under 35 U.S.C. § 371 of International Application No. PCT/EP2021/064684, filed internationally on Jun. 1, 2021, which claims benefit of European Application No. 20178206.7, filed Jun. 4, 2020.

The present invention relates to heterocyclyl pyrimidine and heterocyclyl triazine compounds and the uses thereof for controlling phytopathogenic microorganisms such as phytopathogenic fungi. It also relates to processes and intermediates for preparing these compounds.

Numerous crop protection agents to combat or prevent microorganisms' infestations have been developed until now. However, the need remains for the development of new compounds as such, so as to provide compounds being effective against a broad spectrum of phytopathogenic microorganisms, such as fungi, having low toxicity, high selectivity or that can be used at low application rate whilst still allowing effective pest control. It may also be desired to have new compounds to prevent the emergence of resistances.

The present invention provides new compounds for controlling phytopathogenic microorganisms such as fungi which have advantages over known compounds and compositions in at least some of these aspects.

WO 2020/127780 describes heterocyclyl-substituted Pyridazines as fungicides.

DETAILED DESCRIPTION

Compounds of Formula (I)

The present invention relates to compounds of the formula (I):

(I)

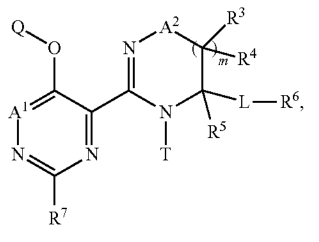

wherein $A^1$ is N or $CR^8$, wherein $R^8$ is hydrogen, halogen, cyano or $C_1$-$C_4$-alkyl, $A^2$ is O, S, C(═O), S(═O), S(═O)$_2$, $NR^1$ or $CR^{2A}R^{R2B}$, wherein $R^1$ is hydrogen, formyl, $C_1$-$C_6$-alkyl or $C_3$-$C_8$-cycloalkyl, wherein $C_1$-$C_6$-alkyl is optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, $R^{2A}$ and $R^{2B}$ are independently hydrogen, $C_1$-$C_6$-alkyl or $C_3$-$C_8$-cycloalkyl, wherein $C_1$-$C_6$-alkyl is optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^{2A}$ and $R^{2B}$ form together with the carbon atom to which they are attached to a $C_3$-$C_8$-cycloalkyl-ring or a 3- to 7-membered heterocyclyl-ring, m is 0, 1 or 2, T is hydrogen, hydroxyl, $C_1$-$C_6$-alkyl, —C(═O)$R^{11}$, —C(═O)($OR^{12}$), —C(═O)N($R^{13}$)$_2$, —S(═O)$R^{14}$, —S(═O)$_2R^{14}$ or —S(═O)$_2$N($R^{14}$)$_2$, wherein $R^{11}$ and $R^{12}$ are independently $C_1$-$C_6$-alkyl, $C_1$-$C_6$-haloalkyl, $C_3$-$C_8$-cycloalkyl or $C_2$-$C_6$-alkenyl, $R^{13}$ and $R^{14}$ are independently hydrogen, $C_1$-$C_6$-alkyl, $C_1$-$C_6$-haloalkyl, $C_3$-$C_8$-cycloalkyl or $C_2$-$C_6$-alkenyl, $R^3$ and $R^4$ are independently hydrogen, halogen, cyano, hydroxyl, formyl, carboxyl, $C_1$-$C_6$-alkyl, $C_1$-$C_6$-alkoxy, $C_1$-$C_6$-alkylcarbonyl, $C_1$-$C_6$-alkylcarbonyloxy, $C_1$-$C_6$-alkoxycarbonyl, $C_2$-$C_6$-alkenyl, $C_2$-$C_6$-alkynyl, $C_3$-$C_8$-cycloalkyl, $C_6$-$C_{14}$-aryl, 5- to 14-membered heteroaryl, 3- to 14-membered heterocyclyl or —O—Si ($C_1$-$C_6$-alkyl)$_3$, wherein $C_1$-$C_6$-alkyl, $C_1$-$C_6$-alkoxy, $C_1$-$C_6$-alkylcarbonyl, $C_1$-$C_6$-alkylcarbonyloxy, $C_1$-$C_6$-alkoxycarbonyl, $C_2$-$C_6$-alkenyl, $C_2$-$C_6$-alkynyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl, $C_6$-$C_{14}$-aryl, 5- to 14-membered heteroaryl and 3- to 14-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^4$ form together with the carbon atom to which they are attached to a carbonyl, a methylidene, a $C_3$-$C_8$-cycloalkyl-ring or a 3- to 7-membered heterocyclyl-ring, wherein $C_3$-$C_8$-cycloalkyl-ring and 3- to 7-membered heterocyclyl-ring are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, $R^5$ is hydrogen, hydroxyl, $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl, $C_3$-$C_8$-cycloalkyl or —O—Si($C_1$-$C_6$-alkyl)$_3$, wherein $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^5$ or $R^4$ and $R^5$ form together with the carbon atom to which they are attached to a $C_3$-$C_8$-cycloalkyl-ring, L is a direct bond, carbonyl, $C_1$-$C_6$-alkylene, $C_2$-$C_6$-alkenylene, $C_2$-$C_6$-alkynylene, —C(═O)—$C_1$-$C_6$-alkylene-, —$C_1$-$C_6$-alkylene-C(═O)—, —$NR^{L1}$—, —$NR^{L2}$(C═O)—, —C(═O)$NR^{L3}$—, —$NR^{L4}$S(═O)$_2$—, —S(═O)$_2NR^{L5}$—, —C(═$NOR^{L6}$)—, —C(═N—N($R^{L7}$)$_2$)—, —C(═$NR^{L8}$)— or a group of formula

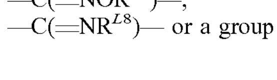

wherein said $C_1$-$C_6$-alkylene, $C_2$-$C_6$-alkenylene, $C_2$-$C_6$-alkynylene, —C(═O)—$C_1$-$C_6$-alkylene- and —$C_1$-$C_6$-alkylene-C(═O)— are optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl, $C_3$-$C_8$-cycloalkenyl and 3- to 7-membered heterocyclyl in turn are optionally substituted with one to three substituents $L^{SC}$, $R^{L1}$, $R^{L2}$, $R^{L3}$ and $R^{L4}$ are independently hydrogen or $C_1$-$C_6$-alkyl, $R^{L5}$, $R^{L6}$, $R^{L7}$ and $R^{L8}$ are independently hydrogen, $C_1$-$C_6$-alkyl, $C_1$-$C_6$-haloalkyl, $C_3$-$C_8$-cycloalkyl or $C_2$-$C_6$-alkenyl, wherein $L^{SA}$ is independently halogen, cyano, hydroxyl, carboxyl, methylidene, halomethylidene, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$ or 3- to 7-membered heterocyclyl, and/or two substituents $L^{SA}$ that are bound to the same carbon atom form together with the carbon atom which they are attached to a $C_3$-$C_8$-cycloalkyl-ring or a 3- to 7-membered heterocyclyl-ring, $L^{SC}$ is independently halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, and/or two $L^{SC}$ substituents form together with the carbon atom to which they are attached to a $C_3$-$C_8$-cycloalkyl-ring, $R^6$ is $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl, 3- to 14-membered heterocyclylsulfonyl, $C_1$-$C_3$-alkoxy, $C_1$-$C_3$-haloalkoxy, $C_1$-$C_3$-alkylsulfanyl, $C_1$-$C_3$-alkylsulfinyl or $C_1$-$C_3$-alkylsulfonyl, wherein $C_1$-$C_3$-alkoxy, $C_1$-$C_3$-haloalkoxy, $C_1$-$C_3$-alkylsulfanyl, $C_1$-$C_3$-alkylsulfinyl and $C_1$-$C_3$-alkylsulfonyl are substituted with one substituent selected from the group consisting of $C_3$-$C_{12}$-carbocyclyl, $C_6$-$C_{14}$-aryl, 3- to 14-membered heterocyclyl and 5- to 14-membered heteroaryl, wherein said $C_3$-$C_{12}$-carbocyclyl, $C_6$-$C_{14}$-aryl, 3- to 14-membered heterocyclyl and 5- to 14-membered heteroaryl in turn are optionally substituted with one to four $R^{6S}$ substituents, wherein $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl and 3- to 14-membered heterocyclylsulfonyl are optionally substituted with one to four $R^{6S}$ substituents, wherein $R^{6S}$ is independently selected from the group consisting of halogen, cyano, isocyano, nitro, hydroxyl, mercapto, pentafluorosulfanyl, oxo, methylidene, halomethylidene, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, $—N(R^{15})_2$, $—O(C{=}O)R^{16}$, $—C({=}O)R^{16}$, $—C({=}O)(OR^{17})$, $—C({=}O)N(R^{18})_2$, $—S({=}O)_2N(R^{19})_2$, —O—Si($C_1$-$C_6$-alkyl)$_3$ and —Si($C_1$-$C_6$-alkyl)$_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are furthermore optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, or two substituents $C_1$-$C_6$-alkyl attached to the same carbon atom from a $C_3$-$C_8$-cycloalkyl-ring, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and wherein $R^{15}$ is independently hydrogen, $C_1$-$C_6$-alkyl or $C_3$-$C_8$-cycloalkyl, wherein said $C_1$-$C_6$-alkyl in turn is optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, and wherein said $C_3$-$C_8$-cycloalkyl in turn is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl and $C_1$-$C_6$-haloalkyl in turn are optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, $R^7$ is hydrogen, halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy, —O—Si($C_1$-$C_6$-alkyl)$_3$, —Si($C_1$-$C_6$-alkyl)$_3$, $—N(R^{20})_2$, $—C({=}NR^{21})R^{22}$, $—NR^{23}C({=}O)R^{24}$, $—C({=}O)(OR^{25})$, $—C({=}O)N(R^{26})_2$, $—S({=}O)_2N(R^{27})_2$ or $—S({=}O)({=}NR^{28})R^{29}$, wherein $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are optionally substituted with one to three $R^{7Sa}$ substituents, wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy are optionally substituted with one to three $R^{7Sc}$ substituents, and wherein $R^{20}$ is independently hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_6$-$C_{14}$-aryl, 5- or 6-membered heteroaryl or 3- to 7-membered heterocyclyl, wherein $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl in turn are optionally substituted with one to three substituents $R^{7Sa}$, and wherein $C_3$-$C_8$-cycloalkyl, $C_3$-$C_8$-halocycloalkyl, $C_6$-$C_{14}$-aryl, 5- or 6-membered heteroaryl and 3- to 7-membered heterocyclyl in turn are optionally substituted with one to three substituents $R^{7Sc}$, $R^{21}$ and $R^{22}$ are independently hydroxyl, amino, cyano, $C_1$-$C_6$-alkyl, $C_1$-$C_6$-haloalkyl, $C_1$-$C_6$-alkoxy, mono-($C_1$-$C_6$-alkyl)amino or di-($C_1$-$C_6$-alkyl)amino, wherein $C_1$-$C_6$-alkyl, $C_1$-$C_6$-haloalkyl, $C_1$-$C_6$-alkoxy, mono-($C_1$-$C_6$-alkyl)amino and di-($C_1$-$C_6$-alkyl)amino in turn are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_6$-alkyl, $C_1$-$C_6$-haloalkyl and $C_3$-$C_8$-cycloalkyl, wherein $C_1$-$C_6$-alkyl and $C_1$-$C_6$-haloalkyl in turn are optionally substituted with one to three $R^{7Sa}$ substituents, and wherein $C_3$-$C_8$-cycloalkyl in turn is optionally substituted with one to three $R^{7Sc}$ substituents, wherein $R^{7Sa}$ is independently cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$, —Si($C_1$-$C_6$-alkyl)$_3$, $C_6$-$C_{14}$-aryl or 3- to 7-membered heterocyclyl, $R^{7Sc}$ is independently halogen, cyano, nitro, hydroxyl, formyl, oxo, methylidene, halomethylidene, $C_1$-$C_6$-alkyl, $C_1$-$C_6$-haloalkyl $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, or two $R^{7Sc}$ substituents $C_1$-$C_6$-alkyl that are bound to the same carbon atom form together a $C_3$-$C_8$-cycloalkyl-ring, Q is $C_6$-$C_{14}$-aryl, $C_3$-$C_{12}$-carbocyclyl, 3- to 14-membered heterocyclyl or 5- to 14-membered heteroaryl, wherein $C_6$-$C_{14}$-aryl, $C_3$-$C_{12}$-carbocyclyl, 3- to 14-membered heterocyclyl or 5- to 14-membered heteroaryl are optionally substituted with one to five substituents $Q^S$ wherein $Q^S$ is independently selected from the group consisting of halogen, cyano, isocyano, nitro, hydroxyl, mercapto, formyl, carboxyl, $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyloxy, $C_3$-$C_6$-cycloalkenyl, 3- to 7-membered heterocyclyl, $C_6$-$C_{14}$-aryl, 5- to 14-membered heteroaryl, —O—Si($C_1$-$C_6$-alkyl)$_3$, —Si($C_1$-$C_6$-alkyl)$_3$, —O—C(═O)$R^{33}$, —N$R^{34}$C(═O)$R^{35}$, —C(═O)N($R^{36}$)$_2$, —C(═S)$R^{37}$, —C(═S)N($R^{38}$)$_2$, —C(═N$R^{39}$)$R^{40}$, —C(═NO$R^{41}$)$R^{42}$ and —N($R^{43}$)$_2$, wherein said $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, said $C_3$-$C_8$-cycloalkyl, $C_3$-$C_8$-cycloalkoxy, $C_3$-$C_6$-cycloalkenyl, 3- to 7-membered heterocyclyl and 5- to 14-membered heteroaryl in turn are optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl, and wherein $R^{33}$ is hydrogen, $C_1$-$C_6$-alkyl, $C_1$-$C_6$-haloalkyl and $C_1$-$C_6$-alkoxy, $R^{34}$, $R^{35}$, $R^{36}$ $R^{37}$ $R^{38}$ $R^{39}$ $R^{40}$ $R^{41}$ and $R^{42}$ are independently hydrogen, $C_1$-$C_6$-alkyl, $C_1$-$C_6$-haloalkyl or $C_1$-$C_6$-alkoxy, wherein said $C_1$-$C_6$-alkyl, $C_1$-$C_6$-haloalkyl and $C_1$-$C_6$-alkoxy in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, and wherein $R^{43}$ is hydrogen, hydroxyl, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl or $C_3$-$C_8$-cycloalkyl, wherein said $C_1$-$C_6$-alkyl, $C_1$-$C_6$-haloalkyl, $C_1$-$C_6$-alkoxy, $C_2$-$C_6$-alkenyl and $C_2$-$C_6$-haloalkenyl in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, wherein said $C_3$-$C_8$-cycloalkyl in turn is optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl, as well as N-oxides, salts, hydrates and hydrates of the salts and N-oxides thereof.

The present invention relates to a composition comprising at least one compound of formula (I) as defined herein and at least one agriculturally suitable auxiliary.

The present invention also relates to the use of a compound of formula (I) as defined herein or a composition as defined herein for controlling phytopathogenic fungi.

The present invention relates to a method for controlling phytopathogenic fungi which comprises the step of applying at least one compound of formula (I) as defined herein or a composition as defined herein to the plants, plant parts, seeds, fruits or to the soil in which the plants grow.

The present invention also relates to processes and intermediates for preparing compounds of formula (I).

Unless otherwise stated, the following definitions apply for the substituents and residues used throughout this specification and claims:

The term "halogen" as used herein refers to fluorine, chlorine, bromine or iodine atom.

The term "methylidene" as used herein refers to a $CH_2$ group connected to a carbon atom via a double bond.

The term "halomethylidene" as used herein refers to a $CX_2$ group connected to a carbon atom via a double bond, wherein X is halogen.

The term "oxo" as used herein refers to an oxygen atom which is bound to a carbon atom or sulfur atom via a double bound.

The term "$C_1$-$C_6$-alkyl" as used herein refers to a saturated, branched or straight hydrocarbon chain having 1, 2, 3, 4, 5 or 6 carbon atoms. Examples of $C_1$-$C_6$-alkyl include but are not limited to methyl, ethyl, propyl (n-propyl), 1-methylethyl (iso-propyl), butyl (n-butyl), 1-methylpropyl (sec-butyl), 2-methylpropyl (iso-butyl), 1,1-dimethylethyl (tert-butyl), pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-di-methylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Particularly, said hydrocarbon chain has 1, 2, 3 or 4 carbon atoms ("$C_1$-$C_4$-alkyl"), e.g. methyl, ethyl, propyl, iso-propyl, butyl, sec-butyl, iso-butyl or tert-butyl.

The term "$C_1$-$C_6$-haloalkyl" as used herein refers to a $C_1$-$C_6$-alkyl group as defined above in which one or more hydrogen atoms are replaced with one or more halogen atoms that may be the same or different. Examples of $C_1$-$C_6$-haloalkyl include but are not limited to chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl. Preferred are fluoromethyl, difluoromethyl, trifluoromethyl, fluoroethyl, 2-fluoroethyl, 2,2-difluoro-ethyl, 2,2,2-trifluoroethyl, pentafluoroethyl and 1,1,1-trifluoroprop-2-yl.

The term "$C_1$-$C_6$-fluoroalkyl" as used herein refers to a $C_1$-$C_6$-alkyl group as defined above in which one or more hydrogen atoms are replaced with one or more fluorine atoms that may be the same or different. Examples of $C_1$-$C_6$-fluoroalkyl include but are not limited to monofluoromethyl, difluoromethyl, trifluoromethyl, 1-fluoroethyl, 1,1-difluoroethyl, 2,2-difluoroethyl and 2,2,2-trifluoroethyl.

The term "$C_1$-$C_6$-alkylene" as used herein refers to a divalent $C_1$-$C_6$-alkyl group as defined herein. Examples of $C_1$-$C_6$-alkylene include but are not limited to methylene, ethylene, propyl-1,3-ene, propyl-1,2-ene, butyl-1,4-ene, butyl-1,3-ene, butyl-1,2-ene, 1,5-pentylene and 1,6-hexylene.

The terms "$C_3$-$C_8$-cycloalkyl" and "$C_3$-$C_8$-cycloalkyl-ring" as used herein refers to a saturated, monocyclic hydrocarbon ring containing 3, 4, 5, 6, 7 or 8 carbon atoms. Examples of $C_3$-$C_8$-cycloalkyl include but are not limited to cyclopropyl, cyclobutyl, cyclopentyl, cyclohexyl, cycloheptyl and cyclooctyl. Particularly, said cycloalkyl has 3 to 6 carbon atoms.

The term "$C_3$-$C_8$-halocycloalkyl" as used herein refers to a saturated hydrocarbon ring system in which all of the ring members, which vary from 3 to 8, are carbon atoms and in which one or more hydrogen atoms are replaced with one or more halogen atoms that may be the same or different.

The term "$C_2$-$C_6$-alkenyl" as used herein refers to an unsaturated, branched or straight hydrocarbon chain having 2, 3, 4, 5 or 6 carbon atoms and comprising at least one double bond. Examples of $C_2$-$C_6$-alkenyl include but are not limited to ethenyl (or "vinyl"), prop-2-en-1-yl (or "allyl"), prop-1-en-1-yl, but-3-enyl, but-2-enyl, but-1-enyl, pent-4-enyl, pent-3-enyl, pent-2-enyl, pent-1-enyl, hex-5-enyl, hex-4-enyl, hex-3-enyl, hex-2-enyl, hex-1-enyl, prop-1-en-2-yl (or "isopropenyl"), 2-methylprop-2-enyl, 1-methylprop-2-enyl, 2-methylprop-1-enyl, 1-methylprop-1-enyl, 3-methylbut-3-enyl, 2-methylbut-3-enyl, 1-methylbut-3-enyl, 3-methylbut-2-enyl, 2-methylbut-2-enyl, 1-methylbut-2-enyl, 3-methylbut-1-enyl, 2-methylbut-1-enyl, 1-methylbut-1-enyl, 1,1-dimethylprop-2-enyl, 1-ethylprop-1-enyl, 1-propyl-vinyl, 1-isopropylvinyl, 4-methylpent-4-enyl, 3-methylpent-4-enyl, 2-methylpent-4-enyl, 1-methylpent-4-enyl, 4-methylpent-3-enyl, 3-methylpent-3-enyl, 2-methylpent-3-enyl, 1-methylpent-3-enyl, 4-methylpent-2-enyl, 3-methylpent-2-enyl, 2-methylpent-2-enyl, 1-methylpent-2-enyl, 4-methylpent-1-enyl, 3-methylpent-1-enyl, 2-methylpent-1-enyl, 1-methylpent-1-enyl, 3-ethylbut-3-enyl, 2-ethylbut-3-enyl, 1-ethylbut-3-enyl, 3-ethylbut-2-enyl, 2-ethylbut-2-enyl, 1-ethylbut-2-enyl, 3-ethylbut-1-enyl, 2-ethylbut-1-enyl, 1-ethylbut-1-enyl, 2-propylprop-2-enyl, 1-propylprop-2-enyl, 2-isopropylprop-2-enyl, 1-isopropylprop-2-enyl, 2-propylprop-1-enyl, 1-propylprop-1-enyl, 2-isopropylprop-1-enyl, 1-isopropylprop-1-enyl, 3,3-dimethylprop-1-enyl, 1-(1,1-dimethylethyl)ethenyl, buta-1,3-dienyl, penta-1,4-dienyl, hexa-1,5-dienyl or methylhexadienyl group.

The term "$C_2$-$C_6$-alkynyl" as used herein refers to a branched or straight hydrocarbon chain having 2, 3, 4, 5 or 6 carbon atoms and comprising at least one triple bond. Examples of $C_2$-$C_6$-alkynyl include but are not limited to ethynyl, prop-1-ynyl, prop-2-ynyl (or "propargyl"), but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl or 3,3-dimethylbut-1-ynyl group.

The term "$C_2$-$C_6$-haloalkenyl" as used herein refers to a $C_2$-$C_6$-alkenyl group as defined above in which one or more hydrogen atoms are replaced with one or more halogen atoms that may be the same or different.

The term "$C_2$-$C_6$-haloalkynyl" as used herein refers to a $C_2$-$C_6$-alkynyl group as defined above in which one or more hydrogen atoms are replaced with one or more halogen atoms that may be the same or different.

The term "$C_1$-$C_6$-alkoxy" as used herein refers to a group of formula ($C_1$-$C_6$-alkyl)-O—, in which the term "$C_1$-$C_6$-alkyl" is as defined herein. Examples of $C_1$-$C_6$-alkoxy include but are not limited to methoxy, ethoxy, n-propoxy, 1-methylethoxy, n-butoxy, 1-methylpropoxy, 2-methylpropoxy, 1,1-dimethylethoxy, n-pentoxy, 1-methylbutoxy, 2-methylbutoxy, 3-methylbutoxy, 2,2-dimethylpropoxy, 1-ethylpropoxy, 1,1-dimethylpropoxy, 1,2-dimethylpropoxy, n-hexyloxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. This definition also applies to alkoxy as part of a composite substituent, for example alkoxyalkyl, alkoxyalkoxy, unless defined elsewhere.

The term "$C_1$-$C_6$-haloalkoxy" as used herein refers to a $C_1$-$C_6$-alkoxy group as defined above in which one or more hydrogen atoms are replaced with one or more halogen atoms that may be the same or different. Examples of $C_1$-$C_6$-haloalkoxy include but are not limited to chloromethoxy, bromomethoxy, dichloromethoxy, trichloromethoxy, fluoromethoxy, difluoromethoxy, trifluoromethoxy, chlorofluoro-methoxy, dichlorofluoromethoxy, chlorodifluoromethoxy, 1-chloroethoxy, 1-bromoethoxy, 1-fluoro-ethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy.

The term "$C_1$-$C_6$-hydroxyalkyl" as used herein refers to a $C_1$-$C_6$-alkyl group as defined above in which at least one hydrogen atom is replaced with a hydroxyl group. Examples of $C_1$-$C_6$-hydroxyalkyl include but are not limited to hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-di-hydroxypropyl and 1,3-dihydroxypropan-2-yl.

The term "$C_3$-$C_8$-cycloalkoxy" as used herein refers to a monocyclic, saturated cycloalkoxy radical having 3 to 8 and preferably 3 to 6 carbon ring members, for example (but not limited to) cyclopropyloxy, cyclobutyloxy, cyclopentyloxy and cyclohexyloxy. This definition also applies to cycloalkoxy as part of a composite substituent, for example cycloalkoxyalkyl, unless defined elsewhere.

The term "$C_3$-$C_8$-halocycloalkoxy" as used herein refers to a $C_3$-$C_8$-cycloalkoxy group as defined above in which one or more hydrogen atoms are replaced with one or more halogen atoms that may be the same or different.

The term $C_2$-$C_6$-alkenyloxy as used herein refers to a formula ($C_2$-$C_6$-alkenyl)-O—, in which the term "$C_1$-$C_6$-alkenyl" group is which the as defined herein. Examples of $C_2$-$C_6$-alkenyl include but are not limited to ethenyloxy (or "vinyloxy"), prop-2-en-1-yloxy (or "allyl"), prop-1-en-1-yloxy, but-3-enyloxy, but-2-enyloxy, but-1-enyloxy, pent-4-enyloxy, pent-3-enyloxy, pent-2-enyloxy, pent-1-enyloxy, hex-5-enyloxy, hex-4-enyloxy, hex-3-enyloxy, hex-2-enyloxy, hex-1-enyloxy, prop-1-en-2-yloxy (or "iso-propenyloxy"), 2-methylprop-2-enyloxy, 1-methylprop-2-enyloxy, 2-methylprop-1-enyloxy, 1-methylprop-1-enyloxy, 3-methylbut-3-enyloxy, 2-methylbut-3-enyloxy, 1-methylbut-3-enyloxy, 3-methylbut-2-enyloxy, 2-methylbut-2-enyloxy, 1-methylbut-2-enyloxy, 3-methylbut-1-enyloxy, 2-methylbut-1-enyloxy, 1-methylbut-1-enyloxy, 1,1-dimethylprop-2-enyloxy, 1-ethylprop-1-enyloxy, 1-propylvinyloxy, 1-isopropylvinyloxy, 4-methylpent-4-enyloxy, 3-methylpent-4-enyloxy, 2-methylpent-4-enyloxy, 1-methylpent-4-enyloxy, 4-methylpent-3-enyloxy, 3-methylpent-3-enyloxy, 2-methylpent-3-enyloxy, 1-methylpent-3-enyloxy, 4-methylpent-2-enyloxy, 3-methylpent-2-enyloxy, 2-methylpent-2-enyloxy, 1-methylpent-2-enyloxy, 4-methylpent-1-enyloxy, 3-methylpent-1-enyloxy, 2-methylpent-1-enyloxy, 1-methylpent-1-enyloxy, 3-ethylbut-3-enyloxy, 2-ethylbut-3-enyloxy, 1-ethylbut-3-enyloxy, 3-ethylbut-2-enyloxy, 2-ethylbut-2-enyloxy, 1-ethylbut-2-enyloxy, 3-ethylbut-1-enyloxy, 2-ethylbut-1-enyloxy, 1-ethylbut-1-enyloxy, 2-propylprop-2-enyloxy, 1-propylprop-2-enyloxy, 2-isopropylprop-2-enyloxy, 1-isopropylprop-2-enyloxy, 2-propylprop-1-enyloxy, 1-propylprop-1-enyloxy, 2-isopropylprop-1-enyloxy, 1-isopropylprop-1-enyloxy, 3,3-dimethylprop-1-enyloxy, 1-(1,1-dimethylethyl)ethenyloxy, buta-1,3-dienyloxy, penta-1,4-dienyloxy, hexa-1,5-dienyloxy or methylhexadienyloxy group.

The term "$C_2$-$C_6$-haloalkenyloxy" as used herein refers to a ($C_2$-$C_6$-alkenyl)-O— group as defined above in which one or more hydrogen atoms are replaced with one or more halogen atoms that may be the same or different.

The term "$C_2$-$C_6$-alkenylene" as used herein refers to a divalent $C_2$-$C_6$-alkenyl group as defined herein. Examples of $C_2$-$C_6$-alkenylene include but are not limited to ethenylene, 1,3-propenylene, butenylene, pentenylene, hexenylene, heptenylene, octenylene, nonenylene, decenylene, undecenylene, dodecenylene, and the like.

The term "$C_2$-$C_6$-haloalkynyloxy" as used herein refers to a ($C_2$-$C_6$-alkynyl)-O— group as defined above in which one or more hydrogen atoms are replaced with one or more halogen atoms that may be the same or different.

The term "$C_1$-$C_6$-alkylsulfanyl" as used herein refers to a saturated, linear or branched group of formula ($C_1$-$C_6$-alkyl)-S—, in which the term "$C_1$-$C_6$-alkyl" is as defined herein. Examples of $C_1$-$C_6$-alkylsulfanyl include but are not limited to methylsulfanyl, ethylsulfanyl, propylsulfanyl, isopropylsulfanyl, butylsulfanyl, sec-butylsulfanyl, isobutylsulfanyl, tert-butylsulfanyl, pentylsulfanyl, isopentylsulfanyl, hexylsulfanyl group.

The term "$C_1$-$C_6$-haloalkylsulfanyl" as used herein refers to a $C_1$-$C_6$-alkylsulfanyl as defined above in which one or more hydrogen atoms are replaced with one or more halogen atoms that may be the same or different.

The term "$C_3$-$C_8$-cycloalkylsulfanyl" as used herein refers to a saturated, monovalent, monocylic hydrocarbon ring which contains 3, 4, 5, 6, 7 or 8 carbon atoms and which is bound to the skeleton via a sulfur atom. Examples of monocyclic $C_3$-$C_8$-cycloalkylsulfanyls include but are not limited to cyclopropylsulfanyl, cyclobutylsulfanyl, cyclopentylsulfanyl, cyclohexylsulfanyl, cycloheptylsulfanyl, or cyclooctylsulfanyl.

The term "$C_1$-$C_6$-alkylsulfinyl" as used herein refers to a saturated, linear or branched group of formula ($C_1$-$C_6$-alkyl)-S(═O)—, in which the term "$C_1$-$C_6$-alkyl" is as defined herein. Examples of $C_1$-$C_6$-alkylsulfinyl include but are not limited to saturated, straight-chain or branched alkylsulfinyl radicals having 1 to 8, preferably 1 to 6 and more preferably 1 to 4 carbon atoms, for example (but not limited to) $C_1$-$C_6$-alkylsulfinyl such as methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl.

The term "$C_1$-$C_6$-haloalkylsulfinyl" as used herein refers to a $C_1$-$C_6$-alkylsulfinyl as defined above in which one or more hydrogen atoms are replaced with one or more halogen atoms that may be the same or different.

The term "$C_3$-$C_8$-cycloalkylsulfinyl" as used herein refers to a saturated, monovalent, monocylic hydrocarbon ring which contains 3, 4, 5, 6, 7 or 8 carbon atoms and which is bound to the skeleton via a —S(═O)— group. Examples of monocyclic $C_3$-$C_8$-cycloalkylsulfinyls include but are not limited to cyclopropylsulfinyl, cyclobutylsulfinyl, cyclopentylsulfinyl, cyclohexylsulfinyl, cycloheptylsulfinyl or cyclooctylsulfinyl.

The term "$C_1$-$C_6$-alkylsulfonyl" s used herein refers to a saturated, linear or branched group of formula ($C_1$-$C_6$-alkyl)-S(═O)$_2$—, in which the term "$C_1$-$C_6$-alkyl" is as defined herein. Examples of $C_1$-$C_6$-alkylsulfonyl include but are not limited to methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, 1,1-dimethylpropylsulfonyl, 1,2-dimethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl.

The term "$C_1$-$C_6$-haloalkylsulfonyl" as used herein refers to a $C_1$-$C_6$-alkylsulfonyl as defined above in which one or more hydrogen atoms are replaced with one or more halogen atoms that may be the same or different.

The term "$C_3$-$C_8$-cycloalkylsulfonyl" as used herein refers to a saturated, monovalent, monocylic hydrocarbon ring which contains 3, 4, 5, 6, 7 or 8 carbon atoms and which is bound to the skeleton via a —S(═O)$_2$— group. Examples of monocyclic $C_3$-$C_8$-cycloalkylsulfonyls include but are not limited to cyclopropylsulfonyl, cyclobutylsulfonyl, cyclopentylsulfonyl, cyclohexylsulfonyl, cycloheptylsulfonyl or cyclooctylsulfonyl.

The term "$C_1$-$C_6$-alkylcarbonyl" as used herein refers to a saturated, linear or branched group of formula ($C_1$-$C_6$-alkyl)-C(═O)—, in which the term "$C_1$-$C_6$-alkyl" is as defined herein.

The term "$C_1$-$C_6$-haloalkylcarbonyl" as used herein refers to a $C_1$-$C_6$-alkylcarbonyl as defined above in which one or more hydrogen atoms are replaced with one or more halogen atoms that may be the same or different.

The term "$C_1$-$C_6$-alkylcarbonyloxy" as used herein refers to a saturated, linear or branched group of formula ($C_1$-$C_6$-alkyl)-C(═O)O—, in which the term "$C_1$-$C_6$-alkyl" is as defined herein.

The term "$C_1$-$C_6$-alkoxycarbonyl" as used herein refers to a saturated, linear or branched group of formula ($C_1$-$C_6$-alkoxy)-C(═O)—, in which the term "$C_1$-$C_6$-alkoxy" is as defined herein.

The term "$C_1$-$C_6$-haloalkoxycarbonyl" as used herein refers to a $C_1$-$C_6$-alkoxycarbonyl as defined above in which one or more hydrogen atoms are replaced with one or more halogen atoms that may be the same or different.

The term "mono-($C_1$-$C_6$-alkyl)amino" as used herein refers to an amino radical having one $C_1$-$C_6$-alkyl group as defined herein. Examples of mono-($C_1$-$C_6$-alkyl)amino include but are not limited to Nmethylamino, N-ethylamino, N-isopropylamino, N-n-propylamino, N-isopropylamino and N-tert-butylamino.

The term "di-($C_1$-$C_6$)-alkylamino" as used herein refers to an amino radical having two independently selected $C_1$-$C_6$-alkyl groups as defined herein. Examples of $C_1$-$C_6$-dialkylamino include but are not limited to N,N-dimethylamino, N,N-diethylamino, N,N-diisopropylamino, N-ethyl-N-methylamino, N-methyl-N-n-propylamino, N-isopropyl-N-n-propylamino and N-tert-butyl-N-methylamino.

The term "$C_3$-$C_{12}$-carbocyclyl" as used herein refers to a saturated or partially unsaturated hydrocarbon ring system in which all of the ring members, which vary from 3 to 12, are carbon atoms. The ring system may be monocyclic or polycyclic (fused, spiro or bridged). $C_3$-$C_{12}$-carbocyclyls include but are not limited to $C_3$-$C_{12}$-cycloalkyl (mono or bicyclic), $C_3$-$C_{12}$-cycloalkenyl (mono or bicyclic), bicylic system comprising an aryl (e.g. phenyl) fused to a monocyclic $C_3$-$C_8$-cycloalkyl (e.g. tetrahydro-naphthalenyl, indanyl, 3-bicyclo[4.2.0]octa-1,3,5-trienyl), bicylic system comprising an aryl (e.g. phenyl) fused to a monocyclic $C_3$-$C_8$-cycloalkenyl (e.g. indenyl, dihydronaphthalenyl) and tricyclic system comprising a cyclopropyl connected through one carbon atom to a bicylic system comprising an aryl (e.g. phenyl) fused to a $C_3$-$C_8$-cycloalkyl or to a $C_3$-$C_8$-cycloalkenyl. The $C_3$-$C_{12}$-carbocyclyl can be attached to the parent molecular moiety through any carbon atom.

The term "$C_3$-$C_{12}$-cycloalkenyl" as used herein refers to an unsaturated, monovalent, mono- or bicylic hydrocarbon ring which contains 3, 4, 5, 6, 7, 8, 9, 10, 11 or 12 carbon atoms and one or two double bonds. Examples of monocyclic $C_3$-$C_8$-cycloalkenyl group include but are not limited to cyclobutenyl, cyclopentenyl, cyclohexenyl, cycloheptenyl and cyclooctenyl group. Examples of bicyclic $C_6$-$C_{12}$-cycloalkenyl group include but are not limited to 3-bicyclo[4.2.0]octa-1,3,5-trienyl, bicyclo[2.2.1]hept-2-enyl or bicyclo[2.2.2]oct-2-enyl.

The term "$C_6$-$C_{14}$-aryl" as used herein refers to an aromatic hydrocarbon ring system in which all of the ring members, which vary from 6 to 14, preferably from 6 to 10, are carbon atoms. The ring system may be monocyclic or fused polycyclic (e.g. bicyclic or tricyclic). Examples of aryl include but are not limited to phenyl, azulenyl and naphthyl.

The term "3- to 14-membered heterocyclyl" as used herein refers to a saturated or partially unsaturated 3-, 4-, 5-, 6-, 7-, 8-, 9-, 10-, 11-, 12-, 13- or 14-membered membered ring system comprising 1 to 4 heteroatoms independently selected from the group consisting of oxygen, nitrogen and sulfur. If the ring system contains more than one oxygen atoms, they are not directly adjacent. Heterocycles include but are not limited to 3- to 7-membered monocyclic heterocycles and 8- to 14-membered polycyclic (e.g. bicyclic or tricyclic) heterocycles. The 3- to 14-membered heterocycle can be connected to the parent molecular moiety through any carbon atom or nitrogen atom contained within the heterocycle. Examples of saturated heterocycles include but are not limited to 3-membered ring such as oxiranyl, aziridinyl, 4-membered ring such as azetidinyl, oxetanyl, thietanyl, 5-membered ring such as tetrahydrofuranyl, 1,3-dioxolanyl, tetrahydrothienyl, pyrrolidinyl, pyrazolidinyl, imidazolidinyl, triazolidinyl, isoxazolidinyl, oxazolidinyl, oxadiazolidinyl, thiazolidinyl, isothiazolidinyl, thiadiazolidinyl, 6-membered ring such as piperidinyl, hexahydropyridazinyl, hexahydropyrimidinyl, piperazinyl, triazinanyl, hexahydrotriazinyl, tetrahydropyranyl, dioxanyl, tetrahydrothiopyranyl, dithianyl, morpholinyl, 1,2-oxazinanyl, oxathianyl, thiomorpholinyl or 7-membered ring such as oxepanyl, azepanyl, 1,4-diazepanyl and 1,4-oxazepanyl.

Examples of unsaturated heterocycles include but are not limited to 5-membered ring such as dihydrofuranyl, 1,3-dioxolyl, dihydrothienyl, pyrrolinyl, dihydroimidazolyl, dihydropyrazolyl, isoxazolinyl, dihydrooxazolyl, dihydrothiazolyl or 6-membered ring such as pyranyl, thiopyranyl, thiazinyl and thiadiazinyl. Bicyclic heterocycles may consist of a monocyclic heteroaryl as defined herein fused to a monocyclic $C_3$-$C_8$-cycloalkyl, a monocyclic $C_3$-$C_8$-cycloalkenyl or a monocyclic heterocycle or may consist of a monocyclic heterocycle fused either to an aryl (e.g. phenyl), a $C_3$-$C_8$-cycloalkyl, a $C_3$-$C_8$-cycloalkenyl or a monocyclic heterocycle. When two monocyclic heterocycles or one monocyclic heterocycle and one monocyclic heteroaryl comprising nitrogen atoms are fused, nitrogen atom may be at the bridgehead (e.g. 4,5,6,7-tetrahydropyrazolo[1,5-a]pyridinyl, 5,6,7,8-tetrahydro-[1,2,4]triazolo[1,5-a]pyridinyl, 5,6,7,8-tetrahydroimidazo[1,2-a]pyridinyl). Tricyclic heterocycles may consist of a monocyclic cycloalkyl connected through one common atom to a bicyclic heterocycle.

The terms "3- to 7-membered heterocyclyl" and "3- to 7-membered heterocyclyl-ring" as used herein refers to a saturated 3-, 4-, 5-, 6- or 7-membered ring system comprising 1 or 2 heteroatoms independently selected from the group consisting of oxygen, nitrogen and sulfur. Examples include but are not limited to oxiranyl, aziridinyl, azetidinyl, oxetanyl, thietanyl, tetrahydrofuranyl, 1,3-dioxolanyl, tetrahydrothienyl, pyrrolidinyl, pyrazolidinyl, imidazolidinyl, triazolidinyl, isoxazolidinyl, oxazolidinyl, oxadiazolidinyl, thiazolidinyl, isothiazolidinyl, thiadiazolidinyl, piperidinyl, hexahydropyridazinyl, hexahydropyrimidinyl, piperazinyl, triazinanyl, hexahydrotriazinyl, tetrahydropyranyl, dioxanyl, tetrahydrothiopyranyl, dithianyl, morpholinyl, 1,2-oxazinanyl, oxathianyl, thiomorpholinyl, oxepanyl, azepanyl, 1,4-diazepanyl and 1,4-oxazepanyl. Preferred 3- to 7-membered heterocyclyl are oxiranyl, aziridinyl, azetidinyl, oxetanyl, tetrahydrofuranyl, 1,3-dioxolanyl, pyrrolidinyl, piperidinyl, piperazinyl, tetrahydropyranyl, dioxanyl, morpholinyl and thiomorpholinyl.

The term "5- to 14-membered heteroaryl" as used herein refers to an aromatic ring system comprising 1 to 4 heteroatoms independently selected from the group consisting of oxygen, nitrogen and sulfur. If the ring system contains more than one oxygen atom, they are not directly adjacent. Aromatic heterocycles include 5- or 6-membered monocyclic heteroaryls and 7- to 14-membered polycyclic (e.g. bicyclic or tricyclic) heteroaryls. The 5- to 14-membered heteroaryl can be connected to the parent molecular moiety through any carbon atom or nitrogen atom contained within the heterocycle.

The term "5- or 6-membered heteroaryl" as used herein refers to a 5- or 6-membered aromatic monocyclic ring system containing 1, 2, 3 or 4 heteroatoms independently selected from the group consisting of oxygen, nitrogen and sulfur. Examples of 5-membered monocyclic heteroaryl include but are not limited to furyl (furanyl), thienyl, pyrrolyl, pyrazolyl, imidazolyl, triazolyl, tetrazolyl, isoxazolyl, oxazolyl, oxadiazolyl, oxatriazolyl, isothiazolyl, thiazolyl, thiadiazolyl and thiatriazolyl. Examples of 6-membered monocyclic heteroaryl include but are not limited to pyridinyl, pyridazinyl, pyrimidinyl, pyrazinyl, triazinyl, tetrazinyl.

The term "7- to 14-membered heteroaryl" as used herein refers to a 7-, 8-, 9-, 10-, 11-, 12-, 13- or 14-membered aromatic polycyclic (e.g. bicyclic or tricyclic) ring system containing 1, 2 or 3 heteroatoms independently selected from the group consisting of oxygen, nitrogen and sulfur. Bicyclic heteroaryls may consist of a monocyclic heteroaryl as defined herein fused to an aryl (e.g. phenyl) or to a monocyclic heteroaryl. Examples of bicyclic heteroaryls include but are not limited to 9-membered ring such as indolyl, indolizinyl, isoindolyl, benzimadozolyl, imidazopyridinyl, indazolyl, benzotriazolyl, purinyl, benzofuranyl, benzothiophenyl, benzothiazolyl, benzoxazolyl and benzisoxazolyl or 10-membered ring such as quinolinyl, isoquinolinyl, cinnolinyl, quinazolinyl, quinoxalinyl, phthalazinyl, naphthyridinyl, pteridinal and benzodioxinyl. In 9- or 10-membered bicyclic heteroaryls comprising two fused 5- or 6-membered monocyclic heteroaryls, nitrogen atom may be at the bridgehead (e.g. imidazo[1,2-a]pyridinyl, [1,2,4]triazolo[4,3-a]pyridinyl, imidazo[1,2-a]pyridinyl, imidazo[2,1-b]oxazolyl, furo[2,3-d]isoxazolyl). Examples of tricyclic aromatic heterocyle include but are not limited to carbazolyl, acridinyl and phenazinyl.

The terms "$C_3$-$C_{12}$-carbocyclyloxy", "$C_3$-$C_8$-cycloalkoxy", "$C_6$-$C_{14}$-aryloxy", "5- to 14-membered heteroaryloxy", "3- to 14-membered heterocyclyloxy" as used herein designate a group of formula —O—R wherein R is respectively a $C_3$-$C_{12}$-carbocyclyl, a $C_3$-$C_8$-cycloalkyl, a $C_6$-$C_{14}$-aryl, a 5- to 14-membered heteroaryl or a 3- to 14-membered heterocyclyl group as defined herein.

The terms "$C_3$-$C_{12}$-carbocyclylsulfanyl", "$C_6$-$C_{14}$-arylsulfanyl", "5- to 14-membered heteroarylsulfanyl", "3- to 14-membered heterocyclylsulfanyl" as used herein designate a group of formula —S—R wherein R is respectively a $C_3$-$C_{12}$-carbocyclyl, a $C_6$-$C_{14}$-aryl, a 5- to 14-membered heteroaryl or a 3- to 14-membered heterocyclyl group as defined herein.

The terms "$C_3$-$C_{12}$-carbocyclylsulfinyl", "$C_6$-$C_{14}$-arylsulfinyl", "5- to 14-membered heteroarylsulfinyl", "3- to 14-membered heterocyclylsulfinyl" as used herein designate a group of formula —(S═O)—R wherein R is respectively a $C_3$-$C_{12}$-carbocyclyl, a $C_6$-$C_{14}$-aryl, a 5- to 14-membered heteroaryl or a 3- to 14-membered heterocyclyl group as defined herein.

The terms "$C_3$-$C_{12}$-carbocyclylsulfonyl", "$C_6$-$C_{14}$-arylsulfonyl", "5- to 14-membered heteroaryl-sulfonyl", "3- to 14-membered heterocyclylsulfonyl" as used herein designate a group of formula —(S═O)$_2$—R wherein R is respectively a $C_3$-$C_{12}$-carbocyclyl, a $C_6$-$C_{14}$-aryl, a 5- to 14-membered heteroaryl or a 3- to 14-membered heterocyclyl group as defined herein.

The term "leaving group" as used herein is to be understood as meaning a group which is displaced from a compound in a substitution or an elimination reaction, for example a halogen atom, a trifluoromethanesulphonate ("triflate") group, alkoxy, methanesulphonate, p-toluenesulphonate, etc.

The terms "as described herein" when referring to a variable Q, E, T, $R^1$, $R^2$, $R^3$, $R^4$, $R^5$, $R^6$, $R^7$ and $R^8$ and m incorporates by reference the broad definition of the variable as well as preferred, more preferred and even more preferred definitions, if any.

Not encompassed herein are compounds resulting from combinations which are against natural laws and which the person skilled in the art would therefore exclude based on his/her expert knowledge. For instance, ring structures having three or more adjacent oxygen atoms are excluded.

The compounds of formula (I) can suitably be in their free form, salt form, N-oxide form or solvate form (e.g. hydrate).

Depending on the nature of the substituents, the compound of formula (I) may be present in the form of different stereoisomers. These stereoisomers are, for example, enantiomers, diastereomers, atropisomers or geometric isomers. Accordingly, the invention encompasses both pure stereoisomers and any mixture of these isomers. Where a compound can be present in two or more tautomer forms in equilibrium, reference to the compound by means of one tautomeric description is to be considered to include all tautomer forms.

Any of the compounds of the present invention can also exist in one or more geometric isomer forms depending on the number of double bonds in the compound. Geometric isomers by nature of substituents about a double bond or a ring may be present in cis (═Z-) or trans (=E-) form. The invention thus relates equally to all geometric isomers and to all possible mixtures, in all proportions.

Depending on the nature of the substituents, the compound of formula (I) may be present in the form of the free compound and/or a salt thereof, such as an agrochemically active salt.

Agrochemically active salts include acid addition salts of inorganic and organic acids well as salts of customary bases. Examples of inorganic acids are hydrohalic acids, such as hydrogen fluoride, hydrogen chloride, hydrogen bromide and hydrogen iodide, sulfuric acid, phosphoric acid and nitric acid, and acidic salts, such as sodium bisulfate and potassium bisulfate. Useful organic acids include, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated fatty acids having 6 to 20 carbon atoms, alkylsulphuric monoesters, alkylsulphonic acids (sulphonic acids having straight-chain or branched alkyl radicals having 1 to 20 carbon atoms), arylsulphonic acids or aryldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulphonic acid, salicylic acid, p-aminosalicylic acid, 2-phenoxybenzoic acid, 2-acetoxybenzoic acid, etc.

Solvates of the compounds of the invention or their salts are stoichiometric compositions of the compounds with solvents.

The compounds of the invention may exist in multiple crystalline and/or amorphous forms. Crystalline forms include unsolvated crystalline forms, solvates and hydrates.

The term "leaving group" as used herein is to be understood as meaning a group which is displaced from a compound in a substitution or an elimination reaction, for example a halogen atom, a trifluoromethanesulphonate ("triflate") group, alkoxy, methanesulphonate, p-toluenesulphonate, etc.

The terms "as described herein" when referring to a variable A, E, Q, L, m, T, $R^1$, $R^2$, $R^3$, $R^4$, $R^5$, $R^6$, $R^7$ and $R^8$ incorporates by reference the broad definition of the variable as well as preferred, more preferred and even more preferred definitions, if any.

The present invention also relates to compounds of the formula (I), wherein $A^1$ is N or $CR^8$,
  wherein $R^1$ is hydrogen or halogen, $A^2$ is O, S, C(═O), S(═O), S(═O)$_2$, $NR^1$ or $CR^{2A}R^{R2B}$,
  wherein
  $R^1$ is hydrogen, $C_1$-$C_6$-alkyl or $C_3$-$C_8$-cycloalkyl,
    wherein $C_1$-$C_6$-alkyl is optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl,
    and
    wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl,
  $R^{2A}$ and $R^{2B}$ are independently hydrogen, $C_1$-$C_6$-alkyl or $C_3$-$C_8$-cycloalkyl,
    wherein $C_1$-$C_6$-alkyl is optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^{2A}$ and $R^{2B}$ form together with the carbon atom to which they are attached to a $C_3$-$C_8$-cycloalkyl-ring or a 3- to 7-membered heterocyclyl-ring, m is 0, 1 or 2, T is hydrogen, hydroxyl, $C_1$-$C_6$-alkyl, —C(═O)$R^{11}$, —C(═O)($OR^{12}$), —C(═O)N($R^{13}$)$_2$, —S(═O)$R^{14}$, —S(═O)$_2R^{14}$ or —S(═O)$_2$N($R^{14}$)$_2$, wherein $R^{11}$ and $R^{12}$ are independently $C_1$-$C_6$-alkyl, $C_1$-$C_6$-haloalkyl, $C_3$-$C_8$-cycloalkyl or $C_2$-$C_6$-alkenyl, $R^{13}$ and $R^{14}$ are independently hydrogen, $C_1$-$C_6$-alkyl, $C_1$-$C_6$-haloalkyl, $C_3$-$C_8$-cycloalkyl or $C_2$-$C_6$-alkenyl, $R^3$ and $R^4$ are independently hydrogen, halogen, cyano, hydroxyl, formyl, carboxyl, $C_1$-$C_6$-alkyl, $C_1$-$C_6$-alkoxy, $C_1$-$C_6$-alkylcarbonyl, $C_1$-$C_6$-alkoxycarbonyl, $C_2$-$C_6$-alkenyl, $C_2$-$C_6$-alkynyl, $C_3$-$C_8$-cycloalkyl, $C_6$-$C_{14}$-aryl, 5- to 14-membered heteroaryl, 3- to 14-membered heterocyclyl or —O—Si($C_1$-$C_6$-alkyl)$_3$, wherein $C_1$-$C_6$-alkyl, $C_1$-$C_6$-alkoxy, $C_1$-$C_6$-alkylcarbonyl, $C_1$-$C_6$-alkoxycarbonyl, $C_2$-$C_6$-alkenyl, $C_2$-$C_6$-alkynyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl, $C_6$-$C_{14}$-aryl, 5- to 14-membered heteroaryl and 3- to 14-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^4$ form together with the carbon atom to which they are attached to a carbonyl, a methylidene, a $C_3$-$C_8$-cycloalkyl-ring or a 3- to 7-membered heterocyclyl-ring, wherein $C_3$-$C_8$-cycloalkyl-ring and 3- to 7-membered heterocyclyl-ring are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, $R^5$ is hydrogen, hydroxyl, $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl, $C_3$-$C_8$-cycloalkyl or —O—Si($C_1$-$C_6$-alkyl)$_3$, wherein $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^5$ or $R^4$ and $R^5$ form together with the carbon atom to which they are attached to a $C_3$-$C_8$-cycloalkyl-ring, L is a direct bond, carbonyl, $C_1$-$C_6$-alkylene, $C_2$-$C_6$-alkenylene, $C_2$-$C_6$-alkynylene, —C(═O)—$C_1$-$C_6$-alkylene-, —$C_1$-$C_6$-alkylene-C(═O)—, —$NR^{L1}$—, —$NR^{L2}$(C═O)—, —C(═O)$NR^{L3}$—, —$NR^{L4}$S(═O)$_2$—, —S(═O)$_2NR^{L5}$—, —C(═$NOR^{L6}$)$_1$, —C(═N—N($R^{L7}$)$_2$)—, —C(═$NR^{L8}$)— or a group of formula

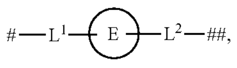

wherein said $C_1$-$C_6$-alkylene, $C_2$-$C_6$-alkenylene, $C_2$-$C_6$-alkynylene, —C(═O)—$C_1$-$C_6$-alkylene- and —$C_1$-$C_6$-alkylene-C(═O)— are optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl, $C_3$-$C_8$-cycloalkenyl and 3- to 7-membered heterocyclyl in turn are optionally substituted with one to three substituents $L^{SC}$, $R^{L1}$, $R^{L2}$, $R^{L3}$ and $R^{L4}$ are independently hydrogen or $C_1$-$C_6$-alkyl, $R^{L5}$, $R^{L6}$, $R^{L7}$ and $R^{L8}$ are independently hydrogen, $C_1$-$C_6$-alkyl, $C_1$-$C_6$-haloalkyl, $C_3$-$C_8$-cycloalkyl or $C_2$-$C_6$-alkenyl, $L^{SA}$ is independently halogen, cyano, hydroxyl, carboxyl, methylidene, halomethylidene, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$ or 3- to 7-membered heterocyclyl, and/or two substituents $L^{SA}$ that are bound to the same carbon atom form together with the carbon atom which they are attached to a $C_3$-$C_8$-cycloalkyl-ring or a 3- to 7-membered heterocyclyl-ring, $L^{SC}$ is independently halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, and/or two $L^{SC}$ substituents form together with the carbon atom to which they are attached to a $C_3$-$C_8$-cycloalkyl-ring, $R^6$ is $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_2$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl, 3- to 14-membered heterocyclylsulfonyl, $C_1$-$C_3$-alkoxy, $C_1$-$C_3$-haloalkoxy, $C_1$-$C_3$-alkylsulfanyl, $C_1$-$C_3$-alkylsulfinyl or $C_1$-$C_3$-alkylsulfonyl, wherein $C_1$-$C_3$-alkoxy, $C_1$-$C_3$-haloalkoxy, $C_1$-$C_3$-alkylsulfanyl, $C_1$-$C_3$-alkylsulfinyl and $C_1$-$C_3$-alkylsulfonyl are substituted with one substituent selected from the group consisting of $C_3$-$C_{12}$-carbocyclyl, $C_6$-$C_{14}$-aryl, 3- to 14-membered heterocyclyl and 5- to 14-membered heteroaryl, wherein said $C_3$-$C_{12}$-carbocyclyl, $C_6$-$C_{14}$-aryl, 3- to 14-membered heterocyclyl and 5- to 14-membered heteroaryl in turn are optionally substituted with one to four $R^{6S}$ substituents, wherein $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl and 3- to 14-membered heterocyclylsulfonyl are optionally substituted with one to four $R^{6S}$ substituents, wherein $R^{6S}$ is independently selected from the group consisting of halogen, cyano, isocyano, nitro, hydroxyl, mercapto, pentafluorosulfanyl, oxo, methylidene, halomethylidene, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, —N($R^{15}$)$_2$, —O(C═O)$R^{16}$, —C(═O)$R^{16}$, —C(═O)(O$R^{17}$), —C(═O)N($R^{18}$)$_2$, —S(═O)$_2$N($R^{19}$)$_2$, —O—Si($C_1$-$C_6$-alkyl)$_3$ and —Si($C_1$-$C_6$-alkyl)$_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are furthermore optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, or two substituents $C_1$-$C_6$-alkyl attached to the same carbon atom from a $C_3$-$C_8$-cycloalkyl-ring, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and wherein $R^{15}$ is independently hydrogen, $C_1$-$C_6$-alkyl or $C_3$-$C_8$-cycloalkyl, wherein said $C_1$-$C_6$-alkyl in turn is optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, and wherein said $C_3$-$C_8$-cycloalkyl in turn is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl and $C_1$-$C_6$-haloalkyl in turn are optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, $R^7$ is hydrogen, halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy, —O—Si($C_1$-$C_6$-alkyl)$_3$, —Si($C_1$-$C_6$-alkyl)$_3$, —N($R^{20}$)$_2$, —C(═$NR^{21}$)$R^{22}$, —$NR^{23}$C(═O)$R^{24}$, —C(═O)($OR^{25}$), —C(═O)N($R^{26}$)$_2$, —S(═O)$_2$N($R^{27}$)$_2$ or —S(═O)(═$NR^{28}$)$R^{29}$, wherein $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are optionally substituted with one to three $R^{7Sa}$ substituents, wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy are optionally substituted with one to three $R^{7Sc}$ substituents, and wherein $R^{20}$ is independently hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_6$-$C_{14}$-aryl, 5- or 6-membered heteroaryl or 3- to 7-membered heterocyclyl, wherein $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl in turn are optionally substituted with one to three substituents $R^{7Sa}$, and wherein $C_3$-$C_8$-cycloalkyl, $C_3$-$C_8$-halocycloalkyl, $C_6$-$C_{14}$-aryl, 5- or 6-membered heteroaryl and 3- to 7-membered heterocyclyl in turn are optionally substituted with one to three substituents $R^{7Sc}$, $R^{21}$ and $R^{22}$ are independently hydroxyl, amino, cyano, $C_1$-$C_6$-alkyl, $C_1$-$C_6$-haloalkyl, $C_1$-$C_6$-alkoxy, mono-($C_1$-$C_6$-alkyl)amino or di-($C_1$-$C_6$-alkyl)amino, wherein $C_1$-$C_6$-alkyl, $C_1$-$C_6$-haloalkyl, $C_1$-$C_6$-alkoxy, mono-($C_1$-$C_6$-alkyl)amino and di-($C_1$-$C_6$-alkyl)amino in turn are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_6$-alkyl, $C_1$-$C_6$-haloalkyl and $C_3$-$C_8$-cycloalkyl, wherein $C_1$-$C_6$-alkyl and $C_1$-$C_6$-haloalkyl in turn are optionally substituted with one to three $R^{7Sa}$ substituents, and wherein $C_3$-$C_8$-cycloalkyl in turn is optionally substituted with one to three $R^{7Sc}$ substituents, wherein $R^{7Sa}$ is independently cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$, —Si($C_1$-$C_6$-alkyl)$_3$, $C_6$-$C_{14}$-aryl or 3- to 7-membered heterocyclyl, $R^{7Sc}$ is independently halogen, cyano, nitro, hydroxyl, formyl, oxo, methylidene, halomethylidene, $C_1$-$C_6$-alkyl, $C_1$-$C_6$-haloalkyl $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, or two $R^{7Sc}$ substituents $C_1$-$C_6$-alkyl that are bound to the same carbon atom form together a $C_3$-$C_8$-cycloalkyl-ring, Q is $C_6$-$C_{14}$-aryl, $C_3$-$C_{12}$-carbocyclyl, 3- to 14-membered heterocyclyl or 5- to 14-membered heteroaryl, wherein $C_6$-$C_{14}$-aryl, $C_3$-$C_{12}$-carbocyclyl, 3- to 14-membered heterocyclyl or 5- to 14-membered heteroaryl are optionally substituted with one to five substituents $Q^S$ wherein $Q^S$ is independently selected from the group consisting of halogen, cyano, isocyano, nitro, hydroxyl, mercapto, formyl, carboxyl, $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyloxy, $C_3$-$C_6$-cycloalkenyl, 3- to 7-membered heterocyclyl, $C_6$-$C_{14}$-aryl, 5- to 14-membered heteroaryl, —O—Si($C_1$-$C_6$-alkyl)$_3$, —Si($C_1$-$C_6$-alkyl)$_3$, —O—C(═O)$R^{33}$, —$NR^{34}$C(═O)$R^{35}$, —C(═O)N($R^{36}$)$_2$, C(═S)$R^{37}$, —C(═S)N($R^{38}$)$_2$, —C(═$NR^{39}$)$R^{40}$, —C(═$NOR^{41}$)$R^{42}$ and —N($R^{43}$)$_2$, wherein said $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —$Si(C_1-C_6\text{-alkyl})_3$ and 3- to 7-membered heterocyclyl, said $C_3$-$C_8$-cycloalkyl, $C_3$-$C_8$-cycloalkoxy, $C_3$-$C_6$-cycloalkenyl, 3- to 7-membered heterocyclyl and 5- to 14-membered heteroaryl in turn are optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl, and wherein $R^{33}$ is hydrogen, $C_1$-$C_6$-alkyl, $C_1$-$C_6$-haloalkyl and $C_1$-$C_6$-alkoxy, $R^{34}$, $R^{35}$, $R^{36}$ $R^{37}$ $R^{38}$ $R^{39}$ $R^{40}$ $R^{41}$ and $R^{42}$ are independently hydrogen, $C_1$-$C_6$-alkyl, $C_1$-$C_6$-haloalkyl or $C_1$-$C_6$-alkoxy, wherein said $C_1$-$C_6$-alkyl, $C_1$-$C_6$-haloalkyl and $C_1$-$C_6$-alkoxy in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —$Si(C_1-C_6\text{-alkyl})_3$ and 3- to 7-membered heterocyclyl, and wherein $R^{43}$ is hydrogen, hydroxyl, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl or $C_3$-$C_8$-cycloalkyl, wherein said $C_1$-$C_6$-alkyl, $C_1$-$C_6$-haloalkyl, $C_1$-$C_6$-alkoxy, $C_2$-$C_6$-alkenyl and $C_2$-$C_6$-haloalkenyl in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —$Si(C_1-C_6\text{-alkyl})_3$ and 3- to 7-membered heterocyclyl, wherein said $C_3$-$C_8$-cycloalkyl in turn is optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl, as well as N-oxides, salts, hydrates and hydrates of the salts and N-oxides thereof.

Preferably the present invention relates to compounds of formula (I), wherein $A^1$ is $CR^8$, wherein $R^8$ is hydrogen, fluoro, chloro or methyl $A^2$ is O, C(=O), $NR^1$ or $CR^{2A}R^{R2B}$, wherein $R^1$ is hydrogen, formyl, $C_1$-$C_4$-alkyl or $C_3$-$C_6$-cycloalkyl, $R^{2A}$ and $R^{2B}$ are independently hydrogen or $C_1$-$C_4$-alkyl, m is 0, 1 or 2, T is hydrogen or $C_1$-$C_4$-alkyl $R^3$ and $R^4$ are independently hydrogen, fluoro, chloro, $C_1$-$C_4$-alkyl $C_1$-$C_4$-alkylcarbonyl, $C_1$-$C_4$-alkylcarbonyloxy, $C_2$-$C_4$-alkenyl, $C_2$-$C_4$-alkynyl or $C_3$-$C_6$-cycloalkyl, $R^5$ is hydrogen or $C_1$-$C_4$-alkyl, L is a direct bond, $C_1$-$C_4$-alkylene or a group of formula

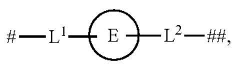

wherein said $C_1$-$C_4$-alkylene is optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl or 3- to 7-membered heterocyclyl, wherein said $C_3$-$C_8$-cycloalkyl and 3- to 7-membered heterocyclyl in turn are optionally substituted with one to three substituents $L^{SC}$ wherein $L^{SA}$ is independently fluoro, chloroor hydroxyl, or two substituents $L^{SA}$ that are bound to the same carbon atom form together with the carbon atom which they are attached to a $C_3$-$C_6$-cycloalkyl-ring or a 4- to 7-membered heterocyclyl-ring, $L^{SC}$ is independently fluoro, chloro hydroxyl, oxo, $C_1$-$C_4$-alkyl, $C_1$-$C_4$-haloalkyl, $C_1$-$C_4$-alkoxy or $C_1$-$C_4$-haloalkoxy, $R^6$ is $C_5$-$C_{10}$-carbocyclyl, phenyl, naphthyl, 5- to 10-membered heterocyclyl or 5- to 10-membered heteroaryl, $C_5$-$C_{10}$-carbocyclyloxy, phenoxy, naphthyloxy, 5- to 10-membered heteroaryloxy, 5- to 10-membered heterocyclyloxy, $C_5$-$C_{10}$-carbocyclylsulfanyl, phenylsulfanyl, naphthylsulfanyl, 5- to 10-membered heteroarylsulfanyl, 5- to 10-membered heterocyclylsulfanyl, $C_1$-$C_3$-alkoxy or $C_1$-$C_3$-haloalkoxy, wherein $C_1$-$C_3$-alkoxy and $C_1$-$C_3$-haloalkoxy are substituted with one substituent selected from the group consisting of $C_5$-$C_{10}$-carbocyclyl, phenyl, naphthyl, 5- to 10-membered heterocyclyl and 5- to 10-membered heteroaryl, wherein said $C_5$-$C_{10}$-carbocyclyl, phenyl, naphthyl, 5- to 10-membered heterocyclyl and 5- to 10-membered heteroaryl in turn are optionally substituted with one to three $R^{6S}$ substituents, wherein $C_5$-$C_{10}$-carbocyclyl, phenyl, naphthyl, 5- to 10-membered heterocyclyl or 5- to 10-membered heteroaryl, $C_5$-$C_{10}$-carbocyclyloxy, phenoxy, naphthyloxy, 5- to 10-membered heteroaryloxy, 5- to 10-membered heterocyclyloxy, $C_5$-$C_{10}$-carbocyclylsulfanyl, phenylsulfanyl, naphthylsulfanyl, 5- to 10-membered heteroarylsulfanyl and 5- to 10-membered heterocyclyl-sulfanyl are optionally substituted with one to three $R^{6S}$ substituents, wherein $R^{6S}$ is independently selected from the group consisting of halogen, cyano, hydroxyl, mercapto, pentafluorosulfanyl, oxo, methylidene, halomethylidene, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylsulfanyl, $C_1$-$C_4$-haloalkylsulfanyl, $C_3$-$C_6$-cycloalkylsulfanyl, $C_3$-$C_6$-cycloalkyl, $C_3$-$C_6$-cycloalkyloxy, 5- or 6-membered heteroaryl, 3- to 7-membered heterocyclyl, —C(═O)$R^{16}$, —C(═O)($OR^{17}$) or —C(═O)N($R^{18}$)$_2$, wherein $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylsulfanyl and $C_1$-$C_4$-haloalkylsulfanyl are furthermore optionally substituted with one to three substituents independently selected from the group consisting of halogen, hydroxyl, $C_1$-$C_4$-alkoxy, $C_1$-$C_4$-haloalkoxy, —Si($C_1$-$C_4$-alkyl)$_3$, $C_3$-$C_6$-cycloalkyl and $C_3$-$C_6$-halocycloalkyl, and wherein $C_3$-$C_6$-cycloalkylsulfanyl, $C_3$-$C_6$-cycloalkyl, $C_3$-$C_6$-cycloalkyloxy, phenyl, naphthyl, 5- or 6-membered heteroaryl and 3- to 7-membered heterocyclyl are furthermore optionally substituted with one to three substituents independently selected from the group consisting of fluoro, chloro, $C_1$-$C_4$-alkyl, $C_1$-$C_4$-haloalkyl, $C_1$-$C_4$-alkoxy and $C_1$-$C_4$-haloalkoxy, and wherein $R^{16}$, $R^{17}$ and $R^{18}$ are independently hydrogen, $C_1$-$C_4$-alkyl or $C_1$-$C_4$-haloalkyl, wherein said $C_1$-$C_4$-alkyl and $C_1$-$C_4$-haloalkyl in turn are optionally substituted with one to three substituents independently selected from the group consisting of halogen, hydroxyl, $C_1$-$C_4$-alkoxy, $C_1$-$C_4$-haloalkoxy, $C_3$-$C_6$-cycloalkyl and $C_3$-$C_6$-halocycloalkyl, $R^7$ is hydrogen, halogen, cyano, hydroxyl, mercapto, $C_1$-$C_4$-alkyl, $C_1$-$C_4$-haloalkyl, $C_1$-$C_4$-hydroxyalkyl, $C_1$-$C_4$-alkoxy, $C_1$-$C_4$-haloalkoxy, $C_1$-$C_4$-alkylcarbonyl, $C_1$-$C_4$-haloalkylcarbonyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylsulfanyl, $C_1$-$C_4$-haloalkylsulfanyl, $C_3$-$C_6$-cycloalkylsulfanyl, $C_1$-$C_4$-alkylsulfinyl, $C_1$-$C_4$-haloalkylsulfinyl, $C_3$-$C_6$-cycloalkylsulfinyl, $C_1$-$C_4$-alkylsulfonyl, $C_1$-$C_4$-haloalkylsulfonyl, $C_3$-$C_6$-cycloalkylsulfonyl, $C_3$-$C_6$-cycloalkyl, $C_3$-$C_6$-cycloalkenyl, phenyl, 5- or 6-membered heteroaryl, 3- to 7-membered heterocyclyl, $C_3$-$C_6$-cycloalkyloxy, phenoxy, 5- or 6-membered heteroaryloxy, 3- to 7-membered heterocyclyloxy, —N($R^{20}$)$_2$, —C(═N$R^{21}$)$R^{22}$, —N$R^{23}$C(═O)$R^{24}$, —C(═O)($OR^{25}$), —C(═O)N($R^{26}$)$_2$, —S(═O)$_2$N($R^{27}$)$_2$ or —S(═O)(═N$R^{28}$)$R^{29}$, wherein $C_1$-$C_4$-alkyl, $C_1$-$C_4$-haloalkyl, $C_1$-$C_4$-hydroxyalkyl, $C_1$-$C_4$-alkoxy, $C_1$-$C_4$-haloalkoxy, $C_1$-$C_4$-alkylcarbonyl, $C_1$-$C_4$-haloalkylcarbonyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylsulfanyl, $C_1$-$C_4$-haloalkylsulfanyl, $C_1$-$C_4$-alkylsulfinyl, $C_1$-$C_4$-haloalkylsulfinyl, $C_1$-$C_4$-alkylsulfonyl and $C_1$-$C_4$-haloalkylsulfonyl are optionally substituted with one to three $R^{7Sa}$ substituents, wherein $C_3$-$C_6$-cycloalkylsulfanyl, $C_1$-$C_4$-alkylsulfinyl, $C_1$-$C_4$-haloalkylsulfinyl, $C_3$-$C_6$-cycloalkylsulfinyl, $C_1$-$C_4$-alkylsulfonyl, $C_1$-$C_4$-haloalkylsulfonyl, $C_3$-$C_6$-cycloalkylsulfonyl, $C_3$-$C_6$-cycloalkyl, $C_3$-$C_6$-cycloalkenyl, phenyl, 5- or 6-membered heteroaryl, 3- to 7-membered heterocyclyl, $C_3$-$C_6$-cycloalkyloxy, phenoxy, 5- or 6-membered heteroaryloxy and 3- to 7-membered heterocyclyloxy are optionally substituted with one to three $R^{7Sc}$ substituents, and wherein $R^{20}$ is independently hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl or $C_3$-$C_6$-cycloalkyl, $R^{21}$ and $R^{22}$ are independently hydroxyl, $C_1$-$C_4$-alkyl, $C_1$-$C_4$-haloalkyl or $C_1$-$C_4$-alkoxy, $R^{23}$, $R^{24}$, $R^{25}$, $R^{26}$, $R^{27}$, $R^{28}$ and $R^{29}$ are independently hydrogen, $C_1$-$C_4$-alkyl, $C_1$-$C_4$-haloalkyl and $C_3$-$C_6$-cycloalkyl, wherein $R^{7Sa}$ is independently hydroxyl, $C_1$-$C_4$-alkoxy, $C_1$-$C_4$-haloalkoxy, $C_3$-$C_6$-cycloalkyl or —Si($C_1$-$C_4$-alkyl)$_3$, $R^{7Sc}$ is independently fluoro, chloro, hydroxyl, oxo, $C_1$-$C_4$-alkyl, $C_1$-$C_4$-haloalkyl $C_1$-$C_4$-alkoxy, $C_1$-$C_4$-haloalkoxy or $C_3$-$C_8$-cycloalkyl, Q is phenyl, naphthyl, $C_5$-$C_{10}$-carbocyclyl, 5- to 10-membered heterocyclyl or 5- to 10-membered heteroaryl, wherein phenyl, naphthyl, $C_5$-$C_{10}$-carbocyclyl, 5- to 10-membered heterocyclyl and 5- to 10-membered heteroaryl are optionally substituted with one to three substituents $Q^S$ wherein $Q^S$ is independently selected from the group consisting of halogen, cyano, nitro, formyl, $C_1$-$C_4$-alkyl, $C_1$-$C_4$-haloalkyl, $C_1$-$C_4$-alkylcarbonyl, $C_1$-$C_4$-haloalkylcarbonyl, $C_1$-$C_4$-alkoxy, $C_1$-$C_4$-haloalkoxy, $C_1$-$C_4$-alkoxycarbonyl, $C_1$-$C_4$-haloalkoxycarbonyl, $C_2$-$C_4$-alkenyl, $C_2$-$C_4$haloalkenyl, $C_2$-$C_4$-alkynyl, $C_2$-$C_4$-haloalkynyl, $C_1$-$C_4$-alkylsulfanyl, $C_1$-$C_4$-haloalkylsulfanyl, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, 3- to 7-membered heterocyclyl, phenyl, 5- or 6-membered heteroaryl, —O—C(═O)$R^{33}$, and —N($R^{43}$)$_2$, wherein said $C_1$-$C_4$-alkyl, $C_1$-$C_4$-haloalkyl, $C_1$-$C_4$-alkylcarbonyl, $C_1$-$C_4$-haloalkylcarbonyl, $C_1$-$C_4$-alkoxy, $C_1$-$C_4$-haloalkoxy, $C_1$-$C_4$-alkoxycarbonyl, $C_1$-$C_4$-haloalkoxycarbonyl, $C_2$-$C_4$-alkenyl, $C_2$-$C_4$haloalkenyl, $C_2$-$C_4$-alkynyl, $C_2$-$C_4$-haloalkynyl, $C_1$-$C_4$-alkylsulfanyl, $C_1$-$C_4$-haloalkylsulfanyl, $C_1$-$C_4$-alkylsulfinyl, $C_1$-$C_4$-haloalkylsulfinyl, $C_1$-$C_4$-alkylsulfonyl and $C_1$-$C_4$-haloalkylsulfonyl in turn are optionally substituted with one to three substituents independently selected from the group consisting of cyano, amino, nitro, hydroxyl, $C_1$-$C_4$-alkoxy, $C_1$-$C_4$-haloalkoxy, $C_1$-$C_4$-alkoxycarbonyl, $C_1$-$C_4$-haloalkoxycarbonyl, $C_3$-$C_6$-cycloalkyl, $C_3$-$C_6$-halocycloalkyl and 3- to 7-membered heterocyclyl, said $C_3$-$C_6$-cycloalkyl, 3- to 7-membered heterocyclyl and 5- or 6-membered heteroaryl in turn are optionally substituted with one to three substituents independently selected from the group consisting of halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxycarbonyl, $C_1$-$C_4$-haloalkoxycarbonyl and $C_3$-$C_6$-cycloalkyl, $R^{33}$ is $C_1$-$C_4$-alkyl or $C_1$-$C_6$-haloalkyl, $R^{43}$ is independently hydrogen, $C_1$-$C_4$-alkyl, $C_1$-$C_4$-haloalkyl or $C_3$-$C_6$-cycloalkyl, as well as N-oxides, salts, hydrates and hydrates of the salts and N-oxides thereof.

Preferably the present invention relates to compounds of formula (I), wherein $A^1$ is N or $CR^8$, wherein $R^1$ is hydrogen or halogen, $A^2$ is O, S, C(=O), S(=O), S(=O)$_2$, $NR^1$ or $CR^{2A}R^{R2B}$, wherein $R^1$ is hydrogen, $C_1$-$C_4$-alkyl or $C_3$-$C_6$-cycloalkyl, wherein $C_1$-$C_4$-alkyl is optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_6$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, $R^{2A}$ and $R^{2B}$ are independently hydrogen, $C_1$-$C_4$-alkyl or $C_3$-$C_6$-cycloalkyl, wherein $C_1$-$C_4$-alkyl is optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_6$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, m is 0, 1 or 2, T is hydrogen, $C_1$-$C_4$-alkyl, $R^3$ and $R^4$ are independently hydrogen, fluoro, chloro, $C_1$-$C_4$-alkyl, $C_2$-$C_4$-alkenyl, $C_2$-$C_4$-alkynyl or $C_3$-$C_6$-cycloalkyl, wherein $C_1$-$C_4$-alkyl, $C_2$-$C_4$-alkenyl and $C_2$-$C_4$-alkynyl are optionally substituted with one to three substituents independently selected from the group consisting of fluoro, chloro, hydroxyl, $C_1$-$C_4$-alkoxy, $C_1$-$C_4$-haloalkoxy, $C_3$-$C_6$-cycloalkyl and $C_3$-$C_6$-halocycloalkyl, and wherein $C_3$-$C_6$-cycloalkyl is optionally substituted with one to three substituents independently selected from the group consisting of fluoro, chloro, hydroxyl, oxo, methylidene, $C_1$-$C_4$-alkyl, $C_1$-$C_4$-haloalkyl, $C_1$-$C_4$-alkoxy, $C_1$-$C_4$-haloalkoxy, $C_2$-$C_4$ alkenyl, $C_3$-$C_6$-cycloalkyl and $C_3$-$C_6$-halocycloalkyl, or $R^5$ is hydrogen, hydroxyl, $C_1$-$C_4$-alkyl, $C_1$-$C_4$-alkoxy or $C_1$-$C_4$-alkylsulfanyl, wherein $C_1$-$C_4$-alkyl, $C_1$-$C_4$-alkoxy and $C_1$-$C_6$-alkylsulfanyl are optionally substituted with one to three substituents independently selected from the group consisting of fluoro, chloro hydroxyl, $C_1$-$C_4$-alkoxy, $C_1$-$C_4$-haloalkoxy, $C_3$-$C_6$-cycloalkyl and $C_3$-$C_6$-halocycloalkyl, and wherein $C_3$-$C_6$-cycloalkyl is optionally substituted with one to three substituents independently selected from the group consisting of fluoro, chloro, hydroxyl, oxo, methylidene, $C_1$-$C_4$-alkyl, $C_1$-$C_4$-haloalkyl, $C_1$-$C_4$-alkoxy, $C_1$-$C_4$-haloalkoxy, $C_2$-$C_4$alkenyl, $C_3$-$C_6$-cycloalkyl and $C_3$-$C_6$-halocycloalkyl, or $R^3$ and $R^5$ or $R^4$ and $R^5$ form together with the carbon atom to which they are attached to a $C_3$-$C_6$-cycloalkyl-ring, L is a direct bond, $C_1$-$C_6$-alkylene or a group of formula

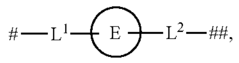

wherein said $C_1$-$C_6$-alkylene is optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_6$-cycloalkyl or 3- to 7-membered heterocyclyl, wherein said $C_3$-$C_6$-cycloalkyl and 3- to 7-membered heterocyclyl in turn are optionally substituted with one to three substituents $L^{SC}$, $L^{SA}$ is independently fluoro, chloro, hydroxyl, $C_1$-$C_4$-alkoxy, $C_1$-$C_4$-haloalkoxy, $C_3$-$C_6$-cycloalkyl and $C_3$-$C_6$-halocycloalkyl, or two substituents $L^{SA}$ that are bound to the same carbon atom form together with the carbon atom which they are attached to a $C_3$-$C_6$-cycloalkyl-ring or a 3- to 7-membered heterocyclyl-ring, $L^{SC}$ is independently fluoro, chloro, hydroxyl, oxo, $C_1$-$C_4$-alkyl, $C_1$-$C_4$-haloalkyl, $C_1$-$C_4$-alkoxy, $C_1$-$C_4$-haloalkoxy, $C_2$-$C_4$alkenyl, $C_3$-$C_6$-cycloalkyl or $C_3$-$C_6$-halocycloalkyl, $R^6$ is $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_1$-$C_3$-alkoxy, $C_1$-$C_3$-haloalkoxy, wherein $C_1$-$C_3$-alkoxy and $C_1$-$C_3$-haloalkoxy are substituted with one substituent selected from the group consisting of $C_3$-$C_{12}$-carbocyclyl, $C_6$-$C_{14}$-aryl, 3- to 14-membered heterocyclyl and 5- to 14-membered heteroaryl, wherein said $C_3$-$C_{12}$-carbocyclyl, $C_6$-$C_{14}$-aryl, 3- to 14-membered heterocyclyl and 5- to 14-membered heteroaryl in turn are optionally substituted with one to three $R^{6S}$ substituents, wherein $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl and 3- to 14-membered heterocyclylsulfanyl are optionally substituted with one to three $R^{6S}$ substituents, wherein $R^{6S}$ is independently selected from the group consisting of halogen, cyano, nitro, hydroxyl, mercapto, pentafluorosulfanyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_1$-$C_6$-haloalkynyl, $C_1$-$C_6$-alkylsulfanyl, $C_1$-$C_6$-haloalkylsulfanyl, $C_3$-$C_6$-cycloalkylsulfanyl, $C_3$-$C_6$-cycloalkyl, $C_3$-$C_6$-cycloalkyloxy, $C_6$-$C_{14}$-aryl, 5- or 6-membered heteroaryl, 3- to 7-membered heterocyclyl, —C(═O)(OR$^{17}$) and —C(═O)N(R$^{18}$)$_2$ wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylsulfanyl and $C_1$-$C_6$-haloalkylsulfanyl in turn are optionally substituted with one to three substituents independently selected from the group consisting of fluoro, chloro, hydroxyl, $C_1$-$C_4$-alkoxy, $C_1$-$C_4$-haloalkoxy, $C_3$-$C_6$-cycloalkyl and $C_3$-$C_6$-halocycloalkyl and wherein $C_3$-$C_6$-cycloalkylsulfanyl, $C_3$-$C_6$-cycloalkyl, $C_3$-$C_6$-cycloalkyloxy, $C_6$-$C_{14}$-aryl, 5- or 6-membered heteroaryl and 3- to 7-membered heterocyclyl in turn are optionally substituted with one to three substituents independently selected from the group consisting of fluoro, chloro, $C_1$-$C_4$-alkyl, $C_1$-$C_4$-haloalkyl, $C_1$-$C_4$-alkoxy and $C_1$-$C_4$-haloalkoxy, and wherein $R^{17}$ and $R^{18}$ are independently hydrogen, $C_1$-$C_4$-alkyl or $C_1$-$C_4$-haloalkyl, wherein said $C_1$-$C_4$-alkyl or $C_1$-$C_4$-haloalkyl in turn are optionally substituted with one to three substituents independently selected from the group consisting of fluoro, chloro, hydroxyl, $C_1$-$C_4$-alkoxy, $C_1$-$C_4$-haloalkoxy, $C_3$-$C_6$-cycloalkyl and $C_3$-$C_6$-halocycloalkyl, $R^7$ is hydrogen, halogen, cyano, hydroxyl, mercapto, $C_1$-$C_4$-alkyl, $C_1$-$C_4$-haloalkyl, $C_1$-$C_4$-hydroxyalkyl, $C_1$-$C_4$-alkoxy, $C_1$-$C_4$-haloalkoxy, $C_1$-$C_4$-alkylcarbonyl, $C_1$-$C_4$haloalkylcarbonyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylsulfanyl, $C_1$-$C_4$-haloalkylsulfanyl, $C_3$-$C_6$-cycloalkylsulfanyl, $C_1$-$C_4$-alkylsulfinyl, $C_1$-$C_4$-haloalkylsulfinyl, $C_3$-$C_6$-cycloalkylsulfinyl, $C_1$-$C_4$-alkylsulfonyl, $C_1$-$C_4$-haloalkylsulfonyl, $C_3$-$C_6$-cycloalkylsulfonyl, $C_3$-$C_6$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_6$-cycloalkyloxy, $C_6$-$C_{14}$-aryloxy, 5- or 6-membered heteroaryloxy, 3- to 7-membered heterocyclyloxy, —N(R$^{20}$)$_2$, —C(═NR$^{21}$)R$^{22}$, —NR$^{23}$C(═O)R$^{24}$, —C(═O)(OR$^{25}$), —C(═O)N(R$^{26}$)$_2$, —S(═O)$_2$N(R$^{27}$)$_2$ or —S(═O)(═NR$^{28}$)R$^{29}$, Wherein $C_1$-$C_4$-alkyl, $C_1$-$C_4$-haloalkyl, $C_1$-$C_4$-hydroxyalkyl, $C_1$-$C_4$-alkoxy, $C_1$-$C_4$-haloalkoxy, $C_1$-$C_4$-alkylcarbonyl, $C_1$-$C_4$haloalkylcarbonyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylsulfanyl, $C_1$-$C_4$-haloalkylsulfanyl, $C_1$-$C_4$-alkylsulfinyl and $C_1$-$C_4$-haloalkylsulfinyl are optionally substituted with one to three $R^{7Sa}$ substituents, wherein $C_3$-$C_6$-cycloalkylsulfanyl, $C_3$-$C_6$-cycloalkylsulfinyl, $C_3$-$C_6$-cycloalkylsulfonyl, $C_3$-$C_6$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_6$-cycloalkyloxy, $C_6$-$C_{14}$-aryloxy, 5- or 6-membered heteroaryloxy and 3- to 7-membered heterocyclyloxy are optionally substituted with one to three $R^{7Sc}$ substituents, and wherein $R^{20}$ is hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl or $C_3$-$C_6$-cycloalkyl, wherein $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl and $C_2$-$C_4$-haloalkynyl in turn are optionally substituted with one to three substituents $R^{7Sa}$, and wherein $C_3$-$C_6$-cycloalkyl in turn is optionally substituted with one to three substituents $R^{7Sc}$, $R^{21}$ and $R^{22}$ are independently hydroxyl, $C_1$-$C_4$-alkyl, $C_1$-$C_4$haloalkyl or $C_1$-$C_4$-alkoxy, wherein $C_1$-$C_4$-alkyl, $C_1$-$C_4$-haloalkyl and $C_1$-$C_4$-alkoxy in turn are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_4$-alkyl, $C_1$-$C_4$-haloalkyl and $C_3$-$C_6$-cycloalkyl, wherein $C_1$-$C_4$-alkyl and $C_1$-$C_4$-haloalkyl in turn are optionally substituted with one or two $R^{7Sa}$ substituents, and wherein $C_3$-$C_6$-cycloalkyl in turn is optionally substituted with one or two $R^{7Sc}$ substituents, wherein $R^{7Sa}$ is independently hydroxyl, $C_1$-$C_4$-alkoxy, $C_1$-$C_4$-haloalkoxy or $C_3$-$C_6$-cycloalkyl, $R^{7Sc}$ is independently fluoro, chloro, hydroxyl, oxo, $C_1$-$C_4$-alkyl, $C_1$-$C_4$-haloalkyl $C_1$-$C_4$-alkoxy, $C_1$-$C_4$-haloalkoxy or $C_3$-$C_6$-cycloalkyl, Q is phenyl, naphthyl, $C_3$-$C_{10}$-carbocyclyl, 5- to 10-membered heterocyclyl or 5- to 10-membered heteroaryl, wherein phenyl, naphthyl, $C_3$-$C_{10}$-carbocyclyl, 5- to 10-membered heterocyclyl and 5- to 10-membered heteroaryl are optionally substituted with one to three substituents $Q^S$ wherein $Q^S$ is independently selected from the group consisting of halogen, cyano, nitro, formyl, carboxyl, $C_1$-$C_4$-alkyl, $C_1$-$C_4$-haloalkyl, $C_1$-$C_4$-alkylcarbonyl, $C_1$-$C_4$-haloalkylcarbonyl, $C_1$-$C_4$-alkoxy, $C_1$-$C_4$-haloalkoxy, $C_1$-$C_4$-alkoxycarbonyl, $C_1$-$C_4$-haloalkoxycarbonyl, $C_2$-$C_4$alkenyl, $C_2$-$C_4$haloalkenyl, $C_2$-$C_4$-alkynyl, $C_2$-$C_4$-haloalkynyl, $C_1$-$C_4$-alkylsulfanyl, $C_1$-$C_4$-haloalkylsulfanyl, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, 3- to 7-membered heterocyclyl, phenyl, 5- or 6-membered heteroaryl, wherein said $C_1$-$C_4$-alkyl, $C_1$-$C_4$-haloalkyl, $C_1$-$C_4$-alkylcarbonyl, $C_1$-$C_4$-haloalkylcarbonyl, $C_1$-$C_4$-alkoxy, $C_1$-$C_4$-haloalkoxy, $C_1$-$C_4$-alkoxycarbonyl, $C_1$-$C_4$-haloalkoxycarbonyl, $C_2$-$C_4$alkenyl, $C_2$-$C_4$haloalkenyl, $C_2$-$C_4$-alkynyl, $C_2$-$C_4$-haloalkynyl, $C_1$-$C_4$-alkylsulfanyl, $C_1$-$C_4$-haloalkylsulfanyl, $C_1$-$C_4$-alkylsulfinyl, $C_1$-$C_4$-haloalkylsulfinyl, $C_1$-$C_4$-alkylsulfonyl and $C_1$-$C_4$-haloalkylsulfonyl in turn are optionally substituted with one to three substituents independently selected from the group consisting of cyano, amino, nitro, hydroxyl, $C_1$-$C_4$-alkoxy, $C_1$-$C_4$-haloalkoxy, $C_3$-$C_6$-cycloalkyl, $C_3$-$C_6$-halocycloalkyl and 3- to 7-membered heterocyclyl, said $C_3$-$C_6$-cycloalkyl, 3- to 7-membered heterocyclyl, phenyl and 5- or 6-membered heteroaryl in turn are optionally substituted with one to three substituents independently selected from the group consisting of fluoro, chloro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxycarbonyl, $C_1$-$C_4$-haloalkoxycarbonyl and $C_3$-$C_6$-cycloalkyl, as well as salts, hydrates and hydrates of the salts thereof.

More preferably the present invention relates to compounds of formula (I), wherein $A^1$ is $CR^8$, wherein $R^8$ is hydrogen, $A^2$ is O, C(=O) or $CR^{2A}R^{R2B}$, wherein $R^{2A}$ and $R^{2B}$ are independently hydrogen, m is 1, T is hydrogen, $R^3$ and $R^4$ are independently hydrogen, fluoro, chloro, $C_1$-$C_4$-alkyl, $C_1$-$C_4$-alkylcarbonyl, $C_1$-$C_4$-alkoxycarbonyl, $C_1$-$C_4$-alkylcarbonyloxy, $C_2$-$C_4$-alkenyl, $C_2$-$C_4$-alkynyl or $C_3$-$C_6$-cycloalkyl, $R^5$ is hydrogen, L is a direct bond, methylene or ethylene, wherein said methylene and ethylene are optionally substituted with one or two substituents $L^{SA}$, wherein $L^{SA}$ is independently fluoro, or two substituents $L^{SA}$ that are bound to the same carbon atom form together with the carbon atom which they are attached to a cyclopropyl- or a cyclobutyl-ring, $R^6$ is indanyl, tetrahydronaphthalenyl, phenyl, naphthyl, 1,3-benzodioxolyl, 1,2,3,4-tetrahydro-quinolinyl, chromanyl, isochromanyl, thiochromanyl, 2,3-dihydro-1,4-benzodioxinyl, tetrahydroquinolinyl, furanyl, thienyl, pyrazolyl, pyridinyl or pyrimidinyl, wherein indanyl, tetrahydronaphthalenyl, phenyl, naphthyl, 1,3-benzodioxolyl, 1,2,3,4-tetrahydroquinolinyl, chromanyl, isochromanyl, thiochromanyl, 2,3-dihydro-1,4-benzodioxinyl, tetrahydroquinolinyl, furanyl, thienyl, pyrazolyl, pyridinyl and pyrimidinyl are optionally substituted with one to three $R^{6S}$ substituents, wherein $R^{6S}$ is independently selected from the group consisting of halogen, cyano, oxo, $C_1$-$C_4$-alkyl, difluoromethyl, trifluoromethyl, $C_1$-$C_4$-alkoxy, difluoromethoxy, trifluoromethoxy, $C_2$-$C_4$-alkenyl, $C_2$-$C_4$-alkynyl, $C_1$-$C_4$-alkylsulfanyl, difluoromethylsulfanyl, trifluoro-methylsulfanyl, $C_3$-$C_6$-cycloalkyl, furanyl, thienyl, pyrazolyl, imidazolyl, triazolyl, oxazolyl, thiazolyl, pyridinyl, pyridazinyl, pyrimidinyl, oxetanyl, tetrahydrofuranyl or —C(=O)$R^{16}$, wherein $C_1$-$C_4$-alkyl, $C_1$-$C_4$-alkoxy, $C_2$-$C_4$-alkenyl, $C_2$-$C_4$-alkynyl and $C_1$-$C_4$-alkylsulfanyl are furthermore optionally substituted with one or two substituents independently selected from the group consisting of hydroxyl, $C_1$-$C_4$-alkoxy, $C_1$-$C_4$-haloalkoxy, —Si($C_1$-$C_4$-alkyl$)_3$ and $C_3$-$C_6$-cycloalkyl and wherein $R^{16}$ is $C_1$-$C_4$-alkyl, $R^7$ is hydrogen, $C_1$-$C_4$-alkyl, difluoromethyl, trifluoromethyl, $C_1$-$C_4$-alkoxy, difluoromethoxy, trifluoromethoxy, $C_1$-$C_4$-alkylsulfanyl or $C_3$-$C_6$-cycloalkyl, Q is phenyl, naphthyl, 3-bicyclo[4.2.0]octa-1,3,5-trienyl, indanyl, tetrahydronaphthalenyl, dihydro-benzofuranyl, indenyl, dihydronaphthalenyl, indolinyl, 1,3-benzodioxolyl, chromanyl, dihydro-1,4-benzodioxinyl, [1,3]dioxolo[4,5-b]pyridinyl, tetrahydroquinolinyl, 6,7-dihydro-5H-cyclopenta[b]pyridinyl, pyrrolyl, furanyl, thienyl, imidazolyl, oxazolyl, thiazolyl, pyridinyl, pyrimidinyl, indolyl, benzimidazolyl, indazolyl, benzofuranyl, benzothiophenyl, benzothiazolyl, benzoxazolyl or quinolinyl, wherein phenyl, naphthyl, 3-bicyclo[4.2.0]octa-1,3,5-trienyl, indanyl, tetrahydronaphthalenyl, dihydrobenzofuranyl, indenyl, dihydronaphthalenyl, indolinyl, 1,3-benzodioxolyl, chromanyl, dihydro-1,4-benzodioxinyl, [1,3]dioxolo[4,5-b]pyridinyl, tetrahydroquinolinyl, 6,7-dihydro-5H-cyclopenta[b]pyridinyl, pyrrolyl, furanyl, thienyl, imidazolyl, oxazolyl, thiazolyl, pyridinyl, pyrimidinyl, indolyl, benzimidazolyl, indazolyl, benzofuranyl, benzothiophenyl, benzothiazolyl, benzoxazolyl and quinolinyl, are optionally substituted with one to three substituents $Q^S$ wherein $Q^S$ is independently selected from the group consisting of halogen, cyano, nitro, formyl, $C_1$-$C_4$-alkyl, difluoromethyl, trifluoromethyl, $C_1$-$C_4$-alkylcarbonyl, $C_1$-$C_4$-alkoxy, difluoromethoxy, trifluoromethoxy, $C_2$-$C_4$-alkenyl, $C_2$-$C_4$haloalkenyl, $C_2$-$C_4$-alkynyl, $C_2$-$C_4$-haloalkynyl, $C_1$-$C_4$-alkylsulfanyl, $C_3$-$C_6$-cycloalkyl oxetanyl, pyrrolidinyl, tetrahydrofuranyl, phenyl, thienyl, furanyl, pyrrolyl, pyridyl, —O(C=O)$R^{33}$ and —N($R^{43}$$)_2$, wherein said $C_1$-$C_4$-alkyl, $C_1$-$C_4$-alkylcarbonyl, $C_1$-$C_4$-alkoxy, $C_2$-$C_4$-alkenyl, $C_2$-$C_4$haloalkenyl, $C_2$-$C_4$-alkynyl, $C_2$-$C_4$-haloalkynyl and $C_1$-$C_4$-alkylsulfanyl in turn are optionally substituted with one or two substituents independently selected from the group consisting of hydroxyl, $C_1$-$C_4$-alkoxy and $C_1$-$C_4$-alkoxycarbonyl $R^{33}$ is $C_1$-$C_4$-alkyl, $R^{43}$ is independently hydrogen or $C_1$-$C_4$-alkyl, as well as N-oxides, salts, hydrates and hydrates of the salts and N-oxides thereof.

Even more preferably the present invention relates to compounds of formula (I), wherein $A^1$ $CR^8$, wherein $R^1$ is hydrogen, $A^2$ is O, m is 1, T is hydrogen, $R^3$ and $R^4$ are independently hydrogen, fluoro or $C_1$-$C_4$-alkyl, $R^5$ is hydrogen, L is a direct bond or $C_1$-$C_4$-alkylene, wherein said $C_1$-$C_4$-alkylene is optionally substituted with one or two substituents $L^{SA}$, $L^{SA}$ is fluoro, or two substituents $L^{SA}$ that are bound to the same carbon atom form together with the carbon atom which they are attached to a cyclopropyl or cyclobutyl, $R^6$ is indanyl, 1,2,3,4-tetrahydronaphthalenyl, phenyl, naphthyl, dihydrobenzofuranyl or dihydro-benzodioxinyl, wherein indanyl, 1,2,3,4-tetrahydronaphthalenyl, phenyl, naphthyl, dihydrobenzofuranyl and di-hydrobenzodioxinyl are optionally substituted with one or two $R^{6S}$ substituents, wherein $R^{6S}$ is independently selected from the group consisting of fluoro, chloro, $C_1$-$C_4$-alkyl, difluoromethyl, trifluoromethyl, $C_1$-$C_4$-alkoxy, difluoromethoxy, trifluoromethoxy, $C_2$-$C_4$-alkenyl, methylcarbonyl, ethylcarbonyl, $C_2$-$C_4$-alkynyl, cyclopropyl, cyclobutyl, oxetanyl, tetrahydrofuranyl, pyrazolyl and pyridyl, $R^7$ is hydrogen, fluoro, chloro, cyano, $C_1$-$C_4$-alkyl, difluoromethyl, trifluoromethyl, methylcarbonyl, ethylcarbonyl, $C_2$-$C_4$-alkenyl, $C_2$-$C_4$-alkynyl, cyclopropyl, cyclobutyl, oxetanyl, pyrrolidinyl or tetrahydrofuranyl, Q is phenyl, wherein phenyl is optionally substituted with one or two substituents $Q^S$, wherein $Q^S$ is independently selected from the group consisting of fluoro, chloro, nitro, $C_1$-$C_4$-alkyl, difluoromethyl, trifluoromethyl, $C_1$-$C_4$-alkoxy, difluoromethoxy, trifluoromethoxy, $C_2$-$C_4$alkenyl, $C_2$-$C_4$-alkynyl, cyclopropyl and cyclobutyl, as well as salts, hydrates and hydrates of the salts thereof.

Not encompassed herein are compounds resulting from combinations which are against natural laws and which the person skilled in the art would therefore exclude based on his/her expert knowledge. For instance, ring structures having three or more adjacent oxygen atoms are excluded.

The compound of formula (I) can suitably be in its free form, salt form, N-oxides form or solvate form (e.g. hydrate).

Depending on the nature of the substituents, the compound of formula (I) may be present in the form of different stereoisomers. These stereoisomers are, for example, enantiomers, diastereomers, atropisomers or geometric isomers. Accordingly, the invention encompasses both pure stereoisomers and any mixture of these isomers. Where a compound can be present in two or more tautomer forms in equilibrium, reference to the compound by means of one tautomeric description is to be considered to include all tautomer forms.

Any of the compounds of the present invention can also exist in one or more geometric isomer forms depending on the number of double bonds in the compound. Geometric isomers by nature of substituents about a double bond or a ring may be present in cis (=Z-) or trans (=E-) form. The invention thus relates equally to all geometric isomers and to all possible mixtures, in all proportions.

Depending on the nature of the substituents, the compound of formula (I) may be present in the form of the free compound and/or a salt thereof, such as an agrochemically active salt.

Agrochemically active salts include acid addition salts of inorganic and organic acids well as salts of customary bases. Examples of inorganic acids are hydrohalic acids, such as hydrogen fluoride, hydrogen chloride, hydrogen bromide and hydrogen iodide, sulfuric acid, phosphoric acid and nitric acid, and acidic salts, such as sodium bisulfate and potassium bisulfate. Useful organic acids include, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated fatty acids having 6 to 20 carbon atoms, alkylsulphuric monoesters, alkylsulphonic acids (sulphonic acids having straight-chain or branched alkyl radicals having 1 to 20 carbon atoms), arylsulphonic acids or aryldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulphonic acid, salicylic acid, p-aminosalicylic acid, 2-phenoxybenzoic acid, 2-acetoxybenzoic acid, etc.

Solvates of the compounds of the invention or their salts are stoichiometric compositions of the compounds with solvents.

The compounds of the invention may exist in multiple crystalline and/or amorphous forms. Crystalline forms include unsolvated crystalline forms, solvates and hydrates.

Preferably, $A^1$ is CH (i.e. $CR^8$, wherein $R^1$ is hydrogen).

Preferably, $A^2$ is O, C(=O), $S(=O)_2$, $NR^1$ or $CR^{2A}R^{2B}$, wherein $R^1$ is hydrogen or $C_1$-$C_4$-alkyl and $R^{2A}$ and $R^{2B}$ are independently hydrogen, halogen or $C_1$-$C_4$-alkyl.

More preferably, $A^2$ is O, (C=O) or $CR^{2A}R^{2B}$, wherein $R^{2A}$ and $R^{2B}$ are independently hydrogen or methyl. Even more preferably, $A^2$ is O.

Likewise more preferably, $A^2$ is O, $NR^1$ or $CR^{2A}R^{2B}$, wherein $R^1$ is hydrogen or $C_1$-$C_4$-alkyl and $R^{2A}$ and $R^{2B}$ are independently hydrogen, halogen or $C_1$-$C_4$-alkyl. Even more preferably, $A^2$ is O.

Even more preferably, m is 1, $A^2$ is O, (C=O) or $CR^{2A}R^{2B}$, wherein $R^{2A}$ and $R^{2B}$ are independently hydrogen or methyl.

More preferably, T is hydrogen and $C_1$-$C_4$-alkyl.

Even more preferably, $A^1$ is CH, $A^2$ is O, m is 1 and T is hydrogen.

Preferably, T is hydrogen and $C_1$-$C_4$-alkyl.

Preferably, $R^3$ and $R^4$ are independently hydrogen, fluorine, chlorine, $C_1$-$C_4$-alkyl, $C_2$-$C_4$-alkenyl, $C_2$-$C_4$-alkynyl and $C_3$-$C_6$-cycloalkyl, or $R^3$ and $R^4$ form together with the carbon atom to which they are attached to a $C_3$-$C_6$-cycloalkyl-ring. More preferably, $R^3$ and $R^4$ are independently hydrogen, fluorine or $C_1$-$C_4$-alkyl.

Preferably $R^5$ is hydrogen, hydroxyl, $C_1$-$C_4$-alkyl or $C_1$-$C_4$-alkoxy. More preferably, $R^5$ is hydrogen.

Even more preferably, $A^1$ is CH, $A^2$ is O, m is 1, T is hydrogen, $R^3$ and $R^4$ are independently hydrogen, fluorine or $C_1$-$C_4$-alkyl and $R^5$ is hydrogen.

Preferably, L is a direct bond, $C_1$-$C_6$-alkylene or a group of formula

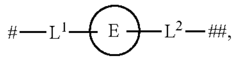

wherein said $C_1$-$C_6$-alkylene is optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl and 3- to 7-membered heterocyclyl in turn are optionally substituted with one to three substituents $L^{SC}$, $L^{SA}$ is independently halogen, hydroxyl, $C_1$-$C_4$-alkoxy, $C_3$-$C_6$-cycloalkyl or 3- to 7-membered heterocyclyl, or two substituents $L^{SA}$ that are bound to the same carbon atom form together with the carbon atom which they are attached to a $C_3$-$C_6$-cycloalkyl-ring or a 3- to 7-membered heterocyclyl-ring, $L^{Sc}$ is independently halogen, hydroxyl, oxo, $C_1$-$C_4$-alkyl, $C_1$-$C_4$-haloalkyl, $C_1$-$C_4$-alkoxy or $C_1$-$C_4$-haloalkoxy, and/or two $L^{Sc}$ substituents form together with the carbon atom to which they are attached to a $C_3$-$C_8$-cycloalkyl-ring.

Preferably, L is a direct bond $C_1$-$C_6$-alkylene or a group of formula

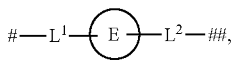

wherein said $C_1$-$C_6$-alkylene is optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl and 3- to 7-membered heterocyclyl in turn are optionally substituted with one to three substituents $L^{SC}$, $L^{SA}$ is independently halogen, hydroxyl, $C_1$-$C_4$-alkoxy, $C_3$-$C_6$-cycloalkyl or 3- to 7-membered heterocyclyl, or two substituents $L^{SA}$ that are bound to the same carbon atom form together with the carbon atom which they are attached to a $C_3$-$C_6$-cycloalkyl-ring or a 3- to 7-membered heterocyclyl-ring, $L^{Sc}$ is independently halogen, hydroxyl, oxo, $C_1$-$C_4$-alkyl, $C_1$-$C_4$-haloalkyl, $C_1$-$C_4$-alkoxy or $C_1$-$C_4$-haloalkoxy, and/or two $L^{Sc}$ substituents form together with the carbon atom to which they are attached to a $C_3$-$C_8$-cycloalkyl-ring.

More preferably, L is a direct bond or $C_1$-$C_4$-alkylene, wherein said $C_1$-$C_4$-alkylene is optionally substituted with one or two substituents $L^{SA}$, $L^{SA}$ is fluoro, or two substituents $L^{SA}$ that are bound to the same carbon atom form together with the carbon atom which they are attached to a cyclopropyl or cyclobutyl.

Even more preferably, L is a direct bond, methylene, monofluoromethylene or difluoromethylene, particularly preferably L is a direct bond or methylene.

Preferably, $R^6$ is $C_3$-$C_{12}$-carbocyclyl, $C_6$-$C_{14}$-aryl, 3- to 14-membered heterocyclyl, 5- to 14-membered heteroaryl, $C_6$-$C_{14}$-aryloxy, $C_1$-$C_3$-alkoxy substituted by a $C_6$-$C_{14}$-aryl or $C_6$-$C_{14}$-arylsulfanyl, wherein $C_3$-$C_{12}$-carbocyclyl, $C_6$-$C_{14}$-aryl, 3- to 14-membered heterocyclyl, 5- to 14-membered heteroaryl, $C_6$-$C_{14}$-aryloxy, $C_1$-$C_3$-alkoxy substituted by a $C_6$-$C_{14}$-aryl and $C_6$-$C_{14}$-arylsulfanyl are optionally substituted with one to four substituents $R^{6S}$, wherein $R^{6S}$ is independently selected from the group consisting of halogen, cyano, nitro, hydroxyl, mercapto, pentafluorosulfanyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylsulfanyl, $C_1$-$C_6$-haloalkylsulfanyl, $C_3$-$C_6$-cycloalkylsulfanyl, $C_3$-$C_6$-cycloalkyl, $C_3$-$C_6$-cycloalkyloxy, $C_6$-$C_{14}$-aryl, 5- or 6-membered heteroaryl, 3- to 7-membered heterocyclyl, —C(=O)($OR^{17}$) and —C(=O)N($R^{18}$)$_2$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylsulfanyl and $C_1$-$C_6$-haloalkylsulfanyl are furthermore optionally substituted with one to three substituents independently selected from the group consisting of fluoro, chloro, hydroxyl, $C_1$-$C_4$-alkoxy, $C_1$-$C_4$-haloalkoxy, $C_3$-$C_6$-cycloalkyl and $C_3$-$C_6$-halocycloalkyl, and wherein $C_3$-$C_6$-cycloalkylsulfanyl, $C_3$-$C_6$-cycloalkyl, $C_3$-$C_6$-cycloalkyloxy, $C_6$-$C_{14}$-aryl, 5- or 6-membered heteroaryl and 3- to 7-membered heterocyclyl are furthermore optionally substituted with one to three substituents independently selected from the group consisting of fluoro, chloro, $C_1$-$C_4$-alkyl, $C_1$-$C_4$-haloalkyl, $C_1$-$C_4$-alkoxy and $C_1$-$C_4$-haloalkoxy, and wherein $R^{17}$ and $R^{18}$ are independently hydrogen, $C_1$-$C_4$-alkyl or $C_1$-$C_4$-haloalkyl, wherein said $C_1$-$C_4$-alkyl or $C_1$-$C_4$-haloalkyl in turn are optionally substituted with one to three substituents independently selected from the group consisting of fluoro, chloro, hydroxyl, $C_1$-$C_4$-alkoxy, $C_1$-$C_4$-haloalkoxy, $C_3$-$C_6$-cycloalkyl and $C_3$-$C_6$-halocycloalkyl.

More preferably, $R^6$ is indanyl, 1,2,3,4-tetrahydronaphthalenyl, bicyclo[4.2.0]octa-1,3,5-trienyl, bi-cyclo[4.2.0]octa-1(6), 2,4-trienyl, indenyl, 1,2-dihydronaphthalenyl, spiro[cyclopropane-2,1'-indane]-1-yl, spiro[cyclopropane-2,1'-tetralin]-1-yl, phenyl, naphthyl, phenoxy, benzyloxy, $OCF_2$-phenyl, phenylsulfanyl, 1,3-dihydrobenzofuranyl, 2,3-dihydrobenzothiophenyl, indolinyl, 1,3-benzodioxolyl, 1,2,3,4-tetrahydroquinolinyl, chromanyl, isochromanyl, thiochromanyl, 2,3-dihydro-1,4-benzodioxinyl, 6,7-dihydro-5H-cyclopenta[b]pyridinyl, 5,6,7,8-tetrahydroquinolinyl, 4,5,6,7-tetrahydrobenzothiophenyl, 4,5,6,7-tetrahydrobenzofuranyl, 4,5,6,7-tetrahydro-1,3-benzoxazolyl, 4,5,6,7-tetrahydro-1,3-benzothiazolyl, 4,5,6,7-tetrahydro-1H-benzimidazolyl, 4,5,6,7-tetrahydro-1H-indazolyl, 4,5,6,7- tetrahydro-2H-isoindolyl, 4,5,6,7-tetrahydro-2-benzothiophenyl, 5,6-dihydro-4H-cyclopenta[b]thiophenyl, 5,6-dihydro-4H-cyclopenta[d]thiazolyl, 4,5,6,7-tetrahydro-pyrazolo[1,5-a]pyridinyl, 5,6,7,8-tetrahydro-[1,2,4]triazolo[1,5-a]pyridinyl, 5,6,7,8-tetrahydroimidazo[1,2-a]pyridinyl, 6,7-dihydro-5H-thieno[3,2-b]pyranyl, spiro[chromane-3,1'-cyclopropane]-yl, spiro[7,8-dihydro-5H-quinoline-6,1'-cyclopropane]-yl, furanyl, thienyl, pyrazolyl, imidazolyl, triazolyl, oxazolyl, oxadiazolyl, thiazolyl, thiadiazolyl, pyridinyl, pyridazinyl and pyrimidinyl, indolyl, benzimadazolyl, indazolyl, benzofuranyl, benzothiophenyl, benzothiazolyl, benzoxazolyl, quinolinyl, isoquinolinyl, quinoxalinyl, pyrrolo[2,3-b]pyridin-3-yl, imidazo[1,2-a]pyridinyl, [1,2,4]triazolo[4,3-a]pyridinyl, thieno[3,2-b]pyrrol-6-yl, thieno[3,2-b]thio-phenyl, imidazo[2,1-b]oxazolyl, furo[2,3-d]isoxazolyl or thieno[2,3-d]isothiazolyl, wherein indanyl, 1,2,3,4-tetrahydronaphthalenyl, bicyclo[4.2.0]octa-1,3,5-trienyl, bicyclo[4.2.0]octa-1(6), 2,4-trienyl, indenyl, 1,2-dihydronaphthalenyl, spiro[cyclopropane-2,1'-indane]-1-yl, spiro[cyclopropane-2,1'-tetralin]-1-yl, phenyl, naphthyl, phenoxy, benzyloxy, $OCF_2$-phenyl, phenylsulfanyl, 3-dihydro-benzofuranyl, 2,3-dihydrobenzothiophenyl, indolinyl, 1,3-benzodioxolyl, 1,2,3,4-tetrahydroquinolinyl, chromanyl, isochromanyl, thiochromanyl, 2,3-dihydro-1,4-benzodioxinyl, 6,7-dihydro-5H-cyclopenta[b]pyridinyl, 5,6,7,8-tetrahydroquinolinyl, 4,5,6,7-tetrahydrobenzothiophenyl, 4,5,6,7-tetrahydro-benzofuranyl, 4,5,6,7-tetrahydro-1,3-benzoxazolyl, 4,5,6,7-tetrahydro-1,3-benzothiazolyl, 4,5,6,7-tetrahydro-1H-benzimidazolyl, 4,5,6,7-tetrahydro-1H-indazolyl, 4,5,6,7-tetrahydro-2H-isoindolyl, 4,5,6,7-tetrahydro-2-benzothiophenyl, 5,6-dihydro-4H-cyclopenta[b]thiophenyl, 5,6-dihydro-4H-cyclopenta[d]thiazolyl, 4,5,6,7-tetrahydro-pyrazolo[1,5-a]pyridinyl, 5,6,7,8-tetrahydro-[1,2,4]triazolo[1,5-a]pyridinyl, 5,6,7,8-tetrahydroimidazo[1,2-a]pyridinyl, 6,7-dihydro-5H-thieno[3,2-b]pyranyl, spiro[chromane-3,1'-cyclopropane]-yl, spiro[7,8-dihydro-5H-quinoline-6,1'-cyclopropane]-yl, furanyl, thienyl, pyrazolyl, imidazolyl, triazolyl, oxazolyl, oxadiazolyl, thiazolyl, thiadiazolyl, pyridinyl, pyridazinyl and pyrimidinyl, indolyl, benzimadazolyl, indazolyl, benzofuranyl, benzothiophenyl, benzothiazolyl, benzoxazolyl, quinolinyl, isoquinolinyl, quinoxalinyl, pyrrolo[2,3-b]pyridin-3-yl, imidazo[1,2-a]pyridinyl, [1,2,4]triazolo[4,3-a]pyridinyl, thieno[3,2-b]pyrrol-6-yl, thieno[3,2-b]thio-phenyl, imidazo[2,1-b]oxazolyl, furo[2,3-d]isoxazolyl and thieno[2,3-d]isothiazolyl are optionally substituted with one to three substituents $R^{6S}$, wherein $R^{6S}$ is independently selected from the group consisting of halogen, cyano, nitro, hydroxyl, mercapto, pentafluorosulfanyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylsulfanyl, $C_1$-$C_6$-haloalkylsulfanyl, $C_3$-$C_6$-cycloalkylsulfanyl, $C_3$-$C_6$-cycloalkyl, $C_3$-$C_6$-cycloalkyloxy, $C_6$-$C_{14}$-aryl, 5- or 6-membered heteroaryl, 3- to 7-membered heterocyclyl, —C(═O)($OR^{17}$) and —C(═O)N($R^{18}$)$_2$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylsulfanyl and $C_1$-$C_6$-haloalkylsulfanyl are furthermore optionally substituted with one to three substituents independently selected from the group consisting of fluoro, chloro, hydroxyl, $C_1$-$C_4$-alkoxy, $C_1$-$C_4$-haloalkoxy, $C_3$-$C_6$-cycloalkyl and $C_3$-$C_6$-halocycloalkyl, and wherein $C_3$-$C_6$-cycloalkylsulfanyl, $C_3$-$C_6$-cycloalkyl, $C_3$-$C_6$-cycloalkyloxy, $C_6$-$C_{14}$-aryl, 5- or 6-membered heteroaryl and 3- to 7-membered heterocyclyl are furthermore optionally substituted with one to three substituents independently selected from the group consisting of fluoro, chloro, $C_1$-$C_4$-alkyl, $C_1$-$C_4$-haloalkyl, $C_1$-$C_4$-alkoxy and $C_1$-$C_4$-haloalkoxy, and wherein $R^{17}$ and $R^{18}$ are independently hydrogen, $C_1$-$C_4$-alkyl or $C_1$-$C_4$-haloalkyl, wherein said $C_1$-$C_4$-alkyl or $C_1$-$C_4$-haloalkyl in turn are optionally substituted with one to three substituents independently selected from the group consisting of fluoro, chloro, hydroxyl, $C_1$-$C_4$-alkoxy, $C_1$-$C_4$-haloalkoxy, $C_3$-$C_6$-cycloalkyl and $C_3$-$C_6$-halocycloalkyl.

Even more preferably, $R^6$ is indanyl, phenyl, dihydrobenzodioxinyl or thienyl, wherein indanyl, phenyl, dihydrobenzodioxinyl and thienyl are optionally substituted with one or two $R^{6S}$ substituents, wherein $R^{6S}$ is independently selected from the group consisting of fluoro, chloro, $C_1$-$C_4$-alkyl, difluoromethyl, trifluoromethyl, $C_1$-$C_4$-alkoxy, difluoromethoxy, trifluoromethoxy, $C_2$-$C_4$-alkenyl, $C_2$-$C_4$-alkynyl, cyclopropyl and cyclobutyl, wherein said $C_2$-$C_4$-alkynyl is optionally substituted with one substituent —Si($CH_3$)$_3$.

Likewise even more preferably, $R^6$ is indanyl, 1,2,3,4-tetrahydronaphthalenyl, phenyl, naphthyl, dihydrobenzofuranyl or dihydrobenzodioxinyl, wherein indanyl, 1,2,3,4-tetrahydronaphthalenyl, phenyl, naphthyl, dihydrobenzofuranyl and dihydrobenzodioxinyl are optionally substituted with one or two $R^{6S}$ substituents, wherein $R^{6S}$ is independently selected from the group consisting of fluoro, chloro, $C_1$-$C_4$-alkyl, difluoromethyl, trifluoromethyl, $C_1$-$C_4$-alkoxy, difluoromethoxy, trifluoromethoxy, $C_2$-$C_4$-alkenyl, methylcarbonyl, ethylcarbonyl, $C_2$-$C_4$-alkynyl, cyclopropyl, cyclobutyl, oxetanyl, tetrahydrofuranyl, pyrazolyl and pyridyl.

In a still even more preferred embodiment, $R^6$ is

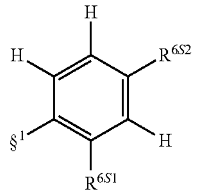

wherein

§ [1] is the attachment to L, $R^{6S1}$ and $R^{6S2}$ are independently hydrogen or $R^{6S}$, wherein $R^{6S}$ is halogen, cyano, $C_1$-$C_4$-alkyl, $C_1$-$C_4$-haloalkyl, $C_1$-$C_4$-alkoxy, $C_1$-$C_6$-haloalkoxy, $C_1$-$C_6$-alkoxycarbonyl, $C_1$-$C_6$-alkylcarbonyl, $C_2$-$C_6$-alkenyl, $C_2$-$C_6$-alkynyl, $C_3$-$C_6$-cycloalkyl, with the proviso that at least one of $R^{6S1}$ and $R^{6S2}$ is different from hydrogen.

Preferably, $R^{6S1}$ and $R^{6S2}$ are independently $R^{6S}$, wherein $R^{6S}$ is halogen, cyano, $C_1$-$C_4$-alkyl, $C_1$-$C_4$-haloalkyl, $C_1$-$C_4$-alkoxy, cyclopropyl, preferably $R^{6S}$ is chloro, fluoro, methyl, trifluoromethyl or methoxy, more preferably methyl.

Preferably $R^7$ is hydrogen, halogen, cyano, $C_1$-$C_6$-alkyl, $C_1$-$C_6$-haloalkyl, $C_1$-$C_6$-hydroxyalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylsulfanyl, $C_1$-$C_6$-alkylsulfinyl, $C_1$-$C_6$-alkylsulfonyl, $C_1$-$C_6$-haloalkylsulfonyl, $C_3$-$C_8$-cycloalkyl, phenyl, naphthyl, 5- or 6-membered heteroaryl, 3- to 7-membered heterocyclyl, —$N(R^{20})_2$, —$C(=NR^{21})R^{22}$, —$C(=O)(OR^{25})$ or —$C(=O)N(R^{26})_2$, wherein $C_1$-$C_6$-alkyl, $C_1$-$C_6$-haloalkyl, $C_1$-$C_6$-hydroxyalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylsulfanyl, $C_1$-$C_6$-alkylsulfinyl, $C_1$-$C_6$-alkylsulfonyl and $C_1$-$C_6$-haloalkylsulfonyl are optionally substituted with one to three $R^{7Sa}$ substituents, wherein $C_3$-$C_8$-cycloalkyl, phenyl, naphthyl, 5- or 6-membered heteroaryl and 3- to 7-membered heterocyclyl are optionally substituted with one to three $R^{7Sc}$ substituents, wherein $R^{20}$ is hydrogen, $C_1$-$C_6$-alkyl, $C_1$-$C_6$-haloalkyl or $C_3$-$C_6$-cycloalkyl, wherein $C_3$-$C_8$-cycloalkyl in turn is optionally substituted with one or two substituents independently selected from the group consisting of halogen and $C_1$-$C_6$-alkyl, $R^{21}$ is hydroxyl, $C_1$-$C_6$-alkyl or $C_1$-$C_6$-alkoxy, $R^{22}$ is hydrogen, $C_1$-$C_6$-alkyl or $C_1$-$C_6$-haloalkyl, $R^{25}$ and $R^{26}$ are independently hydrogen or $C_1$-$C_6$-alkyl, and wherein $R^{7Sa}$ is independently cyano, hydroxyl, $C_1$-$C_6$-alkoxy, $C_1$-$C_6$-haloalkoxy, $C_3$-$C_6$-cycloalkyl, $C_1$-$C_4$-alkoxycarbonyl and phenyl, $R^{7Sc}$ is independently halogen, hydroxyl, $C_1$-$C_4$-alkyl, $C_1$-$C_4$-haloalkyl $C_1$-$C_4$-alkoxy or $C_1$-$C_4$-haloalkoxy.

More preferably $R^7$ is hydrogen, halogen, $C_1$-$C_4$-alkyl, $C_1$-$C_4$-haloalkyl, $C_1$-$C_4$-hydroxyalkyl, $C_1$-$C_4$-alkylcarbonyl, $C_1$-$C_4$-alkoxy, $C_2$-$C_4$-alkenyl, $C_2$-$C_4$-alkynyl, $C_3$-$C_6$-cycloalkyl, pyridinyl, imidazolyl, pyrazolyl, oxetanyl, tetrahydrofuranyl, tetrahydropyranyl, pyrrolidinyl, piperidinyl, —$N(R^{20})_2$, —$C(=NR^{21})R^{22}$ or —$C(=O)(OR^{25})$, wherein $C_1$-$C_4$-alkyl, $C_1$-$C_4$-haloalkyl, $C_1$-$C_4$-hydroxyalkyl, $C_1$-$C_4$-alkylcarbonyl, $C_1$-$C_4$-alkoxy, $C_2$-$C_4$-alkenyl and $C_2$-$C_4$-alkynyl are optionally substituted with one or two $R^{7Sa}$ substituents, wherein $C_3$-$C_6$-cycloalkyl, pyridinyl, imidazolyl, pyrazolyl, oxetanyl, tetrahydrofuranyl, tetrahydropyranyl, pyrrolidinyl, piperidinyl are optionally substituted with one or two $R^{7Sc}$ substituents, wherein $R^{20}$ is hydrogen, $C_1$-$C_4$-alkyl or $C_3$-$C_6$-cycloalkyl, $R^{21}$ is $C_1$-$C_4$-alkyl or $C_1$-$C_4$-alkoxy, $R^{22}$ is $C_1$-$C_4$-alkyl, $R^{25}$ is hydrogen or $C_1$-$C_4$-alkyl, and wherein $R^{7Sa}$ is independently $C_1$-$C_4$-alkoxy or phenyl, $R^{7Sc}$ is independently halogen or $C_1$-$C_4$-alkyl.

Even more preferably $R^7$ is chloro, iodo, $C_1$-$C_4$-alkyl, difluoromethyl, trifluoromethyl, methylcarbonyl, ethylcarbonyl, $C_2$-$C_4$-alkenyl, $C_2$-$C_4$-alkynyl, $C_3$-$C_6$-cycloalkyl, —$N(R^{20})_2$ or —$C(=NR^{21})R^{22}$ wherein $C_1$-$C_4$-alkyl, $C_2$-$C_4$-alkenyl and $C_2$-$C_4$-alkynyl are optionally substituted with one or two $R^{7Sa}$ substituents, wherein $C_3$-$C_6$-cycloalkyl is optionally substituted with one or two $R^{7Sc}$ substituents, $R^{20}$ is hydrogen, cyclopropyl or cyclobutyl, $R^{21}$ is $C_1$-$C_4$-alkyl or $C_1$-$C_4$-alkoxy, $R^{22}$ is $C_1$-$C_4$-alkyl, and wherein $R^{7Sa}$ is independently $C_1$-$C_4$-alkoxy, $R^{7Sc}$ is independently halogen.

Likewise even more preferably $R^7$ is chloro, iodo, $C_1$-$C_4$-alkyl, difluoromethyl, trifluoromethyl, methylcarbonyl, ethylcarbonyl, $C_2$-$C_4$-alkenyl, $C_2$-$C_4$-alkynyl, cyclopropyl, cyclobutyl, oxetanyl, tetrahydrofuranyl or pyrrolidinyl. Particularly preferably $R^7$ is methyl, ethyl, n-propyl, isopropyl or cyclopropyl.

Still even more preferably $R^7$ is methyl, methylsulfanyl or cyclopropyl.

Preferably $R^1$ is hydrogen or fluoro, more preferably $R^1$ is hydrogen.

Even more preferably $R^7$ is methyl, methylsulfanyl or cyclopropyl and $R^1$ is hydrogen.

Preferably Q is phenyl, naphthyl, bicyclo[4.2.0]octa-1(6), 2,4-trienyl, indanyl, tetrahydronaphthalenyl, indenyl, dihydronaphthalenyl, bicyclo[4.2.0]octa-1(6),2,4-trienyl, dihydrobenzofuranyl, 1,3-dihydroiso-benzofuranyl, indolinyl, 1,3-benzodioxolyl, chromanyl, dihydro-1,4-benzodioxinyl, [1,3]dioxolo[4,5-b]pyridinyl, tetrahydroquinolinyl, 6,7-dihydro-5H-cyclopenta[b]pyridinyl, pyrrolyl, furanyl, thienyl, imidazolyl, triazolyl, oxazolyl, thiazolyl, pyridinyl, pyridazinyl, pyrimidinyl, indolyl, benzimidazolyl, indazolyl, benzofuranyl, benzothiophenyl, benzothiazolyl, benzoxazolyl, quinolinyl, furo[3,2-b]pyridinyl, thieno[3,2-b]thiophenyl or thieno[2,3-d]thiazolyl, wherein phenyl, naphthyl, bicyclo[4.2.0]octa-1(6),2,4-trienyl, indanyl, tetrahydronaphthalenyl, indenyl, dihydronaphthalenyl, bicyclo[4.2.0]octa-1(6),2,4-trienyl, dihydrobenzofuranyl, 1,3-dihydroisobenzofuranyl, indolinyl, 1,3-benzodioxolyl, chromanyl, dihydro-1,4-benzodioxinyl, [1,3]dioxolo[4,5-b]pyridinyl, tetrahydro-quinolinyl, 6,7-dihydro-5H-cyclopenta[b]pyridinyl, pyrrolyl, furanyl, thienyl, imidazolyl, triazolyl, oxazolyl, thiazolyl, pyridinyl, pyridazinyl, pyrimidinyl, indolyl, benzimidazolyl, indazolyl, benzofuranyl, benzothiophenyl, benzothiazolyl, benzoxazolyl, quinolinyl, furo[3,2-b]pyridinyl, thieno[3,2-b]thiophenyl and thieno[2,3-d]thiazolyl are optionally substituted with one to four substituents $Q^S$, wherein $Q^S$ is independently selected from group consisting of halogen, cyano, nitro, hydroxyl, formyl, $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylsulfanyl, $C_1$-$C_6$-haloalkylsulfanyl, $C_3$-$C_6$-cycloalkyl, oxetanyl and —$N(R^{43})_2$, wherein said $C_3$-$C_6$-cycloalkyl and oxetanyl in turn are optionally substituted with one or two substituents independently selected from the group consisting of halogen, $C_1$-$C_4$-alkyl and $C_1$-$C_4$-haloalkyl, and wherein $R^{43}$ is hydrogen and $C_1$-$C_6$-alkyl.

More preferably Q is phenyl, naphthyl, bicyclo[4.2.0]octa-1(6),2,4-trienyl, benzodioxolyl, 2,3-dihydrobenzofuranyl, pyridinyl, thienyl or indolyl, wherein phenyl, naphthyl, bicyclo[4.2.0]octa-1(6),2,4-trienyl, benzodioxolyl, 2,3-dihydrobenzofuranyl, pyridinyl, thienyl and indolyl are optionally substituted with one to three substituents $Q^S$, wherein $Q^S$ is independently selected from the group consisting of halogen, cyano, nitro, formyl, $C_1$-$C_4$-alkyl, $C_1$-$C_4$-haloalkyl, $C_1$-$C_4$-alkylcarbonyl, $C_1$-$C_4$-alkoxy, $C_1$-$C_4$-haloalkoxy, $C_2$-$C_4$-alkynyl and $C_3$-$C_6$-cycloalkyl, wherein said $C_3$-$C_6$-cycloalkyl and oxetanyl are in turn optionally substituted with one or two substituents independently selected from the group consisting of fluoro or methyl.

Even more preferably, Q is phenyl, wherein phenyl is substituted with one or two substituents $Q^S$ independently selected from the group consisting of halogen, nitro, $C_1$-$C_4$-alkyl, difluoromethyl, trifluoromethyl, $C_1$-$C_4$-alkoxy, difluoromethoxy, trifluoromethoxy, $C_2$-$C_4$-alkynyl, cyclopropyl and cyclobutyl.

Likewise even more preferably, Q is phenyl, wherein phenyl is substituted with one or two substituents $Q^S$ independently selected from the group consisting of halogen, cyano, nitro, formyl, $C_1$-$C_4$-alkyl, $C_1$-$C_4$-haloalkyl, $C_1$-$C_4$-alkylcarbonyl, $C_1$-$C_4$-alkoxy, $C_1$-$C_4$-haloalkoxy, $C_2$-$C_4$-alkynyl, cyclopropyl and cyclobutyl, wherein said cyclopropyl and cyclobutyl in turn are optionally substituted with one or two substituents independently selected from the group consisting of fluoro or methyl.

Still even more preferably Q is phenyl substituted with one $Q^S$ substituent selected from the group consisting of halogen, cyano, nitro, formyl, $C_1$-$C_4$-haloalkyl, $C_1$-$C_4$-alkylcarbonyl, $C_1$-$C_4$-haloalkoxy, wherein said one $Q^S$ substituent preferably is in position 3 of the phenyl ring, and preferably $Q^S$ is selected from the group consisting of 3-nitro, 3-fluoro, 3-chloro, 3-difluoromethyl or 3-trifluoromethyl. In a particularly preferred embodiment, Q is 3-(trifluoromethyl)phenyl or 3-(nitro)phenyl.

The above specified definitions of $A^1$, $A^2$, Q, T, L, m, $R^1$, $R^2$, $R^3$, $R^4$, $R^5$, $R^6$, $R^7$ and $R^8$ (broad definition as well as preferred, more preferred, even more preferred definitions) can be combined in various manners. These combinations of definitions thus provide sub-classes of compounds according to the invention, such as for instance the ones disclosed below.

The present invention also relates to the compounds of formula (I) disclosed in Table 1.

The compounds of formula (I) may be used as fungicides (for controlling phytopathogenic fungi), in particular in methods for controlling phytopathogenic fungi which comprises the step of applying one or more compounds of formula (I) to the plants, plant parts, seeds, fruits or to the soil in which the plants grow.

Processes for the Preparation of Compounds of Formula (I) and Intermediates

The present invention relates to processes for the preparation of compounds of formula (I) and their intermediates. Unless indicated otherwise, the radicals $A^1$, $A^2$, Q, T, L, m, $R^1$, $R^2$, $R^3$, $R^4$, $R^5$, $R^6$, $R^7$ and $R^8$ have the meanings given above for the compounds of formula (I). These definitions apply not only to the end products of formula (I) but also to all intermediates. Likewise, the preferred definitions, the more preferred definitions, the even more preferred definitions and the particularly preferred definitions of $A^1$, $A^2$, Q, T, L, m, $R^1$, $R^2$, $R^3$, $R^4$, $R^5$, $R^6$, $R^7$ and $R^8$ given above for the compounds of formula (I), apply mutatis mutandis for the compounds of formula (I-a), (I-a-1) and (I-a-2) as well as to all intermediates described in the context of the present invention, in particular the intermediates of formula (1), (2), (3), (4), (5), (6a), (6b), (7), (8), (9), (10), (11), (12), (13) and (14) as defined herein.

Compounds of formula (I-a) is a subset of formula (I). Compounds of formula (I-a-1) and (I-a-2) are various subsets of formula (I-a). All substituents for formula (I-a) and (I-a-1) to (I-a-2) are as defined above for formula (I) unless otherwise noted.

The compounds of formula (I) can be prepared by various routes in analogy to known processes (see e.g. and references therein). Non-limiting examples of suitable processes are herein described.

A compound of formula (I) may be directly obtained by performing any process A to D or may be obtained by conversion or derivatization of another compound of formula (I) prepared in accordance with the processes described herein. For instance, a compound of formula (I) can be converted into another compound of formula (I) by replacing one or more substituents of the starting compound of formula (I) by other substituents.

The processes described herein may be suitably performed using one or more inert organic solvents which is/are customary for the considered reaction. Suitable inert organic solvents can be chosen from the following: aliphatic, alicyclic or aromatic hydrocarbons (e.g. petroleum ether, pentane, hexane, heptane, cyclohexane, methylcyclohexane, ligroin, benzene, toluene, xylene or decalin), halogenated aliphatic, alicyclic or aromatic hydrocarbons (e.g. chlorobenzene, dichlorobenzene, dichloromethane, chloroform, carbon tetrachloride, 1,2-dichloroethane or trichloroethane), ethers (e.g. diethyl ether, diiso-propyl ether, methyl t-butyl ether, methyl t-amyl ether, dioxane, tetrahydrofuran, 2-methyltetrahydrofuran, 1,2-dimethoxyethane, 1,2-diethoxyethane or anisole), ketones (e.g. acetone, methyl ethyl ketone, methyl isopropyl ketone and methyl isobutyl ketone), esters (e.g. methyl acetate, ethyl acetate or butyl acetate), alcohols (e.g. methanol, ethanol, propanol, isopropanol, butanol, tert-butanol), nitriles (e.g. acetonitrile, propionitrile, n- or i-butyronitrile or benzonitrile), amides (e.g. N,N-dimethylformamide, N,N-dimethylacetamide, N-methylformanilide, N-methylpyrrolidone, or hexa-methylphosphoric triamide), sulfoxides (e.g. dimethyl sulfoxide) or sulfones (e.g. sulfolane), ureas (e.g. 1,3-dimethyl-3,4,5,6-tetrahydro-2(1H)-pyrimidinone) or any mixture thereof.

Some processes described herein may require or be optionally performed using one or more inorganic or organic bases which are customary for such reactions. Examples of suitable inorganic and organic bases include, but are not limited to, alkaline earth metal or alkali metal carbonates (e.g. sodium carbonate, potassium carbonate, potassium bicarbonate, sodium bicarbonate or cesium carbonate), alkali metal hydrides (e.g. sodium hydride), alkaline earth metal or alkali metal hydroxides (e.g. sodium hydroxide, calcium hydroxide, potassium hydroxide or other ammonium hydroxide derivatives), alkaline earth metal, alkali metal or ammonium fluorides (e.g. potassium fluoride, cesium fluoride or tetrabutylammonium fluoride), alkali metal or alkaline earth metal acetates (e.g. sodium acetate, lithium acetate, potassium acetate or calcium acetate), alkali metal alcoholates (e.g. potassium tert-butoxide or sodium tert-butoxide), alkali metal phosphates (e.g. tri-potassium phosphate), tertiary amines (e.g. trimethylamine, triethylamine, tributylamine, N,N-dimethylaniline, N,N-dicyclohexylmethylamine, N,N-diisopropylethylamine, N-methylpiperidine, N,N-dimethylaminopyridine, diazabicyclooctane (DABCO), diazabicyclononene (DBN), diazabicycloundecene (DBU), quinuclidine, 3-acetoxyquinuclidine, guanidines or aromatic bases (e.g. pyridines, picolines, lutidines or collidines).

Some of the processes described herein may be optionally performed in the presence of a transition metal catalyst, such as a metal (e.g. copper or palladium) salt or complex, if appropriate in the presence of a ligand.

Suitable copper salts or complexes and their hydrates include, but are not limited to, copper metal, copper(I)

iodide, copper(I) chloride, copper(I) bromide, copper(II) chloride, copper(II) bromide, copper(II) oxide, copper(I) oxide, copper(II) acetate, copper(I) acetate, copper(I) thiophene-2-carboxylate, copper(I) cyanide, copper(II) sulfate, copper(II) bis(2,2,6,6-tetramethyl-3,5-heptane-dionate), copper(II) trifluoromethanesulfonate, tetrakis(acetonitrile) copper(I) hexafluorophosphate, tetrakis(acetonitrile)-copper (I) tetrafluoroborate.

It is also possible to generate in situ a suitable copper complex in the reaction mixture by separate addition to the reaction of a copper salt and a ligand or salt, such as ethylenediamine, N,N-dimethylethylenediamine, N,N'-dimethylethylenediamine, rac-trans-1,2-diaminocyclohexane, rac-trans-N,N'-dimethylcyclohexane-1,2-diamine, 1,1'-binaphthyl-2,2'-diamine, N,N,N',N'-tetramethylethylene-diamine, proline, N,N-dimethylglycine, quinolin-8-ol, pyridine, 2-aminopyridine, 4-(dimethyl-amino)pyridine, 2,2'-bipyridyl, 2,6-di(2-pyridyl)pyridine, 2-picolinic acid, 2-(dimethylaminomethyl)-3-hydroxypyridine, 1,10-phenanthroline, 3,4,7,8-tetramethyl-1,10-phenanthroline, 2,9-dimethyl-1,10-phenanthroline, 4,7-dimethoxy-1,10-phenanthroline, N,N'-bis[(E)-pyridin-2-ylmethylidene]cyclohexane-1,2-diamine, N-[(E)-phenylmethylidene], N-[(E)-phenylmethylidene]-cyclohexanamine, 1,1,1-tris (hydroxymethyl)ethane, n-butylimidazol, ethylene glycol, 2,2,6,6-tetramethylheptane-3,5-dione, 2-(2,2-dimethylpropanoyl)cyclohexanone, acetylacetone, dibenzoylmethane, 2-(2-methylpropanoyl)cyclohexanone, biphenyl-2-yl(di-tert-butyl)phosphane, ethylenebis-(diphenylphosphine), N,N-diethylsalicylamide, 2-hydroxybenzaldehyde oxime, oxo[(2,4,6-trimethylphenyl)amino]acetic acid or 1H-pyrrole-2-carboxylic acid.

Suitable palladium salts or complexes include, but are not limited to, palladium chloride, palladium acetate, tetrakis (triphenylphosphine)palladium(0), bis(dibenzylideneacetone)palladium(0), tris(di-benzylideneacetone)dipalladium (0), bis(triphenylphosphine)palladium(II) dichloride, [1,1'-bis(diphenylphosphino)ferrocene]dichloropalladium(II), bis (cinnamyl)dichlorodipalladium(II), bis(allyl)-dichlorodipalladium(II) or [1,1'-Bis(di-tert-butylphosphino) ferrocene]dichloropalladium(II).

It is also possible to generate a palladium complex in the reaction mixture by separate addition to the reaction of a palladium salt and a ligand or salt, such as triethylphosphine, tri-tert-butylphosphine, tri-tert-butylphosphonium tetrafluoroborate, tricyclohexylphosphine, 2-(dicyclohexylphosphino)biphenyl, 2-(di-tert-butylphosphino)biphenyl, 2-(dicyclohexylphosphino)-2'-(N,N-dimethylamino)biphenyl, 2-(tert-butylphosphino)-2'-(N,N-dimethylamino)biphenyl, 2-di-tert-butylphosphino-2',4',6'-triisopropyl-biphenyl, 2-dicyclohexylphosphino-2',4',6'-triisopropylbiphenyl, 2-dicyclohexylphosphino-2,6'-di-methoxybiphenyl, 2-dicyclohexylphosphino-2',6'-diisopropoxybiphenyl, triphenylphosphine, tris-(o-tolyl)phosphine, sodium 3-(diphenylphosphino)benzenesulfonate, tris-(2-methoxyphenyl)phosphine, 2,2'-bis(diphenylphosphino)-1,1'-binaphthyl, 1,4-bis(diphenylphosphino)butane, 1,2-bis(diphenylphosphino) ethane, 1,4-bis(dicyclohexylphosphino) butane, 1,2-bis(dicyclohexylphosphino)-ethane, 2-(dicyclohexylphosphino)-2'-(N,N-dimethylamino)-biphenyl, 1,1'-bis(diphenylphosphino)-ferrocene, (R)-(−)-1-[(S)-2-diphenylphosphino)ferrocenyl]ethyldicyclohexylphosphine, tris-(2,4-tert-butyl-phenyl)phos-phite, di(1-adamantyl)-2-morpholinophenylphosphine or 1,3-bis(2,4,6-trimethylphenyl)imidazolium chloride.

The appropriate catalyst and/or ligand may be chosen from commercial catalogues such as "Metal Catalysts for Organic Synthesis" by Strem Chemicals or from reviews (Chemical Society Reviews (2014), 43, 3525, Coordination Chemistry Reviews (2004), 248, 2337 and references therein).

Some of the processes described herein may be performed by metallo-photoredox catalysis according to methods reported in the literature (Nature chemistry review, (2017) 0052 and references therein; Science (2016) 352, 6291, 1304; Org. Lett. 2016, 18, 4012, J. Org. Chem 2016, 81, 6898; J. Am. Chem. Soc. 2016, 138, 12715, J. Am. Chem. Soc. 2016, 138, 13862; J. Am. Chem. Soc. 2016, 138, 8034; J. Org. Chem. 2016, 81, 12525, J. Org. Chem. 2015, 80, 7642). The process is then performed in the presence a photosensitizer, such as Ir and Ru complexes or organic dyes, and a metal catalyst such as Ni complexes. The reaction can be performed in the presence of a ligand and if appropriate in the presence of a base under irradiation with blue or white light.

Suitable photosensitizers include, but are not limited to, Ir(III) photocatalyst such as $[Ir(dFCF_3ppy)(bpy)]PF_6$ ($dFCF_3ppy$=2-(2,4-difluorophenyl)-5-trifluoromethylpyridine, bpy=2,2'-bi-pyridine), $[Ir(dFCF_3ppy)_2(dtbbpy)]PF_6$ (dtbbpy=4,4'-di-tert-butyl-2,2'-bipyridine), $Ir(ppy)_2(dtbbpy)PF_6$ (ppy=2-phenylpyridine), $Ir(ppy)_2(bpy)PF_6$, $Ir(dFppy)_3PF_6$ (dFppy=2-(2,4-difluorophenyl)pyridine), fac-$Ir(ppy)_3$, $(Ir[diF(5\text{-}Me)ppy]_2(tetraMePhen)PF_6$ (diF(5-Me)ppy=2-(2,4-difluorophenyl)-5-methylpyridine, tetraMePhen=3,4,7,8-tetramethyl-1,10-phenanthroline), Ru(II) photocatalyst such as $Ru(bpy)_3Cl_2$ or $Ru(bpy)_3(PF_6)_2$ or organic dyes like 9-mesityl-10-acridinium perchlorate or tetrafluoroborate, or 2,4,5,6-tetra-9H-carbazol-9-yl-1,3-benzenedicarbonitrile, 9-fluorenone and 9,10-phenanthrenequinone.

Suitable nickel catalysts include, but are not limited to, bis(1,5-cyclooctadiene)nickel (0), nickel(II) chloride, nickel (II) bromide, nickel(II) iodide under their anhydrous or hydrate forms or as dimethoxyethane complexes, nickel(II) acetylacetonate, nickel(II) nitrate hexahydrate. These nickel catalysts can be used in combination with bipyridine ligand such as 2,2'-bipyridine, 4,4'-di-tert-butyl-2,2'-bipyridine, 4,4'-dimethoxy-2,2'-bipyridine, 4,4'-dimethyl-2,2'-bipyridine or phenantroline such as 1,10-phenanthroline, 4,7-dimethyl-1,10-phenantroline, 4,7-dimethoxy-1,10-phenantroline or diamines such as N,N,N',N'-tetramethylethylenediamine or dione such as tetramethylheptanedione.

The processes described herein may be performed at temperature ranging from −105° C. to 250° C., preferably from −78° C. to 185° C.

The reaction time varies as a function of the scale of the reaction and of the reaction temperature, but is generally between a few minutes and 48 hours.

The processes described herein are generally performed under standard pressure. However, it is also possible to work under elevated or reduced pressure.

In the processes described herein, the starting materials are generally used in approximately equimolar amounts. However, it is also possible to use one of the starting materials in a relatively large excess.

Processes for the Preparation of Compounds of Formula (I)

Process A

A compound of formula (I-a-1), wherein $A^1$, Q, L, $R^3$, $R^4$, $R^5$, $R^6$, $R^7$ and $R^8$ are defined as above and wherein $A^2$ is O, T is hydrogen, m is 1 or 2, may be prepared either when W is hydrogen, by treating the compound of formula (4) with a dehydrating agent, optionally in the presence of a base to obtain directly the compound of formula (I-a-1)

or when W is an aminoprotecting group preferably tert-butoxycarbonyl, benzyl, allyl or (4-methoxyphenyl) methyl, by treating the compound of formula (4) with a dehydrating agent, optionally in the presence of a base, and then performing a deprotection step to obtain the compound of formula (I-a-1) as shown in scheme 1.

Scheme 1: Process A- Synthesis of compounds of formula (I-a-1)

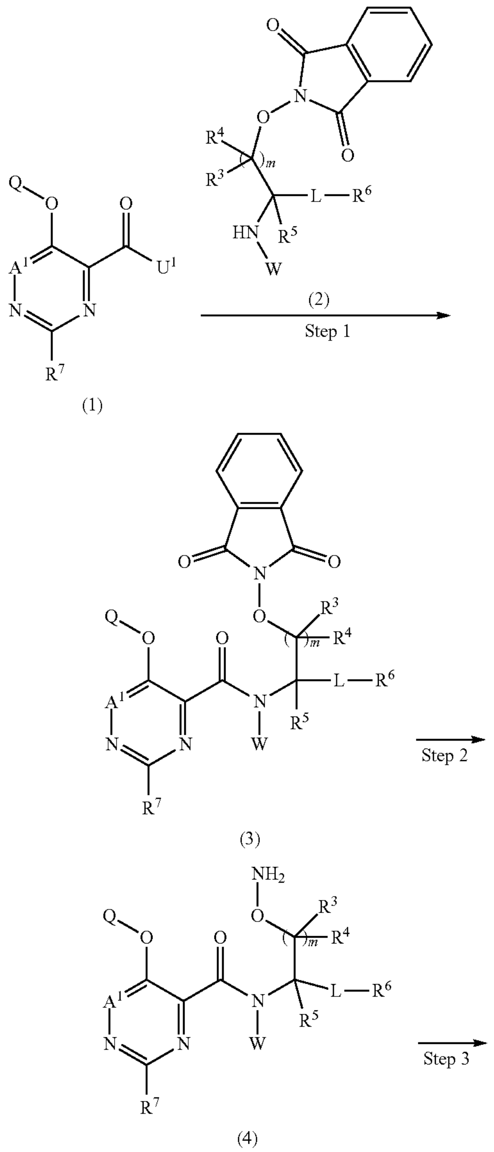

-continued

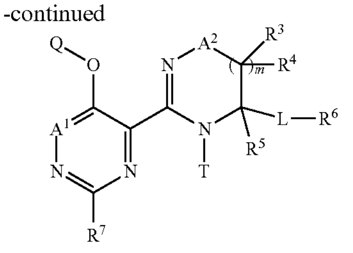

(I-a-1)

The compound of formula (I-a-1) may be obtained by treating a compound of formula (4) with a dehydrating agent such as $POCl_3$, $P_2O_5$ or triflic anhydride, optionally in the presence of a base. Such methods to form oxadiazine rings are known and have been described in the literature (J. Med. Chem. 2017, 60, 2383-2400). The reaction may be performed in any customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin, chlorobenzene, dichlorobenzene, dichloromethane, chloroform, carbon tetrachloride, dichloro-ethane or trichlorethane, ethers, such as diisopropyl ether, methyl t-butyl ether, methyl t-amyl ether, dioxane, tetrahydrofuran, 1,2-dimethoxyethane, 1,2-diethoxyethane or anisole, nitriles, such as acetonitrile, propionitrile, n- or i-butyronitrile or benzonitrile; alcohols, such as ethanol or isopropanol.

When W represents an amino protecting group, step 3 is followed by an additional deprotection step using reaction conditions described in the literature (Greene's Protective Groups in organic Synthesis; Peter G. M. Wuts; Wiley; Fifth Edition; 2014; 895-1194). For example, a tert-butoxycarbonyl group can be removed in acidic medium such as hydrochloric acid or trifluoroacetic acid.

Compound of formula (4), wherein Q, L, $R^1$, $R^2$, $R^3$, $R^4$, $R^5$, $R^6$, $R^7$ and $R^8$ are defined as above, may be obtained by first reacting a compound of formula (1), wherein Q, $R^7$ and $R^8$ are defined as above and $U^1$ is hydroxyl, halogen or $C_1$-$C_6$-alkoxy, with an amine of formula (2), wherein m, L, $R^3$, $R^4$, $R^5$ and $R^6$ are defined as above and W is hydrogen or an aminoprotecting group, preferably tert-butoxycarbonyl, benzyl, allyl or (4-methoxyphenyl)methyl, or a salt thereof, to provide a compound of formula (3), wherein m, W, Q, L, $R^1$, $R^2$, $R^3$, $R^4$, $R^5$, $R^6$, $R^7$ and $R^1$ are defined as above, from which the phthalimide group of compound (3), wherein m, W, Q, L, $R^1$, $R^2$, $R^3$, $R^4$, $R^5$, $R^6$, $R^7$ and $R^8$ are defined as above, is removed to provide a compound of formula (4).

Reaction conditions to remove a phthalimide group are well known and have been reported in the literature (Greene's Protective Groups in organic Synthesis; Peter G. M. Wuts; Wiley; Fifth Edition; 2014; 1012-1014).

Compounds of formula (1) can be prepared by process E described herein.

Amines of formula (2) may be prepared by process G described herein.

Compounds of formula (1) wherein $U^1$ is a hydroxyl group can be reacted with an amine of formula (2) in the presence of a condensing reagent by means of methods described in the literature (e.g. Tetrahedron 2005, 61, 10827-10852). Examples of suitable condensing reagents include, but are not limited to, halogenating reagents (e.g. phosgene, phosphorous tribromide, phosphorous trichloride, phosphorous pentachloride, phosphorous trichloride oxide, oxalyl chloride or thionyl chloride), dehydrating reagents (e.g. ethyl chloroformate, methyl chloroformate, isopropyl chloroformate, isobutyl chloroformate or methanesulfonyl chloride), carbodiimides (e.g. N,N'-dicyclohexylcarbodiimide (DCC)) or other customary condensing (or peptide coupling) reagents (e.g. phosphorous pentoxide, polyphosphoric acid, bis(2-oxo-3-oxazolidinyl)phosphinic chloride, 1-[Bis(dimethylamino)methylene]-1H-1,2,3-triazolo[4,5-b]pyridinium 3-oxide hexafluorophosphate (HATU), N,N'-carbonyldiimidazole, 2-ethoxy-N-ethoxycarbonyl-1,2-dihydroquinoline (EEDQ), triphenylphosphine/tetrachloro-methane, 4-(4,6-dimethoxy[1.3.5]-triazin-2-yl)-4-methylmorpholinium chloride hydrate, bromo-tripyrrolidinophos-phoniumhexafluorophosphate or propanephosphonic anhydride (T3P).

Compounds of formula (1) wherein $U^1$ is a halogen atom can be reacted with an amine of formula (2) in the presence of an acid scavenger by means of well-known methods. Suitable acid scavengers include any inorganic and organic bases, as described herein, which are customary for such reactions. Preference is given to alkali metal carbonates, alkaline earth metal acetates, tertiary amines or aromatic bases.

Compounds of formula (1) wherein $U^1$ is a $C_1$-$C_6$-alkoxy group can be reacted with an excess of amine of formula (2), optionally in the presence of a Lewis acid such as trimethylaluminum.

Process B

A compound of formula (I-a-1), wherein $A^1$, Q, L, $R^3$, $R^4$, $R^5$, $R^6$ and $R^7$ are defined as above and wherein $A^2$ is O, T is hydrogen, m is 1 or 2, may be prepared by reacting a compound of formula (7), wherein m, $A^1$, L, $R^3$, $R^4$, $R^5$, $R^6$ and $R^7$ are defined as above and W is hydrogen, tert-butoxycarbonyl, benzyl, allyl or (4-methoxyphenyl)methyl, X is halogen, preferably bromo, with a compound of formula (8), wherein Q is defined as above, in the presence of a base (e.g. organic or inorganic base) and optionally in the presence of a suitable copper salt or complex, followed by a deprotection step if W is tert-butoxycarbonyl, benzyl, allyl or (4-methoxyphenyl)methyl, as shown in scheme 2.

Scheme 2: Process B- Synthesis of compounds of formula (I-a-1)

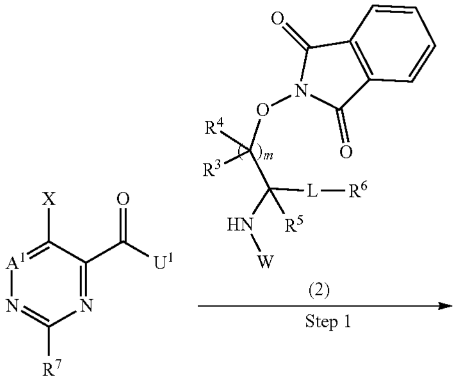

(5)

-continued

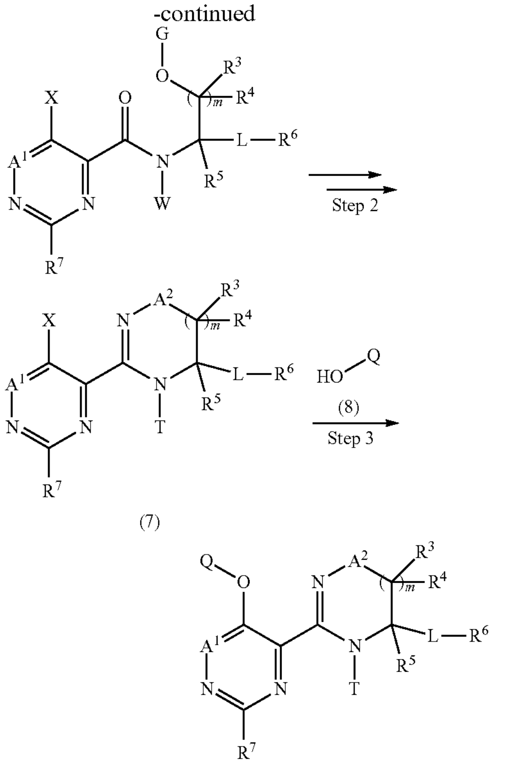

(7)

(I-a-1)

(6a) G=

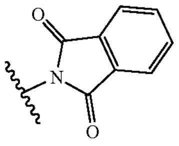

(6b) G = $NH_2$

Compounds of formula (7), wherein m, $A^1$, $A^2$, L, T, W, X, $R^3$, $R^4$, $R^5$, $R^6$ and $R^7$ are defined as above, may be prepared by reacting a compound of formula (5), wherein X and $R^7$ are defined as above and $U^1$ is hydroxyl, halogen or $C_1$-$C_6$-alkoxy, with an amine of formula (2), wherein m, $A^2$, L, W, $R^3$, $R^4$, $R^5$ and $R^6$ are defined as above, or a salt thereof, to obtain a compound of formula (6a), wherein m, $A^1$, $A^2$, L, T, W, X, $R^3$, $R^4$, $R^5$, $R^6$ and $R^7$ are defined as above, and G is phthalimido, or a salt thereof, then removing the phthalimide group of compound (6a) to obtain a compound of formula (6b), wherein m, $A^1$, $A^2$, L, T, W, X, $R^3$, $R^4$, $R^5$, $R^6$ and $R^7$ are defined as above, and G is hydrogen, which is then, when W is hydrogen, directly treated with a dehydrating agent, optionally in the presence of a base to obtain directly the compound of formula (7), or which is then, when W is an aminoprotecting group, treated with a dehydrating agent, optionally in the presence of a base, and finally deprotected to obtain the compound of formula (7), under the same conditions as described herein for process A.

The reaction of compound of formula (7) with a compound of formula (8) may be performed in the presence of a transition metal catalyst such as a copper salt or complex, and if appropriate in the presence of a ligand as described herein.

Compounds of formula (5) are commercially available or may be prepared by process F described herein.

Compounds of formula (8) are commercially available or may be obtained by conversion or derivatization of another compound of formula (8) in accordance to well-known methods.

Process C

A compound of formula (I-a-1), wherein $A^1$, Q, L, $R^3$, $R^4$, $R^5$, $R^6$ and $R^7$ are defined as above and m is 1 or 2, $A^2$ is O or NH, T is hydrogen, may be prepared by first reacting a compound of formula (1), wherein Q, $R^7$ and $R^8$ are defined as above $U^1$ is hydroxyl, halogen or $C_1$-$C_6$-alkoxy, with an amine of formula (9) or one of its salts, wherein m, L, $R^3$, $R^4$, $R^5$ and $R^6$ are defined as above and $E^1$ is hydroxyl or halogen, W is hydrogen, tert-butoxycarbonyl, benzyl, allyl or (4-methoxyphenyl)methyl, to provide a compound of formula (10), wherein m, $E^1$, L, W, $R^3$, $R^4$, $R^5$ and $R^6$ are defined as above, under the conditions as described in process A, which is then treated with a dehydrating agent followed by hydroxylamine or hydrazine ($H_2N$-$E^2$, wherein $E^2$ is hydroxyl or amino), to form a compound of formula (11), wherein m, $E^1$, $E^2$, L, Q, W, $R^3$, $R^4$, $R^5$, $R^6$ and $R^7$ are defined as above, which is finally converted into a compound of formula (I-a-1) or (I-a-2) as shown in scheme 3.

Scheme 3: Process C- Synthesis of compounds of formula (I-a-1) and (I-a-2)

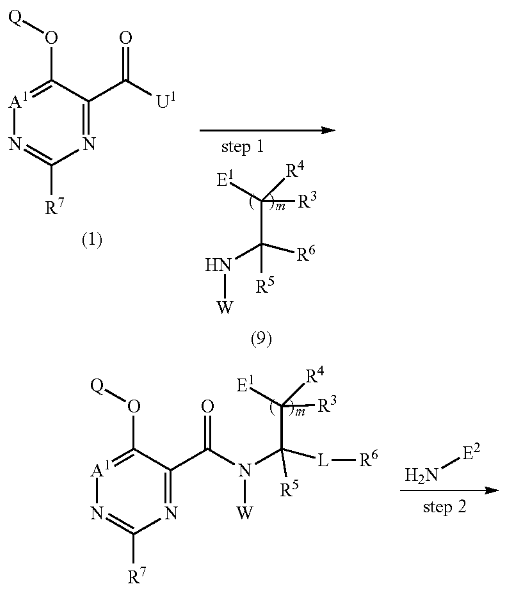

(1)

(9)

(10)

-continued

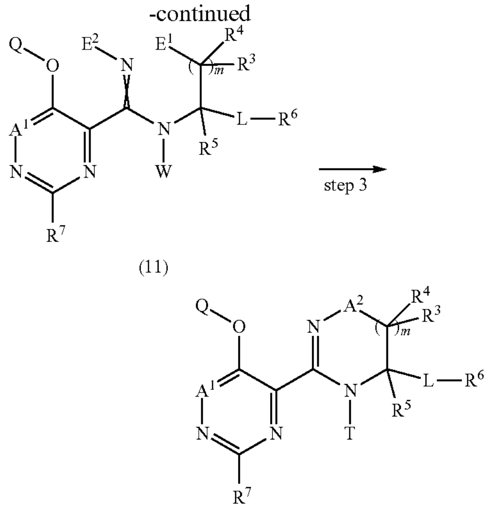

(11)

(I-a-1) $A^2$ = —O—

(I-a-2) $A^2$ = —NH—

When $E^1$ and $E^2$ each are hydroxyl, a compound of formula (11) is converted into a compound of formula (I-a-1) using Mitsunobu reaction conditions known by the skilled person of the art (Strategic Applications of Named Reactions in Organic Synthesis; Laszlo Kürti, Barbara Czako; Elsevier; 2005; 294-295 and reference herein). When $E^1$ is halogen and $E^2$ is hydroxyl or amino, a compound of formula (11) is converted into a compound of formula (I-a-1) or (I-a-2) in the presence of a base.

When W represents an amino protecting group, Step 3 is followed by an additional deprotection step using reaction conditions described in the literature (Greene's Protective Groups in organic Synthesis; Peter G. M. Wuts; Wiley; Fifth Edition; 2014; 895-1194) to provide a compound of formula (I-a-1) or (I-a-2).

Aminoalcohols of formula (9-a, $E^1$=hydroxyl) are commercially available or can be obtained by methods described in the literature (Molecules, 9 (6), 405-426; 2004; WO2017203474). Compounds of formula (9-b, $E^1$=halogen) can be obtained from the corresponding aminoalcohol by well-known methods.

Process D

A compound of formula (I-a-1) or (I-a-2), wherein $A^1$, Q, L, $R^3$, $R^4$, $R^5$, $R^6$ and $R^7$ are defined as above, and $A^2$ is O or NH, T is hydrogen, m is 1 or 2, may be prepared by reacting a compound of formula (5), wherein $R^7$ is defined as above and X is halogen, $U^1$ is hydroxyl, halogen or $C_1$-$C_6$-alkoxy, with an amine of formula (9), wherein m, L, $R^3$, $R^4$, $R^5$ and $R^6$ are defined as above and $E^1$ is hydroxyl or halogen, W is hydrogen, tert-butoxycarbonyl, benzyl, allyl or (4-methoxyphenyl)methyl, to provide a compound of formula (12), wherein m, $E^1$, L, W, X, $R^3$, $R^4$, $R^5$, $R^6$ and $R^7$ are defined as above, under the conditions described in process A, which is then treated with a dehydrating agent followed by hydroxylamine or hydrazine ($H_2N$-$E^2$, wherein $E^2$ is hydroxyl or amino) to form a compound of formula (13), wherein m, $E^1$, L, W, X, $R^3$, $R^4$, $R^5$, $R^6$ and $R^7$ are defined as above, which in the following is converted into compound of formula (7) ($A^2$=O) or of formula (14) ($A^2$=NH), wherein m, $A^1$, L, W, X, $R^3$, $R^4$, $R^5$, $R^6$, $R^7$ and $R^8$ are defined as above, which is finally reacted with a compound of formula (8), wherein Q is defined as above, in the presence of a base (e.g. organic or inorganic base) and optionally in the presence of a suitable copper salt or complex to provide a compound of formula (I-a-1) or (I-a-2) as shown in scheme 4.

Scheme 4: Process D- Synthesis of compounds of formula (I-a-1) and (I-a-2)

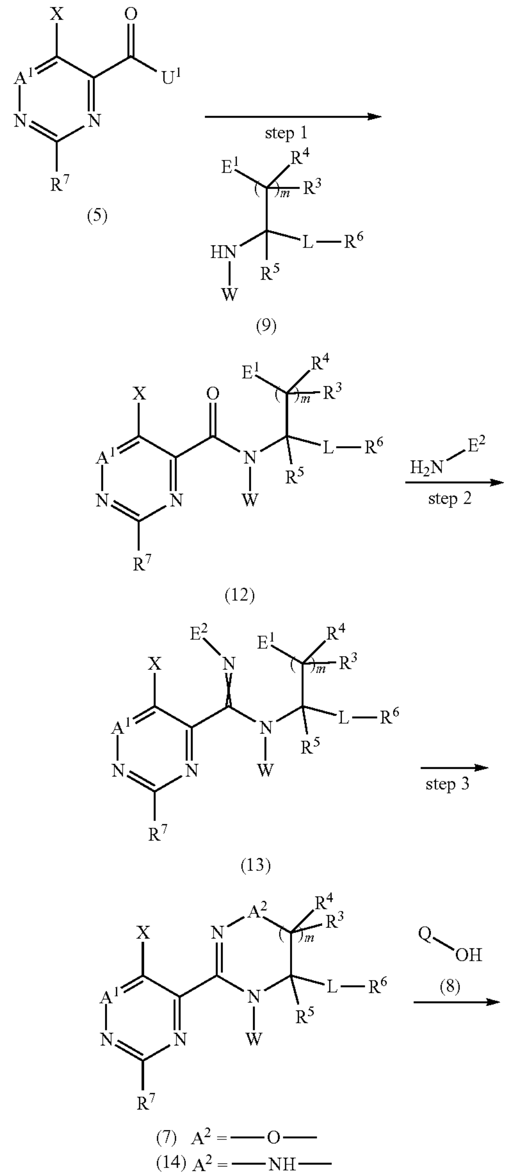

(5)

(9)

(12)

(13)

(7) $A^2$ = —O—

(14) $A^2$ = —NH—

-continued

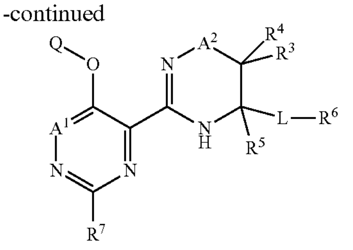

(I-a-1) $A^2$ = —O—

(I-a-2) $A^2$ = —NH—

Step 3 is performed under Mitsunobu reaction conditions when $E^1$ and $E^2$ both are hydroxyl (Strategic Applications of Named Reactions in Organic Synthesis; Laszlo Kürti, Barbara Czako; Elsevier; 2005; 294-295 and reference herein), and in the presence of a base, when $E^1$ is halogen and $E^2$ is hydroxyl or amino.

When W represents an amino protecting group, Step 3 is followed by an additional deprotection step using reaction conditions described in the literature (Greene's Protective Groups in organic Synthesis; Peter G. M. Wuts; Wiley; Fifth Edition; 2014; 895-1194) to provide a compound of formula (I-a-1) or (I-a-2).

Compounds of formula (5) are commercially available or may be prepared by process F described herein.

Processes for the Preparation of a Compound of Formula (1)

Process E

A compound of formula (1) may be directly obtained by performing process E described below or may be obtained by conversion or derivatization of another compound of formula (1) prepared in accordance with the processes described herein. Compounds of formula (1-a), (1-a') and (1-a") are various subsets of formula (1).

A compound of formula (1-a), wherein $A^1$, $R^7$ and Q are defined as above and $U^1$ is $C_1$-$C_6$-alkoxy, can be prepared by a process comprising the step of reacting a compound of formula (5), wherein $A^1$, $R^7$ and A are defined as above and $U^1$ is $C_1$-$C_6$-alkoxy, X is halogen, with compound of formula (8), wherein Q is defined as above, in the presence of a transition metal catalyst, optionally in the presence of a ligand as shown in scheme 5.

Scheme 5: Process E- Synthesis of compounds of formula (1-a)

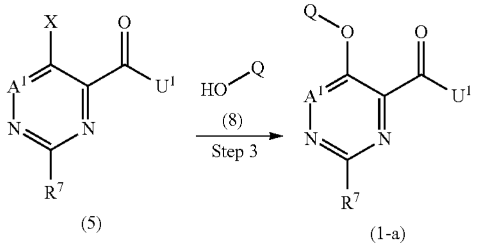

(5)

(1-a)

Compounds of formula (5) are commercially available or may be prepared by process F described herein.

Compounds of formula (8) are commercially available or may be obtained by conversion or derivatization of another compound of formula (8) in accordance to well-known methods.

Compounds of formula (1-a), wherein $U^1$ is $C_1$-$C_6$-alkoxy can be converted to compounds of formula (1-a'), wherein $U^1$ is a hydroxyl group by well-known functional group interconversion methods, for example by hydrolysis of an ester group with LiOH in THF/water.

Compounds of formula (1-a'), wherein $U^1$ is a hydroxyl can be converted to compounds of formula (1-a"), wherein $U^1$ is a halogen in the presence of halogenating agents by well-known methods. Suitable halogenating reagents include, but are not limited to, phosphorous tribromide, phosphorous trichloride, phosphorous pentachloride, phosphorous trichloride oxide, oxalyl chloride or thionyl chloride.

Processes for the Preparation of a Compound of Formula (5)

Process F

A compound of formula (5) as described herein may be directly obtained by performing process F described below or may be obtained by conversion or derivatization of another compound of formula (5) prepared in accordance with the processes described herein. Compounds of formula (5-a), (5-a'), (5-a") and (5-b), (5-b'), (5-b") are various subsets of formula (5).

A compound of formula (5-a), wherein $A^1$ is defined as above and $U^1$ is $C_1$-$C_6$-alkoxy, $R^{7a}$ is halogen, X is halogen, can be converted into a compound of formula (5-b), wherein $A^1$ and $R^8$ are defined as above and $U^1$ is $C_1$-$C_6$-alkoxy, X is halogen, $R^{7b}$ is hydrogen, halogen different from $R^{7a}$, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylsulfanyl, $C_1$-$C_6$-haloalkylsulfanyl, $C_3$-$C_8$-cycloalkylsulfanyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, —$N(R^{21})_2$ or —C(=O)($OR^{21}$), wherein $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylsulfanyl, $C_1$-$C_6$-haloalkylsulfanyl, $C_3$-$C_8$-cycloalkylsulfanyl, $C_3$-$C_8$-cycloalkyl, $C_3$-$C_6$-cycloalkenyl, $C_6$-$C_{14}$-aryl, 5- or 6-membered heteroaryl and 3- to 7-membered heterocyclyl are optionally substituted as defined above, as shown in Scheme 6.

Scheme 6: Process F- Synthesis of compounds of formula (5-b)

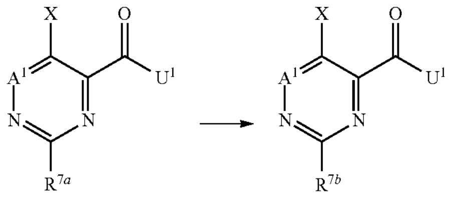

(5-a) (5-b)

Compounds of formula (5-a) are commercially available.

A compound of formula (5-a), wherein $R^{7a}$ is halogen, can be converted into a compound of formula (5-b) wherein $R^{7b}$ is cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylsulfanyl, $C_1$-$C_6$-haloalkylsulfanyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, —$N(R^{21})_2$ or —C(=O)($OR^{21}$) by transition metal catalyzed or metallo-photoredox catalyzed processes as described herein.

Compounds of formula (5-a) and (5-b), wherein $U^1$ is $C_1$-$C_6$-alkoxy can be converted to compounds of formula (5-a') and (5-b'), wherein $U^1$ is a hydroxyl group by well-known functional group interconversion methods, for example by hydrolysis of an ester group with LiOH in THF/water.

Compounds of formula (5-a') and (5-b'), wherein $U^1$ is a hydroxyl group can be converted to compounds of formula (5-a") and (5-a"), wherein $U^1$ is a halogen in the presence of halogenating agents by well-known methods. Suitable halogenating reagents include, but are not limited to, phosphorous tribromide, phosphorous trichloride, phosphorous pentachloride, phosphorous trichloride oxide, oxalyl chloride or thionyl chloride.

Process for the Preparation of Compounds of Formula (2), (9-a) and (9-b)

A compound of formula (9) may be obtained by performing process G described below or may be obtained by conversion or derivatization of another compound of formula (9-a) prepared in accordance with the processes described herein. Compounds of formula (9-a) and (9-b) are various subsets of formula (9).

Process G

A compound of formula (15) may be converted by means of methods described in the literature to the corresponding compounds (9-a) and (2) as shown in scheme 7.

Scheme 7: Process G- Preparation of compounds (2), (9-a) and (9-b)

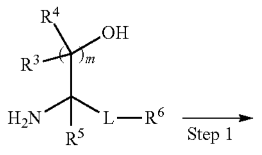

(15)

-continued

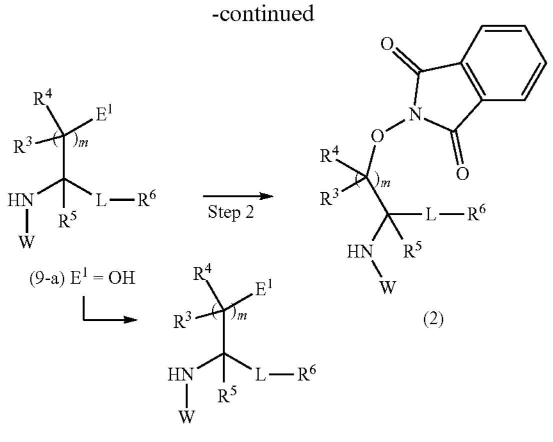

(9-a) $E^1$ = OH (2)

(9-b) $E^1$ = halogen

W = hydrogen, tert-butoxycarbonyl, benzyl, allyl or (4-methoxyphenyl)methyl

The amino function of compound (15) may be first protected (W=tert-butoxycarbonyl, benzyl, allyl or 4-methoxyphenyl)methyl) in accordance with known methods to provide a compound of formula (9-a) (Greene's Protective Groups in organic Synthesis; Peter G. M. Wuts; Wiley; Fifth Edition; 2014; 895-1194).

Subsequently, the compound of formula (9-a) may be converted by Step 2 of Process G into a compound of formula (2) using classical Mitsunobu reaction conditions known by the skilled person of the art (Strategic Applications of Named Reactions in Organic Synthesis; Laszlo Kürti, Barbara Czako; Elsevier; 2005; 294-295 and references therein).

Compounds of formula (9-a) wherein $E^1$ is a hydroxyl may be converted to compounds of formula (9-b) wherein $E^1$ is a halogen in the presence of halogenating agents by well-known methods. Suitable halogenating reagents include, but are not limited to, phosphorous tribromide, phosphorous trichloride, phosphorous pentachloride, phosphorous trichloride oxide, oxalyl chloride or thionyl chloride.

Aminoalcohols of formula (15) are commercially available or may be producible by methods described in the literature (Molecules, 9 (6), 405-426; 2004, WO2017203474).

Alternative Preparation of Compounds of Formula (I)

Process H

A compound of formula (I-a-1), wherein $A^1$, Q, L, $R^3$, $R^4$, $R^6$ and $R^7$ are defined as above and wherein m is 1 or 2, $A^2$ is O, T is hydrogen, $R^5$ is hydrogen, hydroxyl or $C_1$-$C_6$-alkoxy, may be prepared by a process, as shown in scheme 8, comprising the step of adding a reducing agent under acidic conditions to a compound of formula (19), wherein m, Q, L, T, $R^3$, $R^4$, $R^6$ and $R^7$ are defined as above, to provide a compound of formula (I-a-1).

Scheme 8: Process H- Synthesis of compounds of formula (I-a-1)

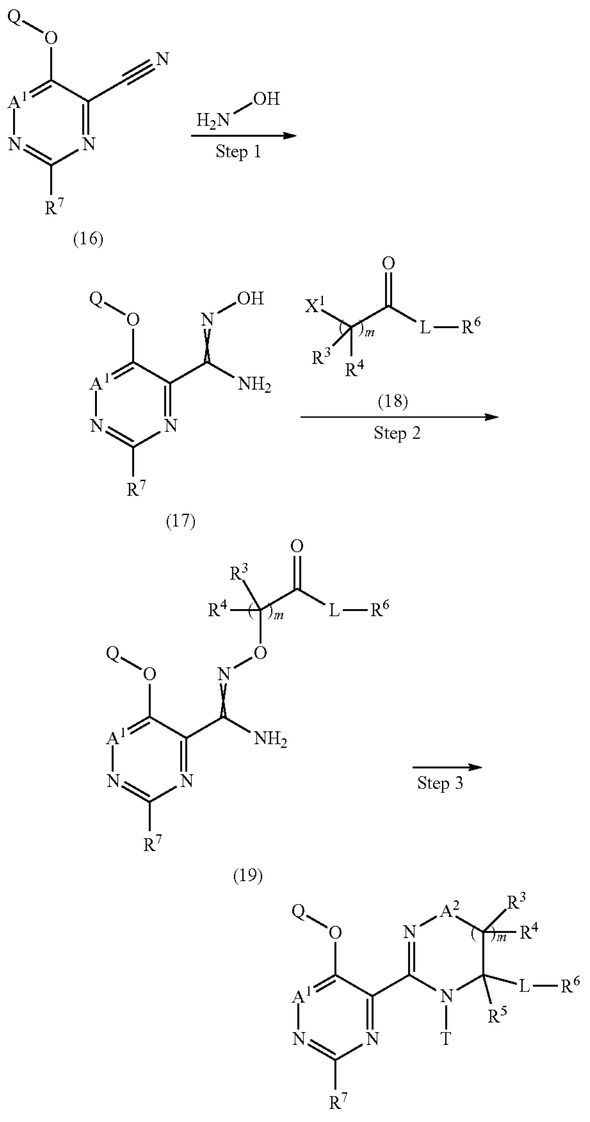

(16)

(17)

(18)

(19)

(I-a-1)

Compounds of formula (19) can be cyclized under acidic conditions in the presence of a reducing agent such as sodium cyanoborohydride to provide a compound of formula (I-a-1). Reaction conditions to form oxadiazine rings with this methodology are known and have been described in the literature (Heterocycles 2016, 92, 2166-2200).

Compounds of formula (19) can be obtained by reacting a compound of formula (17), wherein $A^1$ and Q are defined as above, with a compound of formula (18), wherein m, L, $R^3$, $R^4$ and $R^6$ are defined as above and $X^1$ is halogen, in the presence of a base. Suitable bases are alkali metal hydrides such as sodium hydride, alkali metal carbonates such as potassium carbonate, alkali metal hydroxides such as potassium hydroxide, or phosphazene bases such as BEMP as described in the literature (Heterocycles 2016, 92, 2166-2200).

Compounds of formula (17), wherein $A^1$ and Q are defined as above, can be obtained by reacting a compound of formula (16), wherein $A^1$ and Q are defined as above, with hydroxylamine or a salt thereof. Reaction conditions to perform such transformations are known and have been reported in the literature (WO2010/138600).

Reagents of formula (16) are either commercially available or producible by processes described in the literature (WO2010/099279).

Compounds of formula (18) are either commercially available or can be prepared by processes described in the literature (Eur. J. Med. Chem. 2014, 84, 302, Eur. J. Med. Chem. 2015, 100, 18-23, WO2017031325).

Process I

A compound of formula (I-a), wherein m, $A^1$, $A^2$, L, Q, T, $R^3$, $R^4$, $R^5$ and $R^7$ are defined as above and $R^{6a}$ is indanyl, 1,2,3,4-tetrahydronaphthalenyl, phenyl, naphthyl, dihydrobenzofuranyl or dihydro-benzodioxinyl, wherein indanyl, 1,2,3,4-tetrahydronaphthalenyl, phenyl, naphthyl, dihydrobenzofuranyl and di-hydrobenzodioxinyl are optionally substituted with one or two $R^{6S}$ substituents, wherein $R^{6Sa}$ is halogen, methylsulfonyloxy or trifluoromethylsulfonyloxy, may be converted by means of methods described in the literature to the corresponding compound of formula (I-b), wherein m, $A^1$, $A^2$, L, Q, T, $R^3$, $R^4$, $R^5$, $R^7$, $R^8$ and $R^9$ are defined as above and $R^{6b}$ is indanyl, 1,2,3,4-tetrahydronaphthalenyl, phenyl, naphthyl, dihydrobenzofuranyl or dihydro-benzodioxinyl, wherein indanyl, 1,2,3,4-tetrahydronaphthalenyl, phenyl, naphthyl, dihydrobenzofuranyl and di-hydrobenzodioxinyl are optionally substituted with one or two $R^{6S}$ substituents, wherein $R^{6Sb}$ is independently selected from the group consisting cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylsulfanyl, $C_1$-$C_6$-haloalkylsulfanyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, —$N(R^{20})_2$ or —$C(=O)(OR^{25})$, Wherein $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylsulfanyl, $C_1$-$C_6$-haloalkylsulfanyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl are optionally substituted as defined above and $R^{20}$ and $R^{25}$ are defined as above, in one or more steps as shown in scheme 9.

Scheme 9: Process I- Synthesis of compounds of formula (I-b)

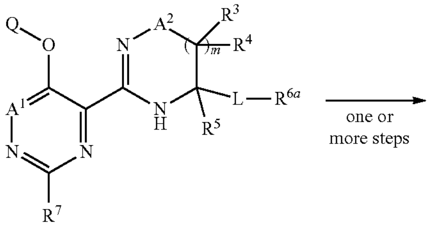

(I-a)

-continued

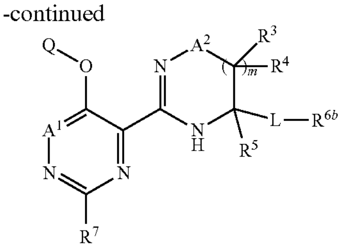

(I-b)

Non-limiting examples of conversions performed in accordance with scheme 17 are provided below.

A compound of formula (I-a), wherein $R^{6Sa}$ is halogen, can be converted into a compound of formula (I-b) wherein $R^{6Sb}$ is cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylsulfanyl, $C_1$-$C_6$-haloalkylsulfanyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, —$N(R^{20})_2$ or —$C(=O)(OR^{25})$ by transition metal catalyzed or metallo-photoredox catalyzed processes as described herein.

A compound of formula (I-a) can be prepared by one or more of the processes herein described or by methods known to the person skilled in the art.

Process J

A compound of formula (I-a-1), wherein $A^1$, L, Q, $R^3$, $R^4$, $R^5$, $R^6$ and $R^7$ are defined as above and wherein $A^2$ is O, T is hydrogen, m is 1 or 2, or a compound of formula (I-a-3), wherein $A^1$, L, Q, $R^3$, $R^4$, $R^5$, $R^6$ and $R^7$ are defined as above and wherein $A^2$ is $CR^1R^2$, wherein $R^1$ and $R^2$ are defined as above, T is hydrogen, m is 1 or 2, or a compound of formula (I-a-4), wherein $A^1$, Q, L, $R^3$, $R^4$, $R^5$, $R^6$ and $R^7$ are defined as above and wherein $A^2$ is C(=O), T is hydrogen, m is 1 or 2, or a compound of formula (I-a-5), wherein $A^1$, L, Q, $R^3$, $R^4$, $R^5$, $R^6$ and $R^7$ are defined as above and wherein $A^2$ is $S(=O)_2$ T is hydrogen, m is 1 or 2, can be prepared by a process comprising the steps of first treating a compound of formula (16), wherein $A^1$, Q and $R^7$ are defined as above, with an alkoxide to provide compound of formula (20), wherein $A^1$, Q and $R^7$ are defined as above and Y is $C_1$-$C_6$-alkyl, which is then reacted with an amine of formula (9c-1), (9c-2), (9c-3) or (9c-4) respectively, wherein each m, L, $R^3$, $R^4$, $R^5$, $R^6$ are defined as above and W is hydrogen or suitable protecting group for amino function and $E^1$ is $NH_2$—O— in compound of formula (9c-1), $E^1$ is $NH_2$—$CR^{44}R^{45}$— in compound of formula (9c-2), wherein $R^{44}$ and $R^{45}$ are hydrogen, $C_1$-$C_6$-alkyl, $C_3$-$C_8$-cycloalkyl, $C_6$-$C_{14}$-aryl, or $R^{44}$ and $R^{45}$ form together with the carbon atom to which they are attached, a $C_3$-$C_8$-cycloalkyl-ring or a 3- to 7-membered heterocyclyl-ring, $E^1$ is $NH_2$—C(═O)— in compound of formula (9c-3), $E^1$ is $NH_2$—S(═O)$_2$— in compound of formula (9c-4), to obtain a compound of formula (I-a-1), (I-a-3), (I-a-4) or (I-a-5) respectively as shown in scheme 10.

Scheme 10: Process R- Synthesis of compounds of formula (I-a-1), (I-a-3), (I-a-4) or (I-a-5)

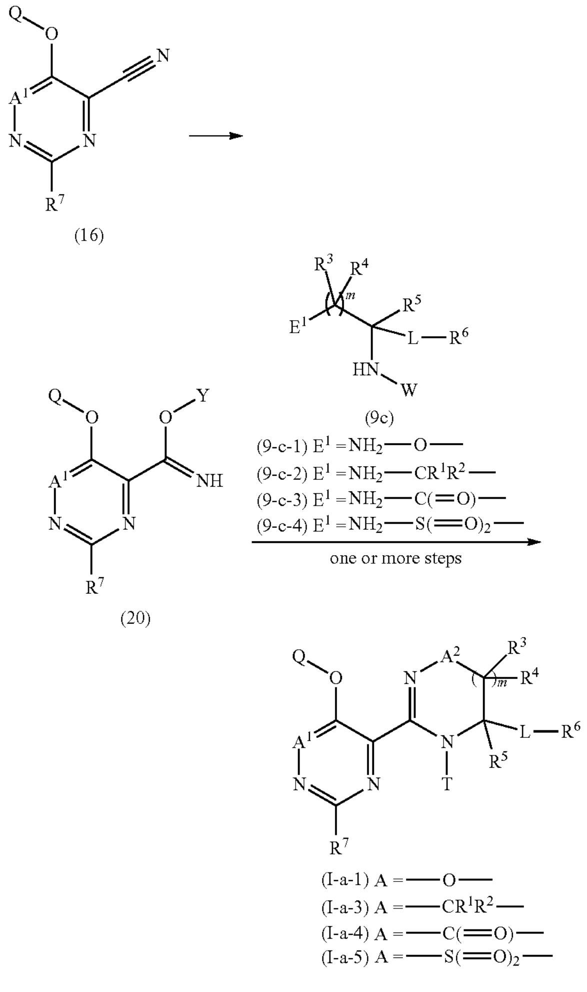

(16)

(9c)

(20)

The compound of formula (20), wherein $A^1$, Q and $R^7$ are defined as above and Y is $C_1$-$C_6$-alkyl, can be obtained by treating a compound of formula (16), wherein $A^1$, Q and $R^7$ are defined as above, with an alkoxide such as sodium methanolate or sodium ethanolate according to methods described in the literature (Heterocycles, 34, 1992, 929-935).

The compound of formula (20), wherein $A^1$, Q and $R^7$ are defined as above and Y is $C_1$-$C_6$-alkyl, is treated with a compound of formula (9-c-1), (9-c-2), (9-c-3) or (9-c-4), wherein m, L, $R^3$, $R^4$, $R^5$, $R^6$ are defined as above, W is hydrogen or suitable protecting group for amino function and $E^1$ is $NH_2$—O— in compound of formula (9c-1), E is $NH_2$—$CR^{44}R^{45}$— in compound of formula (9c-2), wherein $R^{44}$ and $R^{45}$ are defined as above, $E^1$ is $NH_2$—C(═O)— in compound of formula (9c-3), $E^1$ is $NH_2$—S(═O)$_2$— in compound of formula (9c-4), are cyclized under acidic conditions to form respectively a compound of formula (I-a-1), (I-a-3), (I-a-4) or (I-a-5), wherein m, $A^1$, L, Q, T, $R^3$, $R^4$, $R^5$, $R^6$, and $R^7$ are defined as above and $A^2$ is O in compound of formula (I-a-1)

$A^2$ is $CR^1R^2$ in compound of formula (I-a-3)

$A^2$ is C(═O) in compound of formula (I-a-4)

$A^2$ is S(═O)$_2$ in compound of formula (I-a-5).

Reaction conditions to perform such transformations based on this methodology have been described in the literature (Heterocycles 2016, 92, 2166-2200).

Amines of formula (9-c-1), (9-c-2), (9-c-3) or (9-c-4) are either commercially available, or may be prepared by methods described in the literature (Molecules, 9 (6), 405-426; 2004, WO2017/203474; J. Med. Chem 1985, 28, 694-698; J. Med. Chem 2006, 49, 4333-4343) and by Process G of this invention.

Reagents of formula (16) are either commercially available or producible by processes described in the literature (WO2010/099279).

Intermediates

The present invention also relates to intermediates for the preparation of compounds of formula (I).

Some of the intermediates of formula (1) as defined herein are known from the prior art, see for example CN106317027A and U.S. Pat. No. 5,420,129A.

Thus, the present invention relates to compounds of formula (1):

(1)

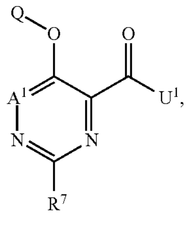

wherein $A^1$ is N or $CR^8$, wherein $R^8$ is hydrogen, halogen, cyano or $C_1$-$C_4$-alkyl, $U^1$ is hydroxyl, halogen or $C_1$-$C_6$-alkoxy, $R^7$ is hydrogen, halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_2$-$C_6$-alkenylsulfanyl, $C_2$-$C_6$-alkynylsulfanyl, $C_1$-$C_6$- alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy, —O—Si($C_1$-$C_6$-alkyl)$_3$, —Si($C_1$-$C_6$-alkyl)$_3$, —N($R^{20}$)$_2$, —C(=N$R^{21}$)$R^{22}$, —N$R^{23}$C(=O)$R^{24}$, —C(=O)(O$R^{25}$), —C(=O)N($R^{26}$)$_2$, —S(=O)$_2$N($R^{27}$)$_2$ or —S(=O)(=N$R^{28}$)$R^{29}$, wherein $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are optionally substituted with one to three $R^{7Sa}$ substituents, wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy are optionally substituted with one to three $R^{7Sc}$ substituents, and wherein $R^{20}$ is independently hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_6$-$C_{14}$-aryl, 5- or 6-membered heteroaryl or 3- to 7-membered heterocyclyl, wherein $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl in turn are optionally substituted with one to three substituents $R^{7Sc}$, and wherein $C_3$-$C_8$-cycloalkyl, $C_3$-$C_8$-halocycloalkyl, $C_6$-$C_{14}$-aryl, 5- or 6-membered heteroaryl and 3- to 7-membered heterocyclyl in turn are optionally substituted with one to three substituents $R^{7Sc}$, $R^{21}$ and $R^{22}$ are independently hydroxyl, amino, cyano, $C_1$-$C_6$-alkyl, $C_1$-$C_6$-haloalkyl, $C_1$-$C_6$-alkoxy, mono-($C_1$-$C_6$-alkyl)amino or di-($C_1$-$C_6$-alkyl)amino, wherein $C_1$-$C_6$-alkyl, $C_1$-$C_6$-haloalkyl, $C_1$-$C_6$-alkoxy, mono-($C_1$-$C_6$-alkyl)amino and di-($C_1$-$C_6$-alkyl)amino in turn are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_6$-alkyl, $C_1$-$C_6$-haloalkyl and $C_3$-$C_8$-cycloalkyl, wherein $C_1$-$C_6$-alkyl and $C_1$-$C_6$-haloalkyl in turn are optionally substituted with one to three $R^{7Sa}$ substituents, and wherein $C_3$-$C_8$-cycloalkyl in turn is optionally substituted with one to three $R^{7Sc}$ substituents, wherein $R^{7Sa}$ is independently cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$, —Si($C_1$-$C_6$-alkyl)$_3$, $C_6$-$C_{14}$-aryl or 3- to 7-membered heterocyclyl, $R^{7Sc}$ is independently halogen, cyano, nitro, hydroxyl, formyl, oxo, methylidene, halomethylidene, $C_1$-$C_6$-alkyl, $C_1$-$C_6$-haloalkyl $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, or two $R^{7Sc}$ substituents $C_1$-$C_6$-alkyl that are bound to the same carbon atom form together a $C_3$-$C_8$-cycloalkyl-ring, Q is $C_6$-$C_{14}$-aryl, $C_3$-$C_{12}$-carbocyclyl, 3- to 14-membered heterocyclyl or 5- to 14-membered heteroaryl, wherein $C_6$-$C_{14}$-aryl, $C_3$-$C_{12}$-carbocyclyl, 3- to 14-membered heterocyclyl or 5- to 14-membered heteroaryl are optionally substituted with one to five substituents $Q^S$ wherein $Q^S$ is independently selected from the group consisting of halogen, cyano, isocyano, nitro, hydroxyl, mercapto, formyl, carboxyl, $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyloxy, $C_3$-$C_6$-cycloalkenyl, 3- to 7-membered heterocyclyl, $C_6$-$C_{14}$-aryl, 5- to 14-membered heteroaryl, —O—Si($C_1$-$C_6$-alkyl)$_3$, —Si($C_1$-$C_6$-alkyl)$_3$, —O—C(=O)$R^{33}$, —N$R^{34}$C(=O)$R^{35}$, —C(=O)N($R^{36}$)$_2$, —C(=S)$R^{37}$, —C(=S)N($R^{38}$)$_2$, —C(=N$R^{39}$)$R^{40}$, —C(=NO$R^{41}$)$R^{42}$ and —N($R^{43}$)$_2$, wherein said $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, said $C_3$-$C_8$-cycloalkyl, $C_3$-$C_8$-cycloalkoxy, $C_3$-$C_6$-cycloalkenyl, 3- to 7-membered heterocyclyl and 5- to 14-membered heteroaryl in turn are optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$- haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl, and wherein $R^{33}$ is hydrogen, $C_1$-$C_6$-alkyl, $C_1$-$C_6$-haloalkyl and $C_1$-$C_6$-alkoxy, $R^{34}$, $R^{35}$, $R^{36}$ $R^{37}$ $R^{38}$ $R^{39}$ $R^{40}$ $R^{41}$ and $R^{42}$ are independently hydrogen, $C_1$-$C_6$-alkyl, $C_1$-$C_6$-haloalkyl or $C_1$-$C_6$-alkoxy, wherein said $C_1$-$C_6$-alkyl, $C_1$-$C_6$-haloalkyl and $C_1$-$C_6$-alkoxy in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, and wherein $R^{43}$ is hydrogen, hydroxyl, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl or $C_3$-$C_8$-cycloalkyl, wherein said $C_1$-$C_6$-alkyl, $C_1$-$C_6$-haloalkyl, $C_1$-$C_6$-alkoxy, $C_2$-$C_6$-alkenyl and $C_2$-$C_6$-haloalkenyl in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, wherein said $C_3$-$C_8$-cycloalkyl in turn is optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl, provided that when in formula (1) A is C—$R^8$ and $R^8$═H, then Q is not 2,5-dichlorophenoxy, if $R^7$ is hydrogen, and provided that the compound of formula (1) is not:

ethyl 2,6-dichloro-5-phenoxypyrimidine-4-carboxylate (CAS 157415-41-3), further preferably provided that when in formula (1) A is C—$R^8$ and $R^8$═H, then $R^7$ is not isopropyl if $U^1$ is hydroxyl.

Thus, the present invention also relates to compounds of formula (1):

(1)

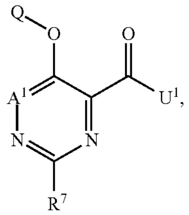

wherein $A^1$ is N or $CR^8$, wherein $R^8$ is hydrogen or halogen, $U^1$ is hydroxyl, halogen or $C_1$-$C_6$-alkoxy, $R^7$ is halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy, —O—Si($C_1$-$C_6$-alkyl)$_3$, —Si($C_1$-$C_6$-alkyl)$_3$, —N($R^{20}$)$_2$, —C(═$NR^{21}$)$R^{22}$, —$NR^{23}$C(═O)$R^{24}$, —C(═O)($OR^{25}$), —C(═O)N($R^{26}$)$_2$, —S(═O)$_2$N($R^{27}$)$_2$ or —S(═O)(═$NR^{28}$)$R^{29}$, wherein $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are optionally substituted with one to three $R^{7Sa}$ substituents, wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy are optionally substituted with one to three $R^{7Sc}$ substituents, and wherein $R^{20}$ is $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_6$-$C_{14}$-aryl, 5- or 6-membered heteroaryl or 3- to 7-membered heterocyclyl, wherein $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$- alkynyl and $C_2$-$C_6$-haloalkynyl are optionally substituted with one to three substituents $R^{7Sa}$, and wherein $C_3$-$C_8$-cycloalkyl, $C_3$-$C_8$-halocycloalkyl, $C_6$-$C_{14}$-aryl, 5- or 6-membered heteroaryl and 3- to 7-membered heterocyclyl are optionally substituted with one to three substituents $R^{7Sc}$, $R^{21}$ and $R^{22}$ are independently hydroxyl, amino, cyano, $C_1$-$C_6$-alkyl, $C_1$-$C_6$-haloalkyl, $C_1$-$C_6$-alkoxy, mono-($C_1$-$C_6$-alkyl)amino or di-($C_1$-$C_6$-alkyl)amino, wherein $C_1$-$C_6$-alkyl, $C_1$-$C_6$-haloalkyl, $C_1$-$C_6$-alkoxy, mono-($C_1$-$C_6$-alkyl)amino and di-($C_1$-$C_6$-alkyl)amino are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_6$-alkyl, $C_1$-$C_6$-haloalkyl and $C_3$-$C_8$-cycloalkyl, wherein $C_1$-$C_6$-alkyl and $C_1$-$C_6$-haloalkyl are optionally substituted with one to three $R^{7Sa}$ substituents, and wherein $C_3$-$C_8$-cycloalkyl is optionally substituted with one to three $R^{7Sc}$ substituents, wherein $R^{7Sa}$ is independently cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$, —Si($C_1$-$C_6$-alkyl)$_3$, $C_6$-$C_{14}$-aryl or 3- to 7-membered heterocyclyl, $R^{7Sc}$ is independently halogen, cyano, nitro, hydroxyl, formyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, or two $R^{7Sc}$ substituents $C_1$-$C_6$-alkyl that are bound to the same carbon atom form together a $C_3$-$C_8$-cycloalkyl, Q is $C_6$-$C_{14}$-aryl, $C_7$-$C_{12}$-carbocyclyl, 6- to 14-membered heterocyclyl or 5- to 14-membered heteroaryl, wherein $C_6$-$C_{14}$-aryl, $C_7$-$C_{12}$-carbocyclyl 6- to 14-membered heterocyclyl or 5- to 14-membered heteroaryl are optionally substituted with one to five substituents $Q^S$, wherein $Q^S$ is independently selected from the group consisting of halogen, cyano, isocyano, nitro, hydroxyl, mercapto, formyl, carboxyl, $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyloxy, $C_3$-$C_6$-cycloalkenyl, 3- to 7-membered heterocyclyl, $C_6$-$C_{14}$-aryl, 5- to 14-membered heteroaryl, —O—Si($C_1$-$C_6$-alkyl)$_3$, —Si($C_1$-$C_6$-alkyl)$_3$, —O—C(═O)$R^{33}$, —$NR^{34}$C(═O)$R^{35}$, —C(═O)N($R^{36}$)$_2$, C(═S)$R^{37}$, —C(═S)N($R^{38}$)$_2$, —C(═$NR^{39}$)$R^{40}$, —C(═$NOR^{41}$)$R^{42}$ and —N($R^{43}$)$_2$, wherein said $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, said $C_3$-$C_8$-cycloalkyl, $C_3$-$C_8$-cycloalkoxy, $C_3$-$C_6$-cycloalkenyl, 3- to 7-membered heterocyclyl and 5- to 14-membered heteroaryl in turn are optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl, and wherein $R^{34}$, $R^{35}$, $R^{36}$ $R^{37}$ $R^{38}$ $R^{39}$ $R^{40}$ $R^{41}$ and $R^{42}$ are independently hydrogen, $C_1$-$C_6$-alkyl, $C_1$-$C_6$-haloalkyl or $C_1$-$C_6$-alkoxy, wherein said $C_1$-$C_6$-alkyl, $C_1$-$C_6$-haloalkyl and $C_1$-$C_6$-alkoxy in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, and wherein $R^{43}$ is hydrogen, hydroxyl, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl or $C_3$-$C_8$-cycloalkyl, wherein said $C_1$-$C_6$-alkyl, $C_1$-$C_6$-haloalkyl, $C_1$-$C_6$-alkoxy, $C_2$-$C_6$-alkenyl and $C_2$-$C_6$-haloalkenyl are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, wherein said $C_3$-$C_8$-cycloalkyl is optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl in turn are optionally substituted with two substituents forming together with the carbon atom to which they are attached to a $C_3$-$C_8$-cycloalkyl, provided that when in formula (1) A is C—$R^8$ and $R^8$ ═H, then Q is not 2,5-dichlorophenoxy, if $R^7$ is hydrogen, and provided that the compound of formula (1) is not:

ethyl 2,6-dichloro-5-phenoxypyrimidine-4-carboxylate (CAS 157415-41-3), further preferably provided that when in formula (1) A is C—$R^8$ and $R^8$ ═H, then $R^7$ is not isopropyl if $U^1$ is hydroxyl.

In advantageous compounds of formula (1), $R^7$ is not hydrogen.

The present invention also relates to compounds of formula (2):

(2)

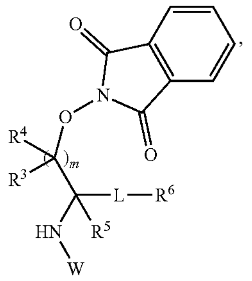

wherein m is 1 or 2, $R^3$ and $R^4$ are independently hydrogen, halogen or $C_1$-$C_6$-alkyl, or $R^3$ and $R^4$ form together with the carbon atom to which they are attached to a $C_3$-$C_8$-cycloalkyl, $R^5$ is hydrogen, hydroxyl, $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl, $C_3$-$C_8$-cycloalkyl or —O—Si($C_1$-$C_6$-alkyl)$_3$, wherein $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^5$ or $R^4$ and $R^5$ form together with the carbon atom to which they are attached to a $C_3$-$C_8$-cycloalkyl, L is a direct bond, carbonyl, $C_1$-$C_6$-alkylene, $C_2$-$C_6$-alkenylene, $C_2$-$C_6$-alkynylene, —C(═O)—$C_1$-$C_6$-alkylene-, —$C_1$-$C_6$-alkylene-C(═O)—, —$NR^{L1}$—, —$NR^{L2}$(C═O)—, —C(═O)$NR^{L3}$—, —$NR^{L4}$S(═O)$_2$—, —S(═O)$_2NR^{L5}$—, —C(═$NOR^{L6}$)—, —C(═N—N($R^{L7}$)$_2$)—, —C(═$NR^{L8}$)— or a group of formula $$\#—L^1—(E)—L^2—\#\#,$$

wherein said $C_1$-$C_6$-alkylene, $C_2$-$C_6$-alkenylene, $C_2$-$C_6$-alkynylene, —C(═O)—$C_1$-$C_6$-alkylene- and —$C_1$-$C_6$-alkylene-C(═O)— are optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl, $C_3$-$C_8$-cycloalkenyl and 3- to 7-membered heterocyclyl in turn are optionally substituted with one to three substituents $L^{SC}$, $R^{L1}$, $R^{L2}$, $R^{L3}$ and $R^{L4}$ are independently hydrogen or $C_1$-$C_6$-alkyl, $R^{L5}$, $R^{L6}$, $R^{L7}$ and $R^{L8}$ are independently hydrogen, $C_1$-$C_6$-alkyl, $C_1$-$C_6$-haloalkyl, $C_3$-$C_8$-cycloalkyl or $C_2$-$C_6$-alkenyl, $L^{SA}$ is independently halogen, cyano, hydroxyl, carboxyl, methylidene, halomethylidene, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$ or 3- to 7-membered heterocyclyl, or two substituents $L^{SA}$ that are bound to the same carbon atom form together with the carbon atom which they are attached to a $C_3$-$C_8$-cycloalkyl-ring or a 3- to 7-membered heterocyclyl-ring, $L^{Sc}$ is independently halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, and/or two $L^{Sc}$ substituents form together with the carbon atom to which they are attached to a $C_3$-$C_8$-cycloalkyl-ring, $R^6$ is $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl, 3- to 14-membered heterocyclylsulfonyl, $C_1$-$C_3$-alkoxy, $C_1$-$C_3$-haloalkoxy, $C_1$-$C_3$-alkylsulfanyl, $C_1$-$C_3$-alkylsulfinyl or $C_1$-$C_3$-alkylsulfonyl, wherein $C_1$-$C_3$-alkoxy, $C_1$-$C_3$-haloalkoxy, $C_1$-$C_3$-alkylsulfanyl, $C_1$-$C_3$-alkylsulfinyl and $C_1$-$C_3$-alkylsulfonyl are substituted with one substituent selected from the group consisting of $C_3$-$C_{12}$-carbocyclyl, $C_6$-$C_{14}$-aryl, 3- to 14-membered heterocyclyl and 5- to 14-membered heteroaryl, wherein said $C_3$-$C_{12}$-carbocyclyl, $C_6$-$C_{14}$-aryl, 3- to 14-membered heterocyclyl and 5- to 14-membered heteroaryl in turn are optionally substituted with one to four $R^{6S}$ substituents, wherein $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl and 3- to 14-membered heterocyclylsulfonyl are optionally substituted with one to four $R^{6S}$ substituents, wherein $R^{6S}$ is selected from the group consisting of halogen, cyano, isocyano, nitro, hydroxyl, mercapto, pentafluorosulfanyl, oxo, methylidene, halomethylidene, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, —$N(R^{15})_2$, —O(C═O)$R^{16}$, —C(═O)$R^{16}$, —C(═O)($OR^{17}$), —C(═O)$N(R^{18})_2$, —S(═O)$_2$$N(R^{19})_2$, —O—Si($C_1$-$C_6$-alkyl)$_3$ or —Si($C_1$-$C_6$-alkyl)$_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, or two substituents $C_1$-$C_6$-alkyl attached to the same carbon atom from a $C_3$-$C_8$-cycloalkyl-ring, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and wherein $R^{15}$ is hydrogen, $C_1$-$C_6$-alkyl or $C_3$-$C_8$-cycloalkyl, wherein said $C_1$-$C_6$-alkyl is optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, and wherein said $C_3$-$C_8$-cycloalkyl is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl or $C_1$-$C_6$-haloalkyl are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, W is hydrogen, tert-butoxycarbonyl, benzyl, allyl or (4-methoxyphenyl)methyl, provided that the compound of formula (2) preferably is not:

| | |
|---|---|
| 2-(2-amino-2-phenylethoxy)-1H-isoindole-1,3(2H)-dione | 1640226-54-5 |
| 2-{[rac-(1R,2R)-1-amino-1-(4-chlorophenyl)propan-2-yl]oxy}-1H-isoindole-1,3(2H)-dione | 2085782-61-0 |
| 2-{[rac-(1S,2S)-1-amino-1-(4-chlorophenyl)propan-2-yl]oxy}-1H-isoindole-1,3(2H)-dione hydrochloride (1:1) | 2085782-62-1 |
| 2-{[1-amino-1-(4-fluorophenyl)-2-methylpropan-2-yl]oxy}-1H-isoindole-1,3(2H)-dione | 1227082-96-3 |

-continued

| | |
|---|---|
| tert-butyl {1-[(1,3-dioxo-1,3-dihydro-2H-isoindol-2-yl)oxy]-3-phenylpropan-2-yl}carbamate | 937641-57-1 |
| tert-butyl {rac-(1R,2R)-1-(4-chlorophenyl)-2-[(1,3-dioxo-1,3-dihydro-2H-isoindol-2-yl)oxy]propyl}carbamate | 2085782-59-6 |
| tert-butyl {2-[(1,3-dioxo-1,3-dihydro-2H-isoindol-2-yl)oxy]-1-(4-fluorophenyl)-2-methylpropyl}carbamate | 1227082-95-2 |
| 2-[rac-2-amino-3-(2,4-dimethylphenyl)propoxy]isoindoline-1,3-dione | 2446130-64-7 |
| 2-[rac-2-amino-3-(2,4-dimethylphenyl)propoxy]isoindoline-1,3-dione 2,2,2-trifluoroacetic acid | 2446130-65-8 |
| 2-[rac-2-amino-3-(2,4-dichlorophenyl)propoxy]isoindoline-1,3-dione | 2446130-81-8 |
| 2-[rac-2-amino-3-(2,4-dichlorophenyl)propoxy]isoindoline-1,3-dione 2,2,2-trifluoroacetic acid | 2446130-82-9 |
| 2-[rac-2-amino-3-(4-bromo-2-chlorophenyl)propoxy]isoindoline-1,3-dione | 2446130-89-6 |
| 2-[rac-2-amino-3-(4-bromo-2-chlorophenyl)propoxy]isoindoline-1,3-dione 2,2,2-trifluoroacetic acid | 2446130-90-9 |
| tert-butyl {1-(2-chloro-4-methylpheny1)-3-[(1,3-dioxo-1,3-dihydro-2H-isoindol-2-yl)oxy]propan-2-yl}carbamate | 2446131-06-0 |
| 2-[2-amino-3-(2-chloro-4-methylphenyl)propoxy]-1H-isoindole-1,3(2H)-dione trifluoroacetate (1:1) | 2446131-05-9 |
| 2-[2-amino-3-(2-chloro-4-methylphenyl)propoxy]-1H-isoindole-1,3(2H)-dione | 2446131-04-8 |
| 2-[2-amino-3-(4-bromo-2-methylphenyl)propoxy]-1H-isoindole-1,3(2H)-dione trifluoroacetate | 2446130-92-1 |
| 2-[2-amino-3-(4-bromo-2-methylphenyl)propoxy]-1H-isoindole-1,3(2H)-dione | 2446130-91-0 |
| 2-[2-amino-3-(3,4-dimethylphenyl)propoxy]-1H-isoindole-1,3(2H)-dione trifluoroacetate (1:1) | 2446130-88-5 |
| 2-[2-amino-3-(3,4-dimethylphenyl)propoxy]-1H-isoindole-1,3(2H)-dione | 2446130-87-4 |
| 2-[2-amino-3-(4-isopropyl-2-methylphenyl)propoxy]-1H-isoindole-1,3(2H)-dione trifluoroacetate (1:1) | 2446130-86-3 |
| 2-[2-amino-3-(4-isopropyl-2-methylphenyl)propoxy]-1H-isoindole-1,3(2H)-dione | 2446130-85-2 |
| 2-[2-amino-3-(2-chloro-4-isopropylphenyl)propoxy]-1H-isoindole-1,3(2H)-dione trifluoroacetate (1:1) | 2446130-84-1 |
| 2-[2-amino-3-(2-chloro-4-isopropylphenyl)propoxy]-1H-isoindole-1,3(2H)-dione | 2446130-83-0 |
| 2-[2-amino-3-(4-cyclopropyl-2-methylphenyl)propoxy]-1H-isoindole-1,3(2H)-dione trifluoroacetate (1:1) | 2446130-80-7 |
| 2-[2-amino-3-(4-cyclopropyl-2-methylphenyl)propoxy]-1H-isoindole-1,3(2H)-dione | 2446130-79-4 |
| 2-[2-amino-3-(2-chloro-4-cyclopropylphenyl)propoxy]-1H-isoindole-1,3(2H)-dione trifluoroacetate (1:1) | 2446130-78-3 |
| 2-[2-amino-3-(2-chloro-4-cyclopropylphenyl)propoxy]-1H-isoindole-1,3(2H)-dione | 2446130-77-2 |
| tert-butyl {(1S)-2-[(1,3-dioxo-1,3-dihydro-2H-isoindol-2-yl)oxy]-1-phenyl-ethyl}carbamate | 2102206-02-8 |

The present invention also relates to compounds of formula (3):

(3)

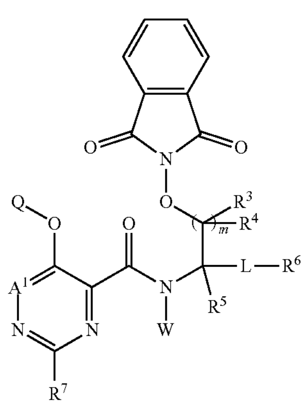

wherein $A^1$ is N or $CR^8$, wherein $R^8$ is hydrogen, halogen, cyano or $C_1$-$C_4$-alkyl, m is 1 or 2, $R^3$ and $R^4$ are independently hydrogen, halogen, cyano, hydroxyl, formyl, carboxyl, $C_1$-$C_6$-alkyl, $C_1$-$C_6$-alkoxy, $C_1$-$C_6$-alkylcarbonyl, $C_1$-$C_6$-alkylcarbonyloxy, $C_1$-$C_6$-alkoxycarbonyl, $C_2$-$C_6$-alkenyl, $C_2$-$C_6$-alkynyl, $C_3$-$C_8$-cycloalkyl, $C_6$-$C_{14}$-aryl, 5- to 14-membered heteroaryl, 3- to 14-membered heterocyclyl or —O—Si($C_1$-$C_6$-alkyl)$_3$, wherein $C_1$-$C_6$-alkyl, $C_1$-$C_6$-alkoxy, $C_1$-$C_6$-alkylcarbonyl, $C_1$-$C_6$-alkylcarbonyloxy, $C_1$-$C_6$-alkoxycarbonyl, $C_2$-$C_6$-alkenyl, $C_2$-$C_6$-alkynyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl, $C_6$-$C_{14}$-aryl, 5- to 14-membered heteroaryl and 3- to 14-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^4$ form together with the carbon atom to which they are attached to a carbonyl, a methylidene, a $C_3$-$C_8$-cycloalkyl-ring or a 3- to 7-membered heterocyclyl-ring, wherein $C_3$-$C_8$-cycloalkyl-ring and 3- to 7-membered heterocyclyl-ring are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, $R^5$ is hydrogen, hydroxyl, $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl, $C_3$-$C_8$-cycloalkyl or —O—Si($C_1$-$C_6$-alkyl)$_3$, wherein $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^5$ or $R^4$ and $R^5$ form together with the carbon atom to which they are attached to a $C_3$-$C_8$-cycloalkyl-ring, L is a direct bond, carbonyl, $C_1$-$C_6$-alkylene, $C_2$-$C_6$-alkenylene, $C_2$-$C_6$-alkynylene, —C(═O)—$C_1$-$C_6$-alkylene-, —$C_1$-$C_6$-alkylene-C(═O)—, —$NR^{L1}$—, —$NR^{L2}$(C═O)—, —C(═O)$NR^{L3}$—, —$NR^{L4}$S(═O)$_2$—, —S(═O)$_2NR^{L5}$—, —C(═$NOR^{L6}$)—, —C(═N—N($R^{L7}$)$_2$)—, —C(═$NR^{L8}$)— or a group of formula

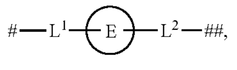

wherein said $C_1$-$C_6$-alkylene, $C_2$-$C_6$-alkenylene, $C_2$-$C_6$-alkynylene, —C(═O)—$C_1$-$C_6$-alkylene- and —$C_1$-$C_6$-alkylene-C(═O)— are optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl, $C_3$-$C_8$-cycloalkenyl and 3- to 7-membered heterocyclyl in turn are optionally substituted with one to three substituents $L^{SC}$, $R^{L1}$, $R^{L2}$, $R^{L3}$ and $R^{L4}$ are independently hydrogen or $C_1$-$C_6$-alkyl, $R^{L5}$, $R^{L6}$, $R^{L7}$ and $R^{L8}$ are independently hydrogen, $C_1$-$C_6$-alkyl, $C_1$-$C_6$-haloalkyl, $C_3$-$C_8$-cycloalkyl or $C_2$-$C_6$-alkenyl, wherein $L^{SA}$ is independently halogen, cyano, hydroxyl, carboxyl, methylidene, halomethylidene, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$ or 3- to 7-membered heterocyclyl, and/or two substituents $L^{SA}$ that are bound to the same carbon atom form together with the carbon atom which they are attached to a $C_3$-$C_8$-cycloalkyl-ring or a 3- to 7-membered heterocyclyl-ring, $L^{SC}$ is independently halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, and/or two $L^{SC}$ substituents form together with the carbon atom to which they are attached to a $C_3$-$C_8$-cycloalkyl-ring, $R^6$ is $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl, 3- to 14-membered heterocyclylsulfonyl, $C_1$-$C_3$-alkoxy, $C_1$-$C_3$-haloalkoxy, $C_1$-$C_3$-alkylsulfanyl, $C_1$-$C_3$-alkylsulfinyl or $C_1$-$C_3$-alkylsulfonyl, wherein $C_1$-$C_3$-alkoxy, $C_1$-$C_3$-haloalkoxy, $C_1$-$C_3$-alkylsulfanyl, $C_1$-$C_3$-alkylsulfinyl and $C_1$-$C_3$-alkylsulfonyl are substituted with one substituent selected from the group consisting of $C_3$-$C_{12}$-carbocyclyl, $C_6$-$C_{14}$-aryl, 3- to 14-membered heterocyclyl and 5- to 14-membered heteroaryl, wherein said $C_3$-$C_{12}$-carbocyclyl, $C_6$-$C_{14}$-aryl, 3- to 14-membered heterocyclyl and 5- to 14-membered heteroaryl in turn are optionally substituted with one to four $R^{6S}$ substituents, wherein $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl and 3- to 14-membered heterocyclylsulfonyl are optionally substituted with one to four $R^{6S}$ substituents, wherein $R^{6S}$ is independently selected from the group consisting of halogen, cyano, isocyano, nitro, hydroxyl, mercapto, pentafluorosulfanyl, oxo, methylidene, halomethylidene, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$- alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, —$N(R^{15})_2$, —O(C═O)$R^{16}$, —C(═O)$R^{16}$, —C(═O)($OR^{17}$), —C(═O)$N(R^{18})_2$, —S(═O)$_2$N$(R^{19})_2$, —O—Si($C_1$-$C_6$-alkyl)$_3$ and —Si($C_1$-$C_6$-alkyl)$_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are furthermore optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, or two substituents $C_1$-$C_6$-alkyl attached to the same carbon atom from a $C_3$-$C_8$-cycloalkyl-ring, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and wherein $R^{15}$ is independently hydrogen, $C_1$-$C_6$-alkyl or $C_3$-$C_8$-cycloalkyl, wherein said $C_1$-$C_6$-alkyl in turn is optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, and wherein said $C_3$-$C_8$-cycloalkyl in turn is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl and $C_1$-$C_6$-haloalkyl in turn are optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, $R^7$ is hydrogen, halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_1$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy, —O—Si($C_1$-$C_6$-alkyl)$_3$, —Si($C_1$-$C_6$-alkyl)$_3$, —$N(R^{20})_2$, —C(═$NR^{21}$)$R^{22}$, —$NR^{23}$C(═O)$R^{24}$, —C(═O)($OR^{25}$), —C(═O)$N(R^{26})_2$, —S(═O)$_2$$N(R^{27})_2$ or —S(═O)(═$NR^{28}$)$R^{29}$, wherein $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are optionally substituted with one to three $R^{7Sa}$ substituents, wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy are optionally substituted with one to three $R^{7Sc}$ substituents, and wherein $R^{20}$ is independently hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_6$-$C_{14}$-aryl, 5- or 6-membered heteroaryl or 3- to 7-membered heterocyclyl, wherein $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl in turn are optionally substituted with one to three substituents $R^{7Sa}$, and wherein $C_3$-$C_8$-cycloalkyl, $C_3$-$C_8$-halocycloalkyl, $C_6$-$C_{14}$-aryl, 5- or 6-membered heteroaryl and 3- to 7-membered heterocyclyl in turn are optionally substituted with one to three substituents $R^{7Sc}$, $R^{21}$ and $R^{22}$ are independently hydroxyl, amino, cyano, $C_1$-$C_6$-alkyl, $C_1$-$C_6$-haloalkyl, $C_1$-$C_6$-alkoxy, mono-($C_1$-$C_6$-alkyl)amino or di-($C_1$-$C_6$-alkyl)amino, wherein $C_1$-$C_6$-alkyl, $C_1$-$C_6$-haloalkyl, $C_1$-$C_6$-alkoxy, mono-($C_1$-$C_6$-alkyl)amino and di-($C_1$-$C_6$-alkyl)amino in turn are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_6$-alkyl, $C_1$-$C_6$-haloalkyl and $C_3$-$C_8$-cycloalkyl, wherein $C_1$-$C_6$-alkyl and $C_1$-$C_6$-haloalkyl in turn are optionally substituted with one to three $R^{7Sa}$ substituents, and wherein $C_3$-$C_8$-cycloalkyl in turn is optionally substituted with one to three $R^{7Sc}$ substituents, wherein $R^{7Sa}$ is independently cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$, —Si($C_1$-$C_6$-alkyl)$_3$, $C_6$-$C_{14}$-aryl or 3- to 7-membered heterocyclyl, $R^{7Sc}$ is independently halogen, cyano, nitro, hydroxyl, formyl, oxo, methylidene, halomethylidene, $C_1$-$C_6$-alkyl, $C_1$-$C_6$-haloalkyl $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, or two $R^{7Sc}$ substituents $C_1$-$C_6$-alkyl that are bound to the same carbon atom form together a $C_3$-$C_8$-cycloalkyl-ring, Q is $C_6$-$C_{14}$-aryl, $C_3$-$C_{12}$-carbocyclyl, 3- to 14-membered heterocyclyl or 5- to 14-membered heteroaryl, wherein $C_6$-$C_{14}$-aryl, $C_3$-$C_{12}$-carbocyclyl, 3- to 14-membered heterocyclyl or 5- to 14-membered heteroaryl are optionally substituted with one to five substituents $Q^S$ wherein $Q^S$ is independently selected from the group consisting of halogen, cyano, isocyano, nitro, hydroxyl, mercapto, formyl, carboxyl, $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyloxy, $C_3$-$C_6$-cycloalkenyl, 3- to 7-membered heterocyclyl, $C_6$-$C_{14}$-aryl, 5- to 14-membered heteroaryl, —O—Si($C_1$-$C_6$-alkyl)$_3$, —Si($C_1$-$C_6$-alkyl)$_3$, —O—C(═O)$R^{33}$, —N$R^{34}$C(═O)$R^{35}$, —C(═O)N($R^{36}$)$_2$, —C(═S)$R^{37}$, —C(═S)N($R^{38}$)$_2$, —C(═N$R^{39}$)$R^{40}$, —C(═NO$R^{41}$)$R^{42}$ and —N($R^{43}$)$_2$, wherein said $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, said $C_3$-$C_8$-cycloalkyl, $C_3$-$C_8$-cycloalkoxy, $C_3$-$C_6$-cycloalkenyl, 3- to 7-membered heterocyclyl and 5- to 14-membered heteroaryl in turn are optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl, and wherein $R^{33}$ is hydrogen, $C_1$-$C_6$-alkyl, $C_1$-$C_6$-haloalkyl and $C_1$-$C_6$-alkoxy, $R^{34}$, $R^{35}$, $R^{36}$ $R^{37}$ $R^{38}$ $R^{39}$ $R^{40}$ $R^{41}$ and $R^{42}$ are independently hydrogen, $C_1$-$C_6$-alkyl, $C_1$-$C_6$-haloalkyl or $C_1$-$C_6$-alkoxy, wherein said $C_1$-$C_6$-alkyl, $C_1$-$C_6$-haloalkyl and $C_1$-$C_6$-alkoxy in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, and wherein $R^{43}$ is hydrogen, hydroxyl, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl or $C_3$-$C_8$-cycloalkyl, wherein said $C_1$-$C_6$-alkyl, $C_1$-$C_6$-haloalkyl, $C_1$-$C_6$-alkoxy, $C_2$-$C_6$-alkenyl and $C_2$-$C_6$-haloalkenyl in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, wherein said $C_3$-$C_8$-cycloalkyl in turn is optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl, W is hydrogen, tert-butoxycarbonyl, benzyl, allyl or (4-methoxyphenyl)methyl.

The present invention also relates to compounds of formula (3):

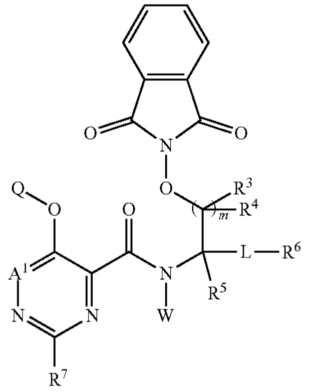

(3)

wherein $A^1$ is N or $CR^8$, wherein $R^1$ is hydrogen or halogen, m is 1 or 2, $R^3$ and $R^4$ are independently hydrogen, halogen, cyano, hydroxyl, formyl, carboxyl, $C_1$-$C_6$-alkyl, $C_1$-$C_6$-alkoxy, $C_1$-$C_6$-alkylcarbonyl, $C_1$-$C_6$-alkoxycarbonyl, $C_2$-$C_6$-alkenyl, $C_2$-$C_6$-alkynyl, $C_3$-$C_8$-cycloalkyl, $C_6$-$C_{14}$-aryl, 5- to 14-membered heteroaryl, 3- to 14-membered heterocyclyl or —O—Si($C_1$-$C_6$-alkyl)$_3$, wherein $C_1$-$C_6$-alkyl, $C_1$-$C_6$-alkoxy, $C_1$-$C_6$-alkylcarbonyl, $C_1$-$C_6$-alkoxycarbonyl, $C_2$-$C_6$-alkenyl, $C_2$-$C_6$-alkynyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl, $C_6$-$C_{14}$-aryl, 5- to 14-membered heteroaryl and 3- to 14-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^4$ form together with the carbon atom to which they are attached to a carbonyl, a methylidene, a $C_3$-$C_8$-cycloalkyl-ring or a 3- to 7-membered heterocyclyl-ring, wherein $C_3$-$C_8$-cycloalkyl and 3- to 7-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, $R^5$ is hydrogen, hydroxyl, $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl, $C_3$-$C_8$-cycloalkyl or —O—Si($C_1$-$C_6$-alkyl)$_3$, wherein $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^5$ or $R^4$ and $R^5$ form together with the carbon atom to which they are attached to a $C_3$-$C_8$-cycloalkyl-ring, L is a direct bond, carbonyl, $C_1$-$C_6$-alkylene, $C_2$-$C_6$-alkenylene, $C_2$-$C_6$-alkynylene, —C(═O)—$C_1$-$C_6$-alkylene-, —$C_1$-$C_6$-alkylene-C(═O)—, —$NR^{L1}$—, —$NR^{L2}$(C═O)—, —C(═O)$NR^{L3}$—, —$NR^{L4}$S(═O)$_2$—, —S(═O)$_2NR^{L5}$—, —C(═$NOR^{L6}$)—, —C(═N—N($R^{L7}$)$_2$)—, —C(═$NR^{L8}$)— or a group of formula

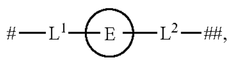

wherein said $C_1$-$C_6$-alkylene, $C_2$-$C_6$-alkenylene, $C_2$-$C_6$-alkynylene, —C(═O)—$C_1$-$C_6$-alkylene- and —$C_1$-$C_6$-alkylene-C(═O)— are optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl, $C_3$-$C_8$-cycloalkenyl and 3- to 7-membered heterocyclyl in turn are optionally substituted with one to three substituents $L^{SC}$, $R^{L1}$, $R^{L2}$, $R^{L3}$ and $R^{L4}$ are independently hydrogen or $C_1$-$C_6$-alkyl, $R^{L5}$, $R^{L6}$, $R^{L7}$ and $R^{L8}$ are independently hydrogen, $C_1$-$C_6$-alkyl, $C_1$-$C_6$-haloalkyl, $C_3$-$C_8$-cycloalkyl or $C_2$-$C_6$-alkenyl, $L^{SA}$ is independently halogen, cyano, hydroxyl, carboxyl, methylidene, halomethylidene, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$ or 3- to 7-membered heterocyclyl, or two substituents $L^{SA}$ that are bound to the same carbon atom form together with the carbon atom which they are attached to a $C_3$-$C_8$-cycloalkyl-ring or a 3- to 7-membered heterocyclyl-ring, $L^{Sc}$ is independently halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, and/or two $L^{Sc}$ substituents form together with the carbon atom to which they are attached to a $C_3$-$C_8$-cycloalkyl-ring, $R^6$ is $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl, 3- to 14-membered heterocyclylsulfonyl, $C_1$-$C_3$-alkoxy, $C_1$-$C_3$-haloalkoxy, $C_1$-$C_3$-alkylsulfanyl, $C_1$-$C_3$-alkylsulfinyl or $C_1$-$C_3$-alkylsulfonyl, wherein $C_1$-$C_3$-alkoxy, $C_1$-$C_3$-haloalkoxy, $C_1$-$C_3$-alkylsulfanyl, $C_1$-$C_3$-alkylsulfinyl and $C_1$-$C_3$-alkylsulfonyl are substituted with one substituent selected from the group consisting of $C_3$-$C_{12}$-carbocyclyl, $C_6$-$C_{14}$-aryl, 3- to 14-membered heterocyclyl and 5- to 14-membered heteroaryl, wherein said $C_3$-$C_{12}$-carbocyclyl, $C_6$-$C_{14}$-aryl, 3- to 14-membered heterocyclyl and 5- to 14-membered heteroaryl in turn are optionally substituted with one to four $R^{6S}$ substituents, wherein $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl and 3- to 14-membered heterocyclylsulfonyl are optionally substituted with one to four $R^{6S}$ substituents, wherein $R^{6S}$ is selected from the group consisting of halogen, cyano, isocyano, nitro, hydroxyl, mercapto, pentafluorosulfanyl, oxo, methylidene, halomethylidene, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, —N($R^{15}$)$_2$, —O(C═O)$R^{16}$, —C(═O)$R^{16}$, —C(═O)($OR^{17}$), —C(═O)N($R^{18}$)$_2$, —S(═O)$_2$N($R^{19}$)$_2$, —O—Si($C_1$-$C_6$-alkyl)$_3$ or —Si($C_1$-$C_6$-alkyl)$_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, or two substituents $C_1$-$C_6$-alkyl attached to the same carbon atom from a $C_3$-$C_8$-cycloalkyl-ring, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and wherein $R^{15}$ is hydrogen, $C_1$-$C_6$-alkyl or $C_3$-$C_8$-cycloalkyl, wherein said $C_1$-$C_6$-alkyl is optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, and wherein said $C_3$-$C_8$-cycloalkyl is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl or $C_1$-$C_6$-haloalkyl are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, $R^7$ is hydrogen, halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy, —O—Si($C_1$-$C_6$-alkyl)$_3$, —Si($C_1$-$C_6$-alkyl)$_3$, —N($R^{20}$)$_2$, —C(═N$R^{21}$)$R^{22}$, —N$R^{23}$C(═O)$R^{24}$, —C(═O)(O$R^{25}$), —C(═O)N($R^{26}$)$_2$, —S(═O)$_2$N($R^{27}$)$_2$ or —S(═O)(═N$R^{28}$)$R^{29}$, wherein $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are optionally substituted with one to three $R^{7Sa}$ substituents, wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy are optionally substituted with one to three $R^{7Sc}$ substituents, and wherein $R^{20}$ is hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_6$-$C_{14}$-aryl, 5- or 6-membered heteroaryl or 3- to 7-membered heterocyclyl, wherein $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl are optionally substituted with one to three substituents $R^{7Sa}$, and wherein $C_3$-$C_8$-cycloalkyl, $C_3$-$C_8$-halocycloalkyl, $C_6$-$C_{14}$-aryl, 5- or 6-membered heteroaryl and 3- to 7-membered heterocyclyl are optionally substituted with one to three substituents $R^{7Sc}$, $R^{21}$ and $R^{22}$ are independently hydroxyl, amino, cyano, $C_1$-$C_6$-alkyl, $C_1$-$C_6$-haloalkyl, $C_1$-$C_6$-alkoxy, mono-($C_1$-$C_6$-alkyl)amino or di-($C_1$-$C_6$-alkyl)amino, wherein $C_1$-$C_6$-alkyl, $C_1$-$C_6$-haloalkyl, $C_1$-$C_6$-alkoxy, mono-($C_1$-$C_6$-alkyl)amino and di-($C_1$-$C_6$-alkyl)amino are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_6$-alkyl, $C_1$-$C_6$-haloalkyl and $C_3$-$C_8$-cycloalkyl, wherein $C_1$-$C_6$-alkyl and $C_1$-$C_6$-haloalkyl are optionally substituted with one to three $R^{7Sa}$ substituents, and wherein $C_3$-$C_8$-cycloalkyl is optionally substituted with one to three $R^{7Sc}$ substituents, wherein $R^{7Sa}$ is independently cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$, —Si($C_1$-$C_6$-alkyl)$_3$, $C_6$-$C_{14}$-aryl or 3- to 7-membered heterocyclyl, $R^{7Sc}$ is independently halogen, cyano, nitro, hydroxyl, formyl, oxo, methylidene, halomethylidene, $C_1$-$C_6$-alkyl, $C_1$-$C_6$-haloalkyl $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, or two $R^{7Sc}$ substituents $C_1$-$C_6$-alkyl that are bound to the same carbon atom form together a $C_3$-$C_8$-cycloalkyl-ring, Q is $C_6$-$C_{14}$-aryl, $C_3$-$C_{12}$-carbocyclyl, 3- to 14-membered heterocyclyl or 5- to 14-membered heteroaryl, wherein $C_6$-$C_{14}$-aryl, $C_3$-$C_{12}$-carbocyclyl 3- to 14-membered heterocyclyl or 5- to 14-membered heteroaryl are optionally substituted with one to five substituents $Q^S$, wherein $Q^S$ is independently selected from the group consisting of halogen, cyano, isocyano, nitro, hydroxyl, mercapto, formyl, carboxyl, $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyloxy, $C_3$-$C_6$-cycloalkenyl, 3- to 7-membered heterocyclyl, $C_6$-$C_{14}$-aryl, 5- to 14-membered heteroaryl, —O—Si($C_1$-$C_6$-alkyl)$_3$, —Si($C_1$-$C_6$-alkyl)$_3$, —O—C(═O)$R^{33}$, —N$R^{34}$C(═O)$R^{35}$, —C(═O)N($R^{36}$)$_2$, C(═S)$R^{37}$, —C(═S)N($R^{38}$)$_2$, —C(═N$R^{39}$)$R^{40}$, —C(═NO$R^{41}$)$R^{42}$ and —N($R^{43}$)$_2$, wherein said $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, said $C_3$-$C_8$-cycloalkyl, $C_3$-$C_8$-cycloalkoxy, $C_3$-$C_6$-cycloalkenyl, 3- to 7-membered heterocyclyl and 5- to 14-membered heteroaryl in turn are optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl, and wherein $R^{34}$, $R^{35}$, $R^{36}$ $R^{37}$ $R^{38}$ $R^{39}$ $R^{40}$ $R^{41}$ and $R^{42}$ are independently hydrogen, $C_1$-$C_6$-alkyl, $C_1$-$C_6$-haloalkyl or $C_1$-$C_6$-alkoxy, wherein said $C_1$-$C_6$-alkyl, $C_1$-$C_6$-haloalkyl and $C_1$-$C_6$-alkoxy in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, and wherein $R^{43}$ is hydrogen, hydroxyl, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl or $C_3$-$C_8$-cycloalkyl, wherein said $C_1$-$C_6$-alkyl, $C_1$-$C_6$-haloalkyl, $C_1$-$C_6$-alkoxy, $C_2$-$C_6$-alkenyl and $C_2$-$C_6$-haloalkenyl are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, wherein said $C_3$-$C_8$-cycloalkyl is optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl in turn are optionally substituted with two substituents forming together with the carbon atom to which they are attached to a $C_3$-$C_8$-cycloalkyl, W is hydrogen, tert-butoxycarbonyl, benzyl, allyl or (4-methoxyphenyl)methyl.

The present invention also relates to compounds of formula (4):

(4)

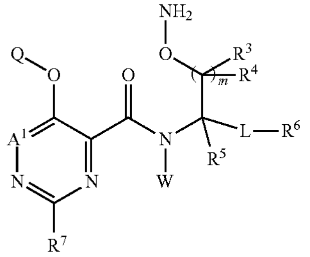

wherein $A^1$ is N or $CR^8$, wherein $R^8$ is hydrogen, halogen, cyano or $C_1$-$C_4$-alkyl, m is 1 or 2, $R^3$ and $R^4$ are independently hydrogen, halogen, cyano, hydroxyl, formyl, carboxyl, $C_1$-$C_6$-alkyl, $C_1$-$C_6$-alkoxy, $C_1$-$C_6$-alkylcarbonyl, $C_1$-$C_6$-alkylcarbonyloxy, $C_1$-$C_6$-alkoxycarbonyl, $C_2$-$C_6$-alkenyl, $C_2$-$C_6$-alkynyl, $C_3$-$C_8$-cycloalkyl, $C_6$-$C_{14}$-aryl, 5- to 14-membered heteroaryl, 3- to 14-membered heterocyclyl or —O—Si($C_1$-$C_6$-alkyl)$_3$, wherein $C_1$-$C_6$-alkyl, $C_1$-$C_6$-alkoxy, $C_1$-$C_6$-alkylcarbonyl, $C_1$-$C_6$-alkylcarbonyloxy, $C_1$-$C_6$-alkoxycarbonyl, $C_2$-$C_6$-alkenyl, $C_2$-$C_6$-alkynyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl, $C_6$-$C_{14}$-aryl, 5- to 14-membered heteroaryl and 3- to 14-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^4$ form together with the carbon atom to which they are attached to a carbonyl, a methylidene, a $C_3$-$C_8$-cycloalkyl-ring or a 3- to 7-membered heterocyclyl-ring, wherein $C_3$-$C_8$-cycloalkyl-ring and 3- to 7-membered heterocyclyl-ring are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, $R^5$ is hydrogen, hydroxyl, $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl, $C_3$-$C_8$-cycloalkyl or —O—Si($C_1$-$C_6$-alkyl)$_3$, wherein $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^5$ or $R^4$ and $R^5$ form together with the carbon atom to which they are attached to a $C_3$-$C_8$-cycloalkyl-ring, L is a direct bond, carbonyl, $C_1$-$C_6$-alkylene, $C_2$-$C_6$-alkenylene, $C_2$-$C_6$-alkynylene, —C(═O)—$C_1$-$C_6$-alkylene-, —$C_1$-$C_6$-alkylene-C(═O)—, —$NR^{L1}$—, —$NR^{L2}$(C═O)—, —C(═O)$NR^{L3}$—, —$NR^{L4}$S(═O)$_2$—, —S(═O)$_2NR^{L5}$—, —C(═$NOR^{L6}$)—, —C(═N—N($R^{L7}$)$_2$)—, —C(═$NR^{L8}$)— or a group of formula

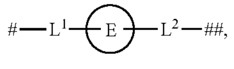

wherein said $C_1$-$C_6$-alkylene, $C_2$-$C_6$-alkenylene, $C_2$-$C_6$-alkynylene, —C(═O)—$C_1$-$C_6$-alkylene- and —$C_1$-$C_6$-alkylene-C(═O)— are optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl, $C_3$-$C_8$-cycloalkenyl and 3- to 7-membered heterocyclyl in turn are optionally substituted with one to three substituents $L^{SC}$, $R^{L1}$, $R^{L2}$, $R^{L3}$ and $R^{L4}$ are independently hydrogen or $C_1$-$C_6$-alkyl, $R^{L5}$, $R^{L6}$, $R^{L7}$ and $R^{L8}$ are independently hydrogen, $C_1$-$C_6$-alkyl, $C_1$-$C_6$-haloalkyl, $C_3$-$C_8$-cycloalkyl or $C_2$-$C_6$-alkenyl, wherein $L^{SA}$ is independently halogen, cyano, hydroxyl, carboxyl, methylidene, halomethylidene, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$ or 3- to 7-membered heterocyclyl, and/or two substituents $L^{SA}$ that are bound to the same carbon atom form together with the carbon atom which they are attached to a $C_3$-$C_8$-cycloalkyl-ring or a 3- to 7-membered heterocyclyl-ring, $L^{SC}$ is independently halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, and/or two $L^{SC}$ substituents form together with the carbon atom to which they are attached to a $C_3$-$C_8$-cycloalkyl-ring, $R^6$ is $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl, 3- to 14-membered heterocyclylsulfonyl, $C_1$-$C_3$-alkoxy, $C_1$-$C_3$-haloalkoxy, $C_1$-$C_3$-alkylsulfanyl, $C_1$-$C_3$-alkylsulfinyl or $C_1$-$C_3$-alkylsulfonyl, wherein $C_1$-$C_3$-alkoxy, $C_1$-$C_3$-haloalkoxy, $C_1$-$C_3$-alkylsulfanyl, $C_1$-$C_3$-alkylsulfinyl and $C_1$-$C_3$-alkylsulfonyl are substituted with one substituent selected from the group consisting of $C_3$-$C_{12}$-carbocyclyl, $C_6$-$C_{14}$-aryl, 3- to 14-membered heterocyclyl and 5- to 14-membered heteroaryl, wherein said $C_3$-$C_{12}$-carbocyclyl, $C_6$-$C_{14}$-aryl, 3- to 14-membered heterocyclyl and 5- to 14-membered heteroaryl in turn are optionally substituted with one to four $R^{6S}$ substituents, wherein $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl and 3- to 14-membered heterocyclylsulfonyl are optionally substituted with one to four $R^{6S}$ substituents, wherein $R^{6S}$ is independently selected from the group consisting of halogen, cyano, isocyano, nitro, hydroxyl, mercapto, pentafluorosulfanyl, oxo, methylidene, halomethylidene, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$- haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, —$N(R^{15})_2$, —O(C═O)$R^{16}$, —C(═O)$R^{16}$, —C(═O)($OR^{17}$), —C(═O)$N(R^{18})_2$, —S(═O)$_2$N$(R^{19})_2$, —O—Si($C_1$-$C_6$-alkyl)$_3$ and —Si($C_1$-$C_6$-alkyl)$_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are furthermore optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, or two substituents $C_1$-$C_6$-alkyl attached to the same carbon atom from a $C_3$-$C_8$-cycloalkyl-ring, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and wherein $R^{15}$ is independently hydrogen, $C_1$-$C_6$-alkyl or $C_3$-$C_8$-cycloalkyl, wherein said $C_1$-$C_6$-alkyl in turn is optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, and wherein said $C_3$-$C_8$-cycloalkyl in turn is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl and $C_1$-$C_6$-haloalkyl in turn are optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, $R^7$ is hydrogen, halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy, —O—Si($C_1$-$C_6$-alkyl)$_3$, —Si($C_1$-$C_6$-alkyl)$_3$, —$N(R^{20})_2$, —C(═$NR^{21}$)$R^{22}$, —$NR^{23}$C(═O)$R^{24}$, —C(═O)($OR^{25}$), —C(═O)N$(R^{26})_2$, —S(═O)$_2$N$(R^{27})_2$ or —S(═O)(═$NR^{28}$)$R^{29}$, wherein $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are optionally substituted with one to three $R^{7Sa}$ substituents, wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy are optionally substituted with one to three $R^{7Sc}$ substituents, and wherein $R^{20}$ is independently hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_6$-$C_{14}$-aryl, 5- or 6-membered heteroaryl or 3- to 7-membered heterocyclyl, wherein $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl in turn are optionally substituted with one to three substituents $R^{7Sa}$, and wherein $C_3$-$C_8$-cycloalkyl, $C_3$-$C_8$-halocycloalkyl, $C_6$-$C_{14}$-aryl, 5- or 6-membered heteroaryl and 3- to 7-membered heterocyclyl in turn are optionally substituted with one to three substituents $R^{7Sc}$, $R^{21}$ and $R^{22}$ are independently hydroxyl, amino, cyano, $C_1$-$C_6$-alkyl, $C_1$-$C_6$-haloalkyl, $C_1$-$C_6$-alkoxy, mono-($C_1$-$C_6$-alkyl)amino or di-($C_1$-$C_6$-alkyl)amino, wherein $C_1$-$C_6$-alkyl, $C_1$-$C_6$-haloalkyl, $C_1$-$C_6$-alkoxy, mono-($C_1$-$C_6$-alkyl)amino and di-($C_1$-$C_6$-alkyl)amino in turn are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_6$-alkyl, $C_1$-$C_6$-haloalkyl and $C_3$-$C_8$-cycloalkyl, wherein $C_1$-$C_6$-alkyl and $C_1$-$C_6$-haloalkyl in turn are optionally substituted with one to three $R^{7Sa}$ substituents, and wherein $C_3$-$C_8$-cycloalkyl in turn is optionally substituted with one to three $R^{7Sc}$ substituents, wherein $R^{7Sa}$ is independently cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$, —Si($C_1$-$C_6$-alkyl)$_3$, $C_6$-$C_{14}$-aryl or 3- to 7-membered heterocyclyl, $R^{7Sc}$ is independently halogen, cyano, nitro, hydroxyl, formyl, oxo, methylidene, halomethylidene, $C_1$-$C_6$-alkyl, $C_1$-$C_6$-haloalkyl $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, or two $R^{7Sc}$ substituents $C_1$-$C_6$-alkyl that are bound to the same carbon atom form together a $C_3$-$C_8$-cycloalkyl-ring, Q is $C_6$-$C_{14}$-aryl, $C_3$-$C_{12}$-carbocyclyl, 3- to 14-membered heterocyclyl or 5- to 14-membered heteroaryl, wherein $C_6$-$C_{14}$-aryl, $C_3$-$C_{12}$-carbocyclyl, 3- to 14-membered heterocyclyl or 5- to 14-membered heteroaryl are optionally substituted with one to five substituents $Q^S$ wherein $Q^S$ is independently selected from the group consisting of halogen, cyano, isocyano, nitro, hydroxyl, mercapto, formyl, carboxyl, $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyloxy, $C_3$-$C_6$-cycloalkenyl, 3- to 7-membered heterocyclyl, $C_6$-$C_{14}$-aryl, 5- to 14-membered heteroaryl, —O—Si($C_1$-$C_6$-alkyl)$_3$, —Si($C_1$-$C_6$-alkyl)$_3$, —O—C(=O)$R^{33}$, —$NR^{34}$C(=O)$R^{35}$, —C(=O)N($R^{36}$)$_2$, —C(=S)$R^{37}$, —C(=S)N($R^{38}$)$_2$, —C(=$NR^{39}$)$R^{40}$, —C(=$NOR^{41}$)$R^{42}$ and —N($R^{43}$)$_2$, wherein said $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, said $C_3$-$C_8$-cycloalkyl, $C_3$-$C_8$-cycloalkoxy, $C_3$-$C_6$-cycloalkenyl, 3- to 7-membered heterocyclyl and 5- to 14-membered heteroaryl in turn are optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl, and wherein $R^{33}$ is hydrogen, $C_1$-$C_6$-alkyl, $C_1$-$C_6$-haloalkyl and $C_1$-$C_6$-alkoxy, $R^{34}$, $R^{35}$, $R^{36}$ $R^{37}$ $R^{38}$ $R^{39}$ $R^{40}$ $R^{41}$ and $R^{42}$ are independently hydrogen, $C_1$-$C_6$-alkyl, $C_1$-$C_6$-haloalkyl or $C_1$-$C_6$-alkoxy, wherein said $C_1$-$C_6$-alkyl, $C_1$-$C_6$-haloalkyl and $C_1$-$C_6$-alkoxy in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, and wherein $R^{43}$ is hydrogen, hydroxyl, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl or $C_3$-$C_8$-cycloalkyl, wherein said $C_1$-$C_6$-alkyl, $C_1$-$C_6$-haloalkyl, $C_1$-$C_6$-alkoxy, $C_2$-$C_6$-alkenyl and $C_2$-$C_6$-haloalkenyl in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, wherein said $C_3$-$C_8$-cycloalkyl in turn is optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl W is hydrogen, tert-butoxycarbonyl, benzyl, allyl or (4-methoxyphenyl)methyl.

The present invention also relates to compounds of formula (4):

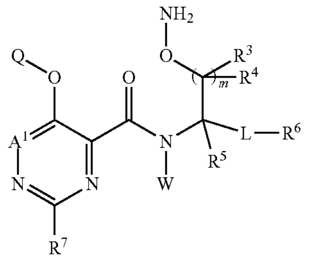

(4)

wherein $A^1$ is N or $CR^8$ wherein $R^8$ is hydrogen or halogen, m is 1 or 2, $R^3$ and $R^4$ are independently hydrogen, halogen, cyano, hydroxyl, formyl, carboxyl, $C_1$-$C_6$-alkyl, $C_1$-$C_6$-alkoxy, $C_1$-$C_6$-alkylcarbonyl, $C_1$-$C_6$-alkoxycarbonyl, $C_2$-$C_6$-alkenyl, $C_2$-$C_6$-alkynyl, $C_3$-$C_8$-cycloalkyl, $C_6$-$C_{14}$-aryl, 5- to 14-membered heteroaryl, 3- to 14-membered heterocyclyl or —O—Si($C_1$-$C_6$-alkyl)$_3$, wherein $C_1$-$C_6$-alkyl, $C_1$-$C_6$-alkoxy, $C_1$-$C_6$-alkylcarbonyl, $C_1$-$C_6$-alkoxycarbonyl, $C_2$-$C_6$-alkenyl, $C_2$-$C_6$-alkynyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl, $C_6$-$C_{14}$-aryl, 5- to 14-membered heteroaryl and 3- to 14-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^4$ form together with the carbon atom to which they are attached to a carbonyl, a methylidene, a $C_3$-$C_8$-cycloalkyl-ring or a 3- to 7-membered heterocyclyl-ring, wherein $C_3$-$C_8$-cycloalkyl and 3- to 7-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, $R^5$ is hydrogen, hydroxyl, $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl, $C_3$-$C_8$-cycloalkyl or —O—Si($C_1$-$C_6$-alkyl)$_3$, wherein $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ or $R^4$, together with $R^5$ form together with the carbon atom to which they are attached to a $C_3$-$C_8$-cycloalkyl, L is a direct bond, carbonyl, $C_1$-$C_6$-alkylene, $C_2$-$C_6$-alkenylene, $C_2$-$C_6$-alkynylene, —C(═O)—$C_1$-$C_6$-alkylene-, —$C_1$-$C_6$-alkylene-C(═O)—, —$NR^{L1}$—, —$NR^{L2}$(C═O)—, —C(═O)$NR^{L3}$—, —$NR^{L4}$S(═O)$_2$—, —S(═O)$_2NR^{L5}$—, —C(═$NOR^{L6}$)—, —C(═N—N($R^{L7}$)$_2$), —C(═$NR^{L8}$)— or a group of formula

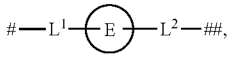

wherein said $C_1$-$C_6$-alkylene, $C_2$-$C_6$-alkenylene, $C_2$-$C_6$-alkynylene, —C(═O)—$C_1$-$C_6$-alkylene- and —$C_1$-$C_6$-alkylene-C(═O)— are optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl, $C_3$-$C_8$-cycloalkenyl and 3- to 7-membered heterocyclyl in turn are optionally substituted with one to three substituents $L^{SC}$, $R^{L1}$, $R^{L2}$, $R^{L3}$ and $R^{L4}$ are independently hydrogen or $C_1$-$C_6$-alkyl, $R^{L5}$, $R^{L6}$, $R^{L7}$ and $R^{L8}$ are independently hydrogen, $C_1$-$C_6$-alkyl, $C_1$-$C_6$-haloalkyl, $C_3$-$C_8$-cycloalkyl or $C_2$-$C_6$-alkenyl, $L^{SA}$ is independently halogen, cyano, hydroxyl, carboxyl, methylidene, halomethylidene, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$ or 3- to 7-membered heterocyclyl, or two substituents $L^{SA}$ that are bound to the same carbon atom form together with the carbon atom which they are attached to a $C_3$-$C_8$-cycloalkyl-ring or a 3- to 7-membered heterocyclyl-ring, $L^{Sc}$ is independently halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, and/or two $L^{Sc}$ substituents form together with the carbon atom to which they are attached to a $C_3$-$C_8$-cycloalkyl-ring, $R^6$ is $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl, 3- to 14-membered heterocyclylsulfonyl, $C_1$-$C_3$-alkoxy, $C_1$-$C_3$-haloalkoxy, $C_1$-$C_3$-alkylsulfanyl, $C_1$-$C_3$-alkylsulfinyl or $C_1$-$C_3$-alkylsulfonyl, wherein $C_1$-$C_3$-alkoxy, $C_1$-$C_3$-haloalkoxy, $C_1$-$C_3$-alkylsulfanyl, $C_1$-$C_3$-alkylsulfinyl and $C_1$-$C_3$-alkylsulfonyl are substituted with one substituent selected from the group consisting of $C_3$-$C_{12}$-carbocyclyl, $C_6$-$C_{14}$-aryl, 3- to 14-membered heterocyclyl and 5- to 14-membered heteroaryl, wherein said $C_3$-$C_{12}$-carbocyclyl, $C_6$-$C_{14}$-aryl, 3- to 14-membered heterocyclyl and 5- to 14-membered heteroaryl in turn are optionally substituted with one to four $R^{6S}$ substituents, wherein $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl and 3- to 14-membered heterocyclylsulfonyl are optionally substituted with one to four $R^{6S}$ substituents, wherein $R^{6S}$ is selected from the group consisting of halogen, cyano, isocyano, nitro, hydroxyl, mercapto, pentafluorosulfanyl, oxo, methylidene, halomethylidene, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, —N($R^{15}$)$_2$, —O(C═O)$R^{16}$, —C(═O)$R^{16}$, —C(═O)(O$R^{17}$), —C(═O)N($R^{18}$)$_2$, —S(═O)$_2$N($R^{19}$)$_2$, —O—Si($C_1$-$C_6$-alkyl)$_3$ or —Si($C_1$-$C_6$-alkyl)$_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, or two substituents $C_1$-$C_6$-alkyl attached to the same carbon atom from a $C_3$-$C_8$-cycloalkyl-ring, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and wherein $R^{15}$ is hydrogen, $C_1$-$C_6$-alkyl or $C_3$-$C_8$-cycloalkyl, wherein said $C_1$-$C_6$-alkyl is optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, and wherein said $C_3$-$C_8$-cycloalkyl is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl or $C_1$-$C_6$-haloalkyl are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, $R^7$ is hydrogen, halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy, —O—Si($C_1$-$C_6$-alkyl)$_3$, —Si($C_1$-$C_6$-alkyl)$_3$, —N($R^{20}$)$_2$, —C(═N$R^{21}$)$R^{22}$, —N$R^{23}$C(═O)$R^{24}$, —C(═O)(O$R^{25}$), —C(═O)N($R^{26}$)$_2$, —S(═O)$_2$N($R^{27}$)$_2$ or —S(═O)(═N$R^{28}$)$R^{29}$, wherein $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are optionally substituted with one to three $R^{7Sa}$ substituents, wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy are optionally substituted with one to three $R^{7Sc}$ substituents, and wherein $R^{20}$ is hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_6$-$C_{14}$-aryl, 5- or 6-membered heteroaryl or 3- to 7-membered heterocyclyl, wherein $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl are optionally substituted with one to three substituents $R^{7Sa}$, and wherein $C_3$-$C_8$-cycloalkyl, $C_3$-$C_8$-halocycloalkyl, $C_6$-$C_{14}$-aryl, 5- or 6-membered heteroaryl and 3- to 7-membered heterocyclyl are optionally substituted with one to three substituents $R^{7Sc}$, $R^{21}$ and $R^{22}$ are independently hydroxyl, amino, cyano, $C_1$-$C_6$-alkyl, $C_1$-$C_6$-haloalkyl, $C_1$-$C_6$-alkoxy, mono-($C_1$-$C_6$-alkyl)amino or di-($C_1$-$C_6$-alkyl)amino, wherein $C_1$-$C_6$-alkyl, $C_1$-$C_6$-haloalkyl, $C_1$-$C_6$-alkoxy, mono-($C_1$-$C_6$-alkyl)amino and di-($C_1$-$C_6$-alkyl)amino are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_6$-alkyl, $C_1$-$C_6$-haloalkyl and $C_3$-$C_8$-cycloalkyl, wherein $C_1$-$C_6$-alkyl and $C_1$-$C_6$-haloalkyl are optionally substituted with one to three $R^{7Sa}$ substituents, and wherein $C_3$-$C_8$-cycloalkyl is optionally substituted with one to three $R^{7Sc}$ substituents, wherein $R^{7Sa}$ is independently cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$, —Si($C_1$-$C_6$-alkyl)$_3$, $C_6$-$C_{14}$-aryl or 3- to 7-membered heterocyclyl, $R^{7Sc}$ is independently halogen, cyano, nitro, hydroxyl, formyl, oxo, methylidene, halomethylidene, $C_1$-$C_6$-alkyl, $C_1$-$C_6$-haloalkyl $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, or two $R^{7Sc}$ substituents $C_1$-$C_6$-alkyl that are bound to the same carbon atom form together a $C_3$-$C_8$-cycloalkyl-ring, $R^8$ is hydrogen or halogen, Q is $C_6$-$C_{14}$-aryl, $C_3$-$C_{12}$-carbocyclyl 3- to 14-membered heterocyclyl or 5- to 14-membered heteroaryl, wherein $C_6$-$C_{14}$-aryl, $C_3$-$C_{12}$-carbocyclyl 3- to 14-membered heterocyclyl or 5- to 14-membered heteroaryl are optionally substituted with one to five substituents $Q^S$, wherein $Q^S$ is independently selected from the group consisting of halogen, cyano, isocyano, nitro, hydroxyl, mercapto, formyl, carboxyl, $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyloxy, $C_3$-$C_6$-cycloalkenyl, 3- to 7-membered heterocyclyl, $C_6$-$C_{14}$-aryl, 5- to 14-membered heteroaryl, —O—Si($C_1$-$C_6$-alkyl)$_3$, —Si($C_1$-$C_6$-alkyl)$_3$, —O—C(═O)$R^{33}$, —N$R^{34}$C(═O)$R^{35}$, —C(═O)N($R^{36}$)$_2$, C(═S)$R^{37}$, —C(═S)N($R^{38}$)$_2$, —C(═N$R^{39}$)$R^{40}$, —C(═NO$R^{41}$)$R^{42}$ and —N($R^{43}$)$_2$, wherein said $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, said $C_3$-$C_8$-cycloalkyl, $C_3$-$C_8$-cycloalkoxy, $C_3$-$C_6$-cycloalkenyl, 3- to 7-membered heterocyclyl and 5- to 14-membered heteroaryl in turn are optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl, and wherein $R^{34}$, $R^{35}$, $R^{36}$ $R^{37}$ $R^{38}$ $R^{39}$ $R^{40}$ $R^{41}$ and $R^{42}$ are independently hydrogen, $C_1$-$C_6$-alkyl, $C_1$-$C_6$-haloalkyl or $C_1$-$C_6$-alkoxy, wherein said $C_1$-$C_6$-alkyl, $C_1$-$C_6$-haloalkyl and $C_1$-$C_6$-alkoxy in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, and wherein $R^{43}$ is hydrogen, hydroxyl, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl or $C_3$-$C_8$-cycloalkyl, wherein said $C_1$-$C_6$-alkyl, $C_1$-$C_6$-haloalkyl, $C_1$-$C_6$-alkoxy, $C_2$-$C_6$-alkenyl and $C_2$-$C_6$-haloalkenyl are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, wherein said $C_3$-$C_8$-cycloalkyl is optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl in turn are optionally substituted with two substituents forming together with the carbon atom to which they are attached to a $C_3$-$C_8$-cycloalkyl, W represents hydrogen, tert-butoxycarbonyl, benzyl, allyl or (4-methoxyphenyl)methyl.

The present invention also relates to compounds of formula (6a) and (6b):

(6a)

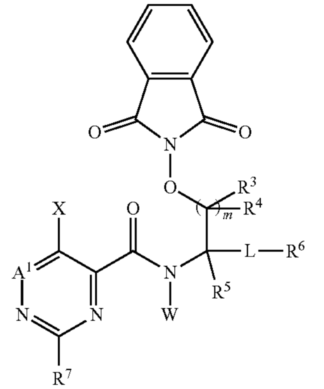

(6b)

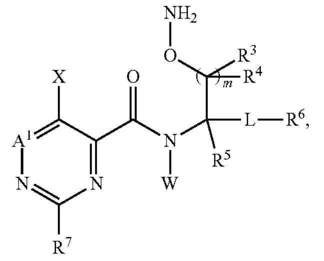

wherein $A^1$ is N or $CR^8$, wherein $R^8$ is hydrogen, halogen, cyano or $C_1$-$C_4$-alkyl, m is 1 or 2, $R^3$ and $R^4$ are independently hydrogen, halogen, cyano, hydroxyl, formyl, carboxyl, $C_1$-$C_6$-alkyl, $C_1$-$C_6$-alkoxy, $C_1$-$C_6$-alkylcarbonyl, $C_1$-$C_6$-alkylcarbonyloxy, $C_1$-$C_6$-alkoxycarbonyl, $C_2$-$C_6$-alkenyl, $C_2$-$C_6$-alkynyl, $C_3$-$C_8$-cycloalkyl, $C_6$-$C_{14}$-aryl, 5- to 14-membered heteroaryl, 3- to 14-membered heterocyclyl or —O—Si($C_1$-$C_6$-alkyl)$_3$, wherein $C_1$-$C_6$-alkyl, $C_1$-$C_6$-alkoxy, $C_1$-$C_6$-alkylcarbonyl, $C_1$-$C_6$-alkylcarbonyloxy, $C_1$-$C_6$-alkoxycarbonyl, $C_2$-$C_6$-alkenyl, $C_2$-$C_6$-alkynyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl, $C_6$-$C_{14}$-aryl, 5- to 14-membered heteroaryl and 3- to 14-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^4$ form together with the carbon atom to which they are attached to a carbonyl, a methylidene, a $C_3$-$C_8$-cycloalkyl-ring or a 3- to 7-membered heterocyclyl-ring, wherein $C_3$-$C_8$-cycloalkyl-ring and 3- to 7-membered heterocyclyl-ring are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, $R^5$ is hydrogen, hydroxyl, $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl, $C_3$-$C_8$-cycloalkyl or —O—Si($C_1$-$C_6$-alkyl)$_3$, wherein $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^5$ or $R^4$ and $R^5$ form together with the carbon atom to which they are attached to a $C_3$-$C_8$-cycloalkyl-ring, L is a direct bond, carbonyl, $C_1$-$C_6$-alkylene, $C_2$-$C_6$-alkenylene, $C_2$-$C_6$-alkynylene, —C(═O)—$C_1$-$C_6$-alkylene-, —$C_1$-$C_6$-alkylene-C(═O)—, —$NR^{L1}$—, —$NR^{L2}$(C═O)—, —C(═O)$NR^{L3}$—, —$NR^{L4}$S(═O)$_2$—, —S(═O)$_2NR^{L5}$—, —C(═$NOR^{L6}$)—, —C(═N—N($R^{L7}$)$_2$)—, —C(═$NR^{L8}$)— or a group of formula

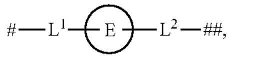, wherein said $C_1$-$C_6$-alkylene, $C_2$-$C_6$-alkenylene, $C_2$-$C_6$-alkynylene, —C(═O)—$C_1$-$C_6$-alkylene- and —$C_1$-$C_6$-alkylene-C(═O)— are optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl, $C_3$-$C_8$-cycloalkenyl and 3- to 7-membered heterocyclyl in turn are optionally substituted with one to three substituents $L^{SC}$, $R^{L1}$, $R^{L2}$, $R^{L3}$ and $R^{L4}$ are independently hydrogen or $C_1$-$C_6$-alkyl, $R^{L5}$, $R^{L6}$, $R^{L7}$ and $R^{L8}$ are independently hydrogen, $C_1$-$C_6$-alkyl, $C_1$-$C_6$-haloalkyl, $C_3$-$C_8$-cycloalkyl or $C_2$-$C_6$-alkenyl, wherein $L^{SA}$ is independently halogen, cyano, hydroxyl, carboxyl, methylidene, halomethylidene, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$ or 3- to 7-membered heterocyclyl, and/or two substituents $L^{SA}$ that are bound to the same carbon atom form together with the carbon atom which they are attached to a $C_3$-$C_8$-cycloalkyl-ring or a 3- to 7-membered heterocyclyl-ring, $L^{SC}$ is independently halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, and/or two $L^{SC}$ substituents form together with the carbon atom to which they are attached to a $C_3$-$C_8$-cycloalkyl-ring, $R^6$ is $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl, 3- to 14-membered heterocyclylsulfonyl, $C_1$-$C_3$-alkoxy, $C_1$-$C_3$-haloalkoxy, $C_1$-$C_3$-alkylsulfanyl, $C_1$-$C_3$-alkylsulfinyl or $C_1$-$C_3$-alkylsulfonyl, wherein $C_1$-$C_3$-alkoxy, $C_1$-$C_3$-haloalkoxy, $C_1$-$C_3$-alkylsulfanyl, $C_1$-$C_3$-alkylsulfinyl and $C_1$-$C_3$-alkylsulfonyl are substituted with one substituent selected from the group consisting of $C_3$-$C_{12}$-carbocyclyl, $C_6$-$C_{14}$-aryl, 3- to 14-membered heterocyclyl and 5- to 14-membered heteroaryl, wherein said $C_3$-$C_{12}$-carbocyclyl, $C_6$-$C_{14}$-aryl, 3- to 14-membered heterocyclyl and 5- to 14-membered heteroaryl in turn are optionally substituted with one to four $R^{6S}$ substituents, wherein $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl and 3- to 14-membered heterocyclylsulfonyl are optionally substituted with one to four $R^{6S}$ substituents, wherein $R^{6S}$ is independently selected from the group consisting of halogen, cyano, isocyano, nitro, hydroxyl, mercapto, pentafluorosulfanyl, oxo, methylidene, halomethylidene, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, —N($R^{15}$)$_2$, —O(C═O)$R^{16}$, —C(═O)$R^{16}$, —C(═O)(O$R^{17}$), —C(═O)N($R^{18}$)$_2$, —S(═O)$_2$N($R^{19}$)$_2$, —O—Si($C_1$-$C_6$-alkyl)$_3$ and —Si($C_1$-$C_6$-alkyl)$_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are furthermore optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, or two substituents $C_1$-$C_6$-alkyl attached to the same carbon atom from a $C_3$-$C_8$-cycloalkyl-ring, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and wherein $R^{15}$ is independently hydrogen, $C_1$-$C_6$-alkyl or $C_3$-$C_8$-cycloalkyl, wherein said $C_1$-$C_6$-alkyl in turn is optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, and wherein said $C_3$-$C_8$-cycloalkyl in turn is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl and $C_1$-$C_6$-haloalkyl in turn are optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, $R^7$ is hydrogen, halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy, —O—Si($C_1$-$C_6$-alkyl)$_3$, —Si($C_1$-$C_6$-alkyl)$_3$, —N($R^{20}$)$_2$, —C(═N$R^{21}$)$R^{22}$, —N$R^{23}$C(═O)$R^{24}$, —C(═O)(O$R^{25}$), —C(═O)N($R^{26}$)$_2$, —S(═O)$_2$N($R^{27}$)$_2$ or —S(═O)(═N$R^{28}$)$R^{29}$, wherein $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are optionally substituted with one to three $R^{7Sa}$ substituents, wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy are optionally substituted with one to three $R^{7Sc}$ substituents, and wherein $R^{20}$ is independently hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_6$-$C_{14}$-aryl, 5- or 6-membered heteroaryl or 3- to 7-membered heterocyclyl, wherein $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl in turn are optionally substituted with one to three substituents $R^{7Sa}$, and wherein $C_3$-$C_8$-cycloalkyl, $C_3$-$C_8$-halocycloalkyl, $C_6$-$C_{14}$-aryl, 5- or 6-membered heteroaryl and 3- to 7-membered heterocyclyl in turn are optionally substituted with one to three substituents $R^{7Sc}$, $R^{21}$ and $R^{22}$ are independently hydroxyl, amino, cyano, $C_1$-$C_6$-alkyl, $C_1$-$C_6$-haloalkyl, $C_1$-$C_6$-alkoxy, mono-($C_1$-$C_6$-alkyl)amino or di-($C_1$-$C_6$-alkyl)amino, wherein $C_1$-$C_6$-alkyl, $C_1$-$C_6$-haloalkyl, $C_1$-$C_6$-alkoxy, mono-($C_1$-$C_6$-alkyl)amino and di-($C_1$-$C_6$-alkyl)amino in turn are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_6$-alkyl, $C_1$-$C_6$-haloalkyl and $C_3$-$C_8$-cycloalkyl, wherein $C_1$-$C_6$-alkyl and $C_1$-$C_6$-haloalkyl in turn are optionally substituted with one to three $R^{7Sa}$ substituents, and wherein $C_3$-$C_8$-cycloalkyl in turn is optionally substituted with one to three $R^{7Sc}$ substituents, wherein $R^{7Sa}$ is independently cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$, —Si($C_1$-$C_6$-alkyl)$_3$, $C_6$-$C_{14}$-aryl or 3- to 7-membered heterocyclyl, $R^{7Sc}$ is independently halogen, cyano, nitro, hydroxyl, formyl, oxo, methylidene, halomethylidene, $C_1$-$C_6$-alkyl, $C_1$-$C_6$-haloalkyl $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, or two $R^{7Sc}$ substituents $C_1$-$C_6$-alkyl that are bound to the same carbon atom form together a $C_3$-$C_8$-cycloalkyl-ring, W is hydrogen, tert-butoxycarbonyl, benzyl, allyl or (4-methoxyphenyl)methyl, X is halogen.

The present invention also relates to compounds of formula (6a) and (6b):

(6a)

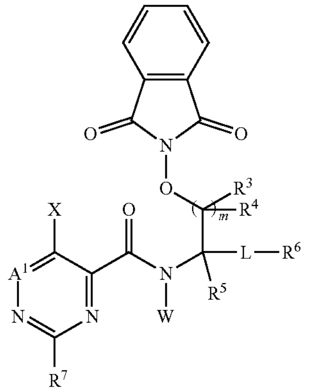

-continued (6b)

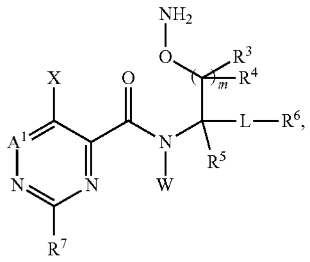

wherein $A^1$ is N or $CR^8$, wherein $R^1$ is hydrogen or halogen, m is 1 or 2, $R^3$ and $R^4$ are independently hydrogen, halogen, cyano, hydroxyl, formyl, carboxyl, $C_1$-$C_6$-alkyl, $C_1$-$C_6$-alkoxy, $C_1$-$C_6$-alkylcarbonyl, $C_1$-$C_6$-alkoxycarbonyl, $C_2$-$C_6$-alkenyl, $C_2$-$C_6$-alkynyl, $C_3$-$C_8$-cycloalkyl, $C_6$-$C_{14}$-aryl, 5- to 14-membered heteroaryl, 3- to 14-membered heterocyclyl or —O—Si($C_1$-$C_6$-alkyl)$_3$, wherein $C_1$-$C_6$-alkyl, $C_1$-$C_6$-alkoxy, $C_1$-$C_6$-alkylcarbonyl, $C_1$-$C_6$-alkoxycarbonyl, $C_2$-$C_6$-alkenyl, $C_2$-$C_6$-alkynyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl, $C_6$-$C_{14}$-aryl, 5- to 14-membered heteroaryl and 3- to 14-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^4$ form together with the carbon atom to which they are attached to a carbonyl, a methylidene, a $C_3$-$C_8$-cycloalkyl-ring or a 3- to 7-membered heterocyclyl-ring, wherein $C_3$-$C_8$-cycloalkyl and 3- to 7-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, $R^5$ is hydrogen, hydroxyl, $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl, $C_3$-$C_8$-cycloalkyl or —O—Si($C_1$-$C_6$-alkyl)$_3$, wherein $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl$)_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl$)_3$ and 3- to 7-membered heterocyclyl, or $R^3$ and $R^5$ or $R^4$ and $R^5$ form together with the carbon atom to which they are attached to a $C_3$-$C_8$-cycloalkyl-ring, L is a direct bond, carbonyl, $C_1$-$C_6$-alkylene, $C_2$-$C_6$-alkenylene, $C_2$-$C_6$-alkynylene, —C(═O)—$C_1$-$C_6$-alkylene-, —$C_1$-$C_6$-alkylene-C(═O)—, —$NR^{L1}$—, —$NR^{L2}$(C═O)—, —C(═O)$NR^{L3}$—, —$NR^{L4}$S(═O$)_2$—, —S(═O$)_2NR^{L5}$—, —C(═$NOR^{L6}$)—, —C(═N—N($R^{L7})_2$), —C(═$NR^{L8}$)— or a group of formula

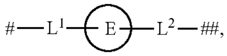

wherein said $C_1$-$C_6$-alkylene, $C_2$-$C_6$-alkenylene, $C_2$-$C_6$-alkynylene, —C(═O)—$C_1$-$C_6$-alkylene- and —$C_1$-$C_6$-alkylene-C(═O)— are optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl, $C_3$-$C_8$-cycloalkenyl and 3- to 7-membered heterocyclyl in turn are optionally substituted with one to three substituents $L^{SC}$, $R^{L1}$, $R^{L2}$, $R^{L3}$ and $R^{L4}$ are independently hydrogen or $C_1$-$C_6$-alkyl, $R^{L5}$, $R^{L6}$, $R^{L7}$ and $R^{L8}$ are independently hydrogen, $C_1$-$C_6$-alkyl, $C_1$-$C_6$-haloalkyl, $C_3$-$C_8$-cycloalkyl or $C_2$-$C_6$-alkenyl, $L^{SA}$ is independently halogen, cyano, hydroxyl, carboxyl, methylidene, halomethylidene, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl$)_3$ or 3- to 7-membered heterocyclyl, or two substituents $L^{SA}$ that are bound to the same carbon atom form together with the carbon atom which they are attached to a $C_3$-$C_8$-cycloalkyl-ring or a 3- to 7-membered heterocyclyl-ring, $L^{Sc}$ is independently halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl$)_3$ or 3- to 7-membered heterocyclyl, and/or two $L^{Sc}$ substituents form together with the carbon atom to which they are attached to a $C_3$-$C_8$-cycloalkyl-ring, $R^6$ is $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl, 3- to 14-membered heterocyclylsulfonyl, $C_1$-$C_3$-alkoxy, $C_1$-$C_3$-haloalkoxy, $C_1$-$C_3$-alkylsulfanyl, $C_1$-$C_3$-alkylsulfinyl or $C_1$-$C_3$-alkylsulfonyl, wherein $C_1$-$C_3$-alkoxy, $C_1$-$C_3$-haloalkoxy, $C_1$-$C_3$-alkylsulfanyl, $C_1$-$C_3$-alkylsulfinyl and $C_1$-$C_3$-alkylsulfonyl are substituted with one substituent selected from the group consisting of $C_3$-$C_{12}$-carbocyclyl, $C_6$-$C_{14}$-aryl, 3- to 14-membered heterocyclyl and 5- to 14-membered heteroaryl, wherein said $C_3$-$C_{12}$-carbocyclyl, $C_6$-$C_{14}$-aryl, 3- to 14-membered heterocyclyl and 5- to 14-membered heteroaryl in turn are optionally substituted with one to four $R^{6S}$ substituents, wherein $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl and 3- to 14-membered heterocyclylsulfonyl are optionally substituted with one to four $R^{6S}$ substituents, wherein $R^{6S}$ is selected from the group consisting of halogen, cyano, isocyano, nitro, hydroxyl, mercapto, pentafluorosulfanyl, oxo, methylidene, halomethylidene, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, —N($R^{15})_2$, —O(C═O)$R^{16}$, —C(═O)$R^{16}$, —C(═O)($OR^{17}$), —C(═O)N($R^{18})_2$, —S(═O$)_2$N($R^{19})_2$, —O—Si($C_1$-$C_6$-alkyl$)_3$ or —Si($C_1$-$C_6$-alkyl$)_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, or two substituents $C_1$-$C_6$-alkyl attached to the same carbon atom from a $C_3$-$C_8$-cycloalkyl-ring, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and wherein $R^{15}$ is hydrogen, $C_1$-$C_6$-alkyl or $C_3$-$C_8$-cycloalkyl, wherein said $C_1$-$C_6$-alkyl is optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, and wherein said $C_3$-$C_8$-cycloalkyl is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl or $C_1$-$C_6$-haloalkyl are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, $R^7$ is hydrogen, halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy, —O—Si($C_1$-$C_6$-alkyl)$_3$, —Si($C_1$-$C_6$-alkyl)$_3$, —N($R^{20}$)$_2$, —C(═N$R^{21}$)$R^{22}$, —N$R^{23}$C(═O)$R^{24}$, —C(═O)(O$R^{25}$), —C(═O)N($R^{26}$)$_2$, —S(═O)$_2$N($R^{27}$)$_2$ or —S(═O)(═N$R^{28}$)$R^{29}$, wherein $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are optionally substituted with one to three $R^{7Sa}$ substituents, wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy are optionally substituted with one to three $R^{7Sc}$ substituents, and wherein $R^{20}$ is hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_6$-$C_{14}$-aryl, 5- or 6-membered heteroaryl or 3- to 7-membered heterocyclyl, wherein $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl are optionally substituted with one to three substituents $R^{7Sa}$, and wherein $C_3$-$C_8$-cycloalkyl, $C_3$-$C_8$-halocycloalkyl, $C_6$-$C_{14}$-aryl, 5- or 6-membered heteroaryl and 3- to 7-membered heterocyclyl are optionally substituted with one to three substituents $R^{7Sc}$, $R^{21}$ and $R^{22}$ are independently hydroxyl, amino, cyano, $C_1$-$C_6$-alkyl, $C_1$-$C_6$-haloalkyl, $C_1$-$C_6$-alkoxy, mono-($C_1$-$C_6$-alkyl)amino or di-($C_1$-$C_6$-alkyl)amino, wherein $C_1$-$C_6$-alkyl, $C_1$-$C_6$-haloalkyl, $C_1$-$C_6$-alkoxy, mono-($C_1$-$C_6$-alkyl)amino and di-($C_1$-$C_6$-alkyl)amino are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_6$-alkyl, $C_1$-$C_6$-haloalkyl and $C_3$-$C_8$-cycloalkyl, wherein $C_1$-$C_6$-alkyl and $C_1$-$C_6$-haloalkyl are optionally substituted with one to three $R^{7Sa}$ substituents, and wherein $C_3$-$C_8$-cycloalkyl is optionally substituted with one to three $R^{7Sc}$ substituents, wherein $R^{7Sa}$ is independently cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$, —Si($C_1$-$C_6$-alkyl)$_3$, $C_6$-$C_{14}$-aryl or 3- to 7-membered heterocyclyl, $R^{7Sc}$ is independently halogen, cyano, nitro, hydroxyl, formyl, oxo, methylidene, halomethylidene, $C_1$-$C_6$-alkyl, $C_1$-$C_6$-haloalkyl $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, or two $R^{7Sc}$ substituents $C_1$-$C_6$-alkyl that are bound to the same carbon atom form together a $C_3$-$C_8$-cycloalkyl, W is hydrogen, tert-butoxycarbonyl, benzyl, allyl or (4-methoxyphenyl)methyl, X is halogen.

The present invention also relates to compounds of formula (7):

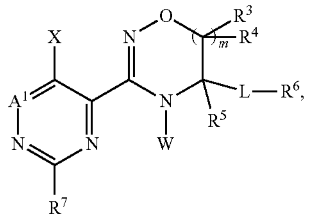

(7)

wherein $A^1$ is N or $CR^8$, wherein $R^8$ is hydrogen, halogen, cyano or $C_1$-$C_4$-alkyl, m is 1 or 2, $R^3$ and $R^4$ are independently hydrogen, halogen, cyano, hydroxyl, formyl, carboxyl, $C_1$-$C_6$-alkyl, $C_1$-$C_6$-alkoxy, $C_1$-$C_6$-alkylcarbonyl, $C_1$-$C_6$-alkylcarbonyloxy, $C_1$-$C_6$-alkoxycarbonyl, $C_2$-$C_6$-alkenyl, $C_2$-$C_6$-alkynyl, $C_3$-$C_8$-cycloalkyl, $C_6$-$C_{14}$-aryl, 5- to 14-membered heteroaryl, 3- to 14-membered heterocyclyl or —O—Si ($C_1$-$C_6$-alkyl)$_3$, wherein $C_1$-$C_6$-alkyl, $C_1$-$C_6$-alkoxy, $C_1$-$C_6$-alkylcarbonyl, $C_1$-$C_6$-alkylcarbonyloxy, $C_1$-$C_6$-alkoxycarbonyl, $C_2$-$C_6$-alkenyl, $C_2$-$C_6$-alkynyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl, $C_6$-$C_{14}$-aryl, 5- to 14-membered heteroaryl and 3- to 14-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^4$ form together with the carbon atom to which they are attached to a carbonyl, a methylidene, a $C_3$-$C_8$-cycloalkyl-ring or a 3- to 7-membered heterocyclyl-ring, wherein $C_3$-$C_8$-cycloalkyl-ring and 3- to 7-membered heterocyclyl-ring are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, $R^5$ is hydrogen, hydroxyl, $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl, $C_3$-$C_8$-cycloalkyl or —O—Si($C_1$-$C_6$-alkyl)$_3$, wherein $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^5$ or $R^4$ and $R^5$ form together with the carbon atom to which they are attached to a $C_3$-$C_8$-cycloalkyl-ring, L is a direct bond, carbonyl, $C_1$-$C_6$-alkylene, $C_2$-$C_6$-alkenylene, $C_2$-$C_6$-alkynylene, —C(═O)—$C_1$-$C_6$-alkylene-, —$C_1$-$C_6$-alkylene-C(═O)—, —$NR^{L1}$—, —$NR^{L2}$(C═O)—, —C(═O)$NR^{L3}$—, —$NR^{L4}$S(═O)$_2$—, —S(═O)$_2NR^{L5}$—, —C(═$NOR^{L6}$)—, —C(═N—N($R^{L7}$)$_2$)—, —C(═$NR^{L8}$)— or a group of formula

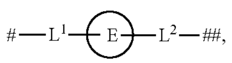

wherein said $C_1$-$C_6$-alkylene, $C_2$-$C_6$-alkenylene, $C_2$-$C_6$-alkynylene, —C(═O)—$C_1$-$C_6$-alkylene- and —$C_1$-$C_6$-alkylene-C(═O)— are optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl, $C_3$-$C_8$-cycloalkenyl and 3- to 7-membered heterocyclyl in turn are optionally substituted with one to three substituents $L^{SC}$, $R^{L1}$, $R^{L2}$, $R^{L3}$ and $R^{L4}$ are independently hydrogen or $C_1$-$C_6$-alkyl, $R^{L5}$, $R^{L6}$, $R^{L7}$ and $R^{L8}$ are independently hydrogen, $C_1$-$C_6$-alkyl, $C_1$-$C_6$-haloalkyl, $C_3$-$C_8$-cycloalkyl or $C_2$-$C_6$-alkenyl, wherein $L^{SA}$ is independently halogen, cyano, hydroxyl, carboxyl, methylidene, halomethylidene, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$ or 3- to 7-membered heterocyclyl, and/or two substituents $L^{SA}$ that are bound to the same carbon atom form together with the carbon atom which they are attached to a $C_3$-$C_8$-cycloalkyl-ring or a 3- to 7-membered heterocyclyl-ring, $L^{SC}$ is independently halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, and/or two $L^{SC}$ substituents form together with the carbon atom to which they are attached to a $C_3$-$C_8$-cycloalkyl-ring, $R^6$ is $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl, 3- to 14-membered heterocyclylsulfonyl, $C_1$-$C_3$-alkoxy, $C_1$-$C_3$-haloalkoxy, $C_1$-$C_3$-alkylsulfanyl, $C_1$-$C_3$-alkylsulfinyl or $C_1$-$C_3$-alkylsulfonyl, wherein $C_1$-$C_3$-alkoxy, $C_1$-$C_3$-haloalkoxy, $C_1$-$C_3$-alkylsulfanyl, $C_1$-$C_3$-alkylsulfinyl and $C_1$-$C_3$-alkylsulfonyl are substituted with one substituent selected from the group consisting of $C_3$-$C_{12}$-carbocyclyl, $C_6$-$C_{14}$-aryl, 3- to 14-membered heterocyclyl and 5- to 14-membered heteroaryl, wherein said $C_3$-$C_{12}$-carbocyclyl, $C_6$-$C_{14}$-aryl, 3- to 14-membered heterocyclyl and 5- to 14-membered heteroaryl in turn are optionally substituted with one to four $R^{6S}$ substituents, wherein $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl and 3- to 14-membered heterocyclylsulfonyl are optionally substituted with one to four $R^{6S}$ substituents, wherein $R^{6S}$ is independently selected from the group consisting of halogen, cyano, isocyano, nitro, hydroxyl, mercapto, pentafluorosulfanyl, oxo, methylidene, halomethylidene, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, —N($R^{15}$)$_2$, —O(C═O)$R^{16}$, —C(═O)$R^{16}$, —C(═O)(O$R^{17}$), —C(═O)N($R^{18}$)$_2$, —S(═O)$_2$N($R^{19}$)$_2$, —O—Si($C_1$-$C_6$-alkyl)$_3$ and —Si($C_1$-$C_6$-alkyl)$_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are furthermore optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, or two substituents $C_1$-$C_6$-alkyl attached to the same carbon atom from a $C_3$-$C_8$-cycloalkyl-ring, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_4$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and wherein $R^{15}$ is independently hydrogen, $C_1$-$C_6$-alkyl or $C_3$-$C_8$-cycloalkyl, wherein said $C_1$-$C_6$-alkyl in turn is optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, and wherein said $C_3$-$C_8$-cycloalkyl in turn is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl and $C_1$-$C_6$-haloalkyl in turn are optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, $R^7$ is hydrogen, halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy, —O—Si($C_1$-$C_6$-alkyl)$_3$, —Si($C_1$-$C_6$-alkyl)$_3$, —N($R^{20}$)$_2$, —C(═N$R^{21}$)$R^{22}$, —N$R^{23}$C(═O)$R^{24}$, —C(═O)(O$R^{25}$), —C(═O)N($R^{26}$)$_2$, —S(═O)$_2$N($R^{27}$)$_2$ or —S(═O)(═N$R^{28}$)$R^{29}$, wherein $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are optionally substituted with one to three $R^{7Sa}$ substituents, wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy are optionally substituted with one to three $R^{7Sc}$ substituents, and wherein $R^{20}$ is independently hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_6$-$C_{14}$-aryl, 5- or 6-membered heteroaryl or 3- to 7-membered heterocyclyl, wherein $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl in turn are optionally substituted with one to three substituents $R^{7Sa}$, and wherein $C_3$-$C_8$-cycloalkyl, $C_3$-$C_8$-halocycloalkyl, $C_6$-$C_{14}$-aryl, 5- or 6-membered heteroaryl and 3- to 7-membered heterocyclyl in turn are optionally substituted with one to three substituents $R^{7Sc}$, $R^{21}$ and $R^{22}$ are independently hydroxyl, amino, cyano, $C_1$-$C_6$-alkyl, $C_1$-$C_6$-haloalkyl, $C_1$-$C_6$-alkoxy, mono-($C_1$-$C_6$-alkyl)amino or di-($C_1$-$C_6$-alkyl)amino, wherein $C_1$-$C_6$-alkyl, $C_1$-$C_6$-haloalkyl, $C_1$-$C_6$-alkoxy, mono-($C_1$-$C_6$-alkyl)amino and di-($C_1$-$C_6$-alkyl)amino in turn are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_6$-alkyl, $C_1$-$C_6$-haloalkyl and $C_3$-$C_8$-cycloalkyl, wherein $C_1$-$C_6$-alkyl and $C_1$-$C_6$-haloalkyl in turn are optionally substituted with one to three $R^{7Sa}$ substituents, and wherein $C_3$-$C_8$-cycloalkyl in turn is optionally substituted with one to three $R^{7Sc}$ substituents, wherein $R^{7Sa}$ is independently cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$, —Si($C_1$-$C_6$-alkyl)$_3$, $C_6$-$C_{14}$-aryl or 3- to 7-membered heterocyclyl, $R^{7Sc}$ is independently halogen, cyano, nitro, hydroxyl, formyl, oxo, methylidene, halomethylidene, $C_1$-$C_6$-alkyl, $C_1$-$C_6$-haloalkyl $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, or two $R^{7Sc}$ substituents $C_1$-$C_6$-alkyl that are bound to the same carbon atom form together a $C_3$-$C_8$-cycloalkyl-ring, W is hydrogen, tert-butoxycarbonyl, benzyl or (4-methoxyphenyl)methyl, X is halogen.

The present invention also relates to compounds of formula (7):

(7)

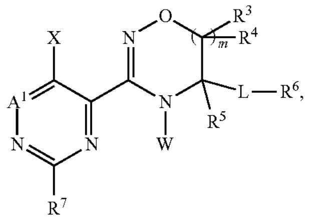

wherein $A^1$ is N or $CR^8$, wherein $R^1$ is hydrogen or halogen, m is 1 or 2, $R^3$ and $R^4$ are independently hydrogen, halogen, cyano, hydroxyl, formyl, carboxyl, $C_1$-$C_6$-alkyl, $C_1$-$C_6$-alkoxy, $C_1$-$C_6$-alkylcarbonyl, $C_1$-$C_6$-alkoxycarbonyl, $C_2$-$C_6$-alkenyl, $C_2$-$C_6$-alkynyl, $C_3$-$C_8$-cycloalkyl, $C_6$-$C_{14}$-aryl, 5- to 14-membered heteroaryl, 3- to 14-membered heterocyclyl or —O—Si($C_1$-$C_6$-alkyl)$_3$, wherein $C_1$-$C_6$-alkyl, $C_1$-$C_6$-alkoxy, $C_1$-$C_6$-alkylcarbonyl, $C_1$-$C_6$-alkoxycarbonyl, $C_2$-$C_6$-alkenyl, $C_2$-$C_6$-alkynyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl, $C_6$-$C_{14}$-aryl, 5- to 14-membered heteroaryl and 3- to 14-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^4$ form together with the carbon atom to which they are attached to a carbonyl, a methylidene, a $C_3$-$C_8$-cycloalkyl-ring or a 3- to 7-membered heterocyclyl-ring, wherein $C_3$-$C_8$-cycloalkyl and 3- to 7-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, $R^5$ is hydrogen, hydroxyl, $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl, $C_3$-$C_8$-cycloalkyl or —O—Si($C_1$-$C_6$-alkyl)$_3$, wherein $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^5$ or $R^4$ and $R^5$ form together with the carbon atom to which they are attached to a $C_3$-$C_8$-cycloalkyl-ring, L is a direct bond, carbonyl, $C_1$-$C_6$-alkylene, $C_2$-$C_6$-alkenylene, $C_2$-$C_6$-alkynylene, —C(═O)—$C_1$-$C_6$-alkylene-, —$C_1$-$C_6$-alkylene-C(═O)—, —$NR^{L1}$—, —$NR^{L2}$(C═O)—, —C(═O)$NR^{L3}$—, —$NR^{L4}$S(═O)$_2$—, —S(═O)$_2NR^{L5}$—, —C(═$NOR^{L6}$)—, —C(═N—N($R^{L7}$)$_2$), —C(═$NR^{L8}$)— or a group of formula

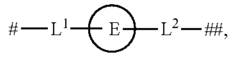

wherein said $C_1$-$C_6$-alkylene, $C_2$-$C_6$-alkenylene, $C_2$-$C_6$-alkynylene, —C(═O)—$C_1$-$C_6$-alkylene- and —$C_1$-$C_6$-alkylene-C(═O)— are optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl, $C_3$-$C_8$-cycloalkenyl and 3- to 7-membered heterocyclyl in turn are optionally substituted with one to three substituents $L^{SC}$, $R^{L1}$, $R^{L2}$, $R^{L3}$ and $R^{L4}$ are independently hydrogen or $C_1$-$C_6$-alkyl, $R^{L5}$, $R^{L6}$, $R^{L7}$ and $R^{L8}$ are independently hydrogen, $C_1$-$C_6$-alkyl, $C_1$-$C_6$-haloalkyl, $C_3$-$C_8$-cycloalkyl or $C_2$-$C_6$-alkenyl, $L^{SA}$ is independently halogen, cyano, hydroxyl, carboxyl, methylidene, halomethylidene, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$ or 3- to 7-membered heterocyclyl, or two substituents $L^{SA}$ that are bound to the same carbon atom form together with the carbon atom which they are attached to a $C_3$-$C_8$-cycloalkyl-ring or a 3- to 7-membered heterocyclyl-ring, $L^{Sc}$ is independently halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, and/or two $L^{Sc}$ substituents form together with the carbon atom to which they are attached to a $C_3$-$C_8$-cycloalkyl-ring, $R^6$ is $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl, 3- to 14-membered heterocyclylsulfonyl, $C_1$-$C_3$-alkoxy, $C_1$-$C_3$-haloalkoxy, $C_1$-$C_3$-alkylsulfanyl, $C_1$-$C_3$-alkylsulfinyl or $C_1$-$C_3$-alkylsulfonyl, wherein $C_1$-$C_3$-alkoxy, $C_1$-$C_3$-haloalkoxy, $C_1$-$C_3$-alkylsulfanyl, $C_1$-$C_3$-alkylsulfinyl and $C_1$-$C_3$-alkylsulfonyl are substituted with one substituent selected from the group consisting of $C_3$-$C_{12}$-carbocyclyl, $C_6$-$C_{14}$-aryl, 3- to 14-membered heterocyclyl and 5- to 14-membered heteroaryl, wherein said $C_3$-$C_{12}$-carbocyclyl, $C_6$-$C_{14}$-aryl, 3- to 14-membered heterocyclyl and 5- to 14-membered heteroaryl in turn are optionally substituted with one to four $R^{6S}$ substituents, wherein $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl and 3- to 14-membered heterocyclylsulfonyl are optionally substituted with one to four $R^{6S}$ substituents, wherein $R^{6S}$ is selected from the group consisting of halogen, cyano, isocyano, nitro, hydroxyl, mercapto, pentafluorosulfanyl, oxo, methylidene, halomethylidene, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, $—N(R^{15})_2$, $—O(C{=}O)R^{16}$, $—C({=}O)R^{16}$, $—C({=}O)(OR^{17})$, $—C({=}O)N(R^{18})_2$, $—S({=}O)_2N(R^{19})_2$, $—O—Si(C_1\text{-}C_6\text{-alkyl})_3$ or $—Si(C_1\text{-}C_6\text{-alkyl})_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $—O—Si(C_1\text{-}C_6\text{-alkyl})_3$ and $—Si(C_1\text{-}C_6\text{-alkyl})_3$ are furthermore optionally substituted with one to three substituents independently selected from the group consisting of cyano, hydroxyl, $C_1$-$C_6$-alkoxy, $C_1$-$C_6$-haloalkoxy, $—O—Si(C_1\text{-}C_6\text{-alkyl})_3$, $—Si(C_1\text{-}C_6\text{-alkyl})_3$, $C_3$-$C_8$-cycloalkyl, $C_3$-$C_8$-halocycloalkyl and 3- to 7-membered heterocyclyl, or two substituents $C_1$-$C_6$-alkyl attached to the same carbon atom from a $C_3$-$C_8$-cycloalkyl, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and wherein $R^{15}$ is hydrogen, $C_1$-$C_6$-alkyl or $C_3$-$C_8$-cycloalkyl, wherein said $C_1$-$C_6$-alkyl is optionally substituted with one to three substituents independently selected from the group consisting of cyano, hydroxyl, $C_1$-$C_6$-alkoxy, $C_1$-$C_6$-haloalkoxy, $—O—Si(C_1\text{-}C_6\text{-alkyl})_3$, $—Si(C_1\text{-}C_6\text{-alkyl})_3$, $C_3$-$C_8$-cycloalkyl, $C_3$-$C_8$-halocycloalkyl and 3- to 7-membered heterocyclyl, and wherein said $C_3$-$C_8$-cycloalkyl is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl or $C_1$-$C_6$-haloalkyl are furthermore optionally substituted with one to three substituents independently selected from the group consisting of cyano, hydroxyl, $C_1$-$C_6$-alkoxy, $C_1$-$C_6$-haloalkoxy, $—O—Si(C_1\text{-}C_6\text{-alkyl})_3$, $—Si(C_1\text{-}C_6\text{-alkyl})_3$, $C_3$-$C_8$-cycloalkyl, $C_3$-$C_8$-halocycloalkyl and 3- to 7-membered heterocyclyl, $R^7$ is hydrogen, halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy, $—O—Si(C_1\text{-}C_6\text{-alkyl})_3$, $—Si(C_1\text{-}C_6\text{-alkyl})_3$, $—N(R^{20})_2$, $—C({=}NR^{21})R^{22}$, $—NR^{23}C({=}O)R^{24}$, $—C({=}O)(OR^{25})$, $—C({=}O)N(R^{26})_2$, $—S({=}O)_2N(R^{27})_2$ or $—S({=}O)({=}NR^{28})R^{29}$, wherein $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are optionally substituted with one to three $R^{7Sa}$ substituents, wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy are optionally substituted with one to three $R^{7Sc}$ substituents, and wherein $R^{20}$ is hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_6$-$C_{14}$-aryl, 5- or 6-membered heteroaryl or 3- to 7-membered heterocyclyl, wherein $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl are optionally substituted with one to three substituents $R^{7Sa}$, and wherein $C_3$-$C_8$-cycloalkyl, $C_3$-$C_8$-halocycloalkyl, $C_6$-$C_{14}$-aryl, 5- or 6-membered heteroaryl and 3- to 7-membered heterocyclyl are optionally substituted with one to three substituents $R^{7Sc}$, $R^{21}$ and $R^{22}$ are independently hydroxyl, amino, cyano, $C_1$-$C_6$-alkyl, $C_1$-$C_6$-haloalkyl, $C_1$-$C_6$-alkoxy, mono-($C_1$-$C_6$-alkyl)amino or di-($C_1$-$C_6$-alkyl)amino, wherein $C_1$-$C_6$-alkyl, $C_1$-$C_6$-haloalkyl, $C_1$-$C_6$-alkoxy, mono-($C_1$-$C_6$-alkyl)amino and di-($C_1$-$C_6$-alkyl)amino are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_6$-alkyl, $C_1$-$C_6$-haloalkyl and $C_3$-$C_8$-cycloalkyl, wherein $C_1$-$C_6$-alkyl and $C_1$-$C_6$-haloalkyl are optionally substituted with one to three $R^{7Sa}$ substituents, and wherein $C_3$-$C_8$-cycloalkyl is optionally substituted with one to three $R^{7Sc}$ substituents, wherein $R^{7Sa}$ is independently cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$, —Si($C_1$-$C_6$-alkyl)$_3$, $C_6$-$C_{14}$-aryl or 3- to 7-membered heterocyclyl, $R^{7Sc}$ is independently halogen, cyano, nitro, hydroxyl, formyl, oxo, methylidene, halomethylidene, $C_1$-$C_6$-alkyl, $C_1$-$C_6$-haloalkyl $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, or two $R^{7Sc}$ substituents $C_1$-$C_6$-alkyl that are bound to the same carbon atom form together a $C_3$-$C_8$-cycloalkyl-ring, W is hydrogen, tert-butoxycarbonyl, benzyl or (4-methoxyphenyl)methyl, X is halogen.

The present invention also relates to compounds of formula (9):

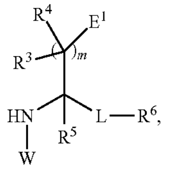

(9)

wherein m is 1,

L is methylidene or difluoromethylidene, $R^3$ and $R^4$ are hydrogen, $R^5$ is hydrogen, $R^6$ is phenyl, wherein phenyl is optionally substituted with one to four $R^{6S}$ substituents, wherein $R^{6S}$ is selected from the group consisting of halogen, cyano, isocyano, nitro, hydroxyl, mercapto, pentafluorosulfanyl, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, —N($R^{15}$)$_2$, —O(C═O)$R^{16}$, —C(═O)$R^{16}$, —C(═O)(O$R^{17}$), —C(═O)N($R^{18}$)$_2$, —S(═O)$_2$N($R^{19}$)$_2$, —O—Si($C_1$-$C_6$-alkyl)$_3$ or —Si($C_1$-$C_6$-alkyl)$_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, or two substituents $C_1$-$C_6$-alkyl attached to the same carbon atom from a $C_3$-$C_8$-cycloalkyl-ring, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$- alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and wherein $R^{15}$ is hydrogen, $C_1$-$C_6$-alkyl or $C_3$-$C_8$-cycloalkyl, wherein said $C_1$-$C_6$-alkyl is optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl$)_3$, —Si($C_1$-$C_6$-alkyl$)_3$, $C_3$-$C_8$-cycloalkyl, $C_3$-$C_8$-halocycloalkyl and 3- to 7-membered heterocyclyl, and wherein said $C_3$-$C_8$-cycloalkyl is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl or $C_1$-$C_6$-haloalkyl are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl$)_3$, —Si($C_1$-$C_6$-alkyl$)_3$, $C_3$-$C_8$-cycloalkyl, $C_3$-$C_8$-halocycloalkyl and 3- to 7-membered heterocyclyl, $E^1$ is chlorine, bromine or iodine, W is hydrogen, tert-butoxycarbonyl, benzyl or (4-methoxyphenyl)methyl and salts, solvates or salts of the solvates thereof, provided that the compound of formula (9) preferably is not:

| | |
|---|---|
| (2RS)-1-chloro-3-phenylpropan-2-amine | 749167-08-6 |
| (2RS)-1-chloro-3-phenylpropan-2-amine | 776253-38-4 |
| 1-chloro-3-phenylpropan-2-amine | 748709-78-6 |
| (2RS)-1-chloro-3-phenylpropan-2-amine hydrochloride (1:1) | 100431-28-5 |
| 1-chloro-3-phenylpropan-2-amine hydrochloride (1:1) | 49557-36-0 |
| (2RS)-1-chloro-3-phenylpropan-2-amine hydrochloride (1:1) | 100431-27-4 |
| 3-(2-amino-3-chloropropyl)phenol | 790605-82-2 |
| 3-(2-amino-3-chloropropyl)phenol hydrochloride (1:1) | 66033-01-0 |
| (2RS)-1-chloro-3-(2,4,5-trifluorophenyl)propan-2-amine | 2101321-88-2 |
| (2RS)-1-chloro-3-(2,4,5-trifluorophenyl)propan-2-amine hydrochloride (1:1) | 2101321-89-3 |
| 1-chloro-3-(3,4,5-trimethoxyphenyl)propan-2-amine | 690946-87-3 |
| 1-chloro-3-(3,4,5-trimethoxyphenyl)propan-2-amine hydrochloride (1:1) | 49557-34-8 |
| 5-[(2RS)-2-amino-3-chloropropyl]-2-methoxybenzenesulfonamide | 855594-92-2 |
| (2RS)-1-chloro-3-phenylpropan-2-amine | 749167-08-6 |
| (2RS)-1-chloro-3-phenylpropan-2-amine | 776253-38-4 |
| 1-chloro-3-phenylpropan-2-amine | 748709-78-6 |
| (2RS)-1-chloro-3-phenylpropan-2-amine hydrochloride (1:1) | 100431-28-5 |
| 1-chloro-3-phenylpropan-2-amine hydrochloride (1:1) | 49557-36-0 |
| (2RS)-1-chloro-3-phenylpropan-2-amine hydrochloride (1:1) | 100431-27-4 |
| 3-(2-amino-3-chloropropyl)phenol | 790605-82-2 |
| 3-(2-amino-3-chloropropyl)phenol hydrochloride (1:1) | 66033-01-0 |
| (2RS)-1-chloro-3-(2,4,5-trifluorophenyl)propan-2-amine | 2101321-88-2 |
| (2RS)-1-chloro-3-(2,4,5-trifluorophenyl)propan-2-amine hydrochloride (1:1) | 2101321-89-3 |
| 1-chloro-3-(3,4,5-trimethoxyphenyl)propan-2-amine | 690946-87-3 |
| 1-chloro-3-(3,4,5-trimethoxyphenyl)propan-2-amine hydrochloride (1:1) | 49557-34-8 |
| 5-[(2RS)-2-amino-3-chloropropyl]-2-methoxybenzenesulfonamide | 855594-92-2 |
| rac-(2RS)-1-chloro-3-(2-chloro-4-methyl-phenyl)propan-2-amine | 2446132-77-8 |
| rac-(2RS)-1-chloro-3-(2-chloro-4-methyl-phenyl)propan-2-amine hydrochloride | 2446132-78-9 |
| rac-(2RS)-1-chloro-3-(2,4-dimethylphenyl)propan-2-amine | 2446130-66-9 |
| rac-(2RS)-1-chloro-3-(2,4-dimethylphenyl)propan-2-amine hydrochloride | 2446130-67-0 |
| (2S)-1-bromo-3-phenylpropan-2-amine trifluoroacetate (1:1) | 2446130-69-2 |
| 1-chloro-3-(3,4-dichlorophenyl)propan-2-amine | 2446132-79-0 |
| 1-(2-bromo-4-methylpheny1)-3-chloropropan-2-amine | 2446132-73-4 |
| 1-chloro-3-[4-(difluoromethyl)phenyl]propan-2-amine | 2446132-71-2 |
| 1-chloro-3-(2-cyclopropyl-4-methylphenyl)propan-2-amine hydrochloride (1:1) | 2446132-98-3 |
| 1-chloro-3-(2-cyclopropyl-4-methylphenyl)propan-2-amine | 2446132-97-2 |
| 1-chloro-3-(3,4-dichlorophenyl)propan-2-amine hydrochloride (1:1) | 2446132-80-3 |
| 1-chloro-3-(3,4-dichlorophenyl)propan-2-amine | 2446132-79-0 |
| 1-(2-bromo-4-methylpheny1)-3-chloropropan-2-amine hydrochloride (1:1) | 2446132-74-5 |
| 1-(2-bromo-4-methylphenyl)-3-chloropropan-2-amine | 2446132-73-4 |
| 1-chloro-3-[4-(difluoromethyl)phenyl]propan-2-amine hydrochloride (1:1) | 2446132-72-3 |
| 1-chloro-3-[4-(difluoromethyl)phenyl]propan-2-amine | 2446132-71-2 |
| 1-chloro-3-[4-(trifluoromethoxy)phenyl]propan-2-amine hydrochloride (1:1) | 2446132-68-7 |
| 1-chloro-3-[4-(trifluoromethoxy)phenyl]propan-2-amine | 2446132-67-6 |
| 3-amino-4-(2,4-dimethylphenyl)butanamide | 2446130-71-6 |
| 4-(2,4-dimethylphenyl)butane-1,3-diamine | 2446130-60-3 |

The present invention also relates to compounds of formula (9):

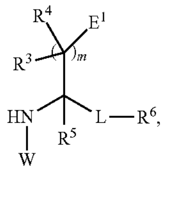

(9)

wherein m is 1 or 2,

L is a direct bond, methylidene, difluoromethylidene or ethylidene, $R^3$ and $R^4$ are hydrogen, $R^5$ is hydrogen, $R^6$ is phenyl or thienyl, wherein phenyl and thienyl are optionally substituted with one to four $R^{6S}$ substituents, wherein $R^{6S}$ is selected from the group consisting of halogen, cyano, isocyano, nitro, hydroxyl, mercapto, pentafluorosulfanyl, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, —$N(R^{15})_2$, —O(C═O)$R^{16}$, —C(═O)$R^{16}$, —C(═O)($OR^{17}$), —C(═O)$N(R^{18})_2$, —$S(═O)_2N(R^{19})_2$, —O—Si($C_1$-$C_6$-alkyl$)_3$ or —Si($C_1$-$C_6$-alkyl$)_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl$)_3$ and —Si($C_1$-$C_6$-alkyl$)_3$ are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl$)_3$, —Si($C_1$-$C_6$-alkyl$)_3$, $C_3$-$C_8$-cycloalkyl, $C_3$-$C_8$-halocycloalkyl and 3- to 7-membered heterocyclyl, or two substituents $C_1$-$C_6$-alkyl attached to the same carbon atom from a $C_3$-$C_8$-cycloalkyl-ring, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and wherein $R^{15}$ is hydrogen, $C_1$-$C_6$-alkyl or $C_3$-$C_8$-cycloalkyl, wherein said $C_1$-$C_6$-alkyl is optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl$)_3$, —Si($C_1$-$C_6$-alkyl$)_3$, $C_3$-$C_8$-cycloalkyl, $C_3$-$C_8$-halocycloalkyl and 3- to 7-membered heterocyclyl, and wherein said $C_3$-$C_8$-cycloalkyl is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl or $C_1$-$C_6$-haloalkyl are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl$)_3$, —Si($C_1$-$C_6$-alkyl$)_3$, $C_3$-$C_8$-cycloalkyl, $C_3$-$C_8$-halocycloalkyl and 3- to 7-membered heterocyclyl, $E^1$ is chlorine, bromine, iodine, aminooxy, amino, aminomethyl, aminocarbonyl or aminosulfonyl, W is hydrogen, tert-butoxycarbonyl, benzyl or (4-methoxyphenyl)methyl and salts, solvates or salts of the solvates thereof, provided that the compound of formula (9) preferably is not:

| | |
|---|---|
| (2RS)-1-chloro-3-phenylpropan-2-amine | 749167-08-6 |
| (2RS)-1-chloro-3-phenylpropan-2-amine | 776253-38-4 |
| 1-chloro-3-phenylpropan-2-amine | 748709-78-6 |
| (2RS)-1-chloro-3-phenylpropan-2-amine hydrochloride (1:1) | 100431-28-5 |
| 1-chloro-3-phenylpropan-2-amine hydrochloride (1:1) | 49557-36-0 |
| (2RS)-1-chloro-3-phenylpropan-2-amine hydrochloride (1:1) | 100431-27-4 |
| 3-(2-amino-3-chloropropyl)phenol | 790605-82-2 |
| 3-(2-amino-3-chloropropyl)phenol hydrochloride (1:1) | 66033-01-0 |
| (2RS)-1-chloro-3-(2,4,5-trifluorophenyl)propan-2-amine | 2101321-88-2 |
| (2RS)-1-chloro-3-(2,4,5-trifluorophenyl)propan-2-amine hydrochloride (1:1) | 2101321-89-3 |
| 1-chloro-3-(3,4,5-trimethoxyphenyl)propan-2-amine | 690946-87-3 |
| 1-chloro-3-(3,4,5-trimethoxyphenyl)propan-2-amine hydrochloride (1:1) | 49557-34-8 |
| 5-[(2RS)-2-amino-3-chloropropyl]-2-methoxybenzenesulfonamide | 855594-92-2 |
| (2RS)-1-chloro-3-phenylpropan-2-amine | 749167-08-6 |
| (2RS)-1-chloro-3-phenylpropan-2-amine | 776253-38-4 |
| 1-chloro-3-phenylpropan-2-amine | 748709-78-6 |
| (2RS)-1-chloro-3-phenylpropan-2-amine hydrochloride (1:1) | 100431-28-5 |
| 1-chloro-3-phenylpropan-2-amine hydrochloride (1:1) | 49557-36-0 |

-continued

| | |
|---|---|
| (2RS)-1-chloro-3-phenylpropan-2-amine hydrochloride (1:1) | 100431-27-4 |
| 3-(2-amino-3-chloropropyl)phenol | 790605-82-2 |
| 3-(2-amino-3-chloropropyl)phenol hydrochloride (1:1) | 66033-01-0 |
| (2RS)-1-chloro-3-(2,4,5-trifluorophenyl)propan-2-amine | 2101321-88-2 |
| (2RS)-1-chloro-3-(2,4,5-trifluorophenyl)propan-2-amine hydrochloride (1:1) | 2101321-89-3 |
| 1-chloro-3-(3,4,5-trimethoxyphenyl)propan-2-amine | 690946-87-3 |
| 1-chloro-3-(3,4,5-trimethoxyphenyl)propan-2-amine hydrochloride (1:1) | 49557-34-8 |
| rac-(2RS)-1-chloro-3-(2-chloro-4-methyl-phenyl)propan-2-amine | 2446132-77-8 |
| rac-(2RS)-1-chloro-3-(2-chloro-4-methyl-phenyl)propan-2-amine hydrochloride | 2446132-78-9 |
| rac-(2RS)-1-chloro-3-(2,4-dimethylphenyl)propan-2-amine | 2446130-66-9 |
| rac-(2RS)-1-chloro-3-(2,4-dimethylphenyl)propan-2-amine hydrochloride | 2446130-67-0 |
| (2S)-1-bromo-3-phenylpropan-2-amine trifluoroacetate (1:1) | 2446130-69-2 |
| 1-chloro-3-(3,4-dichlorophenyl)propan-2-amine | 2446132-79-0 |
| 1-(2-bromo-4-methylpheny1)-3-chloropropan-2-amine | 2446132-73-4 |
| 1-chloro-3-[4-(difluoromethyl)phenyl]propan-2-amine | 2446132-71-2 |
| 1-chloro-3-(2-cyclopropyl-4-methylphenyl)propan-2-amine hydrochloride (1:1) | 2446132-98-3 |
| 1-chloro-3-(2-cyclopropyl-4-methylphenyl)propan-2-amine | 2446132-97-2 |
| 1-chloro-3-(3,4-dichlorophenyl)propan-2-amine hydrochloride (1:1) | 2446132-80-3 |
| 1-chloro-3-(3,4-dichlorophenyl)propan-2-amine | 2446132-79-0 |
| 1-(2-bromo-4-methylphenyl)-3-chloropropan-2-amine hydrochloride (1:1) | 2446132-74-5 |
| 1-(2-bromo-4-methylphenyl)-3-chloropropan-2-amine | 2446132-73-4 |
| 1-chloro-3-[4-(difluoromethyl)phenyl]propan-2-amine hydrochloride (1:1) | 2446132-72-3 |
| 1-chloro-3-[4-(difluoromethyl)phenyl]propan-2-amine | 2446132-71-2 |
| 1-chloro-3-[4-(trifluoromethoxy)phenyl]propan-2-amine hydrochloride (1:1) | 2446132-68-7 |
| 1-chloro-3-[4-(trifluoromethoxy)phenyl]propan-2-amine | 2446132-67-6 |
| 3-amino-4-(2,4-dimethylphenyl)butanamide | 2446130-71-6 |
| 4-(2,4-dimethylphenyl)butane-1,3-diamine | 2446130-60-3 |

The present invention also relates to compounds of formula (10):

(10)

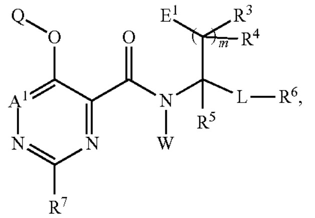

wherein $A^1$ is N or $CR^8$, wherein $R^1$ is hydrogen or halogen, m is 1 or 2, $R^3$ and $R^4$ are hydrogen, $R^5$ is hydrogen, L is a direct bond, carbonyl, $C_1$-$C_6$-alkylene, $C_2$-$C_6$-alkenylene, $C_2$-$C_6$-alkynylene, —C(═O)—$C_1$-$C_6$-alkylene-, —$C_1$-$C_6$-alkylene-C(═O)—, —$NR^{L1}$—, —$NR^{L2}$(C═O)—, —C(═O)$NR^{L3}$—, —$NR^{L4}$S(═O)$_2$—, —S(═O)$_2$$NR^{L5}$—, —C(═$NOR^{L6}$)—, —C(═N—N($R^{L7}$)$_2$), —C(═$NR^{L8}$)— or a group of formula

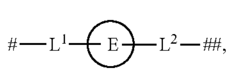

wherein said $C_1$-$C_6$-alkylene, $C_2$-$C_6$-alkenylene, $C_2$-$C_6$-alkynylene, —C(═O)—$C_1$-$C_6$-alkylene- and —$C_1$-$C_6$-alkylene-C(═O)— are optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl, $C_3$-$C_8$-cycloalkenyl and 3- to 7-membered heterocyclyl in turn are optionally substituted with one to three substituents $L^{SC}$, $R^{L1}$, $R^{L2}$, $R^{L3}$ and $R^{L4}$ are independently hydrogen or $C_1$-$C_6$-alkyl, $R^{L5}$, $R^{L6}$, $R^{L7}$ and $R^{L8}$ are independently hydrogen, $C_1$-$C_6$-alkyl, $C_1$-$C_6$-haloalkyl, $C_3$-$C_8$-cycloalkyl or $C_2$-$C_6$-alkenyl, $L^{SA}$ is independently halogen, cyano, hydroxyl, carboxyl, methylidene, halomethylidene, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$ or 3- to 7-membered heterocyclyl, or two substituents $L^{SA}$ that are bound to the same carbon atom form together with the carbon atom which they are attached to a $C_3$-$C_8$-cycloalkyl-ring or a 3- to 7-membered heterocyclyl-ring, $L^{Sc}$ is independently halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, and/or two $L^{Sc}$ substituents form together with the carbon atom to which they are attached to a $C_3$-$C_8$-cycloalkyl-ring, $R^6$ is $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl, 3- to 14-membered heterocyclylsulfonyl, $C_1$-$C_3$-alkoxy, $C_1$-$C_3$-haloalkoxy, $C_1$-$C_3$-alkylsulfanyl, $C_1$-$C_3$-alkylsulfinyl or $C_1$-$C_3$-alkylsulfonyl, wherein $C_1$-$C_3$-alkoxy, $C_1$-$C_3$-haloalkoxy, $C_1$-$C_3$-alkylsulfanyl, $C_1$-$C_3$-alkylsulfinyl and $C_1$-$C_3$-alkylsulfonyl are substituted with one substituent selected from the group consisting of $C_3$-$C_{12}$-carbocyclyl, $C_6$-$C_{14}$-aryl, 3- to 14-membered heterocyclyl and 5- to 14-membered heteroaryl, wherein said $C_3$-$C_{12}$-carbocyclyl, $C_6$-$C_{14}$-aryl, 3- to 14-membered heterocyclyl and 5- to 14-membered heteroaryl in turn are optionally substituted with one to four $R^{6S}$ substituents, wherein $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl and 3- to 14-membered heterocyclylsulfonyl are optionally substituted with one to four $R^{6S}$ substituents, wherein $R^{6S}$ is selected from the group consisting of halogen, cyano, isocyano, nitro, hydroxyl, mercapto, pentafluorosulfanyl, oxo, methylidene, halomethylidene, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, —$N(R^{15})_2$, —$O(C{=}O)R^{16}$, —$C({=}O)R^{16}$, —$C({=}O)(OR^{17})$, —$C({=}O)N(R^{18})_2$, —$S({=}O)_2N(R^{19})_2$, —O—Si($C_1$-$C_6$-alkyl)$_3$ or —Si($C_1$-$C_6$-alkyl)$_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, or two substituents $C_1$-$C_6$-alkyl attached to the same carbon atom from a $C_3$-$C_8$-cycloalkyl-ring, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and wherein $R^{15}$ is hydrogen, $C_1$-$C_6$-alkyl or $C_3$-$C_8$-cycloalkyl, wherein said $C_1$-$C_6$-alkyl is optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, and wherein said $C_3$-$C_8$-cycloalkyl is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl or $C_1$-$C_6$-haloalkyl are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, $R^7$ is hydrogen, halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy, —O—Si($C_1$-$C_6$-alkyl)$_3$, —Si($C_1$-$C_6$-alkyl)$_3$, —$N(R^{20})_2$, —$C({=}NR^{21})R^{22}$, —$NR^{23}C({=}O)R^{24}$, —$C({=}O)(OR^{25})$, —$C({=}O)N(R^{26})_2$, —$S({=}O)_2N(R^{27})_2$ or —$S({=}O)({=}NR^{28})R^{29}$, wherein $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are optionally substituted with one to three $R^{7Sa}$ substituents, wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy are optionally substituted with one to three $R^{7Sc}$ substituents, and wherein $R^{20}$ is hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_6$-$C_{14}$-aryl, 5- or 6-membered heteroaryl or 3- to 7-membered heterocyclyl, wherein $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl are optionally substituted with one to three substituents $R^{7Sa}$, and wherein $C_3$-$C_8$-cycloalkyl, $C_3$-$C_8$-halocycloalkyl, $C_6$-$C_{14}$-aryl, 5- or 6-membered heteroaryl and 3- to 7-membered heterocyclyl are optionally substituted with one to three substituents $R^{7Sc}$, $R^{21}$ and $R^{22}$ are independently hydroxyl, amino, cyano, $C_1$-$C_6$-alkyl, $C_1$-$C_6$-haloalkyl, $C_1$-$C_6$-alkoxy, mono-($C_1$-$C_6$-alkyl)amino or di-($C_1$-$C_6$-alkyl)amino, wherein $C_1$-$C_6$-alkyl, $C_1$-$C_6$-haloalkyl, $C_1$-$C_6$-alkoxy, mono-($C_1$-$C_6$-alkyl)amino and di-($C_1$-$C_6$-alkyl)amino are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_6$-alkyl, $C_1$-$C_6$-haloalkyl and $C_3$-$C_8$-cycloalkyl, wherein $C_1$-$C_6$-alkyl and $C_1$-$C_6$-haloalkyl are optionally substituted with one to three $R^{7Sa}$ substituents, and wherein $C_3$-$C_8$-cycloalkyl is optionally substituted with one to three $R^{7Sc}$ substituents, wherein $R^{7Sa}$ is independently cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$, —Si($C_1$-$C_6$-alkyl)$_3$, $C_6$-$C_{14}$-aryl or 3- to 7-membered heterocyclyl, $R^{7Sc}$ is independently halogen, cyano, nitro, hydroxyl, formyl, oxo, methylidene, halomethylidene, $C_1$-$C_6$-alkyl, $C_1$-$C_6$-haloalkyl $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, or two $R^{7Sc}$ substituents $C_1$-$C_6$-alkyl that are bound to the same carbon atom form together a $C_3$-$C_8$-cycloalkyl-ring, is $C_6$-$C_{14}$-aryl, $C_3$-$C_{12}$-carbocyclyl 3- to 14-membered heterocyclyl or 5- to 14-membered heteroaryl, wherein $C_6$-$C_{14}$-aryl, $C_3$-$C_{12}$-carbocyclyl 3- to 14-membered heterocyclyl or 5- to 14-membered heteroaryl are optionally substituted with one to five substituents $Q^S$ wherein $Q^S$ is independently selected from the group consisting of halogen, cyano, isocyano, nitro, hydroxyl, mercapto, formyl, carboxyl, $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyloxy, $C_3$-$C_6$-cycloalkenyl, 3- to 7-membered heterocyclyl, $C_6$-$C_{14}$-aryl, 5- to 14-membered heteroaryl, —O—Si($C_1$-$C_6$-alkyl)$_3$, —Si($C_1$-$C_6$-alkyl)$_3$, —O—C(═O)$R^{33}$, —$NR^{34}$C(═O)$R^{35}$, —C(═O)N($R^{36}$)$_2$, C(═S)$R^{37}$, —C(═S)N($R^{38}$)$_2$, —C(═$NR^{39}$)$R^{40}$, —C(═$NOR^{41}$)$R^{42}$ and —N($R^{43}$)$_2$, wherein said $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, said $C_3$-$C_8$-cycloalkyl, $C_3$-$C_8$-cycloalkoxy, $C_3$-$C_6$-cycloalkenyl, 3- to 7-membered heterocyclyl and 5- to 14-membered heteroaryl in turn are optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl, and wherein $R^{33}$ is hydrogen, $C_1$-$C_6$-alkyl, $C_1$-$C_6$-haloalkyl and $C_1$-$C_6$-alkoxy, $R^{34}$, $R^{35}$, $R^{36}$ $R^{37}$ $R^{38}$ $R^{39}$ $R^{40}$ $R^{41}$ and $R^{42}$ are independently hydrogen, $C_1$-$C_6$-alkyl, $C_1$-$C_6$-haloalkyl or $C_1$-$C_6$-alkoxy, wherein said $C_1$-$C_6$-alkyl, $C_1$-$C_6$-haloalkyl and $C_1$-$C_6$-alkoxy in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, and wherein $R^{43}$ is hydrogen, hydroxyl, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl or $C_3$-$C_8$-cycloalkyl, wherein said $C_1$-$C_6$-alkyl, $C_1$-$C_6$-haloalkyl, $C_1$-$C_6$-alkoxy, $C_2$-$C_6$-alkenyl and $C_2$-$C_6$-haloalkenyl in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, wherein said $C_3$-$C_8$-cycloalkyl in turn is optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl, $E^1$ is hydroxyl or halogen, W is hydrogen, tert-butoxycarbonyl, benzyl or (4-methoxyphenyl)methyl.

The present invention also relates to compounds of formula (11):

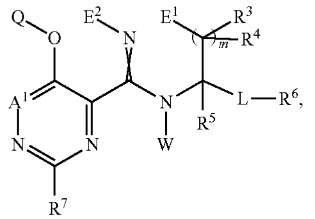

(11)

wherein $A^1$ is N or $CR^8$, wherein $R^1$ is hydrogen or halogen m is 1 or 2, $R^3$ and $R^4$ are independently hydrogen, halogen, cyano, hydroxyl, formyl, carboxyl, $C_1$-$C_6$-alkyl, $C_1$-$C_6$-alkoxy, $C_1$-$C_6$-alkylcarbonyl, $C_1$-$C_6$-alkoxycarbonyl, $C_2$-$C_6$-alkenyl, $C_2$-$C_6$-alkynyl, $C_3$-$C_8$-cycloalkyl, $C_6$-$C_{14}$-aryl, 5- to 14-membered heteroaryl, 3- to 14-membered heterocyclyl or —O—Si($C_1$-$C_6$-alkyl)$_3$, wherein $C_1$-$C_6$-alkyl, $C_1$-$C_6$-alkoxy, $C_1$-$C_6$-alkylcarbonyl, $C_1$-$C_6$-alkoxycarbonyl, $C_2$-$C_6$-alkenyl, $C_2$-$C_6$-alkynyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl, $C_6$-$C_{14}$-aryl, 5- to 14-membered heteroaryl and 3- to 14-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^4$ form together with the carbon atom to which they are attached to a carbonyl, a methylidene, a $C_3$-$C_8$-cycloalkyl-ring or a 3- to 7-membered heterocyclyl-ring, wherein $C_3$-$C_8$-cycloalkyl and 3- to 7-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, $R^5$ is hydrogen, hydroxyl, $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl, $C_3$-$C_8$-cycloalkyl or —O—Si($C_1$-$C_6$-alkyl)$_3$, wherein $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ or $R^4$, together with $R^5$ form together with the carbon atom to which they are attached to a $C_3$-$C_8$-cycloalkyl-ring, L is a direct bond, carbonyl, $C_1$-$C_6$-alkylene, $C_2$-$C_6$-alkenylene, $C_2$-$C_6$-alkynylene, —C(═O)—$C_1$-$C_6$-alkylene-, —$C_1$-$C_6$-alkylene-C(═O)—, —$NR^{L1}$—, —$NR^{L2}$(C═O)—, —C(═O)$NR^{L3}$—, —$NR^{L4}$S(═O)$_2$—, —S(═O)$_2NR^{L5}$—, —C(═$NOR^{L6}$)—, —C(═N—N($R^{L7}$)$_2$), —C(═$NR^{L8}$)— or a group of formula

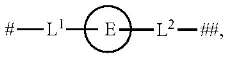

wherein said $C_1$-$C_6$-alkylene, $C_2$-$C_6$-alkenylene, $C_2$-$C_6$-alkynylene, —C(═O)—$C_1$-$C_6$-alkylene- and —$C_1$-$C_6$-alkylene-C(═O)— are optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl, $C_3$-$C_8$-cycloalkenyl and 3- to 7-membered heterocyclyl in turn are optionally substituted with one to three substituents $L^{SC}$, $R^{L1}$, $R^{L2}$, $R^{L3}$ and $R^{L4}$ are independently hydrogen or $C_1$-$C_6$-alkyl, $R^{L5}$, $R^{L6}$, $R^{L7}$ and $R^{L8}$ are independently hydrogen, $C_1$-$C_6$-alkyl, $C_1$-$C_6$-haloalkyl, $C_3$-$C_8$-cycloalkyl or $C_2$-$C_6$-alkenyl, $L^{SA}$ is independently halogen, cyano, hydroxyl, carboxyl, methylidene, halomethylidene, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$ or 3- to 7-membered heterocyclyl, or two substituents $L^{SA}$ that are bound to the same carbon atom form together with the carbon atom which they are attached to a $C_3$-$C_8$-cycloalkyl-ring or a 3- to 7-membered heterocyclyl-ring, $L^{Sc}$ is independently halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, and/or two $L^{Sc}$ substituents form together with the carbon atom to which they are attached to a $C_3$-$C_8$-cycloalkyl-ring, $R^6$ is $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl, 3- to 14-membered heterocyclylsulfonyl, $C_1$-$C_3$-alkoxy, $C_1$-$C_3$-haloalkoxy, $C_1$-$C_3$-alkylsulfanyl, $C_1$-$C_3$-alkylsulfinyl or $C_1$-$C_3$-alkylsulfonyl, wherein $C_1$-$C_3$-alkoxy, $C_1$-$C_3$-haloalkoxy, $C_1$-$C_3$-alkylsulfanyl, $C_1$-$C_3$-alkylsulfinyl and $C_1$-$C_3$-alkylsulfonyl are substituted with one substituent selected from the group consisting of $C_3$-$C_{12}$-carbocyclyl, $C_6$-$C_{14}$-aryl, 3- to 14-membered heterocyclyl and 5- to 14-membered heteroaryl, wherein said $C_3$-$C_{12}$-carbocyclyl, $C_6$-$C_{14}$-aryl, 3- to 14-membered heterocyclyl and 5- to 14-membered heteroaryl in turn are optionally substituted with one to four $R^{6S}$ substituents, wherein $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl and 3- to 14-membered heterocyclylsulfonyl are optionally substituted with one to four $R^{6S}$ substituents, wherein $R^{6S}$ is selected from the group consisting of halogen, cyano, isocyano, nitro, hydroxyl, mercapto, pentafluorosulfanyl, oxo, methylidene, halomethylidene, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, —N($R^{15}$)$_2$, —O(C═O)$R^{16}$, —C(═O)$R^{16}$, —C(═O)($OR^{17}$), —C(═O)N($R^{18}$)$_2$, —S(═O)$_2$N($R^{19}$)$_2$, —O—Si($C_1$-$C_6$-alkyl)$_3$ or —Si($C_1$-$C_6$-alkyl)$_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, or two substituents $C_1$-$C_6$-alkyl attached to the same carbon atom from a $C_3$-$C_8$-cycloalkyl-ring, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and wherein $R^{15}$ is hydrogen, $C_1$-$C_6$-alkyl or $C_3$-$C_8$-cycloalkyl, wherein said $C_1$-$C_6$-alkyl is optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, and wherein said $C_3$-$C_8$-cycloalkyl is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl or $C_1$-$C_6$-haloalkyl are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, $R^7$ is hydrogen, halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy, —O—Si($C_1$-$C_6$-alkyl)$_3$, —Si($C_1$-$C_6$-alkyl)$_3$, —N($R^{20}$)$_2$, —C(═N$R^{21}$)$R^{22}$, —N$R^{23}$C(═O)$R^{24}$, —C(═O)(O$R^{25}$), —C(═O)N($R^{26}$)$_2$, —S(═O)$_2$N($R^{27}$)$_2$ or —S(═O)(═N$R^{28}$)$R^{29}$, wherein $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are optionally substituted with one to three $R^{7Sa}$ substituents, wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy are optionally substituted with one to three $R^{7Sc}$ substituents, and wherein $R^{20}$ is hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_6$-$C_{14}$-aryl, 5- or 6-membered heteroaryl or 3- to 7-membered heterocyclyl, wherein $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl are optionally substituted with one to three substituents $R^{7Sa}$, and wherein $C_3$-$C_8$-cycloalkyl, $C_3$-$C_8$-halocycloalkyl, $C_6$-$C_{14}$-aryl, 5- or 6-membered heteroaryl and 3- to 7-membered heterocyclyl are optionally substituted with one to three substituents $R^{7Sc}$, $R^{21}$ and $R^{22}$ are independently hydroxyl, amino, cyano, $C_1$-$C_6$-alkyl, $C_1$-$C_6$-haloalkyl, $C_1$-$C_6$-alkoxy, mono-($C_1$-$C_6$-alkyl)amino or di-($C_1$-$C_6$-alkyl)amino, wherein $C_1$-$C_6$-alkyl, $C_1$-$C_6$-haloalkyl, $C_1$-$C_6$-alkoxy, mono-($C_1$-$C_6$-alkyl)amino and di-($C_1$-$C_6$-alkyl)amino are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_6$-alkyl, $C_1$-$C_6$-haloalkyl and $C_3$-$C_8$-cycloalkyl, wherein $C_1$-$C_6$-alkyl and $C_1$-$C_6$-haloalkyl are optionally substituted with one to three $R^{7Sa}$ substituents, and wherein $C_3$-$C_8$-cycloalkyl is optionally substituted with one to three $R^{7Sc}$ substituents, wherein $R^{7Sa}$ is independently cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$, —Si($C_1$-$C_6$-alkyl)$_3$, $C_6$-$C_{14}$-aryl or 3- to 7-membered heterocyclyl, $R^{7Sc}$ is independently halogen, cyano, nitro, hydroxyl, formyl, oxo, methylidene, halomethylidene, $C_1$-$C_6$-alkyl, $C_1$-$C_6$-haloalkyl $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, or two $R^{7Sc}$ substituents $C_1$-$C_6$-alkyl that are bound to the same carbon atom form together a $C_3$-$C_8$-cycloalkyl-ring, Q is $C_6$-$C_{14}$-aryl, $C_3$-$C_{12}$-carbocyclyl 3- to 14-membered heterocyclyl or 5- to 14-membered heteroaryl, wherein $C_6$-$C_{14}$-aryl, $C_3$-$C_{12}$-carbocyclyl 3- to 14-membered heterocyclyl or 5- to 14-membered heteroaryl are optionally substituted with one to five substituents $Q^S$ wherein $Q^S$ is independently selected from the group consisting of halogen, cyano, isocyano, nitro, hydroxyl, mercapto, formyl, carboxyl, $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyloxy, $C_3$-$C_6$-cycloalkenyl, 3- to 7-membered heterocyclyl, $C_6$-$C_{14}$-aryl, 5- to 14-membered heteroaryl, —O—Si($C_1$-$C_6$-alkyl$)_3$, —Si($C_1$-$C_6$-alkyl$)_3$, —O—C(═O)$R^{33}$, —$NR^{34}$C(═O)$R^{35}$, —C(═O)N($R^{36})_2$, C(═S)$R^{37}$, —C(═S)N($R^{38})_2$, —C(═$NR^{39}$)$R^{40}$, —C(═$NOR^{41}$)$R^{42}$ and —N($R^{43})_2$, wherein said $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl$)_3$ and —Si($C_1$-$C_6$-alkyl$)_3$ in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl$)_3$ and 3- to 7-membered heterocyclyl, said $C_3$-$C_8$-cycloalkyl, $C_3$-$C_8$-cycloalkoxy, $C_3$-$C_6$-cycloalkenyl, 3- to 7-membered heterocyclyl and 5- to 14-membered heteroaryl in turn are optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl, and wherein $R^{33}$ is hydrogen, $C_1$-$C_6$-alkyl, $C_1$-$C_6$-haloalkyl and $C_1$-$C_6$-alkoxy, $R^{34}$, $R^{35}$, $R^{36}$ $R^{37}$ $R^{38}$ $R^{39}$ $R^{40}$ $R^{41}$ and $R^{42}$ are independently hydrogen, $C_1$-$C_6$-alkyl, $C_1$-$C_6$-haloalkyl or $C_1$-$C_6$-alkoxy, wherein said $C_1$-$C_6$-alkyl, $C_1$-$C_6$-haloalkyl and $C_1$-$C_6$-alkoxy in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl$)_3$ and 3- to 7-membered heterocyclyl, and wherein $R^{43}$ is hydrogen, hydroxyl, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl or $C_3$-$C_8$-cycloalkyl, wherein said $C_1$-$C_6$-alkyl, $C_1$-$C_6$-haloalkyl, $C_1$-$C_6$-alkoxy, $C_2$-$C_6$-alkenyl and $C_2$-$C_6$-haloalkenyl in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl$)_3$ and 3- to 7-membered heterocyclyl, wherein said $C_3$-$C_8$-cycloalkyl in turn is optionally substituted with one to three substituents independently selected from the group consisting of halogen, cyano, amino, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl, $E^1$ is hydroxyl or halogen, $E^2$ is hydroxyl or amino, W is hydrogen, tert-butoxycarbonyl, benzyl or (4-methoxyphenyl)methyl.

The present invention also relates to compounds of formula (12):

(12)

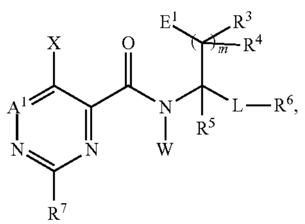

wherein $A^1$ is N or $CR^8$ wherein $R^8$ is hydrogen or halogen, m is 1 or 2, $R^3$ and $R^4$ are hydrogen, $R^5$ is hydrogen, L is a direct bond, carbonyl, $C_1$-$C_6$-alkylene, $C_2$-$C_6$-alkenylene, $C_2$-$C_6$-alkynylene, —C(═O)—$C_1$-$C_6$-alkylene-, —$C_1$-$C_6$-alkylene-C(═O)—, —$NR^{L1}$—, —$NR^{L2}$(C═O)—, —C(═O)$NR^{L3}$—, —$NR^{L4}$S(═O)$_2$—, —S(═O)$_2NR^{L5}$—, —C(═$NOR^{L6}$)$_3$, —C(═N—N($R^{L7}$)$_2$), —C(═$NR^{L8}$)— or a group of formula

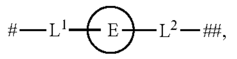

wherein said $C_1$-$C_6$-alkylene, $C_2$-$C_6$-alkenylene, $C_2$-$C_6$-alkynylene, —C(═O)—$C_1$-$C_6$-alkylene- and —$C_1$-$C_6$-alkylene-C(═O)— are optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl, $C_3$-$C_8$-cycloalkenyl and 3- to 7-membered heterocyclyl in turn are optionally substituted with one to three substituents $L^{SC}$, $R^{L1}$, $R^{L2}$, $R^{L3}$ and $R^{L4}$ are independently hydrogen or $C_1$-$C_6$-alkyl, $R^{L5}$, $R^{L6}$, $R^{L7}$ and $R^{L8}$ are independently hydrogen, $C_1$-$C_6$-alkyl, $C_1$-$C_6$-haloalkyl, $C_3$-$C_8$-cycloalkyl or $C_2$-$C_6$-alkenyl, $L^{SA}$ is independently halogen, cyano, hydroxyl, carboxyl, methylidene, halomethylidene, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$ or 3- to 7-membered heterocyclyl, or two substituents $L^{SA}$ that are bound to the same carbon atom form together with the carbon atom which they are attached to a $C_3$-$C_8$-cycloalkyl-ring or a 3- to 7-membered heterocyclyl-ring, $L^{Sc}$ is independently halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, and/or two $L^{Sc}$ substituents form together with the carbon atom to which they are attached to a $C_3$-$C_8$-cycloalkyl-ring, $R^6$ is $C_7$-$C_{12}$-carbocyclyl, $C_6$-$C_{14}$-aryl or 7- to 14-membered heterocyclyl, wherein $C_7$-$C_{12}$-carbocyclyl, $C_6$-$C_{14}$-aryl and 7- to 14-membered heterocyclyl are optionally substituted with one to four $R^{6S}$ substituents, wherein $R^{6S}$ is selected from the group consisting of halogen, cyano, isocyano, nitro, hydroxyl, mercapto, pentafluorosulfanyl, oxo, methylidene, halomethylidene, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, —N($R^{15}$)$_2$, —O(C═O)$R^{16}$, —C(═O)$R^{16}$, —C(═O)($OR^{17}$), —C(═O)N($R^{18}$)$_2$, —S(═O)$_2$N($R^{19}$)$_2$, —O—Si($C_1$-$C_6$-alkyl)$_3$ or —Si($C_1$-$C_6$-alkyl)$_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, or two substituents $C_1$-$C_6$-alkyl attached to the same carbon atom from a $C_3$-$C_8$-cycloalkyl-ring, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and wherein $R^{15}$ is hydrogen, $C_1$-$C_6$-alkyl or $C_3$-$C_8$-cycloalkyl, wherein said $C_1$-$C_6$-alkyl is optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, and wherein said $C_3$-$C_8$-cycloalkyl is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl or $C_1$-$C_6$-haloalkyl are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, $R^7$ is hydrogen, halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy, —O—Si($C_1$-$C_6$-alkyl)$_3$, —Si($C_1$-$C_6$-alkyl)$_3$, —N($R^{20}$)$_2$, —C(═N$R^{21}$)$R^{22}$, —N$R^{23}$C(═O)$R^{24}$, —C(═O)(O$R^{25}$), —C(═O)N($R^{26}$)$_2$, —S(═O)$_2$N($R^{27}$)$_2$ or —S(═O)(═N$R^{28}$)$R^{29}$, wherein $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are optionally substituted with one to three $R^{7Sa}$ substituents, wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy are optionally substituted with one to three $R^{7Sc}$ substituents, and wherein $R^{20}$ is hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_6$-$C_{14}$-aryl, 5- or 6-membered heteroaryl or 3- to 7-membered heterocyclyl, wherein $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl are optionally substituted with one to three substituents $R^{7Sa}$, and wherein $C_3$-$C_8$-cycloalkyl, $C_3$-$C_8$-halocycloalkyl, $C_6$-$C_{14}$-aryl, 5- or 6-membered heteroaryl and 3- to 7-membered heterocyclyl are optionally substituted with one to three substituents $R^{7Sc}$, $R^{21}$ and $R^{22}$ are independently hydroxyl, amino, cyano, $C_1$-$C_6$-alkyl, $C_1$-$C_6$-haloalkyl, $C_1$-$C_6$-alkoxy, mono-($C_1$-$C_6$-alkyl)amino or di-($C_1$-$C_6$-alkyl)amino, wherein $C_1$-$C_6$-alkyl, $C_1$-$C_6$-haloalkyl, $C_1$-$C_6$-alkoxy, mono-($C_1$-$C_6$-alkyl)amino and di-($C_1$-$C_6$-alkyl)amino are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_6$-alkyl, $C_1$-$C_6$-haloalkyl and $C_3$-$C_8$-cycloalkyl, wherein $C_1$-$C_6$-alkyl and $C_1$-$C_6$-haloalkyl are optionally substituted with one to three $R^{7Sa}$ substituents, and wherein $C_3$-$C_8$-cycloalkyl is optionally substituted with one to three $R^{7Sc}$ substituents, wherein $R^{7Sa}$ is independently cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$, —Si($C_1$-$C_6$-alkyl)$_3$, $C_6$-$C_{14}$-aryl or 3- to 7-membered heterocyclyl, $R^{7Sc}$ is independently halogen, cyano, nitro, hydroxyl, formyl, oxo, methylidene, halomethylidene, $C_1$-$C_6$-alkyl, $C_1$-$C_6$-haloalkyl $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, or two $R^{7Sc}$ substituents $C_1$-$C_6$-alkyl that are bound to the same carbon atom form together a $C_3$-$C_8$-cycloalkyl-ring, X is halogen, $E^1$ is hydroxyl or halogen, W is hydrogen, tert-butoxycarbonyl, benzyl or (4-methoxyphenyl)methyl, provided that the compound of formula (12) preferably is not:

| | |
|---|---|
| 5-bromo-2-cyclopropyl-N-[1-(2-fluorophenyl)-3-hydroxypropyl]pyrimidine-4-carboxamide | 2249230-71-3 |
| 5-chloro-N-(3-hydroxy-1-phenylpropyl)-2-isopropyl-N-methylpyrimidine-4-carboxamide | 2071583-58-7 |
| 5-chloro-N-(3-hydroxy-1-phenylpropyl)-2-methylpyrimidine-4-carboxamide | 2069692-16-4 |
| 5-chloro-N-(3-hydroxy-1-phenylpropyl)-2-isopropylpyrimidine-4-carboxamide | 2069116-82-9 |
| 5-chloro-N-(3-hydroxy-1-phenylpropyl)pyrimidine-4-carboxamide | 2062363-89-5 |
| 5-chloro-N-(3-hydroxy-1-phenylpropyl)-N-methylpyrimidine-4-carboxamide | 2059513-53-8 |
| 5-chloro-N-[2-fluoro-1-(2-methylphenyl)ethyl]-2-isopropylpyrimidine-4-carboxamide | 2471404-71-2 |
| 5-chloro-2-ethyl-N-[2-fluoro-1-(2-methylphenyl)ethyl]pyrimidine-4-carboxamide | 2403155-96-2 |
| 5-chloro-N-[(1R)-1-(4-chlorophenyl)-2-hydroxyethyl]-2-ethylpyrimidine-4- | 2398016-15-2 |

-continued

| | |
|---|---|
| carboxamide | |
| 5-chloro-2-ethyl-N-[2-fluoro-1-(4-fluorophenyl)ethyl]pyrimidine-4-carboxamide | 2393328-52-2 |
| 5-chloro-2-ethyl-N-[2-hydroxy-1-(2-methylphenyl)ethyl]-N-methylpyrimidine-4-carboxamide | 2393093-78-0 |
| 5-chloro-N-[2-fluoro-1-(2-methylphenyl)ethyl]-2-methylpyrimidine-4-carboxamide | 2371110-21-1 |
| 5-chloro-N-(2-hydroxy-1-phenylethyl)-2-isopropylpyrimidine-4-carboxamide | 2068919-96-8 |
| 5-chloro-N-[2-hydroxy-1-(3,4,5-trifluorophenyl)ethyl]pyrimidine-4-carboxamide | 2060969-43-7 |
| 5-chloro-N-[1-(4-ethylphenyl)-2-hydroxyethyl]-2-methylpyrimidine-4-carboxamide | 2060546-01-0 |
| 5-chloro-N-[(1S)-2-hydroxy-1-phenylethyl]-2-methylpyrimidine-4-carboxamide | 2060348-97-0 |
| 5-chloro-N-[1-(4-ethylphenyl)-2-hydroxyethyl]pyrimidine-4-carboxamide | 2059923-55-4 |
| 5-chloro-N-[(1R)-2-hydroxy-1-phenylethyl]-2-(methylsulfanyl)pyrimidine-4-carboxamide | 1920522-99-1 |
| 5-chloro-N-[(1S)-2-hydroxy-1-phenylethyl]-2-(methylsulfanyl)pyrimidine-4-carboxamide | 1912038-17-5 |
| 5-chloro-N-(2-hydroxy-1-phenylethyl)-2-(methylsulfanyl)pyrimidine-4-carboxamide | 1493243-27-8 |

The present invention also relates to compounds of formula (13):

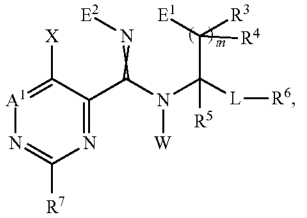

(13)

wherein $A^1$ is N or $CR^8$ wherein $R^8$ is hydrogen or halogen, m is 1 or 2, $R^3$ and $R^4$ are independently hydrogen, halogen, cyano, hydroxyl, formyl, carboxyl, $C_1$-$C_6$-alkyl, $C_1$-$C_6$-alkoxy, $C_1$-$C_6$-alkylcarbonyl, $C_1$-$C_6$-alkoxycarbonyl, $C_2$-$C_6$-alkenyl, $C_2$-$C_6$-alkynyl, $C_3$-$C_8$-cycloalkyl, $C_6$-$C_{14}$-aryl, 5- to 14-membered heteroaryl, 3- to 14-membered heterocyclyl or —O—Si($C_1$-$C_6$-alkyl$)_3$, wherein $C_1$-$C_6$-alkyl, $C_1$-$C_6$-alkoxy, $C_1$-$C_6$-alkylcarbonyl, $C_1$-$C_6$-alkoxycarbonyl, $C_2$-$C_6$-alkenyl, $C_2$-$C_6$-alkynyl and —O—Si($C_1$-$C_6$-alkyl$)_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl$)_3$ and 3- to 7-membered heterocyclyl, and wherein $C_3$-$C_8$-cycloalkyl, $C_6$-$C_{14}$-aryl, 5- to 14-membered heteroaryl and 3- to 14-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl$)_3$ and 3- to 7-membered heterocyclyl, or $R^3$ and $R^4$ form together with the carbon atom to which they are attached to a carbonyl, a methylidene, a $C_3$-$C_8$-cycloalkyl-ring or a 3- to 7-membered heterocyclyl-ring, wherein $C_3$-$C_8$-cycloalkyl and 3- to 7-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl$)_3$ and 3- to 7-membered heterocyclyl, $R^5$ is hydrogen, hydroxyl, $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl, $C_3$-$C_8$-cycloalkyl or —O—Si($C_1$-$C_6$-alkyl$)_3$, wherein $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl and —O—Si($C_1$-$C_6$-alkyl$)_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl$)_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl$)_3$ and 3- to 7-membered heterocyclyl, or $R^3$ or $R^4$, together with $R^5$ form together with the carbon atom to which they are attached to a $C_3$-$C_8$-cycloalkyl-ring, L is a direct bond, carbonyl, $C_1$-$C_6$-alkylene, $C_2$-$C_6$-alkenylene, $C_2$-$C_6$-alkynylene, —C(═O)—$C_1$-$C_6$-alkylene-, —$C_1$-$C_6$-alkylene-C(═O)—, —$NR^{L1}$—, —$NR^{L2}$(C═O)—, —C(═O)$NR^{L3}$—, —$NR^{L4}$S(═O$)_2$—, —S(═O$)_2NR^{L5}$—, —C(═$NOR^{L6}$)—, —C(═N—N($R^{L7})_2$), —C(═$NR^{L8}$)— or a group of formula

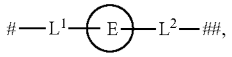

wherein said $C_1$-$C_6$-alkylene, $C_2$-$C_6$-alkenylene, $C_2$-$C_6$-alkynylene, —C(═O)—$C_1$-$C_6$-alkylene- and —$C_1$-$C_6$- alkylene-C(=O)— are optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl, $C_3$-$C_8$-cycloalkenyl and 3- to 7-membered heterocyclyl in turn are optionally substituted with one to three substituents $L^{SC}$, $R^{L1}$, $R^{L2}$, $R^{L3}$ and $R^{L4}$ are independently hydrogen or $C_1$-$C_6$-alkyl, $R^{L5}$, $R^{L6}$, $R^{L7}$ and $R^{L8}$ are independently hydrogen, $C_1$-$C_6$-alkyl, $C_1$-$C_6$-haloalkyl, $C_3$-$C_8$-cycloalkyl or $C_2$-$C_6$-alkenyl, $L^{SA}$ is independently halogen, cyano, hydroxyl, carboxyl, methylidene, halomethylidene, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$ or 3- to 7-membered heterocyclyl, or two substituents $L^{SA}$ that are bound to the same carbon atom form together with the carbon atom which they are attached to a $C_3$-$C_8$-cycloalkyl-ring or a 3- to 7-membered heterocyclyl-ring, $L^{Sc}$ is independently halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, and/or two $L^{Sc}$ substituents form together with the carbon atom to which they are attached to a $C_3$-$C_8$-cycloalkyl-ring, $R^6$ is $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl, 3- to 14-membered heterocyclylsulfonyl, $C_1$-$C_3$-alkoxy, $C_1$-$C_3$-haloalkoxy, $C_1$-$C_3$-alkylsulfanyl, $C_1$-$C_3$-alkylsulfinyl or $C_1$-$C_3$-alkylsulfonyl, wherein $C_1$-$C_3$-alkoxy, $C_1$-$C_3$-haloalkoxy, $C_1$-$C_3$-alkylsulfanyl, $C_1$-$C_3$-alkylsulfinyl and $C_1$-$C_3$-alkylsulfonyl are substituted with one substituent selected from the group consisting of $C_3$-$C_{12}$-carbocyclyl, $C_6$-$C_{14}$-aryl, 3- to 14-membered heterocyclyl and 5- to 14-membered heteroaryl, wherein said $C_3$-$C_{12}$-carbocyclyl, $C_6$-$C_{14}$-aryl, 3- to 14-membered heterocyclyl and 5- to 14-membered heteroaryl in turn are optionally substituted with one to four $R^{6S}$ substituents, wherein $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl and 3- to 14-membered heterocyclylsulfonyl are optionally substituted with one to four $R^{6S}$ substituents, wherein $R^{6S}$ is selected from the group consisting of halogen, cyano, isocyano, nitro, hydroxyl, mercapto, pentafluorosulfanyl, oxo, methylidene, halomethylidene, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, —N($R^{15}$)$_2$, —O(C=O)$R^{16}$, —C(=O)$R^{16}$, —C(=O)(O$R^{17}$), —C(=O)N($R^{18}$)$_2$, —S(=O)$_2$N($R^{19}$)$_2$, —O—Si($C_1$-$C_6$-alkyl)$_3$ or —Si($C_1$-$C_6$-alkyl)$_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, or two substituents $C_1$-$C_6$-alkyl attached to the same carbon atom from a $C_3$-$C_8$-cycloalkyl-ring, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and wherein $R^{15}$ is hydrogen, $C_1$-$C_6$-alkyl or $C_3$-$C_8$-cycloalkyl, wherein said $C_1$-$C_6$-alkyl is optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, and wherein said $C_3$-$C_8$-cycloalkyl is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl or $C_1$-$C_6$-haloalkyl are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, $R^7$ is hydrogen, halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy, —O—Si($C_1$-$C_6$-alkyl)$_3$, —Si($C_1$-$C_6$-alkyl)$_3$, —N($R^{20}$)$_2$, —C(=N$R^{21}$)$R^{22}$, —N$R^{23}$C(=O)$R^{24}$, —C(=O)(O$R^{25}$), —C(=O)N($R^{26}$)$_2$, —S(=O)$_2$N($R^{27}$)$_2$ or —S(=O)(=N$R^{28}$)$R^{29}$, wherein $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are optionally substituted with one to three $R^{7Sa}$ substituents, wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy are optionally substituted with one to three $R^{7Sc}$ substituents, and wherein $R^{20}$ is hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_6$-$C_{14}$-aryl, 5- or 6-membered heteroaryl or 3- to 7-membered heterocyclyl, wherein $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl are optionally substituted with one to three substituents $R^{7Sa}$, and wherein $C_3$-$C_8$-cycloalkyl, $C_3$-$C_8$-halocycloalkyl, $C_6$-$C_{14}$-aryl, 5- or 6-membered heteroaryl and 3- to 7-membered heterocyclyl are optionally substituted with one to three substituents $R^{7Sc}$, $R^{21}$ and $R^{22}$ are independently hydroxyl, amino, cyano, $C_1$-$C_6$-alkyl, $C_1$-$C_6$-haloalkyl, $C_1$-$C_6$-alkoxy, mono-($C_1$-$C_6$-alkyl)amino or di-($C_1$-$C_6$-alkyl)amino, wherein $C_1$-$C_6$-alkyl, $C_1$-$C_6$-haloalkyl, $C_1$-$C_6$-alkoxy, mono-($C_1$-$C_6$-alkyl)amino and di-($C_1$-$C_6$-alkyl)amino are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_6$-alkyl, $C_1$-$C_6$-haloalkyl and $C_3$-$C_8$-cycloalkyl, wherein $C_1$-$C_6$-alkyl and $C_1$-$C_6$-haloalkyl are optionally substituted with one to three $R^{7Sa}$ substituents, and wherein $C_3$-$C_8$-cycloalkyl is optionally substituted with one to three $R^{7Sc}$ substituents, wherein $R^{7Sa}$ is independently cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$, —Si($C_1$-$C_6$-alkyl)$_3$, $C_6$-$C_{14}$-aryl or 3- to 7-membered heterocyclyl, $R^{7Sc}$ is independently halogen, cyano, nitro, hydroxyl, formyl, oxo, methylidene, halomethylidene, $C_1$-$C_6$-alkyl, $C_1$-$C_6$-haloalkyl $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, or two $R^{7Sc}$ substituents $C_1$-$C_6$-alkyl that are bound to the same carbon atom form together a $C_3$-$C_8$-cycloalkyl-ring, X is halogen, $E^1$ is hydroxyl or halogen, $E^2$ is hydroxyl or amino, W is hydrogen, tert-butoxycarbonyl, benzyl or (4-methoxyphenyl)methyl.

The present invention also relates to compounds of formula (14):

(14)

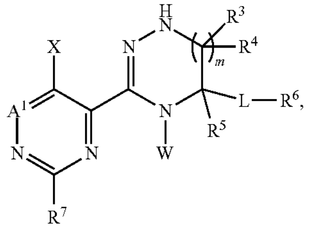

wherein $A^1$ is N or $CR^8$ wherein $R^8$ is hydrogen or halogen, m is 1 or 2, $R^3$ and $R^4$ are independently hydrogen, halogen, cyano, hydroxyl, formyl, carboxyl, $C_1$-$C_6$-alkyl, $C_1$-$C_6$-alkoxy, $C_1$-$C_6$-alkylcarbonyl, $C_1$-$C_6$-alkoxycarbonyl, $C_2$-$C_6$-alkenyl, $C_2$-$C_6$-alkynyl, $C_3$-$C_8$-cycloalkyl, $C_6$-$C_{14}$-aryl, 5- to 14-membered heteroaryl, 3- to 14-membered heterocyclyl or —O—Si($C_1$-$C_6$-alkyl)$_3$, wherein $C_1$-$C_6$-alkyl, $C_1$-$C_6$-alkoxy, $C_1$-$C_6$-alkylcarbonyl, $C_1$-$C_6$-alkoxycarbonyl, $C_2$-$C_6$-alkenyl, $C_2$-$C_6$-alkynyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl, $C_6$-$C_{14}$-aryl, 5- to 14-membered heteroaryl and 3- to 14-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^4$ form together with the carbon atom to which they are attached to a carbonyl, a methylidene, a $C_3$-$C_8$-cycloalkyl-ring or a 3- to 7-membered heterocyclyl-ring, wherein $C_3$-$C_8$-cycloalkyl and 3- to 7-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, $R^5$ is hydrogen, hydroxyl, $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl, $C_3$-$C_8$-cycloalkyl or —O—Si($C_1$-$C_6$-alkyl)$_3$, wherein $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ or $R^4$, together with $R^5$ form together with the carbon atom to which they are attached to a $C_3$-$C_8$-cycloalkyl-ring, L is a direct bond, carbonyl, $C_1$-$C_6$-alkylene, $C_2$-$C_6$-alkenylene, $C_2$-$C_6$-alkynylene, —C(═O)—$C_1$-$C_6$-alkylene-, —$C_1$-$C_6$-alkylene-C(═O)—, —$NR^{L1}$—, —$NR^{L2}$(C═O)—, —C(═O)$NR^{L3}$—, —$NR^{L4}$S(═O)$_2$—, —S(═O)$_2NR^{L5}$—, —C(═$NOR^{L6}$)—, —C(═N—N($R^{L7}$)$_2$), —C(═$NR^{L8}$)— or a group of formula

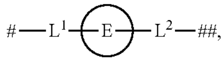

wherein said $C_1$-$C_6$-alkylene, $C_2$-$C_6$-alkenylene, $C_2$-$C_6$-alkynylene, —C(═O)—$C_1$-$C_6$-alkylene- and —$C_1$-$C_6$-alkylene-C(═O)— are optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl, $C_3$-$C_8$-cycloalkenyl and 3- to 7-membered heterocyclyl in turn are optionally substituted with one to three substituents $L^{SC}$, $R^{L1}$, $R^{L2}$, $R^{L3}$ and $R^{L4}$ are independently hydrogen or $C_1$-$C_6$-alkyl, $R^{L5}$, $R^{L6}$, $R^{L7}$ and $R^{L8}$ are independently hydrogen, $C_1$-$C_6$-alkyl, $C_1$-$C_6$-haloalkyl, $C_3$-$C_8$-cycloalkyl or $C_2$-$C_6$-alkenyl, $L^{SA}$ is independently halogen, cyano, hydroxyl, carboxyl, methylidene, halomethylidene, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$ or 3- to 7-membered heterocyclyl, or two substituents $L^{SA}$ that are bound to the same carbon atom form together with the carbon atom which they are attached to a $C_3$-$C_8$-cycloalkyl-ring or a 3- to 7-membered heterocyclyl-ring, $L^{Sc}$ is independently halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, and/or two $L^{Sc}$ substituents form together with the carbon atom to which they are attached to a $C_3$-$C_8$-cycloalkyl-ring, $R^6$ is $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl, 3- to 14-membered heterocyclylsulfonyl, $C_1$-$C_3$-alkoxy, $C_1$-$C_3$-haloalkoxy, $C_1$-$C_3$-alkylsulfanyl, $C_1$-$C_3$-alkylsulfinyl or $C_1$-$C_3$-alkylsulfonyl, wherein $C_1$-$C_3$-alkoxy, $C_1$-$C_3$-haloalkoxy, $C_1$-$C_3$-alkylsulfanyl, $C_1$-$C_3$-alkylsulfinyl and $C_1$-$C_3$-alkylsulfonyl are substituted with one substituent selected from the group consisting of $C_3$-$C_{12}$-carbocyclyl, $C_6$-$C_{14}$-aryl, 3- to 14-membered heterocyclyl and 5- to 14-membered heteroaryl, wherein said $C_3$-$C_{12}$-carbocyclyl, $C_6$-$C_{14}$-aryl, 3- to 14-membered heterocyclyl and 5- to 14-membered heteroaryl in turn are optionally substituted with one to four $R^{6S}$ substituents, wherein $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl and 3- to 14-membered heterocyclylsulfonyl are optionally substituted with one to four $R^{6S}$ substituents, wherein $R^{6S}$ is selected from the group consisting of halogen, cyano, isocyano, nitro, hydroxyl, mercapto, pentafluorosulfanyl, oxo, methylidene, halomethylidene, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, —$N(R^{15})_2$, —$O(C{=}O)R^{16}$, —$C({=}O)R^{16}$, —$C({=}O)(OR^{17})$, —$C({=}O)N(R^{18})_2$, —$S({=}O)_2N(R^{19})_2$, —O—Si($C_1$-$C_6$-alkyl$)_3$ or —Si($C_1$-$C_6$-alkyl$)_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl$)_3$ and —Si($C_1$-$C_6$-alkyl$)_3$ are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl$)_3$, —Si($C_1$-$C_6$-alkyl$)_3$, $C_3$-$C_8$-cycloalkyl, $C_3$-$C_8$-halocycloalkyl and 3- to 7-membered heterocyclyl, or two substituents $C_1$-$C_6$-alkyl attached to the same carbon atom from a $C_3$-$C_8$-cycloalkyl-ring, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, and wherein $R^{15}$ is hydrogen, $C_1$-$C_6$-alkyl or $C_3$-$C_8$-cycloalkyl, wherein said $C_1$-$C_6$-alkyl is optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl$)_3$, —Si($C_1$-$C_6$-alkyl$)_3$, $C_3$-$C_8$-cycloalkyl, $C_3$-$C_8$-halocycloalkyl and 3- to 7-membered heterocyclyl, and wherein said $C_3$-$C_8$-cycloalkyl is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halocycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl or $C_1$-$C_6$-haloalkyl are furthermore optionally substituted with one to three substituents independently selected from the group consisting of cyano, hydroxyl, $C_1$-$C_6$-alkoxy, $C_1$-$C_6$-haloalkoxy, —O—Si($C_1$-$C_6$-alkyl$)_3$, —Si($C_1$-$C_6$-alkyl$)_3$, $C_3$-$C_8$-cycloalkyl, $C_3$-$C_8$-halocycloalkyl and 3- to 7-membered heterocyclyl, $R^7$ is hydrogen, halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cycloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy, —O—Si($C_1$-$C_6$-alkyl$)_3$, —Si($C_1$-$C_6$-alkyl$)_3$, —$N(R^{20})_2$, —$C({=}NR^{21})R^{22}$, —$NR^{23}C$ (=O)$R^{24}$, —C(=O)(O$R^{25}$), —C(=O)N($R^{26}$)$_2$, —S(=O)$_2$N($R^{27}$)$_2$ or —S(=O)(=N$R^{28}$)$R^{29}$, wherein $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are optionally substituted with one to three $R^{7Sa}$ substituents, wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy are optionally substituted with one to three $R^{7Sc}$ substituents, and wherein $R^{20}$ is hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_6$-$C_{14}$-aryl, 5- or 6-membered heteroaryl or 3- to 7-membered heterocyclyl, wherein $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl are optionally substituted with one to three substituents $R^{7Sa}$, and wherein $C_3$-$C_8$-cycloalkyl, $C_3$-$C_8$-halocycloalkyl, $C_6$-$C_{14}$-aryl, 5- or 6-membered heteroaryl and 3- to 7-membered heterocyclyl are optionally substituted with one to three substituents $R^{7Sc}$, $R^{21}$ and $R^{22}$ are independently hydroxyl, amino, cyano, $C_1$-$C_6$-alkyl, $C_1$-$C_6$-haloalkyl, $C_1$-$C_6$-alkoxy, mono-($C_1$-$C_6$-alkyl)amino or di-($C_1$-$C_6$-alkyl)amino, wherein $C_1$-$C_6$-alkyl, $C_1$-$C_6$-haloalkyl, $C_1$-$C_6$-alkoxy, mono-($C_1$-$C_6$-alkyl)amino and di-($C_1$-$C_6$-alkyl)amino are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_6$-alkyl, $C_1$-$C_6$-haloalkyl and $C_3$-$C_8$-cycloalkyl, wherein $C_1$-$C_6$-alkyl and $C_1$-$C_6$-haloalkyl are optionally substituted with one to three $R^{7Sa}$ substituents, and wherein $C_3$-$C_8$-cycloalkyl is optionally substituted with one to three $R^{7Sc}$ substituents, wherein $R^{7Sa}$ is independently cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$, —Si($C_1$-$C_6$-alkyl)$_3$, $C_6$-$C_{14}$-aryl or 3- to 7-membered heterocyclyl, $R^{7Sc}$ is independently halogen, cyano, nitro, hydroxyl, formyl, oxo, methylidene, halomethylidene, $C_1$-$C_6$-alkyl, $C_1$-$C_6$-haloalkyl $C_1$-$C_6$-alkoxy, $C_1$-$C_6$-haloalkoxy, $C_2$-$C_6$ alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, or two $R^{7Sc}$ substituents $C_1$-$C_6$-alkyl that are bound to the same carbon atom form together a $C_3$-$C_8$-cycloalkyl-ring, X is halogen, W is hydrogen, tert-butoxycarbonyl, benzyl or (4-methoxyphenyl)methyl.

The present invention also relates to intermediates of formula (8):

Q-OH (8), wherein

Q is a group of formula

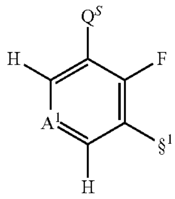

wherein

§ [1] is the point of attachment to oxygen, $A^1$ is CH or N, $Q^S$ is $C_3$-$C_4$-cycloalkyl, $C_3$-$C_8$-halocycloalkyl, $C_2$-$C_6$-alkenyl, $C_2$-$C_6$-haloalkenyl or $C_2$-$C_6$-alkynyl, provided that the compound of formula (8) does not represent:

| | |
|---|---|
| 2-fluoro-3-(3,3,3-trifluoroprop-1-en-2-yl)phenol | 2168012-00-6 |
| 3-(1-ethoxyvinyl)-2-fluorophenol | 2137960-04-2 |
| 1-(2-fluoro-3-hydroxyphenyl)cyclopropanecarbonitrile | 1881320-49-5 |
| 3-(1-aminocyclopropyl)-2-fluorophenol | 1785193-75-0 |
| 1-(2-fluoro-3-hydroxyphenyl)cyclopropanecarboxylic acid | 1507131-96-5 |
| 2-fluoro-3-(prop-1-en-2-yl)phenol | 1375066-38-8 |
| 3-cyclopropyl-2-fluoro-phenol | 2290421-25-7 |
| 2-fluoro-3-(1-fluorocyclopropyl)phenol | 2385918-06-7 |
| 3-(2,2-difluorocyclopropyl)-2-fluoro-phenol | 2435608-24-3 |
| 2-fluoro-3-vinyl-phenol | 2290411-18-4 |
| 2-fluoro-3-[(E)-prop-1-enyl]phenol | 2435608-23-2 |
| 2-fluoro-3-isopropenyl-phenol | 1375066-38-8 |
| 3-ethyl-2-fluoro-phenol | 1243456-02-1 |
| 2-fluoro-3-propyl-phenol | 2284409-52-3 |
| 3-butyl-2-fluoro-phenol | 2284271-78-7 |

Compositions and Formulations

The present invention further relates to compositions, in particular compositions for controlling unwanted microorganisms. The composition may be applied to the microorganisms and/or in their habitat.

The composition comprises at least one compound of formula (I) and at least one agriculturally suitable auxiliary, e.g. carrier(s) and/or surfactant(s).

A carrier is a solid or liquid, natural or synthetic, organic or inorganic substance that is generally inert. The carrier generally improves the application of the compounds, for instance, to plants, plants parts or seeds. Examples of suitable solid carriers include, but are not limited to, ammonium salts, in particular ammonium sulfates, ammonium phosphates and ammonium nitrates, natural rock flours, such as kaolins, clays, talc, chalk, quartz, attapulgite, montmorillonite and diatomaceous earth, silica gel and synthetic rock flours, such as finely divided silica, alumina and silicates. Examples of typically useful solid carriers for preparing granules include, but are not limited to crushed and fractionated natural rocks such as calcite, marble, pumice, sepiolite and dolomite, synthetic granules of inorganic and organic flours and granules of organic material such as paper, sawdust, coconut shells, maize cobs and tobacco stalks. Examples of suitable liquid carriers include, but are not limited to, water, organic solvents and combinations thereof. Examples of suitable solvents include polar and nonpolar organic chemical liquids, for example from the classes of aromatic and nonaromatic hydrocarbons (such as cyclohexane, paraffins, alkylbenzenes, xylene, toluene, tetrahydronaphthalene, alkylnaphthalenes, chlorinated aromatics or chlorinated aliphatic hydrocarbons such as chlorobenzenes, chloroethylenes or methylene chloride), alcohols and polyols (which may optionally also be substituted, etherified and/or esterified, such as ethanol, propanol, butanol, benzylalcohol, cyclohexanol or glycol), ketones (such as acetone, methyl ethyl ketone, methyl isobutyl ketone or cyclohexanone), esters (including fats and oils) and (poly)ethers, unsubstituted and substituted amines, amides (such as dimethylformamide or fatty acid amides) and esters thereof, lactams (such as N-alkylpyrrolidones, in particular N-methylpyrrolidone) and lactones, sulfones and sulfoxides (such as dimethyl sulfoxide), oils of vegetable or animal origin. The carrier may also be a liquefied gaseous extender, i.e. liquid which is gaseous at standard temperature and under standard pressure, for example aerosol propellants such as halohydrocarbons, butane, propane, nitrogen and carbon dioxide.

Preferred solid carriers are selected from clays, talc and silica.

Preferred liquid carriers are selected from water, fatty acid amides and esters thereof, aromatic and nonaromatic hydrocarbons, lactams and carbonic acid esters.

The amount of carrier typically ranges from 1 to 99.99%, preferably from 5 to 99.9%, more preferably from 10 to 99.5%, and most preferably from 20 to 99% by weight of the composition.

Liquid carriers are typically present in a range of from 20 to 90%, for example 30 to 80% by weight of the composition.

Solid carriers are typically present in a range of from 0 to 50%, preferably 5 to 45%, for example 10 to 30% by weight of the composition.

If the composition comprises two or more carriers, the outlined ranges refer to the total amount of carriers.

The surfactant can be an ionic (cationic or anionic), amphoteric or non-ionic surfactant, such as ionic or non-ionic emulsifier(s), foam former(s), dispersant(s), wetting agent(s), penetration enhancer(s) and any mixtures thereof. Examples of suitable surfactants include, but are not limited to, salts of polyacrylic acid, salts of lignosulfonic acid (such as sodium lignosulfonate), salts of phenolsulfonic acid or naphthalenesulfonic acid, polycondensates of ethylene oxide and/or propylene oxide with fatty alcohols, fatty acids or fatty amines (for example, polyoxyethylene fatty acid esters such as castor oil ethoxylate, polyoxyethylene fatty alcohol ethers, for example alkylaryl polyglycol ethers), substituted phenols (preferably alkylphenols or arylphenols) and ethoxylates thereof (such as tristyrylphenol ethoxylate), salts of sulfosuccinic esters, taurine derivatives (preferably alkyl taurates), phosphoric esters of polyethoxylated alcohols or phenols, fatty esters of polyols (such a fatty acid esters of glycerol, sorbitol or sucrose), sulfates (such as alkyl sulfates and alkyl ether sulfates), sulfonates (for example, alkylsulfonates, arylsulfonates and alkylbenzene sulfonates), phosphate esters, protein hydrolysates, lignosulfite waste liquors and methylcellulose. Any reference to salts in this paragraph refers preferably to the respective alkali, alkaline earth and ammonium salts.

Preferred surfactants are selected from polyoxyethylene fatty alcohol ethers, polyoxyethylene fatty acid esters, alkylbenzene sulfonates, such as calcium dodecylbenzenesulfonate, castor oil ethoxylate, sodium lignosulfonate and arylphenol ethoxylates, such as tristyrylphenol ethoxylate.

The amount of surfactants typically ranges from 5 to 40%, for example 10 to 20%, by weight of the composition.

Further examples of suitable auxiliaries include water repellents, siccatives, binders (adhesive, tackifier, fixing agent, such as carboxymethylcellulose, natural and synthetic polymers in the form of powders, granules or latices, such as gum arabic, polyvinyl alcohol and polyvinyl acetate, natural phospholipids such as cephalins and lecithins and synthetic phospholipids, polyvinylpyrrolidone and tylose), thickeners and secondary thickeners (such as cellulose ethers, acrylic acid derivatives, xanthan gum, modified clays, e.g. the products available under the name Bentone, and finely divided silica), stabilizers (e.g. cold stabilizers, preservatives (e.g. dichlorophene and benzyl alcohol hemiformal), antioxidants, light stabilizers, in particular UV stabilizers, or other agents which improve chemical and/or physical stability), dyes or pigments (such as inorganic pigments, e.g. iron oxide, titanium oxide and Prussian Blue; organic dyes, e.g. alizarin, azo and metal phthalocyanine dyes), antifoams (e.g. silicone antifoams and magnesium stearate), antifreezes, stickers, gibberellins and processing auxiliaries, mineral and vegetable oils, perfumes, waxes, nutrients (including trace nutrients, such as salts of iron, manganese, boron, copper, cobalt, molybdenum and zinc), protective colloids, thixotropic substances, penetrants, sequestering agents and complex formers.

The choice of the auxiliaries depends on the intended mode of application of compounds of formula (I) and/or on the physical properties of the compound(s). Furthermore, the auxiliaries may be chosen to impart particular properties (technical, physical and/or biological properties) to the compositions or use forms prepared therefrom. The choice of auxiliaries may allow customizing the compositions to specific needs.

The composition of the invention may be provided to the end user as ready-for-use formulation, i.e. the compositions may be directly applied to the plants or seeds by a suitable device, such as a spraying or dusting device. Alternatively, the compositions may be provided to the end user in the form of concentrates which have to be diluted, preferably with water, prior to use.

The composition of the invention can be prepared in conventional manners, for example by mixing the compounds of formula (I) with one or more suitable auxiliaries, such as disclosed herein above.

The composition comprises a fungicidally effective amount of the compound(s) of formula (I). The term "effective amount" is an amount, which is sufficient for controlling harmful fungi on cultivated plants or in the protection of materials and which does not result in a substantial damage to the treated plants.

Such an amount can vary in a broad range and is dependent on various factors, such as the fungal species to be controlled, the treated cultivated plant or material, the climatic conditions and the specific compound of formula (I) used. Usually, the composition according to the invention contains from 0.01 to 99% by weight, preferably from 0.05 to 98% by weight, more preferred from 0.1 to 95% by weight, even more preferably from 0.5 to 90% by weight, most preferably from 1 to 80% by weight of the compound of formula (I). It is possible that a composition comprises two or more compounds of the invention. In such case the outlined ranges refer to the total amount of compounds of the present invention.

The composition of the invention may be in any customary composition type, such as solutions (e.g aqueous solutions), emulsions, water- and oil-based suspensions, powders (e.g. wettable powders, soluble powders), dusts, pastes, granules (e.g. soluble granules, granules for broadcasting), suspoemulsion concentrates, natural or synthetic products impregnated with the compound of formula (I), fertilizers and also microencapsulations in polymeric substances. The compounds of formula (I) may be present in a suspended, emulsified or dissolved form. Examples of particular suitable composition types are solutions, watersoluble concentrates (e.g. SL, LS), dispersible concentrates (DC), suspensions and suspension concentrates (e.g. SC, OD, OF, FS), emulsifiable concentrates (e.g. EC), emulsions (e.g. EW, EO, ES, ME, SE), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GW, GF). These and further compositions types are defined by the Food and Agriculture Organization of the United Nations (FAO). An overview is given in the "Catalogue of pesticide formulation types and international coding system", Technical Monograph No. 2, 6th Ed. May 2008, Croplife International.

Preferably, the composition of the invention is in form of one of the following types: EC, SC, FS, SE, OD and WG, more preferred EC, SC, OD and WG.

Further details about examples of composition types and their preparation are given below. If two or more compounds of the invention are present, the outlined amount of compound of the invention refers to the total amount of compounds of the present invention. This applies mutatis mutandis for any further component of the composition, if two or more representatives of such component, e.g. wetting agent, binder, are present.

i) Water-Soluble Concentrates (SL, LS)

10-60% by weight of at least one compound of formula (I) and 5-15% by weight surfactant (e.g. polyoxyethylene fatty alcohol ether) are dissolved in such amount of water and/or water-soluble solvent (e.g. alcohols such as propylene glycol or carbonates such as propylene carbonate) to result in a total amount of 100% by weight. Before application the concentrate is diluted with water.

ii) Dispersible Concentrates (DC)

5-25% by weight of at least one compound of formula (I) and 1-10% by weight surfactant and/or binder (e.g. polyvinylpyrrolidone) are dissolved in such amount of organic solvent (e.g. cyclohexanone) to result in a total amount of 100% by weight. Dilution with water gives a dispersion.

iii) Emulsifiable Concentrates (EC)

15-70% by weight of at least one compound of formula (I) and 5-10% by weight surfactant (e.g. a mixture of calcium dodecylbenzenesulfonate and castor oil ethoxylate) are dissolved in such amount of water-insoluble organic solvent (e.g. aromatic hydrocarbon or fatty acid amide) and if needed additional water-soluble solvent to result in a total amount of 100% by weight. Dilution with water gives an emulsion.

iv) Emulsions (EW, EO, ES)

5-40% by weight of at least one compound of formula (I) and 1-10% by weight surfactant (e.g. a mixture of calcium dodecylbenzenesulfonate and castor oil ethoxylate) are dissolved in 20-40% by weight water-insoluble organic solvent (e.g. aromatic hydrocarbon). This mixture is added to such amount of water by means of an emulsifying machine to result in a total amount of 100% by weight. The resulting composition is a homogeneous emulsion. Before application the emulsion may be further diluted with water.

v) Suspensions and Suspension Concentrates v-1) Water-Based (SC, FS)

In a suitable grinding equipment, e.g. an agitated ball mill, 20-60% by weight of at least one compound of formula (I) are comminuted with addition of 2-10% by weight surfactant (e.g. sodium lignosulfonate and polyoxyethylene fatty alcohol ether), 0.1-2% by weight thickener (e.g. xanthan gum) and water to give a fine active substance suspension. The water is added in such amount to result in a total amount of 100% by weight. Dilution with water gives a stable suspension of the active substance. For FS type compositions up to 40% by weight binder (e.g. polyvinylalcohol) is added.

v-2) Oil-Based (OD, OF)

In a suitable grinding equipment, e.g. an agitated ball mill, 20-60% by weight of at least one compound of formula (I) are comminuted with addition of 2-10% by weight surfactant (e.g. sodium lignosulfonate and polyoxyethylene fatty alcohol ether), 0.1-2% by weight thickener (e.g. modified clay, in particular Bentone, or silica) and an organic carrier to give a fine active substance oil suspension. The organic carrier is added in such amount to result in a total amount of 100% by weight. Dilution with water gives a stable dispersion of the active substance.

vi) Water-Dispersible Granules and Water-Soluble Granules (WG, SG)

50-80% by weight of at least one compound of formula (I) are ground finely with addition of surfactant (e.g. sodium lignosulfonate and polyoxyethylene fatty alcohol ether) and converted to water-dispersible or water-soluble granules by means of technical appliances (e.g. extrusion, spray tower, fluidized bed). The surfactant is used in such amount to result in a total amount of 100% by weight. Dilution with water gives a stable dispersion or solution of the active substance.

vii) Water-Dispersible Powders and Water-Soluble Powders (WP, SP, WS)

50-80% by weight of at least one compound of formula (I) are ground in a rotor-stator mill with addition of 1-8% by weight surfactant (e.g. sodium lignosulfonate, polyoxyethylene fatty alcohol ether) and such amount of solid carrier, e.g. silica gel, to result in a total amount of 100% by weight. Dilution with water gives a stable dispersion or solution of the active substance.

viii) Gel (GW, GF)

In an agitated ball mill, 5-25% by weight of at least one compound of formula (I) are comminuted with addition of 3-10% by weight surfactant (e.g. sodium lignosulfonate), 1-5% by weight binder (e.g. carboxymethylcellulose) and such amount of water to result in a total amount of 100% by weight. This results in a fine suspension of the active substance. Dilution with water gives a stable suspension of the active substance.

ix) Microemulsion (ME)

5-20% by weight of at least one compound of formula (I) are added to 5-30% by weight organic solvent blend (e.g. fatty acid dimethylamide and cyclohexanone), 10-25% by weight surfactant blend (e.g. polyoxyethylene fatty alcohol ether and arylphenol ethoxylate), and such amount of water to result in a total amount of 100% by weight. This mixture is stirred for 1 h to produce spontaneously a thermodynamically stable microemulsion.

x) Microcapsules (CS)

An oil phase comprising 5-50% by weight of at least one compound of formula (I), 0-40% by weight water-insoluble organic solvent (e.g. aromatic hydrocarbon), 2-15% by weight acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50% by weight of at least one compound of formula (I), 0-40% by weight water-insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10% by weight of the total CS composition.

xi) Dustable Powders (DP, DS)

1-10% by weight of at least one compound of formula (I) are ground finely and mixed intimately with such amount of solid carrier, e.g. finely divided kaolin, to result in a total amount of 100% by weight.

xii) Granules (GR, FG)

0.5-30% by weight of at least one compound of formula (I) are ground finely and associated with such amount of solid carrier (e.g. silicate) to result in a total amount of 100% by weight. Granulation is achieved by extrusion, spray-drying or the fluidized bed.

xiii) Ultra-Low Volume Liquids (UL)

1-50% by weight of at least one compound of formula (I) are dissolved in such amount of organic solvent, e.g. aromatic hydrocarbon, to result in a total amount of 100% by weight.

The compositions types i) to xiii) may optionally comprise further auxiliaries, such as 0.1-1% by weight preservatives, 0.1-1% by weight antifoams, 0.1-1% by weight dyes and/or pigments, and 5-10% by weight antifreezes.

Mixtures/Combinations

The compound of formula (I) and the composition of the invention can be mixed with other active ingredients like fungicides, bactericides, acaricides, nematicides, insecticides, biological control agents or herbicides. Mixtures with fertilizers, growth regulators, safeners, nitrification inhibitors, semiochemicals and/or other agriculturally beneficial agents are also possible. This may allow to broaden the activity spectrum or to prevent development of resistance. Examples of known fungicides, insecticides, acaricides, nematicides and bactericides are disclosed in the Pesticide Manual, 17th Edition.

Examples of fungicides which could be mixed with the compound of formula (I) and the composition of the invention are:

1) Inhibitors of the ergosterol biosynthesis, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol, (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chloro-cyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) mefentrifluconazole, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluoro-phenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]-phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) ipfentrifluconazole, (1.082) 2-[4-(4-chlorophenoxy)-2-(trifluoromethyl)phenyl]-1-(1H-1,2,4-triazol-1-yl)propan-2-ol, (1.083) 2-[6-(4-bromophenoxy)-2-(trifluoromethyl)-3-pyridyl]-1-(1,2,4-triazol-1-yl)propan-2-ol, (1.084) 2-[6-(4-chlorophenoxy)-2-(trifluoromethyl)-3-pyridyl]-1-(1,2,4-triazol-1-yl)propan-2-ol, (1.085) 3-[2-(1-chlorocyclopropyl)-3-(3-chloro-2-fluoro-phenyl)-2-hydroxypropyl]imidazole-4-carbonitrile, (1.086) 4-[[6-[rac-(2R)-2-(2,4-difluorophenyl)-1,1-difluoro-2-hydroxy-3-(5-thioxo-4H-1,2,4-triazol-1-yl)propyl]-3-pyridyl]oxy]benzonitrile, (1.087) N-isopropyl-N'-[5-methoxy-2-methyl-4-(2,2,2-trifluoro-1-hydroxy-1-phenylethyl)phenyl]-N-methylimidoformamide, (1.088) N'-{5-bromo-2-methyl-6-[(1-propoxypropan-2-yl)oxy]pyridin-3-yl}-N-ethyl-N-methylimidoformamide, (1.089) hexaconazole, (1.090) penconazole, (1.091) fenbuconazole, (1.092) methyl 2-[2-chloro-4-(4-chlorophenoxy)phenyl]-2-hydroxy-3-(1,2,4-triazol-1-yl)propanoate.

2) Inhibitors of the respiratory chain at complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) Isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of syn-epimeric racemate 1RS,4SR,9RS and anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) Pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) inpyrfluxam, (2.029) 3-(difluoromethyl)-1-methyl-N-[(3S)-1,1,3-trimethyl-2,3-dihydro-1H-inden-4-yl]-1H-pyrazole-4-carboxamide, (2.030) fluindapyr, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)-pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) isoflucypram, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-

(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(di-fluoromethyl)-5-fluoro-1-methyl-1H-pyrazole-4-carboxamide, (2.057) pyrapropoyne, (2.058) N-[rac-(1S,2S)-2-(2,4-dichlorophenyl)cyclobutyl]-2-(trifluoromethyl)nicotinamide, (2.059) N-[(1S,2S)-2-(2,4-dichlorophenyl)cyclobutyl]-2-(trifluoromethyl)nicotinamide, (2.060) flubeneteram.

3) Inhibitors of the respiratory chain at complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadone, (3.010) fenamidone, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) fenpicoxamid, (3.026) mandestrobin, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl {5-[3-(2,4-dimethylphenyl)-1H-pyrazol-1-yl]-2-methylbenzyl}carbamate, (3.030) metyltetraprole, (3.031) florylpicoxamid, (3.032) (2S,3S)-3-(o-tolyl)butan-2-yl N-{[4-methoxy-3-(propanoyloxy)-2-pyridyl]carbonyl}-L-alaninate.

4) Inhibitors of the mitosis and cell division, for example (4.001) carbendazim, (4.002) diethofencarb, (4.003) ethaboxam, (4.004) fluopicolide, (4.005) pencycuron, (4.006) thiabendazole, (4.007) thiophanate-methyl, (4.008) zoxamide, (4.009) pyridachlometyl, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine, (4.026) fluopimomide.

5) Compounds capable to have a multisite action, for example (5.001) bordeaux mixture, (5.002) captafol, (5.003) captan, (5.004) chlorothalonil, (5.005) copper hydroxide, (5.006) copper naphthenate, (5.007) copper oxide, (5.008) copper oxychloride, (5.009) copper(2+) sulfate, (5.010) dithianon, (5.011) dodine, (5.012) folpet, (5.013) mancozeb, (5.014) maneb, (5.015) metiram, (5.016) metiram zinc, (5.017) oxine-copper, (5.018) propineb, (5.019) sulfur and sulfur preparations including calcium polysulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.

6) Compounds capable to induce a host defence, for example (6.001) acibenzolar-S-methyl, (6.002) isotianil, (6.003) probenazole, (6.004) tiadinil.

7) Inhibitors of the amino acid and/or protein biosynthesis, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

8) Inhibitors of the ATP production, for example (8.001) silthiofam.

9) Inhibitors of the cell wall synthesis, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Inhibitors of the lipid and membrane synthesis, for example (10.001) propamocarb, (10.002) propamocarb hydrochloride, (10.003) tolclofos-methyl.
11) Inhibitors of the melanin biosynthesis, for example (11.001) tricyclazole, (11.002) tolprocarb.
12) Inhibitors of the nucleic acid synthesis, for example (12.001) benalaxyl, (12.002) benalaxyl-M (kiralaxyl), (12.003) metalaxyl, (12.004) metalaxyl-M (mefenoxam).
13) Inhibitors of the signal transduction, for example (13.001) fludioxonil, (13.002) iprodione, (13.003) procymidone, (13.004) proquinazid, (13.005) quinoxyfen, (13.006) vinclozolin.
14) Compounds capable to act as an uncoupler, for example (14.001) fluazinam, (14.002) meptyldinocap.
15) Further fungicides selected from the group consisting of (15.001) abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenone, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphorous acid and its salts, (15.026) propamocarb-fosetylate, (15.027) pyriofenone (chlazafenone), (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl] ethanone, (15.033) 2-(6-benzylpyridin-2-yl) quinazoline, (15.034) dipymetitrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)-phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl] quinazoline, (15.039) 2-{(5R)-3-[2-(1-{[3,5-bis (difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl}-3-chlorophenyl methanesulfonate, (15.041) ipflufenoquin, (15.042) 2-{2-fluoro-6-[(8-fluoro-2-methylquinolin-3-yl)oxy]phenyl}propan-2-ol, (15.043) fluoxapiprolin, (15.044) 2-{3-[2-(1-{[3,5-bis (difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts, (15.046) 3-(4,4,5-trifluoro-3,3-dimethyl-3,4-dihydroisoquinolin-1-yl)quinoline, (15.047) quinofumelin, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butanoic acid, (15.050) 5-amino-1,3,4-thiadiazole-2-thiol, (15.051) 5-chloro-N'-phenyl-N'-(prop-2-yn-1-yl)thiophene-2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl) methylene]amino}oxy)methyl]pyridin-2-yl}carbamate, (15.062) 5-fluoro-4-imino-3-methyl-1-[(4-methylphenyl)sulfonyl]-3,4-dihydropyrimidin-2 (1H)-one, (15.063) aminopyrifen, (15.064) (N'-[2-chloro-4-(2-fluorophenoxy)-5-methylphenyl]-N-ethyl-N-methylimidoformamide), (15.065) (N'-(2-chloro-5-methyl-4-phenoxyphenyl)-N-ethyl-N-methylimidoformamide), (15.066) (2-{2-[(7,8-difluoro-2-methylquinolin-3-yl)oxy]-6-fluorophenyl}propan-2-ol), (15.067) (5-bromo-1-(5,6-dimethylpyridin-3-yl)-3,3-dimethyl-3,4-dihydroisoquinoline), (15.068) (3-(4,4-difluoro-5,5-dimethyl-4,5-dihydrothieno[2,3-c]pyridin-7-yl) quinoline), (15.069) (1-(4,5-dimethyl-1H-benzimidazol-1-yl)-4,4-difluoro-3,3-dimethyl-3,4-dihydroisoquinoline), (15.070) 8-fluoro-3-(5-fluoro-3,3-dimethyl-3,4-dihydroisoquinolin-1-yl)quinolone, (15.071) 8-fluoro-3-(5-fluoro-3,3,4,4-tetramethyl-3,4-dihydroisoquinolin-1-yl)quinolone, (15.072) 3-(4,4-difluoro-3,3-dimethyl-3,4-dihydroisoquinolin-1-yl)-8-fluoroquinoline, (15.073) (N-methyl-N-phenyl-4-[5-(trifluoromethyl)-1,2,4-oxadiazol-3-yl]benzamide), (15.074) methyl {4-[5-(trifluoromethyl)-1,2,4-oxadiazol-3-yl]phenyl}carbamate, (15.075) (N-{4-[5-(trifluoromethyl)-1,2,4-oxadiazol-3-yl] benzyl}cyclopropanecarboxamide), (15.076) N-methyl-4-(5-(trifluoromethyl)-1,2,4-oxadiazol-3-yl] benzamide, (15.077) N-[(E)-methoxyiminomethyl]-4-[5-(trifluoromethyl)-1,2,4-oxadiazol-3-yl]benzamide, (15.078) N—[(Z)-methoxyiminomethyl]-4-[5-(trifluoromethyl)-1,2,4-oxadiazol-3-yl]benzamide, (15.079) N-[4-[5-(trifluoromethyl)-1,2,4-oxadiazol-3-yl]phenyl]cyclopropanecarboxamide, (15.080) N-(2-fluorophenyl)-4-[5-(trifluoromethyl)-1,2,4-oxadiazol-3-yl] benzamide, (15.081) 2,2-difluoro-N-methyl-2-[4-[5-(trifluoromethyl)-1,2,4-oxadiazol-3-yl]phenyl] acetamide, (15.082) N-allyl-N-[[4-[5-(trifluoromethyl)-1,2,4-oxadiazol-3-yl)phenyl]methyl] acetamide, (15.083) N-[(E)-N-methoxy-C-methyl-carbonimidoyl]-4-(5-(trifluoro-methyl)-1,2,4-oxadiazol-3-yl]benzamide, (15.084) N—[(Z)—N-methoxy-C-methyl-carbonimidoyl]-4-[5-(trifluoromethyl)-1,2,4-oxadiazol-3-yl]benzamide, (15.085) N-allyl-N-[[4-[5-(trifluoromethyl)-1,2,4-oxadiazol-3-yl]phenyl]methyl]propanamide, (15.086) 4,4-dimethyl-1-[[4-[5-(trifluoromethyl)-1,2,4-oxadiazol-3-yl]phenyl]methyl]pyrrolidin-2-one, (15.087) N-methyl-4-[5-(trifluoromethyl)-1,2,4-oxadiazol-3-yl] benzenecarbothioamide, (15.088) 5-methyl-1-[[4-[5-(trifluoromethyl)-1,2,4-oxadiazol-3-yl]phenyl]methyl] pyrrolidin-2-one, (15.089) N-((2,3-difluoro-4-[5-(trifluoromethyl)-1,2,4-oxadiazol-3-yl]phenyl]

methyl]-3,3,3-trifluoro-propanamide, (15.090) 1-methoxy-1-methyl-3-[[4-[5-(trifluoro-methyl}-1,2,4-oxadiazol-3-yl]phenyl]methyl]urea, (15.091) 1,1-diethyl-3-[[4-[5-(trifluoromethyl}-1,2,4-oxadiazol-3-yl]phenyl]methyl]urea, (15.092) N-[[4-[5-(trifluoromethyl)-1,2,4-oxadiazol-3-yl]phenyl]methyl]propanamide, (15.093) N-methoxy-N-[[4-[5-(trifluoromethyl)-1,2,4-oxadiazol-3-yl]phenyl]-methyl]cyclopropanecarboxamide, (15.094) 1-methoxy-3-methyl-1-[[4-[5-(trifluoromethyl)-1,2,4-oxadiazol-3-yl]phenyl]methyl]urea, (15.095) N-methoxy-N-[[4-[5-(trifluoromethyl)-1,2,4-oxadiazol-3-yl]phenyl]methyl)cyclopropanecarboxamide, (15.096) N,2-dimethoxy-N-[[4-[5-(trifluoromethyl}-1,2,4-oxadiazol-3-yl]phenyl]methyl]propanamide, (15.097) N-ethyl-2-methyl-N-[[4-[5-(trifluoromethyl)-1,2,4-oxadiazol-3-yl)phenyl]methyl]propanamide, (15.098) 1-methoxy-3-methyl-1-[[4-[5-(trifluoromethyl)-1,2,4-oxadiazol-3-yl]phenyl]methyl]urea, (15.099) 1,3-dimethoxy-1-[[4-[5-(trifluoromethyl)-1,2,4-oxadiazol-3-yl]phenyl]methyl]urea, (15.100) 3-ethyl-1-methoxy-1-[[4-[5-(trifluoromethyl)-1,2,4-oxadiazol-3-yl]phenyl]methyl]urea, (15.101) 1-[[4-[5-(trifluoromethyl)-1,2,4-oxadiazol-3-yl]phenyl]-methyl]piperidin-2-one, (15.102) 4,4-dimethyl-2-[[4-[5-(trifluoromethyl)-1,2,4-oxadiazol-3-yl]phenyl]-methyl]isooxazolidin-3-one, (15.103) 5,5-dimethyl-2-[[4-[5-(trifluoromethyl)-1,2,4-oxadiazol-3-yl]phenyl]methyl]isoxazolidin-3-one, (15.104) 3,3-dimethyl-1-[[4-[5-(trifluoromethyl)-1,2,4-oxadiazol-3-yl]phenyl]methyl]piperidin-2-one, (15.105) 1-[[3-fluoro-4-(5-(trifluoromethyl)-1,2,4-oxadiazol-3-yl]-phenyl]methyl]azepan-2-one, (15.106) 4,4-dimethyl-2-[[4-(5-(trifluoromethyl)-1,2,4-oxadiazol-3-yl]-phenyl]methyl]isoxazolidin-3-one, (15.107) 5,5-dimethyl-2-[[4-[5-(trifluoromethyl)-1,2,4-oxadiazol-3-yl]phenyl]methyl]isoxazolidin-3-one, (15.108) ethyl 1-{4-[5-(trifluoromethyl)-1,2,4-oxadiazol-3-yl]benzyl}-1H-pyrazole-4-carboxylate, (15.109) N,N-dimethyl-1-{4-[5-(trifluoromethyl)-1,2,4-oxadiazol-3-yl]benzyl}-1H-1,2,4-triazol-3-amine, (15.110) N-{2,3-difluoro-4-[5-(trifluoromethyl)-1,2,4-oxadiazol-3-yl]benzyl}butanamide, (15.111) N-(1-methylcyclopropyl)-4-[5-(trifluoromethyl)-1,2,4-oxadiazol-3-yl]benzamide, (15.112) N-(2,4-difluorophenyl)-4-[5-(trifluoromethyl)-1,2,4-oxadiazol-3-yl]benzamide, (15.113) 1-(5,6-dimethylpyridin-3-yl)-4,4-difluoro-3,3-dimethyl-3,4-dihydroisoquinoline, (15.114) 1-(6-(difluoromethyl)-5-methyl-pyridin-3-yl)-4,4-difluoro-3,3-dimethyl-3,4-dihydroisoquinoline, (15.115) 1-(5-(fluoromethyl)-6-methyl-pyridin-3-yl)-4,4-difluoro-3,3-dimethyl-3,4-dihydroisoquinoline, (15.116) 1-(6-(difluoromethyl)-5-methoxy-pyridin-3-yl)-4,4-difluoro-3,3-dimethyl-3,4-dihydroisoquinoline, (15.117) 4-[5-(trifluoromethyl)-1,2,4-oxadiazol-3-yl]phenyl dimethyl-carbamate, (15.118) N-{4-[5-(trifluoromethyl)-1,2,4-oxadiazol-3-yl]phenyl}propanamide, (15.119) 3-[2-(1-{[5-methyl-3-(trifluoromethyl)-1H-pyrazol-1-yl]acetyl}piperidin-4-yl)-1,3-thiazol-4-yl]-1,5-dihydro-2,4-benzodioxepin-6-yl methanesulfonate, (15.120) 9-fluoro-3-[2-(1-{[5-methyl-3-(trifluoromethyl)-1H-pyrazol-1-yl]acetyl}piperidin-4-yl)-1,3-thiazol-4-yl]-1,5-dihydro-2,4-benzodioxepin-6-yl methanesulfonate, (15.121) 3-[2-(1-{[3,5-bis(difluoromethyl)-1H-pyrazol-1-yl]acetyl}piperidin-4-yl)-1,3-thiazol-4-yl]-1,5-dihydro-2,4-benzodioxepin-6-yl methanesulfonate, (15.122) 3-[2-(1-{[3,5-bis(difluoromethyl)-1H-pyrazol-1-yl]acetyl}piperidin-4-yl)-1,3-thiazol-4-yl]-9-fluoro-1,5-dihydro-2,4-benzodioxepin-6-yl methanesulfonate, (15.123) 1-(6,7-dimethylpyrazolo[1,5-a]pyridin-3-yl)-4,4-difluoro-3,3-dimethyl-3,4-dihydroisoquinoline, (15.124) 8-fluoro-N-(4,4,4-trifluoro-2-methyl-1-phenylbutan-2-yl)quinoline-3-carboxamide, (15.125) 8-fluoro-N-[(2S)-4,4,4-trifluoro-2-methyl-1-phenylbutan-2-yl]quinoline-3-carboxamide, (15.126) N-(2,4-dimethyl-1-phenylpentan-2-yl)-8-fluoroquinoline-3-carboxamide, (15.127) N-[(2S)-2,4-dimethyl-1-phenylpentan-2-yl]-8-fluoroquinoline-3-carboxamide and (15.128) D-tagatose.

All named mixing partners of the classes (1) to (15) as described here above can be present in the form of the free compound or, if their functional groups enable this, an agrochemically active salt thereof.

The compound of formula (I) and the composition of the invention may also be combined with one or more biological control agents.

As used herein, the term "biological control" is defined as control of harmful organisms such as a phytopathogenic fungi and/or insects and/or acarids and/or nematodes by the use or employment of a biological control agent.

As used herein, the term "biological control agent" is defined as an organism other than the harmful organisms and/or proteins or secondary metabolites produced by such an organism for the purpose of biological control. Mutants of the second organism shall be included within the definition of the biological control agent. The term "mutant" refers to a variant of the parental strain as well as methods for obtaining a mutant or variant in which the pesticidal activity is greater than that expressed by the parental strain. The "parent strain" is defined herein as the original strain before mutagenesis. To obtain such mutants the parental strain may be treated with a chemical such as N-methyl-N'-nitro-N-nitrosoguanidine, ethylmethanesulfone, or by irradiation using gamma, x-ray, or UV-irradiation, or by other means well known to those skilled in the art. Known mechanisms of biological control agents comprise enteric bacteria that control root rot by out-competing fungi for space on the surface of the root. Bacterial toxins, such as antibiotics, have been used to control pathogens. The toxin can be isolated and applied directly to the plant or the bacterial species may be administered so it produces the toxin in situ.

A "variant" is a strain having all the identifying characteristics of the NRRL or ATCC Accession Numbers as indicated in this text and can be identified as having a genome that hybridizes under conditions of high stringency to the genome of the NRRL or ATCC Accession Numbers.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

A variant of the indicated NRRL or ATCC Accession Number may also be defined as a strain having a genomic sequence that is greater than 85%, more preferably greater than 90% or more preferably greater than 95% sequence identity to the genome of the indicated NRRL or ATCC Accession Number. A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example, those described in Current Protocols in Molecular Biology (F. M. Ausubel et al., eds., 1987).

NRRL is the abbreviation for the Agricultural Research Service Culture Collection, an international depositary authority for the purposes of deposing microorganism strains under the Budapest treaty on the international recognition of the deposit of microorganisms for the purposes of patent procedure, having the address National Center for Agricultural Utilization Research, Agricultural Research service, U.S. Department of Agriculture, 1815 North university Street, Peroira, Illinois 61604 USA.

ATCC is the abbreviation for the American Type Culture Collection, an international depositary authority for the purposes of deposing microorganism strains under the Budapest treaty on the international recognition of the deposit of microorganisms for the purposes of patent procedure, having the address ATCC Patent Depository, 10801 University Blvd., Manassas, VA 10110 USA.

Examples of biological control agents which may be combined with the compound of formula (I) and the composition of the invention are:

(A) Antibacterial agents selected from the group of:

(A1) bacteria, such as (A1.1) *Bacillus subtilis*, in particular strain QST713/AQ713 (available as SERENADE OPTI or SERENADE ASO from Bayer CropScience LP, US, having NRRL Accession No. B21661, U.S. Pat. No. 6,060,051); (A1.2) *Bacillus* sp., in particular strain D747 (available as DOUBLE NICKEL® from Kumiai Chemical Industry Co., Ltd.), having Accession No. FERM BP-8234, U.S. Pat. No. 7,094,592; (A1.3) *Bacillus pumilus*, in particular strain BU F-33, having NRRL Accession No. 50185 (available as part of the CARTISSA® product from BASF, EPA Reg. No. 71840-19); (A1.4) *Bacillus subtilis* var. *amyloliquefaciens* strain FZB24 having Accession No. DSM 10271 (available from Novozymes as TAEGRO® or TAEGRO® ECO (EPA Registration No. 70127-5)); (A1.5) a *Paenibacillus* sp. strain having Accession No. NRRL B-50972 or Accession No. NRRL B-67129, WO 2016/154297; (A1.6) *Bacillus subtilis* strain BU1814, (available as VELONDIS® PLUS, VELONDIS® FLEX and VELONDIS® EXTRA from BASF SE); (A1.7) *Bacillus mojavensis* strain R3B (Accession No. NCAIM (P) B001389) (WO 2013/034938) from Certis USA LLC, a subsidiary of Mitsui & Co.; (A1.8) *Bacillus subtilis* CX-9060 from Certis USA LLC, a subsidiary of Mitsui & Co.; (A1.9) *Paenibacillus polymyxa*, in particular strain AC-1 (e.g. TOPSEED® from Green Biotech Company Ltd.); (A1.10) *Pseudomonas proradix* (e.g. PRORADIX® from Sourcon Padena); (A1.11) *Pantoea agglomerans*, in particular strain E325 (Accession No. NRRL B-21856) (available as BLOOMTIME BIOLOGICAL™ FD BIOPESTICIDE from Northwest Agri Products); and (A2) fungi, such as (A2.1) *Aureobasidium pullulans*, in particular blastospores of strain DSM14940, blastospores of strain DSM 14941 or mixtures of blastospores of strains DSM14940 and DSM14941 (e.g., BOTECTOR® and BLOSSOM PROTECT® from bioferm, CH); (A2.2) *Pseudozyma aphidis* (as disclosed in WO2011/151819 by Yissum Research Development Company of the Hebrew University of Jerusalem); (A2.3) *Saccharomyces cerevisiae*, in particular strains CNCM No. I-3936, CNCM No. I-3937, CNCM No. I-3938 or CNCM No. I-3939 (WO 2010/086790) from Lesaffre et Compagnie, FR;

(B) biological fungicides selected from the group of:

(B1) bacteria, for example (B1.1) *Bacillus subtilis*, in particular strain QST713/AQ713 (available as SERENADE OPTI or SERENADE ASO from Bayer CropScience LP, US, having NRRL Accession No. B21661 and described in U.S. Pat. No. 6,060,051); (B1.2) *Bacillus pumilus*, in particular strain QST2808 (available as SONATA® from Bayer CropScience LP, US, having Accession No. NRRL B-30087 and described in U.S. Pat. No. 6,245,551); (B1.3) *Bacillus pumilus*, in particular strain GB34 (available as Yield Shield® from Bayer AG, DE); (B1.4) *Bacillus pumilus*, in particular strain BU F-33, having NRRL Accession No. 50185 (available as part of the CARTISSA product from BASF, EPA Reg. No. 71840-19); (B1.5) *Bacillus amyloliquefaciens*, in particular strain D747 (available as Double Nickel™ from Kumiai Chemical Industry Co., Ltd., having accession number FERM BP-8234, U.S. Pat. No. 7,094,592); (B1.6) *Bacillus subtilis* Y1336 (available as BIOBAC® WP from Bion-Tech, Taiwan, registered as a biological fungicide in Taiwan under Registration Nos. 4764, 5454, 5096 and 5277); (B1.7) *Bacillus subtilis* strain MBI 600 (available as SUBTILEX from BASF SE), having Accession Number NRRL B-50595, U.S. Pat. No. 5,061,495; (B1.8) *Bacillus subtilis* strain GB03 (available as Kodiak® from Bayer AG, DE); (B1.9) *Bacillus subtilis* var. *amyloliquefaciens* strain FZB24 having Accession No. DSM 10271 (available from Novozymes as TAEGRO® or TAEGRO® ECO (EPA Registration No. 70127-5)); (B1.10) *Bacillus mycoides*, isolate J, having Accession No. B-30890 (available as BMJ TGAI® or WG and LifeGard™ from Certis USA LLC, a subsidiary of Mitsui & Co.); (B1.11) *Bacillus licheniformis*, in particular strain SB3086, having Accession No. ATCC 55406, WO 2003/000051 (available as ECOGUARD® Biofungicide and GREEN RELEAF™ from Novozymes); (B1.12) a *Paenibacillus* sp. strain having Accession No. NRRL B-50972 or Accession No. NRRL B-67129, WO 2016/154297; (B1.13) *Bacillus subtilis* strain BU1814, (available as VELONDIS® PLUS, VELONDIS® FLEX and VELONDIS® EXTRA from BASF SE); (B1.14) *Bacillus subtilis* CX-9060 from Certis USA LLC, a subsidiary of Mitsui & Co.; (B1.15) *Bacillus amyloliquefaciens* strain F727 (also known as strain MBI110) (NRRL Accession No. B-50768; WO 2014/028521) (STARGUS® from Marrone Bio Innovations); (B1.16) *Bacillus amyloliquefaciens* strain FZB42, Accession No. DSM 23117 (available as RHIZOVITAL® from ABiTEP, DE); (B1.17) *Bacillus licheniformis* FMCH001 and *Bacillus subtilis* FMCH002 (QUARTZO® (WG) and PRESENCE® (WP) from FMC Corporation); (B1.18) *Bacillus mojavensis* strain R3B (Accession No. NCAIM (P) B001389) (WO 2013/034938) from Certis USA LLC, a subsidiary of Mitsui & Co.; (B1.19) *Paenibacillus polymyxa* ssp. *plantarum* (WO 2016/020371) from BASF SE; (B1.20) *Paenibacillus epiphyticus* (WO 2016/020371) from BASF SE; (B.1.21) *Pseudomonas chlororaphis* strain AFS009, having Accession No. NRRL B-50897, WO 2017/019448 (e.g., HOWLER™ and ZIO® from AgBiome Innovations, US); (B1.22) *Pseudomonas chlororaphis*, in particular strain MA342 (e.g. CEDOMON®, CERALL®, and CEDRESS® by Bioagri and Koppert); (B1.23) *Streptomyces lydicus* strain WYEC108 (also known as *Streptomyces lydicus* strain WYCD108US) (ACTINO-IRON® and ACTINO-VATE® from Novozymes); (B1.24) *Agrobacterium radiobacter* strain K84 (e.g. GALLTROL-A® from AgBioChem, CA); (B1.25) *Agrobacterium radiobacter* strain K1026 (e.g. NOGALL™ from BASF SE); (B1.26) *Bacillus subtilis* KTSB strain (FOLI-ACTIVE® from Donaghys); (B1.27) *Bacillus subtilis* IAB/BS03 (AVIV™ from STK Bio-Ag Technologies); (B1.28) *Bacillus subtilis* strain Y1336 (available as BIOBAC® WP from Bion-Tech, Taiwan, registered as a biological fungicide in Taiwan under Registration Nos. 4764, 5454, 5096 and 5277); (B1.29) *Bacillus amyloliquefaciens* isolate B246 (e.g. AVOGREEN™ from University of Pretoria); (B1.30) *Bacillus methylotrophicus* strain BAC-9912 (from Chinese Academy of Sciences' Institute of Applied Ecology); (B1.31) *Pseudomonas proradix* (e.g. PRORADIX® from Sourcon Padena); (B1.32) *Streptomyces griseoviridis* strain K61 (also known as *Streptomyces galbus* strain K61) (Accession No. DSM 7206) (MYCOSTOP® from Verdera; PREFENCE® from BioWorks; cf. Crop Protection 2006, 25, 468-475); (B1.33) *Pseudomonas fluorescens* strain A506 (e.g. BLIGHTBAN® A506 by NuFarm); and (B2) fungi, for example: (B2.1) *Coniothyrium minitans*, in particular strain CON/M/91-8 (Accession No. DSM-9660; e.g. Contans® from Bayer CropScience Biologics GmbH); (B2.2) Metschnikowia fructicola, in particular strain NRRL Y-30752; (B2.3) *Microsphaeropsis ochracea*; (B2.5) *Trichoderma atroviride*, in particular strain SC1 (having Accession No. CBS 122089, WO 2009/116106 and U.S. Pat. No. 8,431,120 (from Bi-PA)), strain 77B (T77 from Andermatt Biocontrol) or strain LU132 (e.g. Sentinel from Agrimm Technologies Limited); (B2.6) *Trichoderma harzianum* strain T-22 (e.g. Trianum-P from Andermatt Biocontrol or Koppert) or strain Cepa Simb-T5 (from Simbiose Agro); (B2.14) *Gliocladium roseum* (also known as *Clonostachys rosea* f, *rosea*), in particular strain 321U from Adjuvants Plus, strain ACM941 as disclosed in Xue (Efficacy of *Clonostachys rosea* strain ACM941 and fungicide seed treatments for controlling the root tot complex of field pea, Can Jour Plant Sci 83(3): 519-524), or strain IK726 (Jensen D F, et al. Development of a biocontrol agent for plant disease control with special emphasis on the near commercial fungal antagonist *Clonostachys rosea* strain 'IK726'; Australas Plant Pathol. 2007; 36:95-101); (B2.35) *Talaromyces flavus*, strain V117b; (B2.36) *Trichoderma viride*, in particular strain B35 (Pietr et al., 1993, Zesz. Nauk. A R w Szczecinie 161: 125-137); (B2.37) *Trichoderma asperellum*, in particular strain SKT-1, having Accession No. FERM P-16510 (e.g. ECO-HOPE® from Kumiai Chemical Industry), strain T34 (e.g. T34 Biocontrol by Biocontrol Technologies S.L., ES) or strain ICC 012 from Isagro; (B2.38) *Trichoderma atroviride*, strain CNCM I-1237 (e.g. Esquive® WP from Agrauxine, FR); (B2.39) *Trichoderma atroviride*, strain no. V08/002387; (B2.40) *Trichoderma atroviride*, strain NMI no. V08/002388; (B2.41) *Trichoderma atroviride*, strain NMI no. V08/002389; (B2.42) *Trichoderma atroviride*, strain NMI no. V08/002390; (B2.43) *Trichoderma atroviride*, strain LC52 (e.g. Tenet by Agrimm Technologies Limited); (B2.44) *Trichoderma atroviride*, strain ATCC 20476 (IMI 206040); (B2.45) *Trichoderma atroviride*, strain T11 (IMI352941/CECT20498); (B2.46) *Trichoderma harmatum*; (B2.47) *Trichoderma harzianum*; (B2.48) *Trichoderma harzianum rifai* T39 (e.g. Trichodex® from Makhteshim, US); (B2.49) *Trichoderma asperellum*, in particular, strain kd (e.g. T-Gro from Andermatt Biocontrol); (B2.50) *Trichoderma harzianum*, strain ITEM 908 (e.g. Trianum-P from Koppert); (B2.51) *Trichoderma harzianum*, strain TH35 (e.g. Root-Pro by Mycontrol); (B2.52) *Trichoderma virens* (also known as *Gliocladium virens*), in particular strain GL-21 (e.g. SoilGard by Certis, US); (B2.53) *Trichoderma viride*, strain TV1(e.g. Trianum-P by Koppert); (B2.54) *Ampelomyces quisqualis*, in particular strain AQ 10 (e.g. AQ 10® by IntrachemBio Italia); (B2.56) *Aureobasidium pullulans*, in particular blastospores of strain DSM14940; (B2.57) *Aureobasidium pullulans*, in particular blastospores of strain DSM 14941; (B2.58) *Aureobasidium pullulans*, in particular mixtures of blastospores of strains DSM14940 and DSM 14941 (e.g. Botector® by bio-ferm, CH); (B2.64) *Cladosporium cladosporioides*, strain H39, having Accession No. CBS122244, US 2010/0291039 (by Stichting Dienst Landbouwkundig Onderzoek); (B2.69) *Gliocladium catenulatum* (Synonym: *Clonostachys rosea* f *catenulate*) strain J1446 (e.g. Prestop® by Lallemand); (B2.70) *Lecanicillium lecanii* (formerly known as *Verticillium lecanii*) conidia of strain KVO1 (e.g. Vertalec® by Koppert/Arysta); (B2.71) *Penicillium vermiculatum*; (B2.72) *Pichia anomala*, strain WRL-076 (NRRL Y-30842), U.S. Pat. No. 7,579,183; (B2.75) *Trichoderma atroviride*, strain SKT-1 (FERM P-16510), JP Patent Publication (Kokai) 11-253151 A; (B2.76) *Trichoderma atroviride*, strain SKT-2 (FERM P-16511), JP Patent Publication (Kokai) 11-253151 A; (B2.77) *Trichoderma atroviride*, strain SKT-3 (FERM P-17021), JP Patent Publication (Kokai) 11-253151 A; (B2.78) *Trichoderma gamsii* (formerly *T. viride*), strain ICC080 (IMI CC 392151 CABI, e.g. BioDerma by AGROBIOSOL DE MEXICO, S.A. DE C.V.); (B2.79) *Trichoderma harzianum*, strain DB 103 (available as T-GRO® 7456 by Dagutat Biolab); (B2.80) *Trichoderma polysporum*, strain IMI 206039 (e.g. Binab TF WP by BINAB Bio-Innovation AB, Sweden); (B2.81) *Trichoderma stromaticum*, having Accession No. Ts3550 (e.g. Tricovab by CEPLAC, Brazil); (B2.83) *Ulocladium oudemansii* strain U3, having Accession No. NM 99/06216 (e.g., BOTRY-ZEN® by Botry-Zen Ltd, New Zealand and BOTRYSTOP® from BioWorks, Inc.); (B2.84) *Verticillium albo-atrum* (formerly *V. dahliae*), strain WCS850 having Accession No. WCS850, deposited at the Central Bureau for Fungi Cultures (e.g., DUTCH TRIG® by Tree Care Innovations); (B2.86) *Verticillium chlamydosporium*; (B2.87) mixtures of *Trichoderma asperellum* strain ICC 012 (also known as *Trichoderma harzianum* ICC012), having Accession No. CABI CC IMI 392716 and *Trichoderma gamsii* (formerly *T. viride*) strain ICC 080, having Accession No. IMI 392151 (e.g., BIOTAM™ from Isagro USA, Inc. and BIODERMA® by Agrobiosol de Mexico, S.A. de C.V.); (B2.88) *Trichoderma asperelloides* JM41R (Accession No. NRRL B-50759) (TRICHO PLUS® from BASF SE); (B2.89) *Aspergillus flavus* strain NRRL 21882 (products known as AFLA-GUARD® from Syngenta/ChemChina); (B2.90) *Chaetomium cupreum* (Accession No. CABI 353812) (e.g. BIOKUPRUM™ by AgriLife); (B2.91) *Saccharomyces cerevisiae*, in particular strain LASO2 (from Agro-Levures et D6riv6s), strain LAS117 cell walls (CEREVISANE® from Lesaffre; ROMEO® from BASF SE), strains CNCM No. 1-3936, CNCM No. 1-3937, CNCM No. I-3938, CNCM No. I-3939 (WO 2010/086790) from Lesaffre et Compagnie, FR; (B2.92) *Trichoderma virens* strain G-41, formerly known as *Gliocladium virens* (Accession No. ATCC 20906) (e.g., ROOTSHIELD® PLUS WP and TURFSHIELD® PLUS WP from BioWorks, US); (B2.93) *Trichoderma hamatum*, having Accession No. ATCC 28012; (B2.94) *Ampelomyces quisqualis* strain AQ10, having Accession No. CNCM I-807 (e.g., AQ 10® by IntrachemBio Italia); (B2.95) *Phlebiopsis gigantea* strain VRA 1992 (ROTSTOP® C from Danstar Ferment); (B2.96) *Penicillium steckii* (DSM 27859; WO 2015/067800) from BASF SE; (B2.97) *Chaetomium globosum* (available as RIVADIOM® by *Rivale*); (B2.98) *Cryptococcus flavescens*, strain 3C (NRRL Y-50378); (B2.99) Dactylaria *candida*; (B2.100) *Dilophosphora alopecuri* (available as TWIST FUNGUS®); (B2.101) *Fusarium oxysporum*, strain Fo47 (available as FUSACLEAN® by Natural Plant Protection); (B2.102) *Pseudozyma flocculosa*, strain PF-A22 UL (available as SPORODEX® L by Plant Products Co., CA); (B2.103) *Trichoderma gamsii* (formerly *T. viride*), strain ICC 080 (IMI CC 392151 CABI) (available as BIODERMA® by AGROBIOSOL DE MEXICO, S.A. DE C.V.); (B2.104) *Trichoderma* fertile (e.g. product TrichoPlus from BASF); (B2.105) Muscodor *roseus*, in particular strain A3-5 (Accession No. NRRL 30548); (B2.106) *Simplicillium lanosoniveum;* biological control agents having an effect for improving plant growth and/or plant health which may be combined in the compound combinations according to the invention including (C1) bacteria selected from the group consisting of *Bacillus pumilus*, in particular strain QST2808 (having Accession No. NRRL No. B-30087); *Bacillus subtilis*, in particular strain QST713/AQ713 (having NRRL Accession No. B-21661 and described in U.S. Pat. No. 6,060,051; available as SERENADE® OPTI or SERENADE® ASO from Bayer CropScience LP, US); *Bacillus subtilis*, in particular strain AQ30002 (having Accession Nos. NRRL B-50421 and described in U.S. patent application Ser. No. 13/330,576); *Bacillus subtilis*, in particular strain AQ30004 (and NRRL B-50455 and described in U.S. patent application Ser. No. 13/330,576); *Sinorhizobium meliloti* strain NRG-185-1 (NITRAGIN® GOLD from Bayer CropScience); *Bacillus subtilis* strain BU1814, (available as TEQUALIS® from BASF SE); *Bacillus subtilis* rm303 (RHIZOMAX® from Biofilm Crop Protection); *Bacillus amyloliquefaciens* pm414 (LOLI-PEPTA® from Biofilm Crop Protection); *Bacillus mycoides* BT155 (NRRL No. B-50921), *Bacillus mycoides* EE118 (NRRL No. B-50918), *Bacillus mycoides* EE141 (NRRL No. B-50916), *Bacillus mycoides* BT46-3 (NRRL No. B-50922), *Bacillus cereus* family member EE128 (NRRL No. B-50917), *Bacillus thuringiensis* BT013A (NRRL No. B-50924) also known as *Bacillus thuringiensis* 4Q7, *Bacillus cereus* family member EE349 (NRRL No. B-50928), *Bacillus amyloliquefaciens* SB3281 (ATCC #PTA-7542; WO 2017/205258), *Bacillus amyloliquefaciens* TJ1000 (available as QUIKROOTS® from Novozymes); *Bacillus firmus*, in particular strain CNMC I-1582 (e.g. VOTIVO® from BASF SE); *Bacillus pumilus*, in particular strain GB34 (e.g. YIELD SHIELD® from Bayer Crop Science, DE); *Bacillus amyloliquefaciens*, in particular strain IN937a; *Bacillus amyloliquefaciens*, in particular strain FZB42 (e.g. RHIZOVITAL® from ABiTEP, DE); *Bacillus amyloliquefaciens* BS27 (Accession No. NRRL B-5015); a mixture of *Bacillus licheniformis* FMCH001 and *Bacillus subtilis* FMCH002 (available as QUARTZO® (WG), PRESENCE® (WP) from FMC Corporation); *Bacillus cereus*, in particular strain BP01 (ATCC 55675; e.g. MEPICHLOR® from Arysta Lifescience, US); *Bacillus subtilis*, in particular strain MBI 600 (e.g. SUBTILEX® from BASF SE); *Bradyrhizobium japonicum* (e.g. OPTIMIZE® from Novozymes); *Mesorhizobium cicer* (e.g., NODULATOR from BASF SE); *Rhizobium leguminosarium biovar viciae* (e.g., NODULATOR from BASF SE); Delftia *acidovorans*, in particular strain RAY209 (e.g. BIOBOOST® from Brett Young Seeds); *Lactobacillus* sp. (e.g. LACTOPLANT® from LactoPAFI); *Paenibacillus polymyxa*, in particular strain AC-1 (e.g. TOPSEED® from Green Biotech Company Ltd.); *Pseudomonas proradix* (e.g. PRORADIX® from Sourcon Padena); *Azospirillum brasilense* (e.g., VIGOR® from KALO, Inc.); *Azospirillum lipoferum* (e.g., VERTEX-IF™ from TerraMax, Inc.); a mixture of *Azotobacter vinelandii* and *Clostridium pasteurianum* (available as INVIGORATE® from Agrinos); *Pseudomonas aeruginosa*, in particular strain PN1; *Rhizobium leguminosarum*, in particular bv. *viceae* strain Z25 (Accession No. CECT 4585); *Azorhizobium caulinodans*, in particular strain ZB-SK-5; *Azotobacter chroococcum*, in particular strain H23; *Azotobacter vinelandii*, in particular strain ATCC 12837; *Bacillus siamensis*, in particular strain KCTC 13613T; *Bacillus* tequilensis, in particular strain NII-0943; *Serratia marcescens*, in particular strain SRM (Accession No. MTCC 8708); *Thiobacillus* sp. (e.g. CROPAID® from Cropaid Ltd UK); and (C2) fungi selected from the group consisting of *Purpureocillium lilacinum* (previously known as *Paecilomyces lilacinus*) strain 251 (AGAL 89/030550; e.g. BioAct from Bayer CropScience Biologics GmbH)*Penicillium* bilaii, strain ATCC 22348 (e.g. JumpStart® from Acceleron BioAg), *Talaromyces flavus*, strain V117b; *Trichoderma atroviride* strain CNCM I-1237 (e.g. Esquive® WP from Agrauxine, FR), *Trichoderma viride*, e.g. strain B35 (Pietr et al., 1993, Zesz. Nauk. A R w Szczecinie 161: 125-137); *Trichoderma atroviride* strain LC52 (also known as *Trichoderma atroviride* strain LU132; e.g. Sentinel from Agrimm Technologies Limited); *Trichoderma atroviride* strain SC1 described in International Application No. PCT/IT2008/000196); *Trichoderma asperellum* strain kd (e.g. T-Gro from Andermatt Biocontrol); *Trichoderma asperellum* strain Eco-T (Plant Health Products, ZA); *Trichoderma harzianum* strain T-22 (e.g. Trianum-P from Andermatt Biocontrol or Koppert); *Myrothecium* verrucaria strain AARC-0255 (e.g. DiTera™ from Valent Biosciences); *Penicillium* bilaii strain ATCC ATCC20851; *Pythium oligandrum* strain M1 (ATCC 38472; e.g. Polyversum from Bioprepraty, CZ); *Trichoderma virens* strain GL-21 (e.g. SoilGard® from Certis, USA); *Verticillium albo-atrum* (formerly *V. dahliae*) strain WCS850 (CBS 276.92; e.g. Dutch Trig from Tree Care Innovations); *Trichoderma atroviride*, in particular strain no. V08/002387, strain no. NMI No. V08/002388, strain no. NMI No. V08/002389, strain no. NMI No. V08/002390; *Trichoderma harzianum* strain ITEM 908; *Trichoderma harzianum*, strain TSTh20; *Trichoderma harzianum* strain 1295-22; *Pythium oligandrum* strain DV74; *Rhizopogon amylopogon* (e.g. comprised in Myco-Sol from Helena Chemical Company); *Rhizopogon fulvigleba* (e.g. comprised in Myco-Sol from Helena Chemical Company); and *Trichoderma virens* strain GI-3;

insecticidally active biological control agents selected from (D1) bacteria selected from the group consisting of *Bacillus thuringiensis* subsp. *aizawai*, in particular strain ABTS-1857 (SD-1372; e.g. XENTARI® from Valent BioSciences); *Bacillus mycoides*, isolate J. (e.g. BmJ from Certis USA LLC, a subsidiary of Mitsui & Co.); *Bacillus sphaericus*, in particular Serotype H5a5b strain 2362 (strain ABTS-1743) (e.g. VECTOLEX® from Valent BioSciences, US); *Bacillus thuringiensis* subsp. *kurstaki* strain BMP 123 from Becker Microbial Products, IL; *Bacillus thuringiensis* subsp. *aizawai*, in particular serotype H-7 (e.g. FLORBAC® WG from Valent BioSciences, US); *Bacillus thuringiensis* subsp. *kurstaki* strain HD-1 (e.g. DIPEL® ES from Valent BioSciences, US); *Bacillus thuringiensis* subsp. *kurstaki* strain BMP 123 by Becker Microbial Products, IL; *Bacillus thuringiensis israelensis* strain BMP 144 (e.g. AQUABAC® by Becker Microbial Products IL); *Burkholderia* spp., in particular *Burkholderia rinojensis* strain A396 (also known as *Burkholderia rinojensis* strain MBI 305) (Accession No. NRRL B-50319; WO 2011/106491 and WO 2013/032693; e.g. MBI-206 TGAI and ZELTO® from Marrone Bio Innovations); *Chromobacterium subtsugae*, in particular strain PRAA4-1T (MBI-203; e.g. GRANDEVO® from Marrone Bio Innovations); *Paenibacillus popilliae* (formerly *Bacillus popilliae*; e.g. MILKY SPORE POWDER™ and MILKY SPORE GRANULAR™ from St. Gabriel Laboratories); *Bacillus thuringiensis* subsp. *israelensis* (serotype H-14) strain AM65-52 (Accession No. ATCC 1276) (e.g. VECTOBAC® by Valent BioSciences, US); *Bacillus thuringiensis* var. *kurstaki* strain EVB-113-19 (e.g., BIOPROTEC® from AEF Global); *Bacillus thuringiensis* subsp. *tenebrionis* strain NB 176 (SD-5428; e.g. NOVODOR® FC from BioFa DE); *Bacillus thuringiensis* var. *japonensis* strain Buibui; *Bacillus thuringiensis* subsp. *kurstaki* strain ABTS 351; *Bacillus thuringiensis* subsp. *kurstaki* strain PB 54; *Bacillus thuringiensis* subsp. *kurstaki* strain SA 11; *Bacillus thuringiensis* subsp. *kurstaki* strain SA 12; *Bacillus thuringiensis* subsp. *kurstaki* strain EG 2348; *Bacillus thuringiensis* var. *Colmeri* (e.g. TIANBAOBTC by Changzhou Jianghai Chemical Factory); *Bacillus thuringiensis* subsp. *aizawai* strain GC-91; *Serratia entomophila* (e.g. INVADE® by Wrightson Seeds); *Serratia marcescens*, in particular strain SRM (Accession No. MTCC 8708); and *Wolbachia pipientis* ZAP strain (e.g., ZAP MALES® from MosquitoMate); and (D2) fungi selected from the group consisting of *Isaria fumosorosea* (previously known as *Paecilomyces* fumosoroseus) strain apopka 97; *Beauveria bassiana* strain ATCC 74040 (e.g. NATURALIS® from Intrachem Bio Italia); *Beauveria bassiana* strain GHA (Accession No. ATCC74250; e.g. BOTANIGUARD® ES and MYCONTROL-O® from Laverlam International Corporation); Zoophtora *radicans; Metarhizium robertsii* 15013-1 (deposited under NRRL accession number 67073), *Metarhizium robertsii* 23013-3 (deposited under NRRL accession number 67075), and *Metarhizium anisopliae* 3213-1 (deposited under NRRL accession number 67074) (WO 2017/066094; Pioneer Hi-Bred International); *Beauveria bassiana* strain ATP02 (Accession No. DSM 24665). Among these, *Isaria fumosorosea* (previously known as *Paecilomyces* fumosoroseus) strain apopka 97 is particularly preferred;

(E) viruses selected from the group consisting of *Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, and *Spodoptera littoralis* (African cotton leafworm) NPV;

(F) bacteria and fungi which can be added as 'inoculant' to plants or plant parts or plant organs and which, by virtue of their particular properties, promote plant growth and plant health. Examples are: *Agrobacterium* spp., *Azorhizobium caulinodans, Azospirillum* spp., *Azotobacter* spp., *Bradyrhizobium* spp., *Burkholderia* spp., in particular *Burkholderia cepacia* (formerly known as *Pseudomonas cepacia*), *Gigaspora* spp., or *Gigaspora monosporum, Glomus* spp., *Laccaria* spp., *Lactobacillus buchneri, Paraglomus* spp., *Pisolithus tinctorus, Pseudomonas* spp., *Rhizobium* spp., in particular *Rhizobium trifolii, Rhizopogon* spp., *Scleroderma* spp., *Suillus* spp., and *Streptomyces* spp.; and (G) plant extracts and products formed by microorganisms including proteins and secondary metabolites which can be used as biological control agents, such as *Allium sativum, Artemisia absinthium*, azadirachtin, Biokeeper WP, *Cassia nigricans, Celastrus angulatus, Chenopodium anthelminticum*, chitin, Armour-Zen, Dryopteris filix-mas, *Equisetum arvense*, Fortune Aza, Fungastop, Heads Up (*Chenopodium quinoa* saponin extract), Pyrethrum/Pyrethrins, *Quassia amara, Quercus*, Quillaja, Regalia, "Requiem™ Insecticide", rotenone, ryania/ryanodine, *Symphytum officinale, Tanacetum vulgare*, thymol, Triact 70, TriCon, *Tropaeulum majus, Urtica dioica*, Veratrin, *Viscum album, Brassicaceae* extract, in particular oilseed rape powder or mustard powder, as well as bioinsecticidal/acaricidal active substances obtained from olive oil, in particular unsaturated fatty/carboxylic acids having carbon chain lengths $C_{16}$-$C_{20}$ as active ingredients, such as, for example, contained in the product with the trade name FLiPPER®.

The compound of formula (I) and the composition of the invention may be combined with one or more active ingredients selected from insecticides, acaricides and nematicides.

"Insecticides" as well as the term "insecticidal" refers to the ability of a substance to increase mortality or inhibit growth rate of insects. As used herein, the term "insects" comprises all organisms in the class "Insecta".

"Nematicide" and "nematicidal" refers to the ability of a substance to increase mortality or inhibit the growth rate of nematodes. In general, the term "nematode" comprises eggs, larvae, juvenile and mature forms of said organism.

"Acaricide" and "acaricidal" refers to the ability of a substance to increase mortality or inhibit growth rate of ectoparasites belonging to the class Arachnida, sub-class Acari.

Examples of insecticides, acaricides and nematicides, respectively, which could be mixed with the compound of formula (I) and the composition of the invention are:

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, such as, for example, cyclodiene-organochlorines, for example chlordane and endosulfan or phenylpyrazoles (fiproles), for example ethiprole and fipronil.

(3) Sodium channel modulators, such as, for example, pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinic acetylcholine receptor (nAChR) competitive modulators, such as, for example, neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, such as, for example, spinosyns, e.g. spinetoram and spinosad.

(6) Glutamate-gated chloride channel (GluCl) allosteric modulators, such as, for example, avermectins/milbemycins, for example abamectin, emamectin benzoate, lepimectin and milbemectin.

(7) Juvenile hormone mimics, such as, for example, juvenile hormone analogues, e.g. hydroprene, kinoprene and methoprene or fenoxycarb or pyriproxyfen.

(8) Miscellaneous non-specific (multi-site) inhibitors, such as, for example, alkyl halides, e.g. methyl bromide and other alkyl halides; or chloropicrine or sulphuryl fluoride or borax or tartar emetic or methyl isocyanate generators, e.g. diazomet and metam.

(9) Modulators of Chordotonal Organs, such as, for example pymetrozine or flonicamid.

(10) Mite growth inhibitors, such as, for example clofentezine, hexythiazox and diflovidazin or etoxazole.

(11) Microbial disruptors of the insect gut membrane, such as, for example *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and B.t. plant proteins: Cry1Ab, Cry1Ac, Cry1Fa, Cry1A.105, Cry2Ab, Vip3A, mCry3A, Cry3Ab, Cry3Bb, Cry34Ab1/35Ab1.

(12) Inhibitors of mitochondrial ATP synthase, such as, ATP disruptors such as, for example, diafenthiuron or organotin compounds, for example azocyclotin, cyhexatin and fenbutatin oxide or propargite or tetradifon.

(13) Uncouplers of oxidative phosphorylation via disruption of the proton gradient, such as, for example, chlorfenapyr, DNOC and sulfluramid.

(14) Nicotinic acetylcholine receptor channel blockers, such as, for example, bensultap, cartap hydrochloride, thiocylam, and thiosultap-sodium.

(15) Inhibitors of chitin biosynthesis, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptor (in particular for Diptera, i.e. dipterans), such as, for example, cyromazine.

(18) Ecdysone receptor agonists, such as, for example, chromafenozide, halofenozide, methoxyfenozide and tebufenozide.

(19) Octopamine receptor agonists, such as, for example, amitraz.

(20) Mitochondrial complex III electron transport inhibitors, such as, for example, hydramethylnone or acequinocyl or fluacrypyrim.

(21) Mitochondrial complex I electron transport inhibitors, such as, for example from the group of the METI acaricides, e.g. fenazaquin, fenpyroximate, pyrimidifen, pyridaben, tebufenpyrad and tolfenpyrad or rotenone (Derris).

(22) Voltage-dependent sodium channel blockers, such as, for example indoxacarb or metaflumizone.

(23) Inhibitors of acetyl CoA carboxylase, such as, for example, tetronic and tetramic acid derivatives, e.g. spirodiclofen, spiromesifen and spirotetramat.

(24) Mitochondrial complex IV electron transport inhibitors, such as, for example, phosphines, e.g. aluminium phosphide, calcium phosphide, phosphine and zinc phosphide or cyanides, e.g. calcium cyanide, potassium cyanide and sodium cyanide.

(25) Mitochondrial complex II electron transport inhibitors, such as, for example, beta-ketonitrile derivatives, e.g. cyenopyrafen and cyflumetofen and carboxanilides, such as, for example, pyflubumide.

(28) Ryanodine receptor modulators, such as, for example, diamides, e.g. chlorantraniliprole, cyantraniliprole and flubendiamide, further active compounds such as, for example, Afidopyropen, Afoxolaner, Azadirachtin, Benclothiaz, Benzoximate, Bifenazate, Broflanilide, Bromopropylate, Chinomethionat, Chloroprallethrin, Cryolite, Cyclaniliprole, Cycloxaprid, Cyhalodiamide, Dicloromezotiaz, Dicofol, epsilon-Metofluthrin, epsilon-Momfluthrin, Flometoquin, Fluazaindolizine, Fluensulfone, Flufenerim, Flufenoxystrobin, Flufiprole, Fluhexafon, Fluopyram, Fluralaner, Fluxametamide, Fufenozide, Guadipyr, Heptafluthrin, Imidaclothiz, Iprodione, kappa-Bifenthrin, kappa-Tefluthrin, Lotilaner, Meperfluthrin, Paichongding, Pyridalyl, Pyrifluquinazon, Pyriminostrobin, Spirobudiclofen, Tetramethylfluthrin, Tetraniliprole, Tetrachlorantraniliprole, Tigolaner, Tioxazafen, Thiofluoximate, Triflumezopyrim and iodomethane; furthermore preparations based on *Bacillus firmus* (I-1582, BioNeem, Votivo), and also the following compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro[indol-3,4'-piperidin]-1(2H)-yl}(2-chloropyridin-4-yl)methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethyl carbonate (known from EP2647626) (CAS 1440516-42-6), 4-(but-2-yn-1-yloxy)-6-(3,5-dimethylpiperidin-1-yl)-5-fluoro-pyrimidine (known from WO2004/099160) (CAS 792914-58-0), PF1364 (known from JP2010/018586) (CAS 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoro-propan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)-benzamide, 4-[5-(3,5-dichlorophenyl)-4,5-dihydro-5-(trifluoromethyl)-3-isoxazolyl]-2-methyl-N-(trans-1-oxido-3-thietanyl)-benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]-propanamide, (+)-N-[3-chloro-1-(3-pyridinyl)-1H-pyrazol-4-yl]-N-ethyl-3-[(3,3,3-trifluoropropyl)sulfinyl]-propanamide and (−)-N-[3-chloro-1-(3-pyridinyl)-1H-pyrazol-4-yl]-N-ethyl-3-[(3,3,3-trifluoropropyl)sulfinyl]-propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-Pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)-pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]-hydrazinecarboxamide (known from CN 101715774 A) (CAS 1232543-85-9); 3-(2,2-dichloroethenyl)-2,2-dimethyl-4-(1H-benzimidazol-2-yl)phenyl-cyclopropanecarboxylic acid ester (known from CN 103524422 A) (CAS 1542271-46-4); (4aS)-7-chloro-2,5-dihydro-2-[[(methoxycarbonyl)[4-[(trifluoromethyl)thio]phenyl]amino]carbonyl]-indeno[1,2-e][1,3,4]oxadiazine-4a(3H)-carboxylic acid methyl ester (known from CN 102391261 A) (CAS 1370358-69-2); 6-deoxy-3-O-ethyl-2,4-di-O-methyl-, 1-[N-[4-[1-[4-(1,1,2,2,2-pentafluoroethoxy)phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethyl-phenoxy)-3-(6-trifluoromethyl-pyridazin-3-yl)-3-aza-bicyclo[3.2.1]octane (CAS 1253850-56-4), (8-anti)-8-(2-cyclopropylmethoxy-4-trifluoromethyl-phenoxy)-3-(6-trifluoromethyl-pyridazin-3-yl)-3-aza-bicyclo[3.2.1]octane (CAS 933798-27-7), (8-syn)-8-(2-cyclopropylmethoxy-4-trifluoromethyl-phenoxy)-3-(6-trifluoromethyl-pyridazin-3-yl)-3-aza-bicyclo[3.2.1]octane (known from WO2007/040280 A1, WO 2007040282 A1) (CAS 934001-66-8), N-[3-chloro-1-(3-pyridinyl)-1H-pyrazol-4-yl]-N-ethyl-3-[(3,3,3-trifluoropropyl)thio]-propanamide (known from WO 2015/058021 A1, WO 2015/058028 A1) (CAS 1477919-27-9) and N-[4-(aminothioxomethyl)-2-methyl-6-[(methylamino)carbonyl]phenyl]-3-bromo-1-(3-chloro-2-pyridinyl)-1H-pyrazole-5-carboxamide (known from CN 103265527 A) (CAS 1452877-50-7), 5-(1,3-dioxan-2-yl)-4-[[4-(trifluoromethyl)phenyl]methoxy]-pyrimidine (known from WO 2013/115391 A1) (CAS 1449021-97-9), 3-(4-chloro-2,6-dimethylphenyl)-4-hydroxy-8-methoxy-1-methyl-1,8-diazaspiro[4.5]dec-3-en-2-one (known from WO 2010/066780 A1, WO 2011/151146 A1) (CAS 1229023-34-0), 3-(4-chloro-2,6-dimethylphenyl)-8-methoxy-1-methyl-1,8-diazaspiro[4.5]decane-2,4-dione (known from WO 2014/187846 A1) (CAS 1638765-58-8), 3-(4-chloro-2,6-dimethylphenyl)-8-methoxy-1-methyl-2-oxo-1,8-diazaspiro[4.5]dec-3-en-4-yl-carbonic acid ethyl ester (known from WO 2010/066780 A1, WO 2011151146 A1) (CAS 1229023-00-0), N-[1-[(6-chloro-3-pyridinyl)methyl]-2(1H)-pyridinylidene]-2,2,2-trifluoro-acetamide (known from DE 3639877 A1, WO 2012029672 A1) (CAS 1363400-41-2), [N(E)]-N-[1-[(6-chloro-3-pyridinyl)methyl]-2(1H)-pyridinylidene]-2,2,2-trifluoro-acetamide, (known from WO 2016005276 A1) (CAS 1689566-03-7), [N(Z)]—N-[1-[(6-chloro-3-pyridinyl)methyl]-2(1H)-pyridinylidene]-2,2,2-trifluoro-acetamide, (CAS 1702305-40-5), 3-endo-3-[2-propoxy-4-(trifluoromethyl)phenoxy]-9-[[5-(trifluoromethyl)-2-pyridinyl]oxy]-9-azabicyclo[3.3.1]nonane (known from WO 2011/105506 A1, WO 2016/133011 A1) (CAS 1332838-17-1).

Examples of herbicides which could be mixed with the compound of formula (I) and the composition of the invention are:

Acetochlor, acifluorfen, acifluorfen-sodium, aclonifen, alachlor, allidochlor, alloxydim, alloxydim-sodium, ametryn, amicarbazone, amidochlor, amidosulfuron, 4-amino-3-chloro-5-fluoro-6-(7-fluoro-1H-indol-6-yl)pyridine-2-carboxylic acid, aminocyclopyrachlor, aminocyclopyrachlor-potassium, aminocyclopyrachlor-methyl, aminopyralid, amitrole, ammoniumsulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyron, bifenox, bilanafos, bilanafos-sodium, bispyribac, bispyribac-sodium, bixlozone, bromacil, bromobutide, bromofenoxim, bromoxynil, bromoxynil-butyrate, -potassium, -heptanoate, and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, 1-{2-chloro-3-[(3-cyclopropyl-5-hydroxy-1-methyl-1H-pyrazol-4-yl)carbonyl]-6-(trifluormethyl)phenyl}piperidin-2-on, 4-{2-chloro-3-[(3,5-dimethyl-1H-pyrazol-1-yl)methyl]-4-(methylsulfonyl)benzoyl}-1,3-dimethyl-1H-pyrazol-5-yl-1,3-dimethyl-1H-pyrazol-4-carboxylat, chlorfenac, chlorfenac-sodium, chlorfenprop, chlorflurenol, chlorflurenol-methyl, chloridazon, chlorimuron, chlorimuron-ethyl, 2-[2-chloro-4-(methylsulfonyl)-3-(morpholin-4-ylmethyl)benzoyl]-3-hydroxycyclohex-2-en-1-on, 4-{2-chloro-4-(methylsulfonyl)-3-[(2,2,2-trifluoroethoxy)methyl]benzoyl}-1-ethyl-1H-pyrazol-5-yl-1,3-dimethyl-1H-pyrazol-4-carboxylat, chlorophthalim, chlorotoluron, chlorthal-dimethyl, 3-[5-chloro-4-(trifluormethyl)pyridine-2-yl]-4-hydroxy-1-methylimidazolidine-2-on, chlorsulfuron, cinidon, cinidon-ethyl, cinmethylin, cinosulfuron, clacyfos, clethodim, clodinafop, clodinafop-propargyl, clomazone, clomeprop, clopyralid, cloransulam, cloransulam-methyl, cumyluron, cyanamide, cyanazine, cycloate, cyclopyranil, cyclopyrimorate, cyclosulfamuron, cycloxydim, cyhalofop, cyhalofop-butyl, cyprazine, 2,4-D, 2,4-D-butotyl, -butyl, -dimethylammonium, -diolamin, -ethyl, -2-ethylhexyl, -isobutyl, -isooctyl, -isopropylammonium, -potassium, -triisopropanolammonium, and -trolamine, 2,4-DB, 2,4-DB-butyl, -dimethylammonium, -isooctyl, -potassium, and -sodium, daimuron (dymron), dalapon, dazomet, n-decanol, desmedipham, detosyl-pyrazolate (DTP), dicamba, dichlobenil, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, 3-(2,6-dimethylphenyl)-6-[(2-hydroxy-6-oxocyclohex-1-en-1-yl)carbonyl]-1-methylchinazolin-2,4(1H,3H)-dion, 1,3-dimethyl-4-[2-(methylsulfonyl)-4-(trifluormethyl)benzoyl]-1H-pyrazol-5-yl-1,3-dimethyl-1H-pyrazol-4-carboxylat, dimetrasulfuron, dinitramine, dinoterb, diphenamid, diquat, diquat-dibromid, dithiopyr, diuron, DMPA, DNOC, endothal, EPTC, esprocarb, ethalfluralin, ethametsulfuron, ethametsulfuron-methyl, ethiozin, ethofumesate, ethoxyfen, ethoxyfen-ethyl, ethoxysulfuron, etobenzanid, ethyl-[(3-{2-chloro-4-fluoro-5-[3-methyl-2,6-dioxo-4-(trifluormethyl)-3,6-dihydropyrimidin-1(2H)-yl]phenoxy}pyridin-2-yl)oxy]acetat, F-9960, F-5231, i.e. N-{2-chloro-4-fluoro-5-[4-(3-fluoropropyl)-5-oxo-4,5-dihydro-1H-tetrazol-1-yl]phenyl}ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxaprop-ethyl, fenoxaprop-P-ethyl, fenoxasulfone, fenquinotrione, fentrazamide, flamprop, flamprop-M-isopropyl, flamprop-M-methyl, flazasulfuron, florasulam, fluazifop, fluazifop-P, fluazifop-butyl, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, flurenol, flurenol-butyl, -dimethylammonium and -methyl, fluoroglycofen, fluoroglycofen-ethyl, flupropanate, flupyrsulfuron, flupyrsulfuron-methyl-sodium, fluridone, flurochloridone, fluroxypyr, fluroxypyr-meptyl, flurtamone, fluthiacet, fluthiacet-methyl, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium, and -trimesium, H-9201, i.e. O-(2,4-dimethyl-6-nitrophenyl)O-ethyl isopropylphosphoramidothioate, halauxifen, halauxifen-methyl, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl-(2,4-dichlorophenoxy)acetate, 4-hydroxy-1-methoxy-5-methyl-3-[4-(trifluormethyl)pyridine-2-yl]imidazolidine-2-on, 4-hydroxy-1-methyl-3-[4-(trifluormethyl)pyridine-2-yl]imidazolidine-2-on, (5-hydroxy-1-methyl-1H-pyrazol-4-yl)(3,3,4-trimethyl-1,1-dioxido-2,3-dihydro-1-benzothiophen-5-yl)methanon, 6-[(2-hydroxy-6-oxocyclohex-1-en-1-yl)carbonyl]-1,5-dimethyl-3-(2-methylphenyl)chinazolin-2,4(1H,3H)-dion, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxynil-octanoate, -potassium and -sodium, ipfencarbazone, isoproturon, isouron, isoxaben, isoxaflutole, karbutilate, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, ketospiradox, lactofen, lenacil, linuron, MCPA, MCPA-butotyl, -dimethylammonium, -2-ethylhexyl, -isopropylammonium, -potassium, and -sodium, MCPB, MCPB-methyl, -ethy,l and -sodium, mecoprop, mecoprop-sodium, and -butotyl, mecoprop-P, mecoprop-P-butotyl, -dimethylammonium, -2-ethylhexyl, and -potassium, mefenacet, mefluidide, mesosulfuron, mesosulfuron-methyl, mesotrione, methabenzthiazuron, metam, metamifop, metamitron, metazachlor, metazosulfuron, methabenzthiazuron, methiopyrsulfuron, methiozolin, 2-({2-[(2-methoxyethoxy) methyl]-6-(trifluormethyl)pyridin-3-yl}carbonyl)cyclohexan-1,3-dion, methyl isothiocyanate, 1-methyl-4-[(3,3,4-trimethyl-1,1-dioxido-2,3-dihydro-1-benzothiophen-5-yl) carbonyl]-1H-pyrazol-5-ylpropan-1-sulfonat, metobromuron, metolachlor, S-metolachlor, metosulam, metoxuron, metribuzin, metsulfuron, metsulfuron-methyl, molinat, monolinuron, monosulfuron, monosulfuron-ester, MT-5950, i.e. N-(3-chloro-4-isopropylphenyl)-2-methylpentan amide, NGGC-011, napropamide, NC-310, i.e. [5-(benzyloxy)-1-methyl-1H-pyrazol-4-yl](2,4-dichlorophenyl)methanone, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxyfluorfen, paraquat, paraquat dichloride, pebulate, pendimethalin, penoxsulam, pentachlorphenol, pentoxazone, pethoxamid, petroleum oils, phenmedipham, picloram, picolinafen, pinoxaden, piperophos, pretilachlor, primisulfuron, primisulfuron-methyl, prodiamine, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, QYM-201, QYR-301, rimsulfuron, saflufenacil, sethoxydim, siduron, simazine, simetryn, SL-261, sulcotrion, sulfentrazone, sulfometuron, sulfometuron-methyl, sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trichloroacetic acid), TCA-sodium, tebuthiuron, tefuryltrione, tembotrione, tepraloxydim, terbacil, terbucarb, terbumeton, terbuthylazin, terbutryn, tetflupyrolimet, thenylchlor, thiazopyr, thiencarbazone, thiencarbazone-methyl, thifensulfuron, thifensulfuron-methyl, thiobencarb, tiafenacil, tolpyralate, topra-mezone, tralkoxydim, triafamone, tri-allate, triasulfuron, triaziflam, tribenuron, tribenuron-methyl, triclopyr, trietazine, trifloxysulfuron, trifloxysulfuron-sodium, trifludimoxazin, trifluralin, triflusulfuron, triflusulfuron-methyl, tritosulfuron, urea sulfate, vernolate, ZJ-0862, i.e. 3,4-dichloro-N-{2-[(4,6-dimethoxypyrimidin-2-yl)oxy]benzyl}aniline.

Examples for plant growth regulators are:

Acibenzolar, acibenzolar-S-methyl, 5-aminolevulinic acid, ancymidol, 6-benzylaminopurine, Brassinolid, catechine, chlormequat chloride, cloprop, cyclanilide, 3-(cycloprop-1-enyl) propionic acid, daminozide, dazomet, n-decanol, dikegulac, dikegulac-sodium, endothal, endothal-dipotassium, -disodium, and -mono(N,N-dimethylalkylammonium), ethephon, flumetralin, flurenol, flurenol-butyl, flurprimidol, forchlorfenuron, gibberellic acid, inabenfide, indol-3-acetic acid (IAA), 4-indol-3-ylbutyric acid, isoprothiolane, probenazole, jasmonic acid, maleic hydrazide, mepiquat chloride, 1-methyl-cyclopropene, methyl jasmonate, 2-(1-naphthyl)acetamide, 1-naphthylacetic acid, 2-naphthyloxyacetic acid, nitrophenolate-mixture, paclobutrazol, N-(2-phenylethyl)-beta-alanine, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P.

Examples of safeners which could be mixed with the compound of formula (I) and the composition of the invention are, for example, benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)-amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Examples of nitrification inhibitors which can be mixed with the compound of formula (I) and the composition of the invention are selected from the group consisting of 2-(3,4-dimethyl-1H-pyrazol-1-yl)succinic acid, 2-(4,5-dimethyl-1H-pyrazol-1-yl)succinic acid, 3,4-dimethyl pyrazolium glycolate, 3,4-dimethyl pyrazolium citrate, 3,4-dimethyl pyrazolium lactate, 3,4-dimethyl pyrazolium mandelate, 1,2,4-triazole, 4-Chloro-3-methylpyrazole, N-((3(5)-methyl-1H-pyrazole-1-yl)methyl)acetamide, N-((3(5)-methyl-1H-pyrazole-1-yl)methyl)formamide, N-((3(5),4-dimethylpyrazole-1-yl)methyl)formamide, N-((4-chloro-3(5)-methyl-pyrazole-1-yl)methyl)formamide; reaction adducts of dicyandiamide, urea and formaldehyde, triazonyl-formaldehyde-dicyandiamide adducts, 2-cyano-1-((4-oxo-1,3,5-triazinan-1-yl)methyl)guanidine, 1-((2-cyanoguanidino)methyl)urea, 2-cyano-1-((2-cyanoguanidino)-methyl)guanidine, 2-chloro-6-(trichloromethyl)-pyridine (nitrapyrin or N-serve), dicyandiamide, 3,4-dimethyl pyrazole phosphate, 4,5-dimethyl pyrazole phosphate, 3,4-dimethylpyrazole, 4,5-dimethyl pyrazole, ammoniumthiosulfate, neem, products based on ingredients of neem, linoleic acid, alpha-linolenic acid, methyl p-coumarate, methyl ferulate, methyl 3-(4-hydroxyphenyl) propionate, karanjin, brachialacton, p-benzoquinone sorgoleone, 4-amino-1,2,4-triazole hydrochloride, 1-amido-2-thiourea, 2-amino-4-chloro-6-methylpyrimidine, 2-mercapto-benzothiazole, 5-ethoxy-3-trichloromethyl-1,2,4-thiodiazole (terrazole, etridiazole), 2-sulfanilamidothiazole, 3-methylpyrazol, 1,2,4-triazol thiourea, cyan amide, melamine, zeolite powder, catechol, benzoquinone, sodium tetraborate, allylthiourea, chlorate salts, and zinc sulfate.

The compound of formula (I) and the composition of the invention may be combined with one or more agriculturally beneficial agents.

Examples of agriculturally beneficial agents include biostimulants, plant growth regulators, plant signal molecules, growth enhancers, microbial stimulating molecules, biomolecules, soil amendments, nutrients, plant nutrient enhancers, etc., such as lipo-chitooligosaccharides (LCO), chitooligosaccharides (CO), chitinous compounds, flavonoids, jasmonic acid or derivatives thereof (e.g., jasmonates), cytokinins, auxins, gibberellins, absiscic acid, ethylene, brassinosteroids, salicylates, macro- and micro-nutrients, linoleic acid or derivatives thereof, linolenic acid or derivatives thereof, karrikins, and beneficial microorganisms (e.g., *Rhizobium* spp., *Bradyrhizobium* spp., *Sinorhizobium* spp., *Azorhizobium* spp., *Glomus* spp., *Gigaspora* spp., *Hymenoscyphous* spp., *Oidiodendron* spp., *Laccaria* spp., *Pisolithus* spp., *Rhizopogon* spp., *Scleroderma* spp., *Rhizoctonia* spp., *Acinetobacter* spp., *Arthrobacter* spp., *Arthrobotrys* spp., *Aspergillus* spp., *Azospirillum* spp., *Bacillus* spp., *Burkholderia* spp., *Candida* spp., *Chryseomonas* spp.,

*Enterobacter* spp., *Eupenicillium* spp., *Exiguobacterium* spp., *Klebsiella* spp., *Kluyvera* spp., *Microbacterium* spp., *Mucor* spp., *Paecilomyces* spp., *Paenibacillus* spp., *Penicillium* spp., *Pseudomonas* spp., *Serratia* spp., *Stenotrophomonas* spp., *Streptomyces* spp., *Streptosporangium* spp., *Swaminathania* spp., *Thiobacillus* spp., *Torulospora* spp., *Vibrio* spp., *Xanthobacter* spp., *Xanthomonas* spp., etc.), and combinations thereof.

Methods and Uses

The compound of formula (I) and the composition of the invention have potent microbicidal activity and/or plant defense modulating potential. They can be used for controlling unwanted microorganisms, such as unwanted fungi and bacteria, on plants. They can be particularly useful in crop protection (they control microorganisms that cause plants diseases) or for protecting materials (e.g. industrial materials, timber, storage goods) as described in more details herein below. More specifically, the compound of formula (I) and the composition of the invention can be used to protect seeds, germinating seeds, emerged seedlings, plants, plant parts, fruits, harvest goods and/or the soil in which the plants grow from unwanted microorganisms.

Control or controlling as used herein encompasses protective, curative and eradicative treatment of unwanted microorganisms. Unwanted microorganisms may be pathogenic bacteria, pathogenic virus, pathogenic oomycetes or pathogenic fungi, more specifically phytopathogenic bacteria, phytopathogenic virus, phytopathogenic oomycetes or phytopathogenic fungi. As detailed herein below, these phytopathogenic microorganism are the causal agents of a broad spectrum of plants diseases.

More specifically, the compound of formula (I) and the composition of the invention can be used as fungicides. For the purpose of the specification, the term "fungicide" refers to a compound or composition that can be used in crop protection for the control of unwanted fungi, such as Plasmodiophoromycetes, Chytridiomycetes, Zygomycetes, Ascomycetes, Basidiomycetes and Deuteromycetes and/or for the control of Oomycetes.

The compound of formula (I) and the composition of the invention may also be used as antibacterial agent. In particular, they may be used in crop protection, for example for the control of unwanted bacteria, such as Pseudomonadaceae, Rhizobiaceae, Xanthomonadaceae, Enterobacteriaceae, Corynebacteriaceae and Streptomycetaceae.

The compound of formula (I) and the composition of the invention may also be used as antiviral agent in crop protection. For example the compound of formula (I) and the composition of the invention may have effects on diseases from plant viruses, such as the tobacco mosaic virus (TMV), tobacco rattle virus, tobacco stunt virus (TStuV), tobacco leaf curl virus (VLCV), tobacco nervilia mosaic virus (TVBMV), tobacco necrotic dwarf virus (TNDV), tobacco streak virus (TSV), potato virus X (PVX), potato viruses Y, S, M, and A, potato acuba mosaic virus (PAMV), potato mop-top virus (PMTV), potato leaf-roll virus (PLRV), alfalfa mosaic virus (AMV), cucumber mosaic virus (CMV), cucumber green mottlemosaic virus (CGMMV), cucumber yellows virus (CuYV), watermelon mosaic virus (WMV), tomato spotted wilt virus (TSWV), tomato ringspot virus (TomRSV), sugarcane mosaic virus (SCMV), rice dwarf virus, rice stripe virus, rice black-streaked dwarf virus, strawberry mottle virus (SMoV), strawberry vein banding virus (SVBV), strawberry mild yellow edge virus (SMYEV), strawberry crinkle virus (SCrV), broad beanwilt virus (BBWV), and melon necrotic spot virus (MNSV).

The present invention also relates to a method for controlling unwanted microorganisms, such as unwanted fungi, oomycetes and bacteria, on plants comprising the step of applying at least one compound of formula (I) or at least one composition of the invention to the microorganisms and/or their habitat (to the plants, plant parts, seeds, fruits or to the soil in which the plants grow).

Typically, when the compound of formula (I) and the composition of the invention are used in curative or protective methods for controlling phytopathogenic fungi and/or phytopathogenic oomycetes, an effective and plant-compatible amount thereof is applied to the plants, plant parts, fruits, seeds or to the soil or substrates in which the plants grow. Suitable substrates that may be used for cultivating plants include inorganic based substrates, such as mineral wool, in particular stone wool, perlite, sand or gravel; organic substrates, such as peat, pine bark or sawdust; and petroleum based substrates such as polymeric foams or plastic beads. Effective and plant-compatible amount means an amount that is sufficient to control or destroy the fungi present or liable to appear on the cropland and that does not entail any appreciable symptom of phytotoxicity for said crops. Such an amount can vary within a wide range depending on the fungus to be controlled, the type of crop, the crop growth stage, the climatic conditions and the respective compound or composition of the invention used. This amount can be determined by systematic field trials that are within the capabilities of a person skilled in the art.

Plants and Plant Parts

The compound of formula (I) and the composition of the invention may be applied to any plants or plant parts.

Plants mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the genetically modified plants (GMO or transgenic plants) and the plant cultivars which are protectable and non-protectable by plant breeders' rights.

Plant cultivars are understood to mean plants which have new properties ("traits") and have been obtained by conventional breeding, by mutagenesis or by recombinant DNA techniques. They can be cultivars, varieties, bio- or genotypes.

Plant parts are understood to mean all parts and organs of plants above and below the ground, such as shoots, leaves, needles, stalks, stems, flowers, fruit bodies, fruits, seeds, roots, tubers and rhizomes. The plant parts also include harvested material and vegetative and generative propagation material, for example cuttings, tubers, rhizomes, slips and seeds.

Plants which may be treated in accordance with the methods of the invention include the following: cotton, flax, grapevine, fruit, vegetables, such as Rosaceae sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce),

*Umbelliferae* sp., *Cruciferae* sp., *Chenopodiaceae* sp., *Cucurbitaceae* sp. (for example cucumber), *Alliaceae* sp. (for example leek, onion), *Papilionaceae* sp. (for example peas); major crop plants, such as Gramineae sp. (for example maize, turf, cereals such as wheat, rye, rice, barley, oats, millet and triticale), *Asteraceae* sp. (for example sunflower), Brassicaceae sp. (for example white cabbage, red cabbage, broccoli, cauliflower, Brussels sprouts, pak choi, kohlrabi, radishes, and oilseed rape, mustard, horseradish and cress), *Fabacae* sp. (for example bean, peanuts), *Papilionaceae* sp. (for example soya bean), *Solanaceae* sp. (for example potatoes), *Chenopodiaceae* sp. (for example sugar beet, fodder beet, swiss chard, beetroot); useful plants and ornamental plants for gardens and wooded areas; and genetically modified varieties of each of these plants.

Plants and plant cultivars which may be treated by the above disclosed methods include plants and plant cultivars which are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may be treated by the above disclosed methods include those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may be treated by the above disclosed methods include those plants characterized by enhanced yield characteristics. Increased yield in said plants may be the result of, for example, improved plant physiology, growth and development, such as water use efficiency, water retention efficiency, improved nitrogen use, enhanced carbon assimilation, improved photosynthesis, increased germination efficiency and accelerated maturation. Yield may furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content and composition for example cotton or starch, protein content, oil content and composition, nutritional value, reduction in anti-nutritional compounds, improved processability and better storage stability.

Plants and plant cultivars which may be treated by the above disclosed methods include plants and plant cultivars which are hybrid plants that already express the characteristic of heterosis or hybrid vigor which results in generally higher yield, vigor, health and resistance towards biotic and abiotic stresses.

Transgenic Plants, Seed Treatment and Integration Events

The compound of formula (I) can be advantageously used to treat transgenic plants, plant cultivars or plant parts that received genetic material which imparts advantageous and/or useful properties (traits) to these plants, plant cultivars or plant parts. Therefore, it is contemplated that the present invention may be combined with one or more recombinant traits or transgenic event(s) or a combination thereof. For the purposes of this application, a transgenic event is created by the insertion of a specific recombinant DNA molecule into a specific position (locus) within the chromosome of the plant genome. The insertion creates a novel DNA sequence referred to as an "event" and is characterized by the inserted recombinant DNA molecule and some amount of genomic DNA immediately adjacent to/flanking both ends of the inserted DNA. Such trait(s) or transgenic event(s) include, but are not limited to, pest resistance, water use efficiency, yield performance, drought tolerance, seed quality, improved nutritional quality, hybrid seed production, and herbicide tolerance, in which the trait is measured with respect to a plant lacking such trait or transgenic event. Concrete examples of such advantageous and/or useful properties (traits) are better plant growth, vigor, stress tolerance, standability, lodging resistance, nutrient uptake, plant nutrition, and/or yield, in particular improved growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products, and increased resistance against animal and microbial pests, such as against insects, arachnids, nematodes, mites, slugs and snails.

Among DNA sequences encoding proteins which confer properties of tolerance to such animal and microbial pests, in particular insects, mention will particularly be made of the genetic material from *Bacillus thuringiensis* encoding the Bt proteins widely described in the literature and well known to those skilled in the art. Mention will also be made of proteins extracted from bacteria such as *Photorhabdus* (WO97/17432 and WO98/08932). In particular, mention will be made of the Bt Cry or VIP proteins which include the CryIA, CryIAb, CryIAc, CryIIA, CryIIIA, CryIIIB2, Cry9c Cry2Ab, Cry3Bb and CryIF proteins or toxic fragments thereof and also hybrids or combinations thereof, especially the CryIF protein or hybrids derived from a CryIF protein (e.g. hybrid CryIA-CryIF proteins or toxic fragments thereof), the CryIA-type proteins or toxic fragments thereof, preferably the Cry1Ac protein or hybrids derived from the Cry1Ac protein (e.g. hybrid Cry1Ab-Cry1Ac proteins) or the Cry1Ab or Bt2 protein or toxic fragments thereof, the Cry2Ae, Cry2Af or Cry2Ag proteins or toxic fragments thereof, the Cry1A.105 protein or a toxic fragment thereof, the VIP3Aa19 protein, the VIP3Aa20 protein, the VIP3A proteins produced in the COT202 or COT203 cotton events, the VIP3Aa protein or a toxic fragment thereof as described in Estruch et al. (1996), Proc Natl Acad Sci USA. 28; 93(11):5389-94, the Cry proteins as described in WO2001/47952, the insecticidal proteins from Xenorhabdus (as described in WO98/50427), *Serratia* (particularly from *S. entomophila*) or *Photorhabdus* species strains, such as Tc-proteins from *Photorhabdus* as described in WO98/08932. Also any variants or mutants of any one of these proteins differing in some amino acids (1-10, preferably 1-5) from any of the above named sequences, particularly the sequence of their toxic fragment, or which are fused to a transit peptide, such as a plastid transit peptide, or another protein or peptide, is included herein.

Another and particularly emphasized example of such properties is conferred tolerance to one or more herbicides, for example imidazolinones, sulphonylureas, glyphosate or phosphinothricin. Among DNA sequences encoding proteins which confer properties of tolerance to certain herbicides on the transformed plant cells and plants, mention will be particularly be made to the bar or PAT gene or the *Streptomyces coelicolor* gene described in WO2009/152359 which confers tolerance to glufosinate herbicides, a gene encoding a suitable EPSPS (5-Enolpyruvylshikimat-3-phosphat-synthase) which confers tolerance to herbicides having EPSPS as a target, especially herbicides such as glyphosate and its salts, a gene encoding glyphosate-n-acetyltransferase, or a gene encoding glyphosate oxidoreductase. Further suitable herbicide tolerance traits include at least one ALS (acetolactate synthase) inhibitor (e.g. WO2007/024782), a mutated *Arabidopsis* ALS/AHAS gene (e.g. U.S. Pat. No. 6,855,533), genes encoding 2,4-D-monooxygenases conferring tolerance to 2,4-D (2,4-dichlorophenoxyacetic acid) and genes encoding Dicamba monooxygenases conferring tolerance to dicamba (3,6-dichloro-2-methoxybenzoic acid).

Yet another example of such properties is resistance to one or more phytopathogenic fungi, for example Asian Soybean Rust. Among DNA sequences encoding proteins which confer properties of resistance to such diseases, mention will particularly be made of the genetic material from *Glycine tomentella*, for example from any one of publically available accession lines PI441001, PI483224, PI583970, PI446958, PI499939, PI505220, PI499933, PI441008, PI505256 or PI446961 as described in WO2019/103918.

Further and particularly emphasized examples of such properties are increased resistance against bacteria and/or viruses owing, for example, to systemic acquired resistance (SAR), systemin, phytoalexins, elicitors and also resistance genes and correspondingly expressed proteins and toxins.

Particularly useful transgenic events in transgenic plants or plant cultivars which can be treated with preference in accordance with the invention include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control—herbicide tolerance, deposited as PTA-6233, described in WO2005/103266 or US-A 2005-216969); Event 3006-210-23 (cotton, insect control—herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control—herbicide tolerance, deposited as ATCC PTA-11508, described in WO 11/075593); Event 43A47 (corn, insect control—herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLR1 (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480);); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control—herbicide tolerance, deposited as ATCC PTA 11384, described in US-A 2006-070139); Event DAS-59132 (corn, insect control—herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); Event EE-I (brinjal, insect control, not deposited, described in WO 07/091277); Event Fil 17 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO98/044140); Event GHB119 (cotton, insect control—herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-

2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait—herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control—herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MSl 1 (oilseed rape, pollination control—herbicide tolerance, deposited as ATCC PTA-850 or PTA-2485, described in WO2001/031042); Event MS8 (oilseed rape, pollination control—herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control—herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHT0H2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control—herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control—herbicide tolerance, not deposited, described in US-A 2005-039226 or WO2004/099447); Event VTP1034 (corn, insect control—herbicide tolerance, deposited as ATCC PTA-3925, described in WO2003/052073), Event 32316 (corn, insect control—herbicide tolerance, deposited as PTA-11507, described in WO2011/084632), Event 4114 (corn, insect control—herbicide tolerance, deposited as PTA-11506, described in WO2011/084621), event EE-GM3/FG72 (soybean, herbicide tolerance, ATCC Accession No PTA-11041) optionally stacked with event EE-GM1/LL27 or event EE-GM2/LL55 (WO2011/063413A2), event DAS-68416-4 (soybean, herbicide tolerance, ATCC Accession No PTA-10442, WO2011/066360A1), event DAS-68416-4 (soybean, herbicide tolerance, ATCC Accession No PTA-10442, WO2011/066384A1), event DP-040416-8 (corn, insect control, ATCC Accession No PTA-11508, WO2011/075593A1), event DP-043A47-3 (corn, insect control, ATCC Accession No PTA-11509, WO2011/075595A1), event DP-004114-3 (corn, insect control, ATCC Accession No PTA-11506, WO2011/084621A1), event DP-032316-8 (corn, insect control, ATCC Accession No PTA-11507, WO2011/084632A1), event MON-88302-9 (oilseed rape, herbicide tolerance, ATCC Accession No PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession No. PTA-10296, WO2012/051199A2), event DAS-44406-6 (soybean, stacked herbicide tolerance, ATCC Accession No. PTA-11336, WO2012/075426A1), event DAS-14536-7 (soybean, stacked herbicide tolerance, ATCC Accession No. PTA-11335, WO2012/075429A1), event SYN-000H2-5 (soybean, herbicide tolerance, ATCC Accession No. PTA-11226, WO2012/082548A2), event DP-061061-7 (oilseed rape, herbicide tolerance, no deposit No available, WO2012071039A1), event DP-073496-4 (oilseed rape, herbicide tolerance, no deposit No available, US2012131692), event 8264.44.06.1 (soybean, stacked herbicide tolerance, Accession No PTA-11336, WO2012075426A2), event 8291.45.36.2 (soybean, stacked herbicide tolerance, Accession No. PTA-11335, WO2012075429A2), event SYHT0H2 (soybean, ATCC Accession No. PTA-11226, WO2012/082548A2), event MON88701 (cotton, ATCC Accession No PTA-11754, WO2012/134808A1), event KK179-2 (alfalfa, ATCC Accession No PTA-11833, WO2013/003558A1), event pDAB8264.42.32.1 (soybean, stacked herbicide tolerance, ATCC Accession No PTA-11993, WO2013/010094A1), event MZDT09Y (corn, ATCC Accession No PTA-13025, WO2013/012775A1).

Further, a list of such transgenic event(s) is provided by the United States Department of Agriculture's (USDA) Animal and Plant Health Inspection Service (APHIS) and can be found on their website on the world wide web at aphis.usda.gov. For this application, the status of such list as it is/was on the filing date of this application, is relevant.

The genes/events which impart the desired traits in question may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape.

Traits which are particularly emphasized are the increased resistance of the plants to insects, arachnids, nematodes and slugs and snails, as well as the increased resistance of the plants to one or more herbicides.

Commercially available examples of such plants, plant parts or plant seeds that may be treated with preference in accordance with the invention include commercial products, such as plant seeds, sold or distributed under the GENUITY®, DROUGHTGARD®, SMARTSTAX®, RIB COMPLETE®, ROUNDUP READY®, VT DOUBLE PRO®, VT TRIPLE PRO®, BOLLGARD II®, ROUNDUP READY 2 YIELD®, YIELDGARD®, ROUNDUP READY® 2 XTEND™, INTACTA RR2 PRO®, VISTIVE GOLD®, and/or XTENDFLEX™ trade names.

Pathogens

Non-limiting examples of pathogens of fungal diseases which may be treated in accordance with the invention include:

- diseases caused by powdery mildew pathogens, for example Blumeria species, for example Blumeria *graminis; Podosphaera* species, for example *Podosphaera leucotricha; Sphaerotheca* species, for example *Sphaerotheca fuliginea; Uncinula* species, for example *Uncinula necator;*
- diseases caused by rust disease pathogens, for example *Gymnosporangium* species, for example *Gymnosporangium sabinae; Hemileia* species, for example *Hemileia vastatrix; Phakopsora* species, for example *Phakopsora pachyrhizi* or *Phakopsora meibomiae; Puccinia* species, for example *Puccinia recondita, Puccinia graminis oder Puccinia striiformis; Uromyces* species, for example *Uromyces appendiculatus;*
- diseases caused by pathogens from the group of the Oomycetes, for example *Albugo* species, for example *Albugo candida; Bremia* species, for example *Bremia lactucae; Peronospora* species, for example *Peronospora pisi* or *P. brassicae; Phytophthora* species, for example *Phytophthora infestans; Plasmopara* species, for example *Plasmopara viticola; Pseudoperonospora* species, for example *Pseudoperonospora humuli* or *Pseudoperonospora cubensis; Pythium* species, for example *Pythium ultimum;*
- leaf blotch diseases and leaf wilt diseases caused, for example, by *Alternaria* species, for example *Alternaria solani; Cercospora* species, for example *Cercospora beticola; Cladiosporium* species, for example *Cladiosporium cucumerinum; Cochliobolus* species, for example *Cochliobolus sativus* (conidial form: *Drechslera*, syn: *Helminthosporium*) or *Cochliobolus miyabeanus; Colletotrichum* species, for example *Colletotrichum lindemuthanium; Corynespora* species, for example *Corynespora cassiicola; Cycloconium* species, for example *Cycloconium oleaginum; Diaporthe* species, for example *Diaporthe citri; Elsinoe* species, for example *Elsinoe fawcettii; Gloeosporium* species, for example *Gloeosporium laeticolor; Glomerella* species, for example *Glomerella cingulata; Guignardia* species, for example *Guignardia bidwelli; Leptosphaeria* species, for example *Leptosphaeria maculans; Magnaporthe* species, for example *Magnaporthe grisea; Microdochium* species, for example *Microdochium nivale; Mycosphaerella* species, for example *Mycosphaerella graminicola, Mycosphaerella arachidicola* or *Mycosphaerella fijiensis; Phaeosphaeria* species, for example *Phaeosphaeria nodorum; Pyrenophora* species, for example *Pyrenophora teres* or *Pyrenophora tritici repentis; Ramularia* species, for example *Ramularia collo-cygni* or *Ramularia areola; Rhynchosporium* species, for example *Rhynchosporium secalis; Septoria* species, for example *Septoria apii* or *Septoria lycopersici; Stagonospora* species, for example *Stagonospora nodorum; Typhula* species, for example *Typhula incarnata; Venturia* species, for example *Venturia inaequalis;*
- root and stem diseases caused, for example, by *Corticium* species, for example *Corticium graminearum; Fusarium* species, for example *Fusarium oxysporum; Gaeumannomyces* species, for example *Gaeumannomyces graminis; Plasmodiophora* species, for example *Plasmodiophora brassicae; Rhizoctonia* species, for example *Rhizoctonia solani; Sarocladium* species, for example *Sarocladium oryzae; Sclerotium* species, for example *Sclerotium oryzae; Tapesia* species, for example *Tapesia acuformis; Thielaviopsis* species, for example *Thielaviopsis basicola;*
- ear and panicle diseases (including corn cobs) caused, for example, by *Alternaria* species, for example *Alternaria* spp.; *Aspergillus* species, for example *Aspergillus flavus; Cladosporium* species, for example *Cladosporium cladosporioides; Claviceps* species, for example *Claviceps purpurea; Fusarium* species, for example *Fusarium culmorum; Gibberella* species, for example *Gibberella zeae; Monographella* species, for example *Monographella nivalis; Stagnospora* species, for example *Stagnospora nodorum*; diseases caused by smut fungi, for example *Sphacelotheca* species, for example *Sphacelotheca reiliana; Tilletia* species, for example *Tilletia caries* or *Tilletia controversa; Urocystis* species, for example *Urocystis occulta; Ustilago* species, for example *Ustilago nuda;*
- fruit rot caused, for example, by *Aspergillus* species, for example *Aspergillus flavus; Botrytis* species, for example *Botrytis cinerea; Monilinia* species, for example *Monilinia laxa; Penicillium* species, for example *Penicillium expansum* or *Penicillium purpurogenum; Rhizopus* species, for example *Rhizopus stolonifer; Sclerotinia* species, for example *Sclerotinia sclerotiorum; Verticilium* species, for example *Verticilium alboatrum;*
- seed- and soil-borne rot and wilt diseases, and also diseases of seedlings, caused, for example, by *Alternaria* species, for example *Alternaria brassicicola; Aphanomyces* species, for example *Aphanomyces euteiches; Ascochyta* species, for example *Ascochyta lentis; Aspergillus* species, for example *Aspergillus flavus; Cladosporium* species, for example *Cladosporium herbarum; Cochliobolus* species, for example *Cochliobolus sativus* (conidial form: *Drechslera, Bipolaris* Syn: *Helminthosporium*); *Colletotrichum* species, for example *Colletotrichum coccodes; Fusarium* species, for example *Fusarium culmorum; Gibberella* species, for example *Gibberella zeae; Macrophomina* species, for example *Macrophomina phaseolina; Microdochium* species, for example *Microdochium nivale; Monographella* species, for example *Monographella nivalis; Penicillium* species, for example *Penicillium expansum; Phoma* species, for example *Phoma lingam; Phomopsis* species, for example *Phomopsis sojae; Phytophthora* species, for example *Phytophthora cactorum; Pyrenophora* species, for example *Pyrenophora graminea; Pyricularia* species, for example *Pyricularia oryzae; Pythium* species, for example *Pythium ultimum; Rhizoctonia* species, for example *Rhizoctonia solani; Rhizopus* species, for example *Rhizopus oryzae; Sclerotium* species, for example *Sclerotium rolfsii; Septoria* species, for example *Septoria nodorum; Typhula* species, for example *Typhula incarnata; Verticillium* species, for example *Verticillium dahliae;* cancers, galls and witches' broom caused, for example, by *Nectria* species, for example *Nectria galligena;* wilt diseases caused, for example, by *Verticillium* species, for example *Verticillium longisporum; Fusarium* species, for example *Fusarium oxysporum;* deformations of leaves, flowers and fruits caused, for example, by *Exobasidium* species, for example *Exobasidium vexans; Taphrina* species, for example *Taphrina deformans;* degenerative diseases in woody plants, caused, for example, by *Esca* species, for example *Phaeomoniella chlamydospora, Phaeoacremonium aleophilum or Fomitiporia mediterranea; Ganoderma* species, for example *Ganoderma boninense;* diseases of plant tubers caused, for example, by *Rhizoctonia* species, for example *Rhizoctonia solani; Helminthosporium* species, for example *Helminthosporium solani;* diseases caused by bacterial pathogens, for example *Xanthomonas* species, for example *Xanthomonas campestris* pv. *oryzae; Pseudomonas* species, for example *Pseudomonas syringae* pv. *lachrymans; Erwinia* species, for example *Erwinia amylovora; Liberibacter* species, for example *Liberibacter asiaticus; Xyella* species, for example *Xylella fastidiosa; Ralstonia* species, for example *Ralstonia solanacearum; Dickeya* species, for example *Dickeya solani; Clavibacter* species, for example *Clavibacter michiganensis; Streptomyces* species, for example *Streptomyces scabies.*

Diseases of Soya Beans:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), *Cercospora* leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), *pyrenochaeta* leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), sudden death syndrome (*Fusarium virguliforme*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), *phytophthora* rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Mycotoxins

In addition, the compound of formula (I) and the composition of the invention may reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticilihoides*, and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusiformis, C. paspali, C. africana, Stachybotrys* spec. and others.

Material Protection

The compound of formula (I) and the composition of the invention may also be used in the protection of materials, especially for the protection of industrial materials against attack and destruction by phytopathogenic fungi.

In addition, the compound of formula (I) and the composition of the invention may be used as antifouling compositions, alone or in combinations with other active ingredients.

Industrial materials in the present context are understood to mean inanimate materials which have been prepared for use in industry. For example, industrial materials which are to be protected from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The compound of formula (I) and the composition of the invention may prevent adverse effects, such as rotting, decay, discoloration, decoloration or formation of mould.

In the case of treatment of wood the compound of formula (I) and the composition of the invention may also be used against fungal diseases liable to grow on or inside timber.

Timber means all types of species of wood, and all types of working of this wood intended for construction, for example solid wood, high-density wood, laminated wood, and plywood. In addition, the compound of formula (I) and the composition of the invention may be used to protect objects which come into contact with saltwater or brackish water, especially hulls, screens, nets, buildings, moorings and signalling systems, from fouling.

The compound of formula (I) and the composition of the invention may also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, may be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The compound of formula (I) and the composition of the invention may prevent adverse effects, such as rotting, decay, discoloration, decoloration or formation of mould.

Microorganisms capable of degrading or altering industrial materials include, for example, bacteria, fungi, yeasts, algae and slime organisms. The compound of formula (I) and the composition of the invention preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis; Aspergillus*, such as *Aspergillus niger; Chaetomium*, such as *Chaetomium globosum; Coniophora*, such as *Coniophora puetana; Lentinus*, such as *Lentinus tigrinus; Penicillium*, such as *Penicillium glaucum; Polyporus*, such as *Polyporus versicolor; Aureobasidium*, such as *Aureobasidium pullulans; Sclerophoma*, such as *Sclerophoma pityophila; Trichoderma*, such as *Trichoderma viride; Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli; Pseudomonas*, such as *Pseudomonas aeruginosa; Staphylococcus*, such as *Staphylococcus aureus, Candida* spp. and *Saccharomyces* spp., such as *Saccharomyces cerevisae.*

Seed Treatment

The compound of formula (I) and the composition of the invention may also be used to protect seeds from unwanted microorganisms, such as phytopathogenic microorganisms, for instance phytopathogenic fungi or phytopathogenic oomycetes. The term seed(s) as used herein include dormant seeds, primed seeds, pregerminated seeds and seeds with emerged roots and leaves.

Thus, the present invention also relates to a method for protecting seeds from unwanted microorganisms which comprises the step of treating the seeds with the compound of formula (I) or the composition of the invention.

The treatment of seeds with the compound of formula (I) or the composition of the invention protects the seeds from phytopathogenic microorganisms, but also protects the germinating seeds, the emerging seedlings and the plants after emergence from the treated seeds. Therefore, the present invention also relates to a method for protecting seeds, germinating seeds and emerging seedlings.

The seeds treatment may be performed prior to sowing, at the time of sowing or shortly thereafter.

When the seeds treatment is performed prior to sowing (e.g. so-called on-seed applications), the seeds treatment may be performed as follows: the seeds may be placed into a mixer with a desired amount of the compound of formula (I) or the composition of the invention, the seeds and the compound of formula (I) or the composition of the invention are mixed until an homogeneous distribution on seeds is achieved. If appropriate, the seeds may then be dried.

The invention also relates to seeds coated with the compound of formula (I) or the composition of the invention.

Preferably, the seeds are treated in a state in which it is sufficiently stable for no damage to occur in the course of treatment. In general, seeds can be treated at any time between harvest and shortly after sowing. It is customary to use seeds which have been separated from the plant and freed from cobs, shells, stalks, coats, hairs or the flesh of the fruits. For example, it is possible to use seeds which have been harvested, cleaned and dried down to a moisture content of less than 15% by weight. Alternatively, it is also possible to use seeds which, after drying, for example, have been treated with water and then dried again, or seeds just after priming, or seeds stored in primed conditions or pre-germinated seeds, or seeds sown on nursery trays, tapes or paper.

The amount of the compound of formula (I) or the composition of the invention applied to the seeds is typically such that the germination of the seed is not impaired, or that the resulting plant is not damaged.

This must be ensured particularly in case the compound of formula (I) would exhibit phytotoxic effects at certain application rates. The intrinsic phenotypes of transgenic plants should also be taken into consideration when determining the amount of the compound of formula (I) to be applied to the seed in order to achieve optimum seed and germinating plant protection with a minimum amount of compound being employed.

The compound of formula (I) can be applied as such, directly to the seeds, i.e. without the use of any other components and without having been diluted. Also the composition of the invention can be applied to the seeds.

The compound of formula (I) and the composition of the invention are suitable for protecting seeds of any plant variety. Preferred seeds are that of cereals (such as wheat, barley, rye, millet, triticale, and oats), oilseed rape, maize, cotton, soybean, rice, potatoes, sunflower, beans, coffee, peas, beet (e.g. sugar beet and fodder beet), peanut, vegetables (such as tomato, cucumber, onions and lettuce), lawns and ornamental plants. More preferred are seeds of wheat, soybean, oilseed rape, maize and rice.

The compound of formula (I) and the composition of the invention may be used for treating transgenic seeds, in particular seeds of plants capable of expressing a polypeptide or protein which acts against pests, herbicidal damage or abiotic stress, thereby increasing the protective effect. Seeds of plants capable of expressing a polypeptide or protein which acts against pests, herbicidal damage or abiotic stress may contain at least one heterologous gene which allows the expression of said polypeptide or protein. These heterologous genes in transgenic seeds may originate, for example, from microorganisms of the species *Bacillus, Rhizobium, Pseudomonas, Serratia, Trichoderma, Clavibacter, Glomus* or *Gliocladium*. These heterologous genes preferably originate from *Bacillus* sp., in which case the gene product is effective against the European corn borer and/or the Western corn rootworm. Particularly preferably, the heterologous genes originate from *Bacillus thuringiensis.*

Application

The compound of formula (I) can be applied as such, or for example in the form of as ready-to-use solutions, emulsions, water- or oil-based suspensions, powders, wettable powders, pastes, soluble powders, dusts, soluble granules, granules for broadcasting, suspoemulsion concentrates, natural products impregnated with the compound of formula (I), synthetic substances impregnated with the compound of formula (I), fertilizers or microencapsulations in polymeric substances.

Application is accomplished in a customary manner, for example by watering, spraying, atomizing, broadcasting, dusting, foaming or spreading-on. It is also possible to deploy the compound of formula (I) by the ultra-low volume method, via a drip irrigation system or drench application, to apply it in-furrow or to inject it into the soil stem or trunk. It is further possible to apply the compound of formula (I) by means of a wound seal, paint or other wound dressing.

The effective and plant-compatible amount of the compound of formula (I) which is applied to the plants, plant parts, fruits, seeds or soil will depend on various factors, such as the compound/composition employed, the subject of the treatment (plant, plant part, fruit, seed or soil), the type of treatment (dusting, spraying, seed dressing), the purpose of the treatment (curative and protective), the type of microorganisms, the development stage of the microorganisms, the sensitivity of the microorganisms, the crop growth stage and the environmental conditions.

When the compound of formula (I) is used as a fungicide, the application rates can vary within a relatively wide range, depending on the kind of application. For the treatment of plant parts, such as leaves, the application rate may range from 0.1 to 10 000 g/ha, preferably from 10 to 1000 g/ha, more preferably from 50 to 300 g/ha (in the case of application by watering or dripping, it is even possible to reduce the application rate, especially when inert substrates such as rockwool or perlite are used). For the treatment of seeds, the application rate may range from 0.1 to 200 g per 100 kg of seeds, preferably from 1 to 150 g per 100 kg of seeds, more preferably from 2.5 to 25 g per 100 kg of seeds, even more preferably from 2.5 to 12.5 g per 100 kg of seeds. For the treatment of soil, the application rate may range from 0.1 to 10 000 g/ha, preferably from 1 to 5000 g/ha.

These application rates are merely examples and are not intended to limit the scope of the present invention.

The compound of formula (I) and the composition of the invention can be used in combination with models e.g. embedded in computer programs for site specific crop management, satellite farming, precision farming or precision agriculture. Such models support the site specific management of agricultural sites with data from various sources such as soils, weather, crops (e.g. type, growth stage, plant health), weeds (e.g. type, growth stage), diseases, pests, nutrients, water, moisture, biomass, satellite data, yield etc. with the purpose to optimize profitability, sustainability and protection of the environment. In particular, such models can help to optimize agronomical decisions, control the precision of pesticide applications and record the work performed.

As an example, the compound of formula (I) can be applied to a crop plant according to appropriate dose regime if a model models the development of a fungal disease and calculates that a threshold has been reached for which it is recommendable to apply the compound of formula (I) to the crop plant.

Commercially available systems which include agronomic models are e.g. FieldScripts™ from The Climate Corporation, Xarvio™ from BASF, AGLogic™ from John Deere, etc.

The compound of formula (I) can also be used in combination with smart spraying equipment such as e.g. spot spraying or precision spraying equipment attached to or housed within a farm vehicle such as a tractor, robot, helicopter, airplane, unmanned aerial vehicle (UAV) such as a drone, etc. Such an equipment usually includes input sensors (such as e.g. a camera) and a processing unit configured to analyze the input data and configured to provide a decision based on the analysis of the input data to apply the compound of the invention to the crop plants (respectively the weeds) in a specific and precise manner. The use of such smart spraying equipment usually also requires positions systems (e.g. GPS receivers) to localize recorded data and to guide or to control farm vehicles; geographic information systems (GIS) to represent the information on intelligible maps, and appropriate farm vehicles to perform the required farm action such as the spraying.

In an example, fungal diseases can be detected from imagery acquired by a camera. In an example fungal diseases can be identified and/or classified based on that imagery. Such identification/classification can make use of image processing algorithms. Such image processing algorithms can utilize machine learning algorithms, such as trained neutral networks, decision trees and utilize artificial intelligence algorithms. In this manner, the compounds described herein can be applied only where needed.

Aspects of the present teaching may be further understood in light of the following examples, which should not be construed as limiting the scope of the present teaching in any way.

A. EXAMPLES

A-1. Generality

A-1.1. Measurement of Log P Values

Measurement of Log P values as provided herein was performed according to EEC directive 79/831 Annex V.A8 by HPLC (High Performance Liquid Chromatography) on reversed phase columns with the following methods:

[a] Log P value is determined by measurement of LC-UV, in an acidic range, with 0.1% formic acid in water and acetonitrile as eluent (linear gradient from 10% acetonitrile to 95% acetonitrile).

[b] Log P value is determined by measurement of LC-UV, in a neutral range, with 0.001 molar ammonium acetate solution in water and acetonitrile as eluent (linear gradient from 10% acetonitrile to 95% acetonitrile).

[c] Log P value is determined by measurement of LC-UV, in an acidic range, with 0.1% phosphoric acid and acetonitrile as eluent (linear gradient from 10% acetonitrile to 95% acetonitrile).

If more than one Log P value is available within the same method, all the values are given and separated by "+".

Calibration was done with straight-chain alkan2-ones (with 3 to 16 carbon atoms) with known Log P values (measurement of Log P values using retention times with linear interpolation between successive alkanones). Lambda-max-values were determined using UV-spectra from 200 nm to 400 nm and the peak values of the chromatographic signals

A-1.2. $^1$H-NMR Data $^1$H-NMR data of selected examples as provided herein are written in form of $^1$H-NMR-peak lists. To each signal peak are listed the 6-value in ppm and the signal intensity in round brackets. Between the δ-value—signal intensity pairs are semicolons as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally, they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore, their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

The following examples illustrate in a non-limiting manner the preparation and biological activity of the compounds of formula (I) according to the invention.

A-3. Synthesis of Compounds of Formula (I) and Intermediates

Preparation Example 1: Preparation of (5RS)-3-{2-cyclopropyl-5-[3-(trifluoro-methyl)phenoxy]pyrimidin-4-yl}-5-(2,4-dimethylbenzyl)-5,6-dihydro-4H-1,2,4-oxadiazine (compound I-001)

Step 1: Preparation of 2-cyclopropyl-5-[3-(trifluoromethyl)phenoxy]pyrimidine-4-carboxylic acid (Compound 1-02)

In a microwave vial, a mixture of 5-bromo-2-cyclopropylpyrimidine-4-carboxylic acid (200 mg, 0.82 mmol), 3-(trifluoromethyl)phenol (226 mg, 1.39 mmol), N-(n-butyl) imidazole (30 mg, 0.25 mmol), cesium carbonate (536 mg, 1.64 mmol) and copper(I)iodide (31.3 mg, 0.16 mmol) were dissolved in dioxane (4.5 mL). The tube was sealed and the reaction mixture was heated in a microwave at 130° C. for 30 min. The reaction was diluted with dichloromethane and filtered over Celite®. The organic layers were concentrated under reduced pressure. Purification of the residue by preparative HPLC afforded, after evaporation of the solvents, 23 mg (98% purity, 10% yield) of 2-cyclopropyl-5-[3-(trifluoromethyl)phenoxy]pyrimidine-4-carboxylic acid as a white solid.

Step 2: Preparation of 2-cyclopropyl-N-{(2RS)-1-(2,4-dimethylphenyl)-3-[(1,3-dioxo-1,3-dihydro-2H-isoindol-2-yl)oxy]propan-2-yl}-5-[3-(trifluoromethyl)phenoxy]pyrimidine-4-carboxamide (Compound 3-01)

Under argon, to a mixture of 2-cyclopropyl-5-[3-(trifluoromethyl)phenoxy]pyrimidine-4-carboxylic acid (23 mg, 0.07 mmol) and HATU (30 mg, 0.07 mmol) in DMF (1 mL) were added at 0° C., 2-{[(2RS)-2-amino-3-(2,4-dimethylphenyl)propyl]oxy}-1H-isoindole-1,3(2H)-dione.trifluoroacetate (34 mg, 0.07 mmol) and N,N-Diisopropylethylamine (0.04 mL, 0.21 mmol). After 15 min at 0° C., the reaction mixture was stirred for 18 h at room temperature. It was then diluted with water and extracted with ethyl acetate (2×50 mL). The organic extracts were dried over magnesium sulfate, filtered and concentrated under reduced pressure. Purification of the residue by column chromatography on silica gel (gradient heptane/ethyl acetate) afforded, after evaporation of the solvents, 34 mg (100% purity, 76% yield) of 2-cyclopropyl-N-{(2RS)-1-(2,4-dimethylphenyl)-3-[(1,3-dioxo-1,3-dihydro-2H-isoindol-2-yl)oxy]propan-2-yl}-5-[3-(trifluoromethyl)phenoxy]pyrimidine-4-carboxamide as a white solid.

Step 3: Preparation of N-[(2RS)-1-(aminooxy)-3-(2,4-dimethylphenyl)propan-2-yl]-2-cyclopropyl-5-[3-(trifluoromethyl)phenoxy]pyrimidine-4-carboxamide (Compound 4-01)

Under argon, hydrazine monohydrate (0.01 mL, 0.16 mmol) was added to a solution of 2-cyclopropyl-N-{(2RS)-1-(2,4-dimethylphenyl)-3-[(1,3-dioxo-1,3-dihydro-2H-isoindol-2-yl)oxy]propan-2-yl}-5-[3-(trifluoromethyl)phenoxy]pyrimidine-4-carboxamide (34 mg, 0.05 mmol) in dichloromethane/methanol (1 mL, 1:1). The reaction mixture was stirred for 2 h at room temperature and concentrated. It was then diluted with water and extracted with dichloromethane (2×50 mL). The organic extracts were dried over magnesium sulfate, filtered and concentrated under reduced pressure. Evaporation of the solvents afforded 27 mg (100% purity, 98% yield) of N-[(2RS)-1-(aminooxy)-3-(2,4-dimethylphenyl)propan-2-yl]-2-cyclopropyl-5-[3-(trifluoromethyl)phenoxy]pyrimidine-4-carboxamide as a colorless oil.

Step 4: Preparation of (5RS)-3-{2-cyclopropyl-5-[3-(trifluoromethyl)phenoxy]pyrimidin-4-yl}-5-(2,4-dimethylbenzyl)-5,6-dihydro-4H-1,2,4-oxadiazine Under argon, $POCl_3$ (0.02 mL, 0.18 mmol) was added at 85° C. to a solution N-[(2RS)-1-(aminooxy)-3-(2,4-dimethylphenyl)propan-2-yl]-2-cyclopropyl-5-[3-(trifluoromethyl)phenoxy]pyrimidine-4-carboxamide (27 mg, 0.06 mmol) in Acetonitrile (5 mL). The reaction mixture was stirred for 2 h at 85° C. After cooling to room temperature, the mixture was poured into a saturated sodium bicarbonate solution and extracted with ethyl acetate (2×50 mL). The organic extracts were dried over magnesium sulfate, filtered and concentrated under reduced pressure. Purification of the residue by column chromatography on silica gel (gradient heptane/ethyl acetate) afforded, after evaporation of the solvents, 11.3 mg (100% purity, 39% yield) of (5RS)-3-{2-cyclopropyl-5-[3-(trifluoromethyl)phenoxy]pyrimidin-4-yl}-5-(2,4-dimethylbenzyl)-5,6-dihydro-4H-1,2,4-oxadiazine as a yellow oil.

Preparation Example 2: Preparation of (5RS)-5-(2,4-dimethylbenzyl)-3-{2-methyl-5-[3-(trifluoromethyl)phenoxy]pyrimidin-4-yl}-5,6-dihydro-4H-1,2,4-oxadiazine (Compound I-002)

Step 1: Preparation of 5-bromo-N-{(2RS)-1-(2,4-dimethylphenyl)-3-[(1,3-dioxo-1,3-dihydro-2H-isoindol-2-yl)oxy]propan-2-yl}-2-methylpyrimidine-4-carboxamide Under argon, to a mixture of 5-bromo-2-methylpyrimidine-4-carboxylic acid (150 mg, 0.07 mmol) and HATU (289 mg, 0.76 mmol) in DMF (6.5 mL) were added at 0° C., 2-{[(2RS)-2-amino-3-(2,4-dimethylphenyl)propyl]oxy}-1H-isoindole-1,3(2H)-dione trifluoroacetate (333 mg, 0.76 mmol) and N,N-Diisopropylethylamine (0.36 mL, 2.07 mmol). After 15 min at 0° C., the reaction mixture was stirred for 18 h at room temperature. It was then diluted with water and extracted with ethyl acetate (2×200 mL). The organic extracts were dried over magnesium sulfate, filtered and concentrated under reduced pressure. Purification of the residue by column chromatography on silica gel (gradient heptane/ethyl acetate) afforded, after evaporation of the solvents, 211 mg (100% purity, 58% yield) of 5-bromo-N-{(2RS)-1-(2,4-dimethylphenyl)-3-[(1,3-dioxo-1,3-dihydro-2H-isoindol-2-yl)oxy]propan-2-yl}-2-methylpyrimidine-4-carboxamide as a yellow solid.

Step 2: Preparation of N-[(2RS)-1-(aminooxy)-3-(2,4-dimethylphenyl)propan-2-yl]-5-bromo-2-methylpyrimidine-4-carboxamide Under argon, hydrazine monohydrate (0.07 mL, 1.2 mmol) was added to a solution of 5-bromo-N-{(2RS)-1-(2,4-dimethylphenyl)-3-[(1,3-dioxo-1,3-dihydro-2H-isoindol-2-yl)oxy]propan-2-yl}-2-methylpyrimidine-4-carboxamide (210 mg, 0.40 mmol) in dichloromethane/methanol (6 mL, 1:1). The reaction mixture was stirred for 2 h at room temperature and concentrated. It was then diluted with water and extracted with dichloromethane (2×100 mL). The organic extracts were dried over magnesium sulfate, filtered and concentrated under reduced pressure. Evaporation of the solvents afforded 161 mg (76% purity, 77% yield) of N-[(2RS)-1-(aminooxy)-3-(2,4-dimethylphenyl)propan-2-yl]-5-bromo-2-methylpyrimidine-4-carboxamide as a yellow oil.

Step 3: Preparation of (5RS)-5-(2,4-dimethylbenzyl)-3-{2-methyl-5-[3-(trifluoro-methyl)phenoxy]pyrimidin-4-yl}-5,6-dihydro-4H-1,2,4-oxadiazine (Compound 7-01)

Under argon, $POCl_3$ (0.11 mL, 1.16 mmol) was added at 85° C. to a solution N-[(2RS)-1-(aminooxy)-3-(2,4-dimethylphenyl)propan-2-yl]-5-bromo-2-methylpyrimidine-4-carboxamide (152 mg, 0.38 mmol) in Acetonitrile (5 mL). The reaction mixture was stirred for 1 h at 85° C. After cooling to room temperature, the mixture was poured into a saturated sodium bicarbonate solution and extracted with ethyl acetate (2×50 mL). The organic extracts were dried over magnesium sulfate, filtered and concentrated under reduced pressure. Purification of the residue by column chromatography on silica gel (gradient heptane/EtOAc) afforded, after evaporation of the solvents, 32 mg (91% purity, 20% yield) of (5RS)-5-(2,4-dimethylbenzyl)-3-{2-methyl-5-[3-(trifluoromethyl)phenoxy]pyrimidin-4-yl}-5,6-dihydro-4H-1,2,4-oxadiazine as a yellow oil.

Step 4: Preparation of (5RS)-5-(2,4-dimethylbenzyl)-3-{2-methyl-5-[3-(trifluoro-methyl)phenoxy]pyrimidin-4-yl}-5,6-dihydro-4H-1,2,4-oxadiazine In a microwave vial, a mixture of (5RS)-3-(5-bromo-2-methylpyrimidin-4-yl)-5-(2,4-dimethylbenzyl)-5,6-dihydro-4H-1,2,4-oxadiazine (26 mg, 0.06 mmol), 3-(trifluoromethyl)phenol (16.5 mg, 0.1 mmol), N-(n-butyl)imidazole (4.2 mg, 0.03 mmol), cesium carbonate (44.4 mg, 0.14 mmol) and copper(I)iodide (1.3 mg, 0.007 mmol) were dissolved in dioxane (2.5 mL). The tube was sealed and the reaction mixture was heated in a microwave at 130° C. for 30 min. The reaction was diluted with dichloromethane and filtered over Celite®. The organic layers were concentrated under reduced pressure. Purification of the residue by preparative HPLC afforded, after evaporation of the solvents, 13.7 mg (100% purity, 44% yield) of (5RS)-5-(2,4-dimethylbenzyl)-3-{2-methyl-5-[3-(trifluoromethyl)phenoxy]pyrimidin-4-yl}-5,6-dihydro-4H-1,2,4-oxadiazine as a brown oil.

Preparation Example 3: Preparation of (5RS)-5-(2,4-dimethylbenzyl)-3-[2-methyl-5-(3-nitro-phenoxy)pyrimidin-4-yl]-5,6-dihydro-4H-1,2,4-oxadiazine (Compound I-003)

Step 1: Preparation of 5-bromo-N-[(2RS)-1-chloro-3-(2,4-dimethylphenyl)propan-2-yl]-2-methyl-pyrimidine-4-carboxamide (Compound 12.01)

Under argon, to a solution of 5-bromo-2-methylpyrimidine-4-carboxylic acid (200 mg, 0.92 mmol) and propylphosphonic anhydride (1.1 g, 3.41 mmol, 50% in THF) in dichloromethane (6 mL) was added N,N-Diisopropylethylamine (0.59 mL, 3.36 mmol) and (2RS)-1-chloro-3-(2,4-dimethylphenyl)propan-2-aminium chloride (237 mg, 1 mmol). The reaction mixture was stirred at room temperature for 1 h, diluted with water and extracted with dichloromethane (3×200 mL). The organic extracts were washed with a saturated aqueous sodium bicarbonate solution and brine, dried over magnesium sulfate, filtered and concentrated under reduced pressure. Purification of the residue by column chromatography on silica gel (gradient heptane/EtOAc) afforded, after evaporation of the solvents, 256 mg (100% purity, 70% yield) of 5-bromo-N-[(2RS)-1-chloro-3-(2,4-dimethylphenyl)propan-2-yl]-2-methylpyrimidine-4-carboxamide.

Step 2: Preparation of 5-bromo-N-[(2RS)-1-chloro-3-(2,4-dimethylphenyl)propan-2-yl]-N'-hydroxy-2-methylpyrimidine-4-carboximidamide (Compound 13.01)

To a solution of 5-bromo-N-[(2RS)-1-chloro-3-(2,4-dimethylphenyl)propan-2-yl]-2-methylpyrimidine-4-carboxamide (233 mg, 0.59 mmol) in toluene (6 mL) was added phosphorous pentachloride (183 mg, 0.54 mmol). The reaction mixture was stirred at 75° C. for 2 h, then concentrated under reduced pressure. The residue was dissolved in Acetonitrile (3 mL) and added to a solution of hydroxylamine (0.72 mL, 11.7 mmol, 50% in water) in Acetonitrile (3 mL). After stirring at room temperature for 15 min, the reaction mixture was diluted with water and extracted with ethyl acetate (3×200 mL). The organic extracts were washed with water and brine, dried over sodium sulfate, filtered and concentrated under reduced pressure. Purification of the residue by column chromatography on silica gel (gradient heptane/EtOAc) afforded, after evaporation of the solvents, 127 mg (100% purity, 53% yield) of 5-bromo-N-[(2RS)-1-chloro-3-(2,4-dimethylphenyl)propan-2-yl]-N'-hydroxy-2-methylpyrimidine-4-carboximidamide as a yellow oil.

Step 3: Preparation of (5RS)-3-(5-bromo-2-methylpyrimidin-4-yl)-5-(2,4-dimethylbenzyl)-5,6-dihydro-4H-1,2,4-oxadiazine (Compound 7.01)

To a solution of 5-bromo-N-[(2RS)-1-chloro-3-(2,4-dimethylphenyl)propan-2-yl]-N'-hydroxy-2-methylpyrimidine-4-carboximidamide (124 mg, 0.3 mmol) in Acetonitrile (2.9 mL) was added potassium phosphate (96 mg, 0.45 mmol). The reaction mixture was stirred at room temperature for 18 h, then diluted with water and extracted with ethyl acetate (3×200 mL). The organic extracts were dried over magnesium sulfate, filtered and concentrated under reduced pressure. Evaporation of the solvents afforded 91.5 mg (100% purity, 81% yield) of (5RS)-3-(5-bromo-2-methylpyrimidin-4-yl)-5-(2,4-dimethylbenzyl)-5,6-dihydro-4H-1,2,4-oxadiazine as a yellow oil.

Step 4: Preparation of (5RS)-5-(2,4-dimethylbenzyl)-3-[2-methyl-5-(3-nitrophenoxy)pyrimidin-4-yl]-5,6-dihydro-4H-1,2,4-oxadiazine In a microwave vial, a mixture of (5RS)-3-(5-bromo-2-methylpyrimidin-4-yl)-5-(2,4-dimethylbenzyl)-5,6-dihydro-4H-1,2,4-oxadiazine (85 mg, 0.22 mmol), 3-nitrophenol (47 mg, 0.34 mmol), N-(n-butyl)imidazole (14 mg, 0.11 mmol), cesium carbonate (148 mg, 0.45 mmol) and copper(I)iodide (4.3 mg, 0.02 mmol) were dissolved in dioxane (4 mL). The tube was sealed and the reaction mixture was heated in a microwave at 130° C. for 30 min. The reaction was diluted with dichloromethane and filtered over Celite®. The organic layers were concentrated under reduced pressure. Purification of the residue by preparative HPLC afforded, after evaporation of the solvents, 19.6 mg (100% purity, 20% yield) of (5RS)-5-(2,4-dimethylbenzyl)-3-[2-methyl-5-(3-nitrophenoxy)pyrimidin-4-yl]-5,6-dihydro-4H-1,2,4-oxadiazine as a brown oil.

Preparation Example 4: Preparation of (5RS)-3-[5-(3-chlorophenoxy)-2-methyl-pyrimidin-4-yl]-5-indan-5-yl-5,6-dihydro-4H-1,2,4-oxadiazine (Compound 1-014)

Step 1: Preparation of 5-(3-chlorophenoxy)-N'-hydroxy-2-methyl-pyrimidine-4-carboxamidine (Compound 17-01)

To a solution of 5-(3-chlorophenoxy)-2-methyl-pyrimidine-4-carbonitrile (59 mg, 0.243 mmol) in ethanol (1.5 mL) was added hydroxylamine-hydrochloride (42 mg, 0.67 mmol) and potassium carbonate (84 mg, 0.67 mmol). The reaction mixture was stirred 2 h at 60° C., then the reaction mixture was cooled down to room temperature and filtered. The filtrate was concentrated, and the residue was diluted with water and extracted with ethyl acetate. The combined organic layers were dried with $MgSO_4$, filtered and concentrated to give 45 mg (94% purity, 63% yield) of (5-(3-chlorophenoxy)-N'-hydroxy-2-methyl-pyrimidine-4-carboxamidine as a white solid.

Step 2: Preparation of (5-(3-chlorophenoxy)-N'-(2-indan-5-yl-2-oxo-ethoxy)-2-methyl-pyrimidine-4-carboxamidine (Compound 19-01)

To a solution of 5-(3-chlorophenoxy)-N'-hydroxy-2-methyl-pyrimidine-4-carboxamidine (42 mg, 0.151 mmol) in acetonitrile (1.5 mL) was added 2-tert-butylimino-2-diethylamino-1,3-dimethylperhydro-1,3,2-diazaphosphorine (0.052 mL, 0.181 mmol) at room temperature. After stirring for 15 min, 2-bromo-1-indan-5-yl-ethanone (54 mg, 0.226 mmol) in acetonitrile (1 mL) was added and the mixture was stirred for 15 min at room temperature. The reaction mixture was quenched with saturated aqueous solution of ammonium chloride, then extracted with ethyl acetate. The organic phase was dried with $MgSO_4$, filtered and concentrated to give 95 mg (61% purity, 88% yield) of (5-(3-chlorophenoxy)-N'-(2-indan-5-yl-2-oxo-ethoxy)-2-methyl-pyrimidine-4-carboxamidine. The product was converted without further purification.

Step 3: Preparation of (5RS)-3-[5-(3-chlorophenoxy)-2-methyl-pyrimidin-4-yl]-5-indan-5-yl-5,6-dihydro-4H-1,2,4-oxadiazine (Compound 1-014)

A solution of (5-(3-chlorophenoxy)-N'-(2-indan-5-yl-2-oxo-ethoxy)-2-methyl-pyrimidine-4-carboxamidine (93 mg, 0, 213 mmol) in a mixture of methanol (1.6 mL) and acetic acid (0.4 mL) was heated for 1 h at 60° C. Then sodium cyanoborohydride (15 mg, 0.234 mmol) was added and the reaction mixture was stirred at 60° C. for an additional 2 h. The reaction mixture was poured into 1N NaOH solution and extracted with ethyl acetate. The combined organic layers were washed with brine, dried over $MgSO_4$ and concentrated. The residue was purified by preparative HPLC to afford 18 mg (99% purity, 20% yield) of (5RS)-3-[5-(3-chlorophenoxy)-2-methyl-pyrimidin-4-yl]-5-indan-5-yl-5,6-dihydro-4H-1,2,4-oxadiazine as a transparent oil.

Preparation Example 5: Preparation of (5RS)-5-[(4-ethynyl-2-methyl-phenyl)methyl]-3-[2-methyl-5-[3-(trifluoromethyl)phenoxy]pyrimidin-4-yl]-5,6-dihydro-4H-1,2,4-oxadiazine (Compound I-026)

Step 1: Preparation of trimethyl-[2-[3-methyl-4-[[(5RS)-3-[2-methyl-5-[3-(trifluoro-methyl)phenoxy]pyrimidin-4-yl]-5,6-dihydro-4H-1,2,4-oxadiazin-5-yl]methyl]phenyl]ethynyl]silane (Compound 1-010)

In a sealed vial, (5RS)-5-[(4-bromo-2-methyl-phenyl)methyl]-3-[2-methyl-5-[3-(trifluoro-methyl)phenoxy]pyrimidin-4-yl]-5,6-dihydro-4H-1,2,4-oxadiazine (200 mg, 0.38 mmol) (compound I-021), trimethylsilylacetylene (0.273 mL, 1.92 mmol), tetrakis(triphenylphosphine)palladium (44 mg, 0.04 mmol), zinc dibromide (173 mg, 0.77 mmol) and diisopropylamine (0.27 mL, 1.92 mmol) were suspended in degassed toluene (4 mL). The reaction mixture was stirred at 120° C. under microwave irradiation during 35 min. The reaction mixture was poured over brine and diluted with ethyl acetate. The organic layer was dried over $MgSO_4$ anhydrous, filtered and then concentrated under reduced pressure. This crude product was purified by flash silica gel chromatography (10% to 80% ethyl acetate in n-heptane) to afford 102 mg (80% purity, 40% yield) of trimethyl-[2-[3-methyl-4-[[(5RS)-3-[2-methyl-5-[3-(trifluoromethyl)phenoxy]pyrimidin-4-yl]-5,6-dihydro-4H-1,2,4-oxadiazin-5-yl]methyl]phenyl]ethynyl]silane.

Step 2: Preparation of (5RS)-5-[(4-ethynyl-2-methyl-phenyl)methyl]-3-[2-methyl-5-[3-(trifluoromethyl)phenoxy]pyrimidin-4-yl]-5,6-dihydro-4H-1,2,4-oxadiazine (Compound I-026)

To a solution of trimethyl-[2-[3-methyl-4-[[(5RS)-3-[2-methyl-5-[3-(trifluoromethyl)phenoxy]pyrimidin-4-yl]-5,6-dihydro-4H-1,2,4-oxadiazin-5-yl]methyl]phenyl]ethynyl]silane (96 mg, 80% purity, 0.143 mmol) in THF (3 mL) at 0° C. was added tetra-n-butylammonium fluoride (0.143 mL, 0.143 mmol, 1 M solution in THF). After 30 min. at 0° C., the reaction mixture was poured into the brine, and extracted with ethyl acetate. The collected organic layer was dried over $MgSO_4$ anhydrous, filtered then concentrated over reduced pressure. The crude product was purified by preparative HPLC to afford 28 mg (99% purity, 42% yield) of (5RS)-5-[(4-ethynyl-2-methyl-phenyl)methyl]-3-[2-methyl-5-[3-(trifluoromethyl)phenoxy]pyrimidin-4-yl]-5,6-dihydro-4H-1,2,4-oxadiazine as a transparent oil.

Preparation Example 6: Preparation of (5RS)-5-[(4-cyclopropyl-2-methyl-phenyl)methyl]-3-[2-methyl-5-[3-(trifluoromethyl)phenoxy]pyrimidin-4-yl]-5,6-dihydro-4H-1,2,4-oxadiazine (Compound I-029)

In a sealed vial(5RS)-5-[(4-bromo-2-methyl-phenyl)methyl]-3-[2-methyl-5-[3-(trifluoro-methyl)phenoxy]pyrimidin-4-yl]-5,6-dihydro-4H-1,2,4-oxadiazine (100 mg, 0.19 mmol) (compound I-021), 2-cyclopropyl-4,4,5,5-tetramethyl-1,3,2-dioxaborolane (64 mg, 0.38 mmol), cesium carbonate (94 mg, 0.29 mmol) and [1,1'-bis(diphenylphosphino)ferrocene]dichloropalladium(II) (7.5 mg, 0.009 mmol) were suspended in a mixture of 1,4-dioxane (1 mL) and water (0.5 mL). The reaction mixture was stirred at 130° C. under microwave irradiation during 45 min. The reaction mixture was diluted with ethyl acetate and washed with a saturated aqueous solution of $K_2CO_3$. The organic layer was dried over $MgSO_4$ anhydrous, filtered then concentrated over reduced pressure. This crude product was purified by preparative HPLC to afford 9 mg (96% purity, 9% yield) of (5RS)-5-[(4-cyclopropyl-2-methyl-phenyl)methyl]-3-[2-methyl-5-[3-(trifluoromethyl)phenoxy]pyrimidin-4-yl]-5,6-dihydro-4H-1,2,4-oxadiazine.

Preparation Example 7: Preparation of (6RS)-2-[5-(3-chlorophenoxy)-2-methyl-pyrimidin-4-yl]-6-[(2,4-dimethylphenyl)methyl]-5,6-dihydro-1H-pyrimidin-4-one (Compound I-011)

Step 1: Preparation of methyl 5-(3-chlorophenoxy)-2-methyl-pyrimidine-4-carboximidate (compound 20-01)

To a solution of 5-(3-chlorophenoxy)-2-methyl-pyrimidine-4-carbonitrile (120 mg, 0.48 mmol) in methanol (1 mL) at 0° C. was added sodium methoxide (29 mg, 0.53 mmol). The reaction was stirred for 2 h at 0° C., and then 30 min at room temperature. The reaction mixture was kept as a solution and used directly without further purification for the following step.

Step 2: Preparation of (6RS)-2-[5-(3-chlorophenoxy)-2-methyl-pyrimidin-4-yl]-6-[(2,4-dimethylphenyl)methyl]-5,6-dihydro-1H-pyrimidin-4-one (Compound I-011)

A solution of methyl 5-(3-chlorophenoxy)-2-methyl-pyrimidine-4-carboximidate (135 mg, 0.48 mmol) and 3-amino-4-(2,4-dimethylphenyl)butanamide (151 mg, 0.73 mmol) in methanol (1 mL) and acetic acid (28 μL, 0.48 mmol) was stirred at 60° C. during 18 h. The reaction mixture was cooled down to room temperature and concentrated. The crude product was purified directly by flash silica gel chromatography (10% to 80% ethyl acetate in n-heptane) to afford 93 mg (99% purity, 43% yield) of (6RS)-2-[5-(3-chlorophenoxy)-2-methyl-pyrimidin-4-yl]-6-[(2,4-dimethylphenyl)methyl]-5,6-dihydro-1H-pyrimidin-4-one as a white powder.

Preparation Example 8: Preparation of 5-(3-chlorophenoxy)-2-methyl-4-[(6RS)-6-[(2,4-dimethyl-phenyl)methyl]-1,4,5,6-tetrahydropyrimidin-2-yl]pyrimidine (Compound T-022)

Step 1: Preparation of methyl 5-(3-chlorophenoxy)-2-methyl-pyrimidine-4-carboximidate (compound 20-01)

To a solution of 5-(3-chlorophenoxy)-2-methyl-pyrimidine-4-carbonitrile (120 mg, 0.48 mmol) in methanol (1 mL) at 0° C. was added sodium methoxide (29 mg, 0.53 mmol). The reaction was stirred for 2 h at 0° C., and then 30 min at room temperature. The reaction mixture was kept as a solution and used directly treated for the following step.

Step 2: Preparation of 5-(3-chlorophenoxy)-2-methyl-4-[(6RS)-6-[(2,4-dimethylphenyl)methyl]-1,4,5,6-tetrahydropyrimidin-2-yl]pyrimidine (Compound I-022)

A solution of methyl 5-(3-chlorophenoxy)-2-methyl-pyrimidine-4-carboximidate (135 mg, 0.48 mmol) and 4-(2,4-dimethylphenyl)butane-1,3-diamine (140 mg, 0.72 mmol) in methanol (1.5 mL) and acetic acid (13 μL, 0.24 mmol) was stirred at room temperature during 18 h. The reaction mixture was cooled down to room temperature and concentrated. The crude product was purified directly by flash silica gel chromatography (10% to 80% ethyl acetate in n-heptane) to afford 113 mg (99% purity, 55% yield) of 5-(3-chlorophenoxy)-2-methyl-4-[(6RS)-6-[(2,4-dimethylphenyl)methyl]-1,4,5,6-tetrahydropyrimidin-2-yl]pyrimidine as a yellow oil.

The compounds as shown in Table 1 below were prepared in accordance with the examples provided above or following methods described herein.

TABLE 1
| Compounds according to formula (I) | | | |
|---|---|---|---|
| Ex No | Structure | $^{1}$H-NMR Peak List | LogP |
| I-001 | 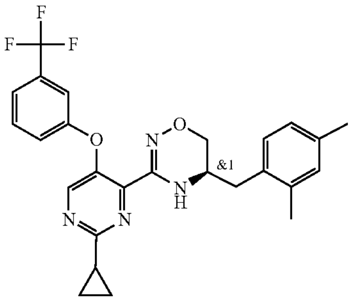 [SMILES: Cc1ccc(C[C@@H]2CON=C(c3nc(C4CC4)ncc3Oc3cccc(C(F)(F)F)c3)N2)c(C)c1] | I-001: $^{1}$H-NMR(500.1 MHz, CDCl3): δ = 8.3657 (6.1); 7.4320 (0.8); 7.4164 (2.0); 7.4007 (1.2); 7.3317 (2.0); 7.3163 (1.4); 7.2591 (20.8); 7.1034 (4.5); 7.0867 (1.4); 7.0681 (1.4); 7.0521 (5.3); 7.0359 (2.4); 7.0201 (0.9); 6.3216 (1.8); 5.2981 (5.9); 4.0471 (1.2); 4.0403 (1.3); 4.0254 (1.3); 4.0185 (1.4); 3.7989 (0.6); 3.7931 (0.8); 3.7874 (0.9); 3.7814 (0.9); 3.7760 (0.8); 3.7699 (0.6); 3.6441 (1.5); 3.6324 (1.3); 3.6224 (1.4); 3.6106 (1.2); 2.9374 (1.0); 2.9259 (1.0); 2.9102 (1.3); 2.8987 (1.3); 2.7473 (1.3); 2.7297 (1.3); 2.7201 (1.1); 2.7023 (1.0); 2.3290 (14.3); 2.3119 (15.1); 2.3014 (0.7); 2.2908 (0.8); 2.2843 (0.9); 2.2747 (1.3); 2.2652 (0.9); 2.2589 (0.8); 2.2491 (0.4); 1.5413 (16.0); 1.2847 (0.3); 1.2556 (1.3); 1.1475 (0.4); 1.1342 (0.6); 1.1216 (1.6); 1.1186 (1.6); 1.1065 (2.0); 1.0940 (1.8); 1.0808 (1.1); 1.0748 (1.2); 1.0640 (1.5); 1.0537 (1.0); 1.0501 (1.1); 1.0394 (1.4); 1.0274 (0.6); 1.0229 (0.8); 0.8807 (0.4); 0.1539 (0.5); 0.0692 (12.6); −0.0002 (27.7) | 5.16[a] |
| I-002 | 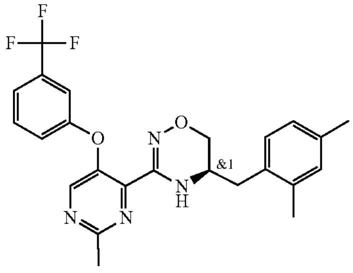 | I-002: $^{1}$H-NMR(500.1 MHz, CDCl3): δ = 8.4314 (3.7); 7.4542 (0.5); 7.4377 (1.0); 7.4207 (0.8); 7.3566 (1.3); 7.3411 (0.9); 7.2596 (8.5); 7.1300 (2.7); 7.1176 (1.0); 7.0612 (1.2); 7.0459 (2.2); 7.0361 (2.0); 7.0076 (1.3); 6.9921 (0.7); 6.4383 (1.1); 5.2980 (1.5); 4.1429 (0.6); 4.1287 (1.7); 4.1144 (1.7); 4.1001 (0.6); 3.9901 (0.8); 3.9833 (0.8); 3.9683 (0.9); 3.9615 (0.9); 3.8113 (0.5); 3.8051 (0.5); 3.8001 (0.6); 3.6697 (1.0); 3.6587 (0.9); 3.6479 (0.9); 3.6370 (0.8); 2.9187 (0.5); 2.9056 (0.6); 2.8913 (1.0); 2.8782 (0.9); 2.8249 (1.0); 2.8088 (0.9); 2.7975 (0.6); 2.7814 (0.6); 2.7464 (11.4); 2.3168 (16.0); 2.0435 (7.2); 2.0043 (0.4); 1.5580 (1.7); 1.2729 (2.0); 1.2586 (4.2); 1.2444 (1.9); 0.0694 (2.8); −0.0002 (11.0) | 4.33[a] |
| I-003 | 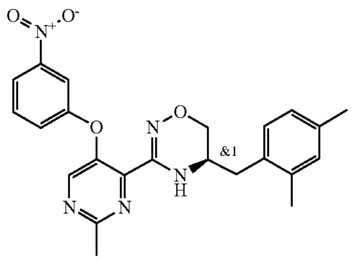 | I-003: $^{1}$H-NMR(400.1 MHz, CDCl3): δ = 8.5025 (3.2); 7.9443 (1.5); 7.9251 (1.8); 7.5818 (2.5); 7.5102 (1.0); 7.4904 (1.9); 7.4706 (1.3); 7.3293 (1.7); 7.3110 (1.6); 7.2606 (1.0); 7.0383 (5.2); 7.0137 (3.0); 6.9957 (1.7); 6.4866 (2.1); 5.2950 (2.0); 3.9648 (1.3); 3.9394 (1.5); 3.7880 (1.4); 3.6532 (1.2); 3.6404 (1.3); 3.6275 (1.3); 3.6144 (1.1); 2.9151 (0.7); 2.8987 (0.9); 2.8815 (1.5); 2.8660 (1.5); 2.8223 (1.5); 2.8016 (1.9); 2.7739 (10.5); 2.3143 (16.0); 2.0430 (0.6); 2.0027 (0.3); 1.6337 (0.6); 1.2576 (0.6); 1.2416 (0.4); −0.0002 (1.0) | 3.78[a] |
| I-004 | 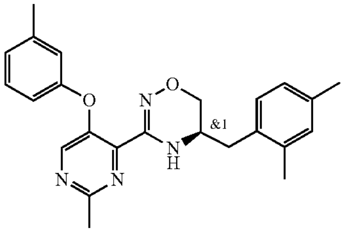 [SMILES: Cc1cccc(Oc2cnc(C)nc2C2=NOC[C@@H](Cc3ccc(C)cc3C)N2)c1] | I-004: $^{1}$H-NMR(400.1 MHz, CDCl3): δ = 8.3507 (0.8); 7.2598 (6.3); 7.2177 (0.7); 7.1983 (1.4); 7.1787 (0.8); 7.0686 (1.0); 7.0495 (1.7); 7.0291 (1.9); 6.9946 (1.2); 6.9752 (0.8); 6.9363 (1.1); 6.9176 (0.9); 6.7803 (1.6); 6.7637 (1.0); 6.7428 (0.8); 6.4083 (0.9); 5.2977 (1.0); 4.1306 (0.9); 4.1127 (1.0); 4.0949 (0.4); 4.0651 (0.4); 4.0347 (0.6); 4.0273 (0.6); 4.0073 (0.6); 4.0005 (0.7); 3.8135 (0.5); 3.7152 (0.6); 3.7016 (0.6); 3.6881 (0.6); 3.6741 (0.5); 2.9395 (0.4); 2.9233 (0.4); 2.9054 (0.8); 2.8893 (0.8); 2.8352 (0.8); 2.8148 (0.8); 2.8011 (0.5); 2.7809 (0.4); 2.7082 (5.6); 2.3195 (10.0); 2.3132 (16.0); 2.0436 (5.0); 1.5769 (5.6); 1.2764 (1.2); 1.2585 (2.3); 1.2407 (1.1); 0.9356 (0.6); 0.0695 (1.8); −0.0002 (8.3) | 3.95[a] |
| I-005 | 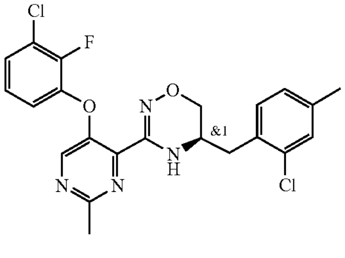 [SMILES: Cc1ccc(C[C@@H]2CON=C(c3nc(C)ncc3Oc3cccc(Cl)c3F)N2)c(Cl)c1] | I-005: $^{1}$H-NMR(400.1 MHz, CDCl3): δ = 8.3346 (4.0); 7.2600 (13.8); 7.2368 (2.7); 7.1991 (0.8); 7.1954 (0.8); 7.1833 (0.9); 7.1792 (1.6); 7.1750 (1.1); 7.1631 (1.0); 7.1593 (1.0); 7.1382 (1.9); 7.1189 (2.7); 7.0482 (1.7); 7.0338 (1.3); 7.0297 (1.9); 7.0135 (1.7); 7.0092 (1.6); 6.9929 (0.9); 6.9886 (0.9); 6.8965 (1.0); 6.8928 (1.0); 6.8786 (1.2); 6.8754 (1.6); 6.8581 (0.8); 6.8543 (0.7); 6.4425 (1.3); 5.2984 (3.9); 3.9830 (0.9); 3.9751 (1.6); 3.9546 (2.4); 3.9486 (1.8); 3.9309 (0.4); 3.7852 (0.9); 3.7709 (1.3); 3.7558 (1.1); 3.7417 (0.6); 3.0733 (0.5); 3.0563 (0.5); 3.0391 (1.4); 3.0232 (1.4); 3.0013 (1.2); 2.9825 (1.1); 2.9669 (0.6); 2.9494 (0.5); 2.7229 (16.0); 2.3512 (0.3); 2.3327 (11.8); 1.5770 (3.8); 1.2554 (0.4); 0.0694 (2.3); −0.0002 (18.0) | 4.19[a] |

TABLE 1-continued
Compounds according to formula (I)
| Ex No | Structure | $^1$H-NMR Peak List | LogP |
|---|---|---|---|
| I-006 | 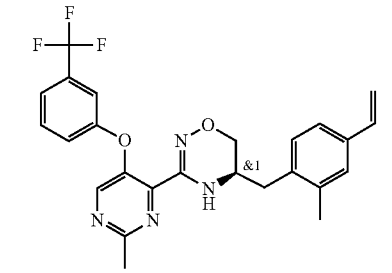 [SMILES: C=Cc1ccc(C[C@@H]2CON=C(c3nc(C)ncc3Oc3cccc(C(F)(F)F)c3)N2)c(C)c1] | I-006: $^1$H-NMR(400.1 MHz, CDCl3): δ = 8.4345 (4.8); 7.4618 (0.8); 7.4419 (1.8); 7.4206 (1.4); 7.3624 (2.4); 7.3427 (1.6); 7.2593 (17.6); 7.2340 (2.5); 7.1355 (7.4); 7.1181 (3.7); 6.7222 (1.1); 6.6948 (1.3); 6.6782 (1.3); 6.6510 (1.3); 6.4384 (2.1); 5.7629 (2.5); 5.7191 (2.3); 5.2979 (5.2); 5.2540 (2.5); 5.2267 (2.4); 3.9792 (1.2); 3.9708 (1.3); 3.9519 (1.5); 3.9438 (1.6); 3.8232 (1.2); 3.7044 (1.6); 3.6914 (1.4); 3.6773 (1.4); 3.6646 (1.1); 2.9541 (0.7); 2.9369 (0.7); 2.9198 (1.7); 2.9035 (1.7); 2.8757 (1.7); 2.8557 (1.7); 2.8417 (0.8); 2.8217 (0.7); 2.7426 (16.0); 2.3516 (14.3); 2.3270 (0.7); 2.0435 (1.0); 1.5574 (7.0); 1.2767 (0.5); 1.2584 (1.3); 1.2412 (0.4); 0.0694 (4.2); −0.0002 (15.9) | 4.44[a] |
| I-007 | 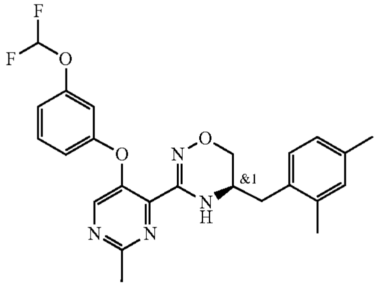 [SMILES: Cc1ccc(C[C@@H]2CON=C(c3nc(C)ncc3Oc3cccc(OC(F)F)c3)N2)c(C)c1] | I-007: $^1$H-NMR(400.1 MHz, CDCl3): δ = 8.4266 (0.3); 7.3093 (0.8); 7.2886 (1.6); 7.2598 (6.2); 7.0664 (1.0); 7.0470 (2.1); 7.0361 (2.1); 7.0080 (1.4); 6.9890 (0.7); 6.8597 (1.0); 6.8402 (0.9); 6.7736 (1.0); 6.7530 (0.9); 6.7033 (1.8); 6.6727 (0.8); 6.4886 (1.7); 6.4289 (0.8); 6.3045 (0.8); 4.1305 (0.4); 4.1125 (0.4); 3.9993 (0.6); 3.9793 (0.6); 3.8049 (0.6); 3.6896 (0.6); 3.6756 (0.6); 3.6630 (0.6); 3.6497 (0.4); 2.9307 (0.4); 2.9145 (0.4); 2.8967 (0.8); 2.8809 (0.8); 2.8323 (0.8); 2.8125 (0.8); 2.7986 (0.5); 2.7784 (0.5); 2.7290 (3.7); 2.3186 (16.0); 2.0436 (2.1); 1.5667 (5.9); 1.2764 (0.6); 1.2585 (1.2); 1.2408 (0.5); 0.0696 (2.3); −0.0002 (7.9) | 3.94[a] |
| I-008 | 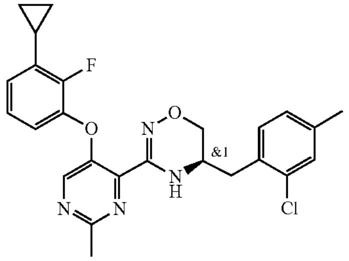 [SMILES: Cc1ccc(C[C@@H]2CON=C(c3nc(C)ncc3Oc3cccc(C4CC4)c3F)N2)c(Cl)c1] | I-008: $^1$H-NMR(400.1 MHz, CDCl3): δ = 8.3966 (0.5); 8.2610 (5.0); 7.2605 (12.4); 7.2321 (4.4); 7.1655 (0.6); 7.1485 (2.4); 7.1296 (3.2); 7.1104 (0.4); 7.0901 (0.3); 7.0314 (2.6); 7.0133 (2.1); 6.9958 (1.4); 6.9754 (2.6); 6.9560 (1.6); 6.9341 (0.3); 6.8654 (1.4); 6.8466 (2.3); 6.8266 (1.2); 6.7104 (1.5); 6.6933 (2.3); 6.6761 (1.2); 6.4399 (2.6); 5.2984 (8.5); 4.0014 (1.7); 3.9769 (3.8); 3.8093 (1.3); 3.7985 (1.6); 3.7834 (1.5); 3.0913 (0.7); 3.0760 (0.8); 3.0581 (1.6); 3.0418 (1.7); 3.0110 (1.7); 2.9928 (1.6); 2.9785 (0.8); 2.9591 (0.7); 2.7892 (1.6); 2.7013 (16.0); 2.3260 (14.9); 2.2767 (1.6); 2.1151 (0.5); 2.0931 (1.1); 2.0806 (1.6); 2.0694 (1.1); 2.0482 (0.5); 1.5741 (24.2); 1.2564 (0.9); 1.0379 (0.4); 1.0096 (3.6); 0.9887 (3.6); 0.7414 (4.5); 0.7283 (4.3); 0.0698 (5.2); −0.0002 (14.9) | 4.49[a] |
| I-009 | 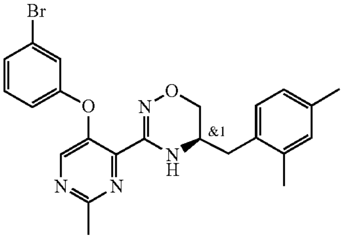 [SMILES: Cc1ccc(C[C@@H]2CON=C(c3nc(C)ncc3Oc3cccc(Br)c3)N2)c(C)c1] | I-009: $^1$H-NMR(400.1 MHz, CDCl3): δ = 8.4127 (3.2); 7.2592 (2.5); 7.2354 (0.6); 7.2154 (1.6); 7.1995 (1.3); 7.1796 (1.7); 7.1597 (0.6); 7.0676 (1.0); 7.0484 (2.0); 7.0331 (2.6); 7.0278 (2.1); 7.0227 (1.4); 7.0089 (1.3); 6.9897 (0.7); 6.9122 (0.9); 6.9095 (0.8); 6.8921 (0.8); 6.4162 (1.1); 4.0111 (0.7); 4.0026 (0.8); 3.9839 (0.8); 3.9755 (0.8); 3.8113 (0.5); 3.8056 (0.6); 3.6858 (0.9); 3.6721 (0.8); 3.6587 (0.8); 3.6449 (0.7); 2.9318 (0.4); 2.9156 (0.5); 2.8977 (0.9); 2.8815 (0.8); 2.8323 (0.9); 2.8122 (0.9); 2.7982 (0.5); 2.7780 (0.5); 2.7330 (10.1); 2.3192 (16.0); 1.5950 (1.0); 0.0706 (0.6); −0.0002 (3.1) | 4.44[a] |
| I-010 | 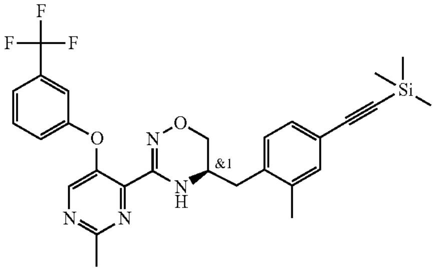 [SMILES: Cc1ncc(Oc2cccc(C(F)(F)F)c2)c(C2=NOC[C@@H](Cc3ccc(C#C[Si](C)(C)C)cc3C)N2)n1] | I-010: $^1$H-NMR(400.1 MHz, CDCl3): δ = 8.4403 (1.3); 8.4373 (1.9); 7.4435 (0.6); 7.4226 (0.5); 7.3647 (1.1); 7.3382 (1.0); 7.2992 (0.6); 7.2792 (0.6); 7.2596 (5.9); 7.1326 (1.5); 7.1048 (0.7); 7.0853 (0.6); 7.0400 (0.4); 6.4021 (0.5); 5.2976 (2.7); 3.9361 (0.3); 3.9283 (0.4); 3.9091 (0.4); 3.9013 (0.5); 3.8095 (0.3); 3.7030 (0.4); 3.6915 (0.4); 3.6758 (0.3); 2.9103 (0.5); 2.8940 (0.5); 2.8849 (0.7); 2.8659 (0.6); 2.8583 (0.3); 2.7495 (7.4); 2.4018 (0.4); 2.3526 (0.4); 2.3253 (2.0); 2.3113 (3.6); 1.5514 (6.9); 0.2988 (2.2); 0.2499 (16.0); 0.2343 (2.0); 0.2070 (1.7); 0.0697 (4.5); −0.0002 (6.1) | 5.79[a] |

TABLE 1-continued
Compounds according to formula (I)
| Ex No | Structure | $^1$H-NMR Peak List | LogP |
|---|---|---|---|
| I-011 | 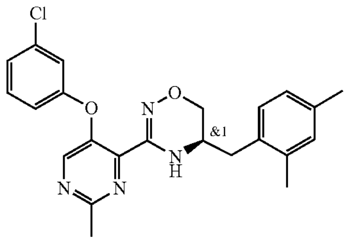 [SMILES: Cc1ccc(C[C@@H]2CON=C(c3nc(C)ncc3Oc3cccc(Cl)c3)N2)c(C)c1] | I-011: $^1$H-NMR(400.1 MHz, CDCl3): δ = 9.3618 (1.0); 8.5704 (5.3); 7.2588 (5.0); 7.2373 (2.7); 7.2168 (1.8); 7.1056 (1.1); 7.1034 (1.3); 7.1008 (1.3); 7.0986 (1.3); 7.0856 (0.9); 7.0833 (1.0); 7.0808 (1.1); 7.0786 (1.0); 6.9243 (3.0); 6.9055 (2.3); 6.8887 (1.6); 6.8832 (2.5); 6.8779 (1.8); 6.8430 (1.2); 6.8238 (0.8); 6.7625 (1.1); 6.7603 (1.2); 6.7564 (1.1); 6.7543 (1.1); 6.7418 (1.0); 6.7396 (1.1); 6.7357 (1.1); 6.7335 (1.0); 5.2963 (1.0); 3.9460 (0.5); 3.9386 (0.4); 3.9323 (0.6); 3.9246 (0.6); 3.9188 (0.6); 3.9111 (0.6); 3.9048 (0.4); 3.8974 (0.6); 2.8976 (0.8); 2.8835 (0.8); 2.8630 (0.9); 2.8490 (0.9); 2.8328 (0.4); 2.7826 (16.0); 2.5798 (1.0); 2.5583 (1.0); 2.5452 (0.8); 2.5238 (0.8); 2.4495 (0.9); 2.4354 (1.0); 2.4076 (1.3); 2.3935 (1.2); 2.2596 (9.7); 2.2049 (1.7); 2.1948 (10.7); 2.1778 (1.7); 2.1630 (1.3); 2.1454 (0.3); 2.1358 (1.2); 1.5810 (0.7); 1.2550 (0.5); 0.0704 (0.8); −0.0002 (6.4); −0.0084 (0.3) | 4.01[a] |
| I-012 | 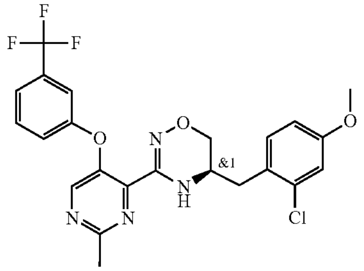 [SMILES: COc1ccc(C[C@@H]2CON=C(c3nc(C)ncc3Oc3cccc(C(F)(F)F)c3)N2)c(Cl)c1] | I-012: $^1$H-NMR(400.1 MHz, CDCl3): δ = 8.4365 (5.0); 7.4638 (0.8); 7.4439 (1.7); 7.4228 (1.3); 7.3625 (2.2); 7.3436 (1.5); 7.2611 (8.3); 7.1420 (7.3); 7.1219 (4.2); 6.9718 (2.8); 6.9660 (3.0); 6.8046 (1.7); 6.7987 (1.6); 6.7835 (1.5); 6.7777 (1.4); 6.4705 (1.9); 5.2990 (4.1); 3.9168 (2.7); 3.8957 (2.4); 3.8053 (16.0); 3.7878 (0.9); 3.7552 (0.3); 3.7356 (1.1); 3.7220 (1.5); 3.7063 (1.3); 3.6936 (0.8); 3.0216 (0.5); 3.0058 (0.6); 2.9879 (1.6); 2.9710 (1.7); 2.9601 (1.8); 2.9425 (1.7); 2.9264 (0.6); 2.9073 (0.5); 2.7566 (15.3); 2.0444 (0.8); 1.5732 (3.4); 1.2765 (0.4); 1.2589 (0.8); 0.0699 (3.2); −0.0002 (10.8) | 4.08[a] |
| I-013 | 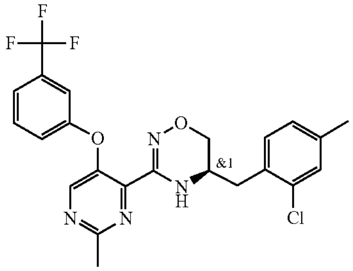 [SMILES: Cc1ccc(C[C@@H]2CON=C(c3nc(C)ncc3Oc3cccc(C(F)(F)F)c3)N2)c(Cl)c1] | I-013: $^1$H-NMR(400.1 MHz, CDCl3): δ = 8.4349 (5.1); 7.4639 (0.8); 7.4440 (1.9); 7.4227 (1.3); 7.3628 (2.4); 7.3440 (1.6); 7.2609 (10.2); 7.2372 (3.8); 7.1405 (5.7); 7.1232 (3.9); 7.1035 (3.3); 7.0491 (2.4); 7.0300 (1.5); 6.4816 (2.1); 3.9297 (2.8); 3.9038 (2.1); 3.8970 (1.5); 3.7350 (1.2); 3.7235 (1.5); 3.7078 (1.3); 3.6970 (0.9); 3.0500 (0.6); 3.0327 (0.6); 3.0160 (1.7); 2.9997 (1.7); 2.9841 (1.7); 2.9658 (1.6); 2.9512 (0.7); 2.9322 (0.6); 2.8426 (0.3); 2.7561 (16.0); 2.3541 (0.4); 2.3337 (14.1); 1.5758 (12.4); 1.2582 (0.6); 0.0698 (1.1); −0.0002 (12.7) | 4.47[a] |
| I-014 | 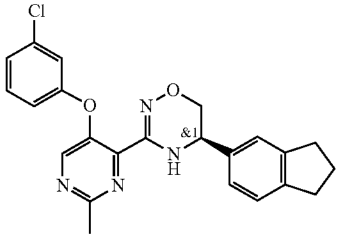 [SMILES: Cc1ncc(Oc2cccc(Cl)c2)c(C2=NOC[C@@H](c3ccc4c(c3)CCC4)N2)n1] | I-014: $^1$H-NMR(400.1 MHz, CDCl3): δ = 8.4634 (5.2); 7.2843 (1.2); 7.2641 (4.3); 7.2593 (12.8); 7.2444 (1.7); 7.0752 (1.2); 7.0731 (1.0); 6.9320 (1.1); 6.9265 (2.4); 6.9214 (1.8); 6.9156 (1.5); 6.9136 (1.5); 6.9096 (0.8); 6.8951 (1.1); 6.8933 (1.1); 6.8891 (0.9); 6.8873 (0.8); 6.6338 (1.3); 5.2981 (11.8); 4.6799 (0.6); 4.6700 (0.7); 4.6650 (0.7); 4.6549 (0.7); 4.2441 (0.7); 4.2416 (0.8); 4.2342 (0.8); 4.2315 (0.7); 4.2168 (0.8); 4.2142 (0.9); 4.2068 (0.8); 4.2042 (0.8); 3.6221 (1.3); 3.6037 (1.3); 3.5948 (1.3); 3.5764 (1.2); 2.9379 (3.0); 2.9193 (5.9); 2.9007 (3.4); 2.7868 (0.4); 2.7366 (16.0); 2.6872 (0.3); 2.1360 (0.6); 2.1173 (1.8); 2.1088 (0.4); 2.0986 (2.6); 2.0803 (1.8); 2.0615 (0.5); 2.0437 (1.3); 1.5497 (7.2); 1.2766 (0.5); 1.2587 (1.1); 1.2409 (0.4); 0.0693 (7.2); 0.0603 (0.4); 0.0502 (0.4); 0.0078 (0.6); −0.0002 (17.4); −0.0083 (0.9); −0.0500 (0.3) | 4.05[a] |
| I-015 | 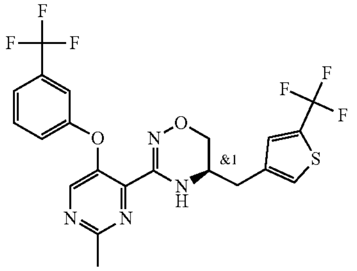 [SMILES: Cc1ncc(Oc2cccc(C(F)(F)F)c2)c(C2=NOC[C@@H](Cc3csc(C(F)(F)F)c3)N2)n1] | I-015: $^1$H-NMR(400.1 MHz, CDCl3): δ = 8.4461 (5.2); 7.4708 (0.6); 7.4499 (1.3); 7.4291 (1.0); 7.3709 (1.6); 7.3513 (3.5); 7.2601 (11.1); 7.1447 (2.8); 6.5029 (1.2); 5.2983 (3.5); 3.9409 (0.9); 3.9329 (1.1); 3.9137 (1.2); 3.9057 (1.4); 3.8561 (3.1); 7.1917 (2.2); 7.0999 (2.2); 7.0954 (1.5); 7.0930 (1.3); 7.0801 (0.4); 3.8475 (0.6); 3.8391 (0.8); 3.8310 (0.8); 3.8226 (0.6); 3.8121 (0.4); 3.7536 (1.3); 3.7427 (1.1); 3.7264 (1.0); 3.7155 (0.8); 2.9406 (1.6); 2.9269 (2.2); 2.9088 (1.6); 2.7809 (0.3); 2.7495 (16.0); 1.5707 (1.0); 0.0697 (1.3); 0.0078 (0.5); −0.0002 (13.6) | 4.17[a] |

TABLE 1-continued
Compounds according to formula (I)
| Ex No | Structure | $^1$H-NMR Peak List | LogP |
|---|---|---|---|
| I-016 | 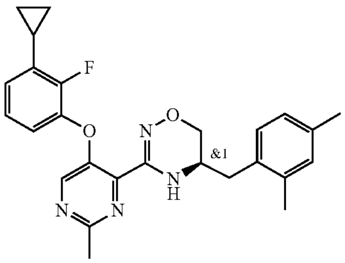 [SMILES: Cc1ccc(C[C@@H]2CON=C(c3nc(C)ncc3Oc3cccc(C4CC4)c3F)N2)c(C)c1] | I-016: $^1$H-NMR(400.1 MHz, CDCl3): δ = 8.3952 (0.8); 8.2538 (4.8); 7.2595 (9.2); 7.0803 (2.4); 7.0622 (3.4); 7.0260 (4.8); 6.9899 (5.1); 6.9701 (6.0); 6.9198 (0.6); 6.9024 (0.4); 6.8579 (1.7); 6.8386 (2.7); 6.8192 (1.5); 6.7065 (2.0); 6.6901 (2.7); 6.4108 (3.2); 5.2978 (1.1); 4.3651 (0.4); 4.1368 (0.4); 4.0594 (1.9); 4.0339 (2.2); 3.8401 (1.9); 3.7518 (1.9); 3.7424 (1.7); 3.7289 (1.7); 3.7155 (1.4); 2.9564 (1.0); 2.9412 (1.2); 2.9227 (2.0); 2.9090 (1.9); 2.8605 (1.9); 2.8426 (1.9); 2.8313 (1.4); 2.7946 (2.6); 2.6921 (15.2); 2.3295 (16.0); 2.3077 (15.7); 2.2728 (3.1); 2.0781 (1.9); 1.5679 (17.8); 1.2545 (0.7); 1.0058 (4.7); 0.9857 (4.2); 0.7381 (5.7); 0.7269 (5.3); 0.0695 (4.8); −0.0002 (11.2) | 4.41[a] |
| I-017 | 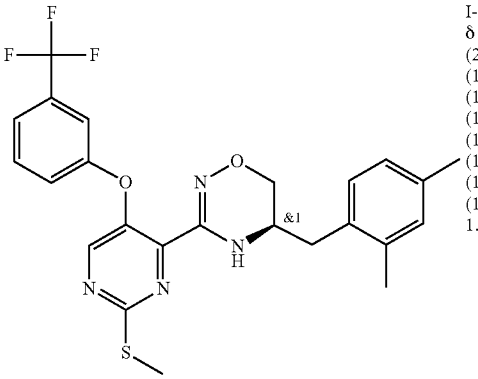 | I-017: $^1$H-NMR(400.1 MHz, CDCl3): δ = 8.3643 (5.3); 7.4496 (0.8); 7.4296 (1.7); 7.4087 (1.3); 7.3445 (2.2); 7.3251 (1.5); 7.2601 (9.5); 7.1179 (5.1); 7.1022 (2.0); 7.0579 (1.8); 7.0374 (5.0); 7.0045 (2.6); 6.9857 (1.3); 6.2481 (2.1); 5.2981 (1.2); 4.1305 (0.8); 4.1127 (0.8); 4.0949 (0.3); 4.0420 (1.2); 4.0340 (1.3); 4.0151 (1.5); 4.0071 (1.5); 3.8130 (1.0); 3.8066 (1.1); 3.7997 (1.2); 3.7928 (1.1); 3.6697 (1.5); 3.6552 (1.4); 3.6425 (1.4); 3.6281 (1.2); 2.9288 (1.0); 2.9142 (1.0); 2.8947 (1.5); 2.8803 (1.4); 2.7699 (1.4); 2.7477 (1.4); 2.7359 (1.1); 2.7134 (0.9); 2.5791 (0.3); 2.4820 (16.0); 2.3138 (15.4); 2.3041 (15.8); 2.0438 (3.2); 1.5658 (17.2); 1.2765 (1.2); 1.2586 (2.5); 1.2409 (1.1); 0.0698 (4.5); −0.0002 (11.7) | 5.09[a] |
| I-018 | 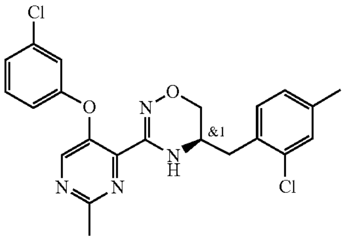 | I-018: $^1$H-NMR(400.1 MHz, CDCl3): δ = 8.5242 (0.7); 8.4198 (5.0); 7.2604 (11.2); 7.2402 (6.3); 7.1553 (0.9); 7.1258 (2.7); 7.1070 (3.9); 7.0842 (3.0); 7.0640 (2.7); 7.0475 (3.4); 7.0291 (2.2); 6.9841 (0.6); 6.9628 (0.6); 6.9163 (0.7); 6.8884 (4.4); 6.8691 (2.8); 6.8473 (2.4); 6.8126 (0.4); 6.4431 (3.0); 5.2975 (1.0); 4.3623 (0.4); 4.0849 (0.4); 3.9413 (4.1); 3.9196 (3.7); 3.7457 (1.6); 3.7343 (2.0); 3.7181 (1.8); 3.7060 (1.3); 3.0556 (1.0); 3.0402 (1.0); 3.0229 (2.1); 3.0076 (2.1); 2.9838 (2.1); 2.9657 (2.1); 2.9339 (0.8); 2.8261 (2.1); 2.7407 (16.0); 2.3325 (15.3); 2.2805 (2.2); 1.5616 (16.9); 1.2599 (0.4); 0.0695 (2.2); −0.0002 (12.3) | 4.22[a] |
| I-019 | 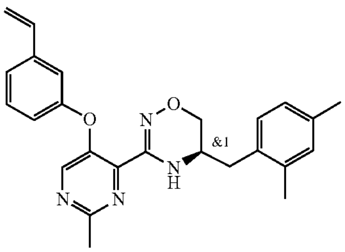 [SMILES: C=Cc1cccc(Oc2cnc(C)nc2C2=NOC[C@@H](Cc3ccc(C)cc3C)N2)c1] | I-019: $^1$H-NMR(400.1 MHz, CDCl3): δ = 8.3693 (3.5); 7.2950 (0.9); 7.2755 (2.1); 7.2590 (8.9); 7.1671 (1.9); 7.1479 (1.4); 7.0667 (1.5); 7.0474 (2.5); 7.0255 (4.2); 6.9956 (2.0); 6.9770 (1.2); 6.8524 (1.4); 6.8320 (1.3); 6.6818 (0.9); 6.6547 (1.0); 6.6377 (1.0); 6.6109 (1.0); 6.4156 (1.8); 5.7236 (2.0); 5.6795 (1.8); 5.2975 (2.7); 5.2730 (2.0); 5.2458 (1.9); 4.1478 (0.4); 4.1301 (1.1); 4.1125 (1.2); 4.0947 (0.4); 4.0223 (1.1); 3.9956 (1.2); 3.8159 (1.0); 3.7081 (1.2); 3.6950 (1.0); 3.6811 (1.0); 3.6677 (0.8); 2.9367 (0.6); 2.9212 (0.6); 2.9034 (1.2); 2.8872 (1.2); 2.8346 (1.2); 2.8144 (1.2); 2.8017 (0.7); 2.7806 (0.6); 2.7155 (11.5); 2.3161 (16.0); 2.0431 (4.6); 2.0038 (0.5); 1.5839 (3.2); 1.2761 (1.5); 1.2584 (2.9); 1.2405 (1.4); 0.0694 (0.9); −0.0002 (11.2) | 4.09[a] |
| I-020 | 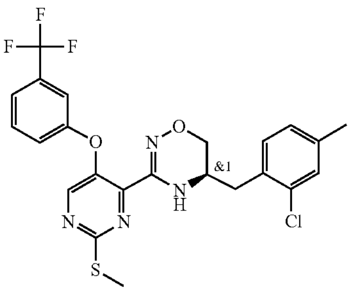 [SMILES: CSc1ncc(Oc2cccc(C(F)(F)F)c2)c(C2=NOC[C@@H](Cc3ccc(C)cc3Cl)N2)n1] | I-020: $^1$H-NMR(400.1 MHz, CDCl3): δ = 8.3709 (5.4); 7.4499 (0.7); 7.4305 (1.7); 7.4111 (1.1); 7.3466 (1.8); 7.3273 (1.2); 7.2592 (3.6); 7.2343 (2.9); 7.1252 (4.6); 7.1182 (2.5); 7.0981 (3.7); 7.0507 (1.9); 7.0314 (1.1); 6.2571 (1.6); 5.2957 (0.5); 3.9663 (0.9); 3.9583 (1.5); 3.9481 (0.7); 3.9356 (2.4); 3.9068 (0.4); 3.7270 (0.8); 3.7138 (1.3); 3.6991 (1.2); 3.6847 (0.5); 3.0519 (0.7); 3.0373 (0.7); 3.0181 (1.2); 3.0037 (1.2); 2.9266 (1.1); 2.9063 (1.0); 2.8928 (0.7); 2.8730 (0.7); 2.5190 (16.0); 2.3312 (12.4); 1.5638 (0.9); 1.2573 (0.5); 0.0708 (0.9); −0.0002 (3.9) | 5.14[a] |

TABLE 1-continued
| Compounds according to formula (I) | | | |
|---|---|---|---|
| Ex No | Structure | $^1$H-NMR Peak List | LogP |
| I-021 | 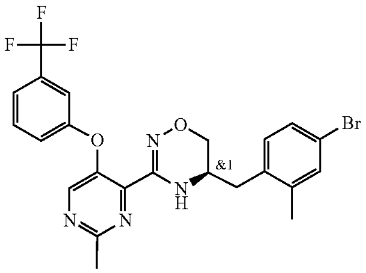 [SMILES: Cc1ncc(Oc2cccc(C(F)(F)F)c2)c(C2=NOC[C@@H](Cc3ccc(Br)cc3C)N2)n1] | I-021: $^1$H-NMR(400.1 MHz, CDCl3): δ = 8.4411 (5.1); 7.4685 (0.6); 7.4471 (1.2); 7.4262 (0.9); 7.3666 (3.9); 7.3474 (1.1); 7.3262 (1.2); 7.3215 (1.0); 7.3061 (1.3); 7.3013 (1.2); 7.2603 (11.8); 7.1421 (1.4); 7.1267 (3.4); 7.0407 (2.3); 7.0204 (2.0); 6.4208 (1.2); 5.2988 (1.5); 3.9325 (0.9); 3.9244 (1.0); 3.9053 (1.2); 3.8972 (1.3); 3.8185 (0.6); 3.8101 (0.7); 3.8019 (0.8); 3.7934 (0.6); 3.7823 (0.4); 3.7221 (1.4); 3.7104 (1.1); 3.6950 (1.0); 3.6834 (0.8); 2.9195 (0.4); 2.9029 (0.5); 2.8853 (1.5); 2.8685 (1.5); 2.8590 (1.6); 2.8453 (0.6); 2.8393 (1.4); 2.8248 (0.5); 2.8050 (0.4); 2.7500 (16.0); 2.3260 (12.1); 1.5618 (8.2); 1.2542 (0.3); 0.0696 (3.9); 0.0076 (0.6); −0.0002 (14.4); −0.0083 (0.6) | 4.48[a] |
| I-022 | 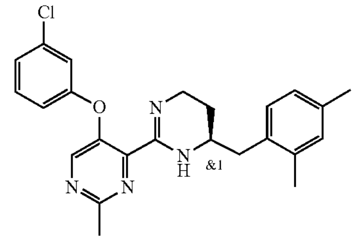 [SMILES: Cc1ccc(C[C@@H]2CCN=C(c3nc(C)ncc3Oc3cccc(Cl)c3)N2)c(C)c1] | I-022: $^1$H-NMR(400.1 MHz, CDCl3): δ = 8.3434 (5.6); 7.4024 (1.1); 7.3822 (2.8); 7.3620 (1.9); 7.2982 (1.7); 7.2762 (1.2); 7.2628 (6.0); 7.1484 (1.4); 7.1432 (2.8); 7.1384 (2.0); 7.1257 (1.6); 7.1054 (1.2); 7.1011 (1.0); 7.0236 (1.8); 7.0035 (3.2); 6.8907 (1.4); 6.8720 (1.1); 5.2985 (9.4); 4.0352 (0.4); 4.0239 (0.9); 4.0123 (0.5); 3.9977 (0.6); 3.9864 (1.1); 3.9749 (0.5); 3.9328 (0.6); 3.9210 (0.7); 3.9087 (0.6); 3.7209 (0.3); 3.7151 (0.5); 3.7040 (0.7); 3.6910 (0.6); 3.6791 (0.8); 3.6669 (0.5); 3.6537 (0.5); 3.6429 (0.4); 3.0879 (0.7); 3.0727 (0.7); 3.0527 (1.1); 3.0378 (1.1); 2.9497 (1.1); 2.9272 (1.1); 2.9148 (0.8); 2.8923 (0.7); 2.7140 (16.0); 2.3051 (12.3); 2.2697 (12.1); 2.2529 (1.2); 2.2407 (0.7); 2.2290 (0.9); 2.2186 (1.0); 2.2073 (0.4); 2.1691 (6.2); 1.9680 (1.7); 1.9177 (0.4); 1.9063 (0.5); 1.8950 (0.7); 1.8836 (0.5); 1.8719 (0.6); 1.8607 (0.4); 1.2528 (0.4); 1.2352 (0.4); 0.0700 (1.9); 0.0078 (0.4); −0.0002 (8.4) | 2.59[a] |
| I-023 | 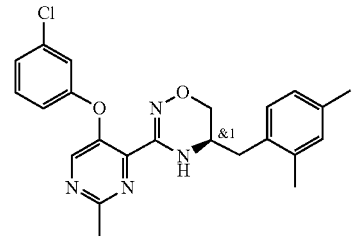 | I-023: $^1$H-NMR(400.1 MHz, CDCl3): δ = 8.4175 (0.8); 7.2596 (5.2); 7.2405 (1.6); 7.2203 (1.0); 7.0809 (1.2); 7.0653 (1.6); 7.0473 (2.0); 7.0356 (2.0); 7.0083 (1.3); 6.9893 (0.7); 6.8796 (1.8); 6.8618 (1.1); 6.8412 (0.9); 6.4155 (0.9); 4.0118 (0.6); 4.0040 (0.6); 3.9846 (0.7); 3.9765 (0.7); 3.8049 (0.6); 3.6879 (0.7); 3.6741 (0.6); 3.6608 (0.6); 3.6471 (0.5); 2.9310 (0.4); 2.9150 (0.5); 2.8970 (0.9); 2.8810 (0.8); 2.8312 (0.8); 2.8111 (0.8); 2.7971 (0.5); 2.7770 (0.5); 2.7323 (6.0); 2.3188 (16.0); 1.5786 (2.3); 0.0697 (1.3); −0.0002 (6.1) | 4.15[a] |
| I-024 | 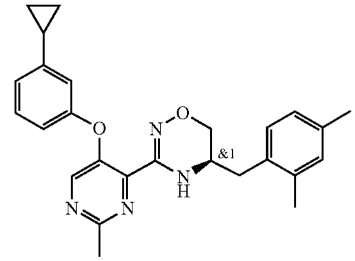 [SMILES: Cc1ccc(C[C@@H]2CON=C(c3nc(C)ncc3Oc3cccc(C4CC4)c3)N2)c(C)c1] | I-024: $^1$H-NMR(400.1 MHz, CDCl3): δ = 8.3315 (5.0); 7.2600 (10.0); 7.2068 (1.1); 7.1867 (2.1); 7.1654 (1.4); 7.0695 (1.9); 7.0503 (3.2); 7.0293 (3.5); 6.9942 (2.3); 6.9752 (1.4); 6.8477 (2.1); 6.8288 (1.9); 6.7105 (5.1); 6.6956 (2.1); 6.4109 (2.0); 5.2981 (2.0); 4.1484 (0.5); 4.1306 (1.5); 4.1126 (1.5); 4.0951 (0.6); 4.0349 (1.2); 4.0266 (1.3); 4.0079 (1.4); 3.9996 (1.5); 3.8163 (1.1); 3.7163 (1.6); 3.7026 (1.3); 3.6892 (1.4); 3.6756 (1.2); 2.9411 (0.8); 2.9250 (0.8); 2.9072 (1.6); 2.8912 (1.5); 2.8372 (1.5); 2.8168 (1.5); 2.8029 (0.9); 2.7827 (0.9); 2.7466 (0.5); 2.7047 (16.0); 2.3219 (15.9); 2.3138 (15.7); 2.0439 (6.3); 2.0046 (0.4); 1.8820 (0.4); 1.8706 (0.7); 1.8617 (0.9); 1.8497 (1.4); 1.8372 (0.9); 1.8289 (0.8); 1.8158 (0.4); 1.5732 (7.2); 1.2766 (1.9); 1.2587 (3.9); 1.2409 (1.9); 0.9711 (0.8); 0.9548 (2.8); 0.9379 (2.8); 0.9227 (1.1); 0.8831 (0.3); 0.6869 (0.9); 0.6745 (3.4); 0.6594 (3.3); 0.6471 (0.9); 0.0697 (3.4); −0.0002 (13.1) | 4.55[a] |
| I-025 | 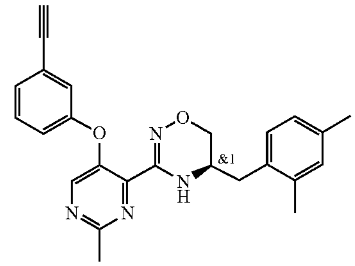 [SMILES: C#Cc1cccc(Oc2cnc(C)nc2C2=NOC[C@@H](Cc3ccc(C)cc3C)N2)c1] | I-025: $^1$H-NMR(400.1 MHz, CDCl3): δ = 8.3969 (2.6); 7.2993 (0.5); 7.2805 (1.4); 7.2601 (6.9); 7.2360 (2.4); 6.9801 (3.4); 6.4017 (1.3); 5.2983 (4.9); 4.0091 (0.7); 4.0016 (0.8); 3.9820 (0.9); 3.9752 (0.9); 3.8042 (0.7); 3.6825 (0.9); 3.6687 (0.8); 3.6558 (0.8); 3.6418 (0.6); 3.0562 (2.7); 2.9303 (0.4); 2.9138 (0.5); 2.8961 (0.9); 2.8799 (0.9); 2.8292 (0.9); 2.8093 (0.9); 2.7955 (0.5); 2.7751 (0.4); 2.7265 (8.3); 2.3181 (16.0); 1.5555 (5.8); 1.2604 (0.7); 0.8825 (0.4); 0.0695 (1.2); −0.0002 (8.4) | 3.85[a] |

TABLE 1-continued
| Compounds according to formula (I) | | | |
|---|---|---|---|
| Ex No | Structure | $^1$H-NMR Peak List | LogP |
| I-026 | 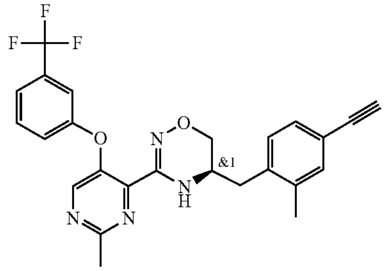 [SMILES: C#Cc1ccc(C[C@@H]2CON=C(c3nc(C)ncc3Oc3cccc(C(F)(F)F)c3)N2)c(C)c1] | I-026: $^1$H-NMR(400.1 MHz, CDCl3): δ = 8.4392 (5.2); 7.4671 (0.6); 7.4461 (1.4); 7.4251 (1.0); 7.3616 (3.3); 7.3464 (1.2); 7.3315 (1.3); 7.3119 (1.5); 7.2600 (15.1); 7.1319 (4.6); 7.1129 (2.1); 6.4275 (1.3); 5.2987 (10.8); 3.9488 (0.9); 3.9405 (1.1); 3.9216 (1.2); 3.9134 (1.4); 3.8416 (0.6); 3.8334 (0.7); 3.8251 (0.8); 3.8172 (0.6); 3.8055 (0.4); 3.7214 (1.4); 3.7094 (1.1); 3.6942 (1.1); 3.6823 (0.9); 3.0645 (5.3); 2.9637 (0.5); 2.9472 (0.5); 2.9295 (1.5); 2.9130 (1.4); 2.8993 (1.5); 2.8792 (1.4); 2.8650 (0.5); 2.8458 (0.6); 2.7464 (16.0); 2.3298 (12.2); 2.0442 (1.3); 2.0054 (0.6); 1.5681 (2.0); 1.2768 (0.5); 1.2589 (1.1); 1.2412 (0.4); 0.0694 (2.0); 0.0076 (1.1); −0.0002 (21.2) | 3.99[a] |
| I-027 | 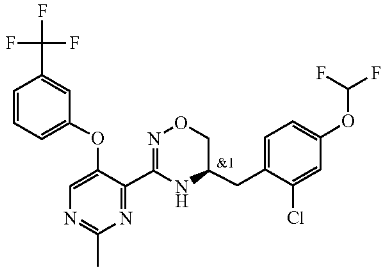 [SMILES: Cc1ncc(Oc2cccc(C(F)(F)F)c2)c(C2=NOC[C@@H](Cc3ccc(OC(F)F)cc3Cl)N2)n1] | I-027: $^1$H-NMR(400.1 MHz, CDCl3): δ = 8.4451 (5.1); 7.4715 (1.0); 7.4516 (2.1); 7.4309 (1.5); 7.3708 (2.6); 7.3518 (1.8); 7.2612 (14.0); 7.2377 (5.5); 7.2183 (3.5); 7.1364 (5.0); 7.0940 (0.4); 7.0733 (0.4); 7.0430 (2.0); 7.0222 (1.7); 6.6961 (1.3); 6.5134 (2.8); 6.4740 (2.3); 6.3310 (1.4); 5.3002 (1.2); 3.9568 (1.5); 3.9487 (1.6); 3.9414 (1.3); 3.8936 (1.4); 3.8862 (1.3); 3.8657 (2.2); 3.8584 (2.0); 3.7947 (1.8); 3.7852 (1.9); 3.7676 (1.2); 3.7573 (1.1); 3.0868 (0.5); 3.0695 (0.7); 3.0533 (2.2); 3.0355 (3.8); 3.0159 (2.2); 2.9820 (0.7); 2.8449 (0.8); 2.7519 (16.0); 1.5671 (9.0); 1.2553 (0.8); 0.0695 (2.0); −0.0002 (18.3) | 4.15[a] |
| I-028 | 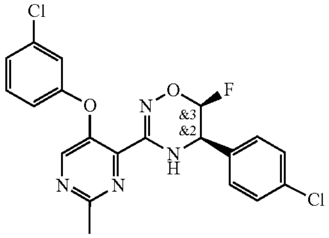 [SMILES: Cc1ncc(Oc2cccc(Cl)c2)c(C2=NO[C@@H](F)[C@@H](c3ccc(Cl)cc3)N2)n1] | I-028: $^1$H-NMR(400.1 MHz, CDCl3): δ = 8.4847 (5.1); 7.4584 (1.0); 7.4517 (0.7); 7.4362 (8.1); 7.4295 (6.2); 7.4068 (1.1); 7.3093 (0.4); 7.2979 (1.3); 7.2776 (2.8); 7.2596 (14.2); 7.1237 (1.3); 7.1212 (1.4); 7.1010 (1.2); 6.9604 (1.4); 6.9549 (2.6); 6.9498 (1.8); 6.9197 (1.4); 6.9139 (1.1); 6.8990 (1.2); 6.8943 (1.0); 6.6907 (1.5); 5.9713 (1.4); 5.8407 (1.4); 5.2984 (5.4); 4.6366 (1.2); 4.6329 (1.3); 4.5890 (1.2); 4.5852 (1.2); 4.1304 (0.4); 4.1125 (0.4); 2.8034 (0.3); 2.7540 (16.0); 2.0437 (1.6); 1.5449 (12.9); 1.2766 (0.7); 1.2586 (1.4); 1.2408 (0.6); 0.0782 (0.4); 0.0693 (6.5); 0.0496 (0.5); −0.0002 (18.4); −0.0506 (0.3) | 3.79[a] |
| I-029 | 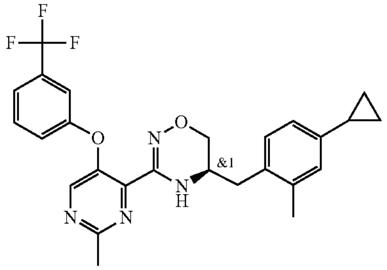 [SMILES: Cc1ncc(Oc2cccc(C(F)(F)F)c2)c(C2=NOC[C@@H](Cc3ccc(C4CC4)cc3C)N2)n1] | I-029: $^1$H-NMR(400.1 MHz, CDCl3): δ = 8.4305 (5.2); 7.4578 (0.6); 7.4373 (1.4); 7.4161 (1.1); 7.3570 (1.8); 7.3377 (1.2); 7.2592 (5.3); 7.1306 (4.2); 7.1148 (1.5); 7.0566 (1.9); 7.0372 (2.5); 6.9268 (2.7); 6.8958 (1.6); 6.8763 (1.3); 6.4262 (1.6); 5.2965 (5.9); 4.1300 (0.5); 4.1121 (0.5); 3.9836 (1.0); 3.9752 (1.1); 3.9564 (1.2); 3.9481 (1.3); 3.7969 (0.8); 3.7901 (0.8); 3.7696 (0.4); 3.6717 (1.4); 3.6581 (1.2); 3.6445 (1.2); 3.6310 (1.0); 2.9146 (0.7); 2.8982 (0.7); 2.8804 (1.4); 2.8640 (1.4); 2.8218 (1.4); 2.8019 (1.4); 2.7876 (0.8); 2.7768 (0.3); 2.7677 (0.7); 2.7448 (16.0); 2.3127 (12.7); 2.0429 (2.1); 2.0024 (1.3); 1.8794 (0.6); 1.8710 (0.7); 1.8584 (1.2); 1.8459 (0.7); 1.8375 (0.7); 1.8247 (0.4); 1.5738 (2.0); 1.2760 (0.8); 1.2581 (1.8); 1.2404 (0.7); 0.9754 (0.6); 0.9652 (2.0); 0.9607 (2.2); 0.9517 (1.2); 0.9443 (2.1); 0.9397 (2.1); 0.9300 (0.9); 0.6956 (0.9); 0.6832 (2.4); 0.6793 (2.0); 0.6716 (2.4); 0.6588 (0.9); 0.0704 (2.5); −0.0002 (5.2) | 4.70[a] |
| I-030 | 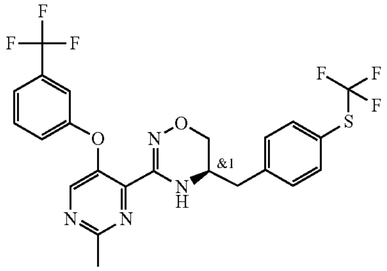 [SMILES: Cc1ncc(Oc2cccc(C(F)(F)F)c2)c(C2=NOC[C@@H](Cc3ccc(SC(F)(F)F)cc3)N2)n1] | I-030: $^1$H-NMR(400.1 MHz, CDCl3): δ = 8.4394 (5.3); 7.6589 (3.0); 7.6387 (3.4); 7.4702 (0.6); 7.4492 (1.2); 7.4362 (0.3); 7.4280 (1.0); 7.3699 (1.5); 7.3508 (1.0); 7.3072 (3.7); 7.2868 (3.3); 7.2597 (11.6); 7.1454 (1.5); 7.1304 (2.7); 6.4490 (1.1); 5.2982 (5.7); 3.9489 (0.9); 3.9408 (1.1); 3.9218 (1.1); 3.9137 (1.4); 3.8684 (0.6); 3.8603 (0.7); 3.8521 (0.7); 3.8437 (0.6); 3.8325 (0.4); 3.7535 (1.3); 3.7422 (1.1); 3.7264 (1.0); 3.7151 (0.8); 2.9848 (0.4); 2.9683 (0.4); 2.9514 (1.5); 2.9340 (2.6); 2.9133 (1.4); 2.8997 (0.4); 2.8800 (0.5); 2.8419 (0.5); 2.7224 (16.0); 1.5447 (7.8); 1.2584 (0.4); 0.0695 (3.4); −0.0002 (18.0); −0.0082 (0.8) | 4.62[a] |

TABLE 1-continued

| Compounds according to formula (I) | | | |
|---|---|---|---|
| Ex No | Structure | $^1$H-NMR Peak List | LogP |
| I-031 | 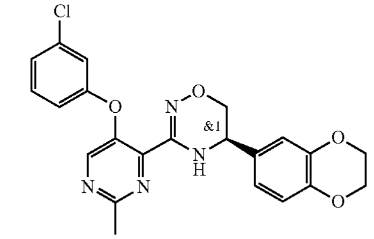 [SMILES: Cc1ncc(Oc2cccc(Cl)c2)c(C2=NOC[C@@H](c3ccc4c(c3)OCCO4)N2)n1] | I-031: $^1$H-NMR(400.1 MHz, CDCl3): δ = 8.4569 (3.2); 7.2798 (1.0); 7.2606 (5.0); 7.2391 (1.4); 7.0949 (1.2); 7.0924 (1.2); 7.0905 (1.1); 7.0768 (0.9); 7.0749 (1.0); 7.0724 (1.0); 7.0705 (0.9); 6.9372 (1.3); 6.9319 (2.2); 6.9268 (1.5); 6.8986 (2.8); 6.8925 (1.3); 6.8906 (1.2); 6.8780 (3.7); 6.8719 (1.3); 6.8452 (2.1); 6.8402 (2.5); 6.8097 (1.6); 6.8047 (1.3); 6.7890 (1.1); 6.7839 (0.9); 6.6034 (1.4); 4.6067 (0.6); 4.5962 (0.8); 4.5922 (0.8); 4.5818 (0.7); 4.2672 (16.0); 4.2172 (1.0); 4.2070 (0.8); 4.1895 (0.9); 4.1873 (0.9); 4.1797 (0.9); 3.5977 (1.0); 3.5795 (1.1); 3.5703 (1.0); 3.5522 (1.0); 2.7431 (11.9); 2.0036 (1.1); 1.2551 (0.5); 0.0705 (0.5); -0.0002 (4.7) | 3.04[a] |
| I-032 | 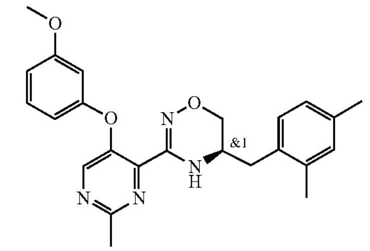 [SMILES: COc1cccc(Oc2cnc(C)nc2C2=NOC[C@@H](Cc3ccc(C)cc3C)N2)c1] | I-032: $^1$H-NMR(400.1 MHz, CDCl3): δ = 8.3822 (2.3); 7.2601 (10.2); 7.2249 (1.2); 7.2043 (2.4); 7.1837 (1.3); 7.0677 (1.6); 7.0484 (2.7); 7.0300 (3.0); 6.9984 (2.0); 6.9798 (1.1); 6.6754 (1.4); 6.6715 (1.4); 6.6547 (1.3); 6.6506 (1.3); 6.5522 (2.8); 6.5094 (1.5); 6.4892 (1.4); 6.4105 (1.6); 5.2980 (1.8); 4.1482 (0.5); 4.1306 (1.5); 4.1127 (1.5); 4.0950 (0.6); 4.0652 (0.5); 4.0281 (1.0); 4.0201 (1.0); 4.0012 (1.1); 3.9931 (1.2); 3.8129 (1.0); 3.7729 (15.2); 3.7098 (1.2); 3.6963 (1.0); 3.6827 (1.1); 3.6689 (0.9); 2.9366 (0.7); 2.9210 (0.7); 2.9028 (1.3); 2.8868 (1.2); 2.8346 (1.3); 2.8146 (1.2); 2.8007 (0.8); 2.7803 (0.7); 2.7101 (11.5); 2.3192 (16.0); 2.0437 (7.8); 2.0044 (0.3); 1.6267 (0.4); 1.5764 (7.0); 1.2765 (1.9); 1.2586 (3.8); 1.2408 (1.8); 0.9539 (0.4); 0.9356 (0.8); 0.9174 (0.4); 0.0695 (2.1); −0.0002 (13.6) | 3.66[a] |
| I-033 | 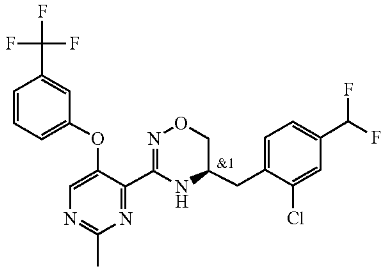 [SMILES: Cc1ncc(Oc2cccc(C(F)(F)F)c2)c(C2=NOC[C@@H](Cc3ccc(C(F)F)cc3Cl)N2)n1] | I-033: $^1$H-NMR(400.1 MHz, CDCl3): δ = 8.4461 (5.2); 7.5799 (1.9); 7.4711 (0.5); 7.4512 (1.1); 7.4422 (0.4); 7.4308 (0.9); 7.3929 (0.7); 7.3718 (2.5); 7.3507 (1.0); 7.3401 (2.2); 7.3204 (1.1); 7.2599 (11.0); 7.1462 (1.4); 7.1387 (1.9); 7.1335 (2.1); 6.7626 (1.0); 6.6222 (2.1); 6.4818 (1.2); 6.4702 (0.9); 6.4625 (1.0); 5.2983 (7.5); 4.0030 (0.5); 3.9944 (0.7); 3.9856 (0.8); 3.9765 (0.6); 3.9677 (0.4); 3.8893 (0.8); 3.8814 (0.7); 3.8617 (1.6); 3.8537 (1.4); 3.8123 (1.3); 3.8024 (1.2); 3.7849 (0.7); 3.7749 (0.6); 3.1161 (1.2); 3.0997 (2.3); 3.0816 (1.2); 3.0668 (0.4); 3.0482 (0.3); 2.7475 (16.0); 1.5478 (7.0); 0.0696 (2.5); 0.0080 (0.5); −0.0002 (17.2); -0.0084 (0.9) | 4.02[a] |
| I-034 | 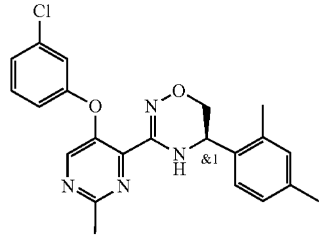 [SMILES: Cc1ccc([C@@H]2CON=C(c3nc(C)ncc3Oc3cccc(Cl)c3)N2)c(C)c1] | I-034: $^1$H-NMR(400.1 MHZ, CDCl3): δ = 9.5693 (1.5); 8.5899 (5.3); 7.2592 (5.4); 7.2033 (1.3); 7.1830 (2.8); 7.1626 (1.8); 7.0758 (1.8); 7.0737 (1.8); 7.0557 (1.3); 6.9268 (2.9); 6.8631 (1.4); 6.8434 (1.8); 6.8183 (2.0); 6.8132 (2.9); 6.8080 (1.9); 6.7345 (2.7); 6.7150 (2.0); 6.6838 (1.5); 6.6785 (1.4); 6.6636 (1.4); 6.6578 (1.3); 5.2971 (1.5); 5.0366 (1.1); 5.0229 (1.2); 5.0043 (1.2); 4.9906 (1.2); 2.8163 (16.0); 2.7454 (1.2); 2.7317 (1.2); 2.7030 (1.4); 2.6894 (1.4); 2.3731 (1.5); 2.3406 (1.6); 2.3307 (1.4); 2.2980 (1.9); 2.2849 (12.8); 2.2189 (13.3); 1.5609 (2.9); 1.2557 (0.4); 0.0700 (1.6); −0.0002 (7.6) | 3.80[a] |
| I-035 | 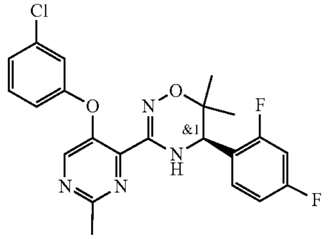 [SMILES: Cc1ncc(Oc2cccc(Cl)c2)c(C2=NOC(C)(C)[C@@H](c3ccc(F)cc3F)N2)n1] | I-035: $^1$H-NMR(400.1 MHz, CDCl3): δ = 8.4956 (5.2); 7.5391 (0.4); 7.5223 (0.4); 7.2795 (1.0); 7.2601 (13.1); 7.2395 (1.6); 7.2273 (0.7); 7.2058 (1.3); 7.1895 (1.3); 7.1682 (0.7); 7.0932 (1.6); 7.0911 (1.6); 7.0723 (1.4); 6.9154 (0.4); 6.9040 (1.4); 6.9001 (2.0); 6.8806 (4.8); 6.8781 (4.8); 6.8560 (1.4); 6.8341 (0.8); 6.8285 (1.0); 6.8223 (0.8); 6.8027 (1.4); 6.7807 (1.1); 6.7749 (1.0); 6.7559 (0.4); 6.7497 (0.3); 6.7053 (1.3); 6.6979 (1.3); 4.8804 (0.6); 4.8708 (0.6); 4.7657 (2.3); 4.7565 (2.3); 2.7620 (0.7); 2.7467 (16.0); 2.6199 (0.6); 2.6098 (0.6); 2.0049 (1.0); 1.9606 (1.2); 1.5531 (6.3); 1.4010 (0.7); 1.2960 (12.6); 1.2544 (0.7); 1.0992 (3.8); 0.9838 (10.6); 0.0695 (3.6); −0.0002 (15.8) | 3.84[a] |

The following compounds of formula (I) may be prepared according to the processes disclosed herein:

3-[6-(3-chloro-2-fluorophenoxy)-3-methyl-1,2,4-triazin-5-yl]-5-(2-chloro-4-methylbenzyl)-5,6-dihydro-4H-1,2,4-oxadiazine 3-[6-(3-chloro-2-fluorophenoxy)-3-methyl-1,2,4-triazin-5-yl]-5-(2,4-dimethylbenzyl)-5,6-dihydro-4H-1,2,4-oxadiazine 3-[6-(3-cyclopropyl-2-fluorophenoxy)-3-methyl-1,2,4-triazin-5-yl]-5-(2,4-dimethylbenzyl)-5,6-dihydro-4H-1,2,4-oxadiazine 5-(2-chloro-4-methylbenzyl)-3-[6-(3-cyclopropyl-2-fluorophenoxy)-3-methyl-1,2,4-triazin-5-yl]-5,6-dihydro-4H-1,2,4-oxadiazine 5-(2-chloro-4-methylbenzyl)-3-{3-methyl-6-[3-(trifluoromethyl)phenoxy]-1,2,4-triazin-5-yl}-5,6-dihydro-4H-1,2,4-oxadiazine 5-(2,4-dimethylbenzyl)-3-{3-methyl-6-[3-(trifluoromethyl)phenoxy]-1,2,4-triazin-5-yl}-5,6-dihydro-4H-1,2,4-oxadiazine 5-(4-bromo-2-methylbenzyl)-3-{3-methyl-6-[3-(trifluoromethyl)phenoxy]-1,2,4-triazin-5-yl}-5,6-dihydro-4H-1,2,4-oxadiazine 5-(4-bromo-2-methylbenzyl)-3-[6-(3-cyclopropyl-2-fluorophenoxy)-3-methyl-1,2,4-triazin-5-yl]-5,6-dihydro-4H-1,2,4-oxadiazine 5-(4-bromo-2-methylbenzyl)-3-[6-(3-chloro-2-fluorophenoxy)-3-methyl-1,2,4-triazin-5-yl]-5,6-dihydro-4H-1,2,4-oxadiazine 3-[6-(3-chloro-2-fluorophenoxy)-3-methyl-1,2,4-triazin-5-yl]-5-(3,4-dimethylbenzyl)-5,6-dihydro-4H-1,2,4-oxadiazine 3-[6-(3-cyclopropyl-2-fluorophenoxy)-3-methyl-1,2,4-triazin-5-yl]-5-(3,4-dimethylbenzyl)-5,6-dihydro-4H-1,2,4-oxadiazine 5-(3,4-dimethylbenzyl)-3-{3-methyl-6-[3-(trifluoromethyl)phenoxy]-1,2,4-triazin-5-yl}-5,6-dihydro-4H-1,2,4-oxadiazine.

Compounds of Formula (1)

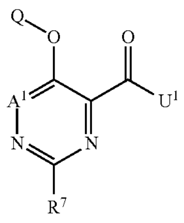

(1)

TABLE 2

| Compounds according to formula (1), their $^1$H-NMR data and LogP values | | | |
|---|---|---|---|
| Ex No | Structure | $^1$H-NMR Peak List | LogP |
| 1-01 | 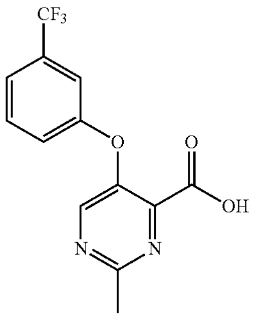 [SMILES: Cc1ncc(Oc2cccc(C(F)(F)F)c2)c(C(=O)O)n1] | 1-01: $^1$H-NMR(300.2 MHz, CDCl3): δ = 8.6429 (5.5); 7.5904 (0.6); 7.5646 (1.8); 7.5384 (1.6); 7.5149 (2.1); 7.4891 (0.9); 7.3041 (48.7); 7.2543 (1.3); 7.2302 (1.1); 5.3438 (0.6); 2.8770 (16.0); 1.8227 (0.5); 1.7542 (0.6); 1.7206 (0.6); 1.6818 (0.6); 1.6615 (0.6); 1.4810 (0.4); 1.2972 (1.1); 0.0530 (1.4); 0.0423 (41.8); 0.0313 (1.4) | 1.69[a] |
| 1-02 | 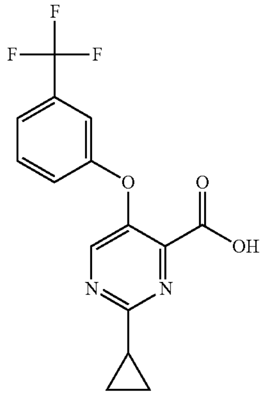 [SMILES: O=C(O)c1nc(C2CC2)ncc1Oc1cccc(C(F)(F)F)c1] | 1-02: $^1$H-NMR(500.1 MHz, $d_6$-DMSO): δ = 8.7173 (16.0); 7.6068 (2.4); 7.5908 (5.5); 7.5746 (3.6); 7.4986 (5.0); 7.4831 (3.7); 7.3759 (6.5); 7.2830 (3.6); 7.2786 (3.4); 7.2665 (3.3); 7.2621 (3.0); 5.7533 (10.0); 3.3171 (4.3); 2.5006 (40.2); 2.3175 (0.8); 2.3082 (1.8); 2.3008 (2.2); 2.2920 (3.6); 2.2830 (2.2); 2.2760 (1.9); 2.2664 (0.9); 1.2356 (1.3); 1.1240 (1.6); 1.1157 (4.3); 1.1097 (6.7); 1.1028 (4.3); 1.0997 (4.3); 1.0938 (6.0); 1.0876 (2.6); 1.0735 (0.7); 1.0587 (0.6); 1.0430 (2.7); 1.0364 (6.6); 1.0278 (7.7); 1.0222 (5.5); 1.0135 (1.7); −0.0002 (26.6) | 2.49[a] |
| 1-03 | 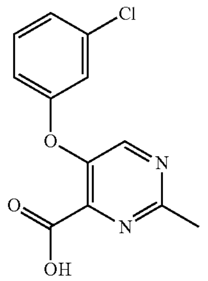 [SMILES: Cc1ncc(Oc2cccc(Cl)c2)c(C(=O)O)n1] | 1-03: $^1$H-NMR(400.2 MHz, $d_6$-DMSO): δ = 14.2640 (0.5); 14.0604 (1.1); 8.7553 (3.8); 7.4006 (12.1); 7.2186 (16.0); 7.2009 (15.0); 7.1446 (11.9); 6.9896 (9.1); 6.8525 (0.5); 6.8009 (0.4); 4.0581 (0.6); 4.0401 (1.5); 4.0224 (1.4); 4.0053 (0.6); 3.5546 (0.4); 3.5099 (0.4); 3.4704 (0.4); 3.4393 (0.4); 3.4185 (0.4); 3.3805 (0.4); 3.3407 (0.4); 3.3267 (0.4); 3.2691 (0.4); 3.2579 (0.4); 3.2405 (0.4); 3.2114 (0.4); 3.1952 (0.4); 3.1334 (0.4); 3.1179 (0.4); 3.1057 (0.4); 3.0752 (0.4); 3.0061 (0.9); 2.6805 (12.8); 2.5514 (79.7); 2.5126 (22.9); 2.3772 (1.0); 2.3437 (0.6); 2.2288 (0.3); 1.9935 (7.0); 1.9164 (0.7); 1.2324 (0.4); 1.1943 (1.7); 1.1767 (3.1); 1.1590 (1.6); 0.0003 (10.4) | 2.00[a] |

TABLE 2-continued
Compounds according to formula (1), their $^1H$-NMR data and LogP values
| Ex No | Structure | $^1H$-NMR Peak List | LogP |
|---|---|---|---|
| 1-04 | 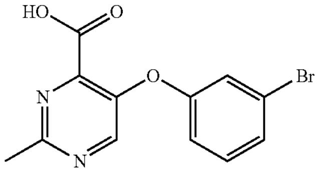 [SMILES: Cc1ncc(Oc2cccc(Br)c2)c(C(=O)O)n1] | 1-04: $^1H$-NMR(400.2 MHz, $d_6$-DMSO): δ = 8.5628 (5.6); 7.3290 (1.1); 7.3086 (9.9); 7.3044 (6.4); 7.2957 (12.0); 7.2767 (0.8); 7.1761 (6.6); 7.0085 (0.7); 6.9977 (2.4); 6.9917 (2.6); 6.9863 (3.7); 6.9779 (2.6); 6.9753 (2.4); 6.9688 (2.0); 3.5251 (0.4); 3.5052 (0.5); 3.3435 (1.5); 3.1515 (0.4); 2.7775 (0.4); 2.6717 (2.3); 2.6673 (2.0); 2.6196 (16.0); 2.5071 (175.0); 2.5028 (218.8); 2.4986 (157.8); 2.3337 (1.1); 2.3297 (1.4); 0.0000 (8.0) | 2.15[a] |
| 1-05 | 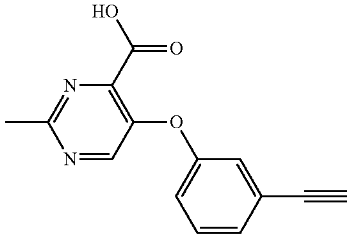 [SMILES: C#Cc1cccc(Oc2cnc(C)nc2C(=O)O)c1] | 1-05: $^1H$-NMR(300.1 MHz, $d_6$-DMSO): δ = 8.7047 (6.2); 7.4169 (0.9); 7.4078 (0.4); 7.3915 (1.5); 7.3873 (1.3); 7.3817 (0.6); 7.3716 (0.5); 7.3615 (1.6); 7.2660 (2.1); 7.2405 (1.4); 7.0836 (4.0); 7.0716 (1.6); 7.0624 (1.4); 7.0596 (1.4); 7.0540 (0.7); 4.2707 (6.1); 3.3512 (0.6); 2.6734 (16.0); 2.5097 (4.3); 2.5038 (5.6); 2.4980 (3.9); 0.2351 (0.4); 0.1991 (0.8); −0.0004 (1.5); −0.1305 (0.8) | 1.77[a] |
| 1-06 | 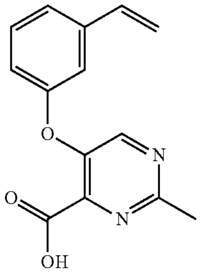 [SMILES: C=Cc1cccc(Oc2cnc(C)nc2C(=O)O)c1] | 1-06: $^1H$-NMR(300.1 MHz, $d_6$-DMSO): δ = 8.7319 (3.0); 8.6371 (6.0); 7.3811 (0.9); 7.3551 (2.6); 7.3466 (2.0); 7.3435 (2.1); 7.3370 (1.1); 7.3287 (2.5); 7.2988 (0.4); 7.2864 (2.0); 7.2589 (1.9); 7.2553 (1.6); 7.2486 (0.9); 7.1603 (1.6); 7.1535 (2.1); 7.0388 (0.5); 7.0297 (0.8); 7.0185 (0.7); 7.0082 (0.5); 6.9999 (0.4); 6.9221 (1.1); 6.9169 (1.1); 6.8956 (1.0); 6.8901 (1.0); 6.7652 (1.0); 6.7288 (1.1); 6.7063 (1.2); 6.6699 (1.2); 5.8898 (2.0); 5.8323 (1.7); 5.3169 (2.0); 5.2797 (1.9); 3.3461 (1.1); 2.6771 (8.3); 2.6644 (16.0); 2.5095 (5.8); 2.5037 (7.7); 2.4979 (5.6); 1.9896 (0.4); −0.0003 (1.5) | 1.87[a] |
| 1-07 | 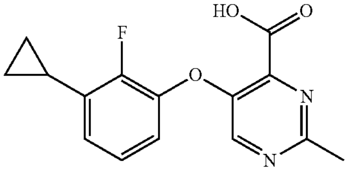 [SMILES: Cc1ncc(Oc2cccc(C3CC3)c2F)c(C(=O)O)n1] | 1-07: $^1H$-NMR(300.1 MHz, $d_6$-DMSO): δ = 8.5949 (5.4); 7.0746 (0.6); 7.0513 (1.5); 7.0479 (1.6); 7.0248 (1.0); 7.0211 (1.1); 6.8868 (0.8); 6.8818 (1.0); 6.8599 (1.4); 6.8553 (1.6); 6.8332 (0.7); 6.8281 (0.8); 6.8229 (1.0); 6.8179 (0.8); 6.7962 (1.4); 6.7739 (0.8); 3.3294 (1.9); 2.6544 (16.0); 2.5138 (3.7); 2.5081 (7.8); 2.5022 (10.6); 2.4964 (7.7); 2.1023 (0.5); 2.0908 (0.6); 2.0745 (1.0); 2.0572 (0.6); 2.0463 (0.6); 1.9891 (0.7); 1.1744 (0.4); 1.0423 (0.7); 1.0276 (2.0); 1.0201 (2.2); 1.0067 (1.2); 0.9993 (2.0); 0.9919 (2.1); 0.9787 (0.9); 0.7847 (0.9); 0.7711 (2.2); 0.7643 (2.4); 0.7542 (2.2); 0.7473 (2.4); 0.7322 (0.8); −0.0005 (2.1) | 2.20[a] |
| 1-08 | 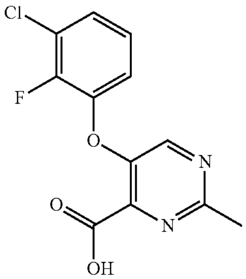 [SMILES: Cc1ncc(Oc2cccc(Cl)c2F)c(C(=O)O)n1] | 1-08: $^1H$-NMR(300.1 MHz, $d_6$-DMSO): δ = 14.3903 (0.6); 14.3754 (0.6); 14.3570 (0.6); 14.2915 (0.7); 14.2611 (0.6); 14.2262 (0.7); 14.1136 (0.8); 14.0584 (0.8); 14.0448 (0.7); 14.0278 (0.8); 13.9874 (0.7); 13.9793 (0.7); 13.9631 (0.7); 13.9391 (0.6); 13.9085 (0.7); 13.8304 (0.6); 13.8039 (0.6); 13.7190 (0.6); 13.6818 (0.6); 13.6109 (0.5); 12.2188 (2.7); 10.4179 (0.7); 10.3529 (5.6); 9.2084 (0.6); 9.1381 (2.0); 9.0430 (0.6); 8.9501 (1.2); 8.8078 (3.4); 8.7775 (3.2); 8.7364 (2.5); 8.6655 (1.5); 8.6130 (1.1); 8.5996 (1.0); 8.5157 (0.6); 8.4798 (0.6); 8.2939 (0.6); 7.8826 (2.3); 7.8604 (2.4); 7.8245 (0.7); 7.6469 (0.5); 7.4451 (2.5); 7.3724 (16.0); 7.3023 (1.8); 7.1866 (13.1); 7.0688 (6.9); 7.0347 (7.4); 7.0092 (8.6); 6.9828 (10.4); 6.9574 (12.1); 6.9430 (15.3); 6.9306 (11.2); 6.9197 (11.0); 6.8393 (1.0); 6.8087 (0.7); 6.7649 (0.8); 4.0682 (0.6); 4.0424 (1.6); 4.0173 (1.8); 3.9946 (5.4); 3.9768 (5.6); 3.9200 (0.7); 3.8879 (0.7); 3.8615 (0.8); 3.8425 (0.6); 3.6561 (1.1); 3.5695 (5.0); 3.5187 (1.4); 3.4690 (1.3); 3.4449 (1.5); 3.4271 (1.4); 3.3755 (1.4); 3.3126 (1.2); 3.2266 (1.0); 3.1840 (0.9); 3.1686 (0.8); 3.1389 (0.8); 3.0900 (0.6); 3.0560 (0.7); 3.0202 (0.6); 2.9951 (0.6); 2.9616 (0.8); 2.6906 (9.5); 2.5070 (191.5); 2.3890 (4.6); 2.2791 (3.4); 2.1831 (1.9); 2.0976 (1.4); 2.0236 (1.2); 1.9906 (8.7); 1.9118 (1.2); 1.8578 (0.9); 1.8281 (0.9); 1.8003 (0.8); 1.7742 (0.9); 1.6946 (0.7); 1.6278 (0.6); 1.5835 (0.7); 1.5496 (0.6); 1.5343 (0.6); 1.4365 (0.6); 1.4011 (0.6); 1.3809 (0.6); 1.3530 (0.6); 1.2353 (0.8); 1.1985 (1.7); 1.1754 (3.3); 1.1508 (1.8); 1.1207 (0.6); 0.9980 (0.5); 0.7819 (0.5); -0.0004 (15.0) | 1.91[a] |

Compounds of Formula (2)
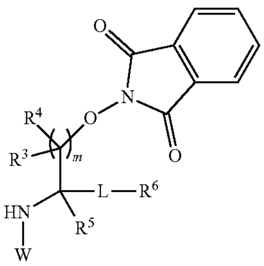
(2)
TABLE 3
| Compounds according to formula (2), their $^1$H-NMR data and LogP values | | | |
|---|---|---|---|
| Ex No | Structure | $^1$H-NMR Peak List | LogP |
| 2-01 | 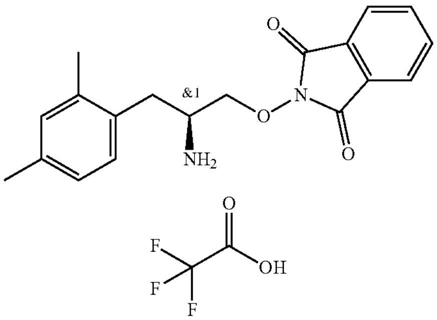 | 2-01: $^1$H-NMR(300.1 MHz, $d_6$-DMSO): δ = 8.4567 (2.3); 7.8866 (16.0); 7.1956 (1.5); 7.1703 (1.8); 6.9824 (2.5); 6.9715 (1.6); 6.9447 (1.0); 4.3276 (0.5); 4.3060 (0.6); 4.2909 (1.0); 4.2697 (1.0); 4.2311 (1.0); 4.2196 (1.1); 4.1945 (0.6); 4.1830 (0.5); 3.7230 (0.6); 3.7140 (0.6); 3.0236 (0.4); 2.9970 (1.1); 2.9786 (1.7); 2.9487 (0.9); 2.9341 (0.3); 2.5156 (1.9); 2.5101 (2.4); 2.5047 (1.8); 2.3112 (0.3); 2.2747 (8.8); 2.2526 (0.6); 2.2218 (8.4) | 1.55[a] |
Compounds of Formula (3)
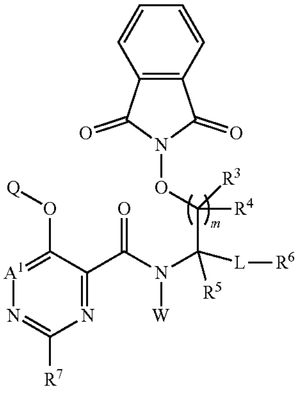
(3)

TABLE 4
Compounds according to formula (2), their $^1$H-NMR data and LogP values
| Ex No | Structure | $^1$H-NMR Peak List | LogP |
|---|---|---|---|
| 3-01 | 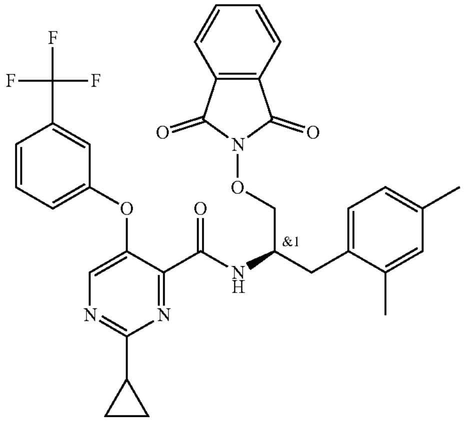 [SMILES: Cc1ccc(C[C@H](CON2C(=O)c3ccccc3C2=O)NC(=O)c2nc(C3CC3)ncc2Oc2cccc(C(F)(F)F)c2)c(C)c1] | 3-01: $^1$H-NMR(500.1 MHz, CDCl3): δ = 8.5619 (1.3); 8.5457 (1.3); 8.4307 (7.6); 7.8398 (3.0); 7.8336 (3.3); 7.8289 (3.4); 7.8228 (4.7); 7.8145 (0.6); 7.7712 (0.6); 7.7629 (4.6); 7.7567 (3.5); 7.7520 (3.4); 7.7458 (3.2); 7.7386 (0.4); 7.4408 (1.0); 7.4249 (2.3); 7.4088 (1.5); 7.3490 (2.1); 7.3335 (1.5); 7.2591 (16.8); 7.2396 (2.6); 7.2041 (2.7); 7.1166 (1.5); 7.1122 (1.4); 7.1002 (1.3); 7.0958 (1.2); 6.9854 (5.8); 6.9696 (1.6); 5.2977 (1.3); 4.4436 (0.4); 4.4354 (0.6); 4.4282 (1.0); 4.4207 (0.9); 4.4123 (0.9); 4.4059 (2.8); 4.3995 (1.1); 4.3868 (2.1); 4.3801 (1.4); 4.1425 (1.4); 4.1359 (1.7); 4.1235 (1.6); 4.1167 (1.2); 3.1330 (4.1); 3.1181 (4.1); 2.5649 (1.5); 2.4959 (1.4); 2.4345 (0.4); 2.4250 (0.8); 2.4184 (0.9); 2.4091 (1.7); 2.3994 (1.1); 2.3853 (16.0); 2.3348 (0.6); 2.2836 (15.1); 2.2009 (0.6); 1.5472 (13.8); 1.3019 (0.6); 1.2944 (1.0); 1.2863 (1.2); 1.2774 (1.7); 1.2684 (1.2); 1.2563 (0.6); 1.2487 (0.4); 1.2267 (0.6); 1.2175 (1.2); 1.2079 (0.9); 1.2009 (0.8); 1.1981 (0.7); 1.1927 (1.1); 1.1785 (3.3); 1.1729 (1.6); 1.1705 (1.6); 1.1623 (2.7); 1.1540 (1.7); 0.0697 (7.7); 0.0626 (0.4); 0.0060 (0.9); −0.0002 (22.7); −0.0065 (1.1) | 5.40[a] |
| 3-02 | 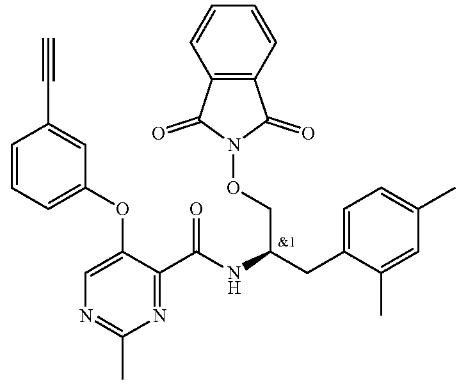 [SMILES: C#Cc1cccc(Oc2cnc(C)nc2C(=O)N[C@@H](CON2C(=O)c3ccccc3C2=O)Cc2ccc(C)cc2C)c1] | 3-02: $^1$H-NMR(400.1 MHz, CDCl3): δ = 8.6256 (1.7); 8.6060 (1.7); 8.4559 (5.1); 8.0181 (1.1); 7.8343 (4.1); 7.8243 (4.3); 7.7651 (4.6); 7.7569 (4.2); 7.3133 (1.0); 7.2932 (2.7); 7.2607 (18.0); 7.2455 (3.7); 7.0786 (3.5); 7.0339 (2.1); 7.0145 (2.0); 6.9868 (6.3); 6.9645 (2.3); 4.4601 (1.2); 4.4523 (1.3); 4.4315 (2.7); 4.4067 (2.1); 4.1617 (1.7); 4.1547 (1.8); 4.1382 (1.7); 3.7141 (0.4); 3.1567 (4.8); 3.1387 (4.0); 3.0482 (5.0); 2.9562 (5.3); 2.9340 (0.6); 2.8835 (6.2); 2.8176 (16.0); 2.8032 (6.7); 2.4068 (15.0); 2.3684 (0.4); 2.3418 (0.4); 2.3257 (0.5); 2.2842 (15.2); 2.2118 (0.5); 1.5789 (8.4); 1.5200 (1.3); 1.4925 (3.1); 1.4763 (2.9); 1.4478 (2.8); 1.4308 (2.7); 1.2576 (1.2); 0.2067 (0.5); 0.0699 (7.0); −0.0002 (15.1); −0.0875 (0.5) | 4.41[a] |
| 3-03 | 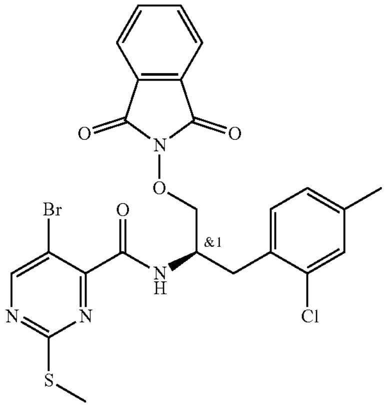 [SMILES: CSc1ncc(Br)c(C(=O)N[C@@H](CON2C(=O)c3ccccc3C2=O)Cc2ccc(C)cc2Cl)n1] | 3-03: $^1$H-NMR(400.1 MHz, CDCl3): δ = 8.7200 (5.6); 8.3767 (0.9); 8.3568 (0.9); 7.8451 (2.2); 7.8373 (2.5); 7.8314 (2.5); 7.8237 (3.6); 7.8136 (0.6); 7.7735 (0.5); 7.7635 (3.5); 7.7559 (2.5); 7.7499 (2.6); 7.7421 (2.3); 7.3768 (2.0); 7.3574 (2.3); 7.2601 (16.1); 7.1837 (2.5); 7.0555 (1.3); 7.0359 (1.2); 4.6562 (0.4); 4.6467 (0.8); 4.6366 (0.7); 4.6266 (0.8); 4.6171 (0.5); 4.4620 (1.0); 4.4519 (1.0); 4.4365 (1.4); 4.4263 (1.3); 4.2830 (1.3); 4.2728 (1.3); 4.2574 (1.1); 4.2472 (1.0); 3.3855 (0.6); 3.3661 (0.4); 3.3510 (1.4); 3.3308 (1.9); 3.3091 (1.4); 3.2929 (0.5); 3.2747 (0.4); 2.8032 (4.8); 2.6423 (0.3); 2.6217 (16.0); 2.3013 (11.0); 2.2365 (0.6); 1.5505 (7.4); 1.2558 (0.6); 0.0694 (3.5); −0.0002 (21.0) | 4.62[a] |

Compounds of Formula (4)
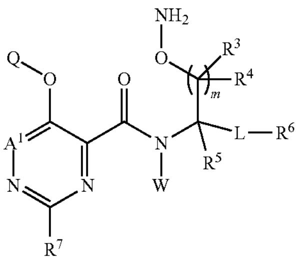
(4)
TABLE 4
| Compounds according to formula (4), their $^1$H-NMR data and LogP values | | | |
|---|---|---|---|
| Ex No | Structure | $^1$H-NMR Peak List | LogP |
| 4-01 | 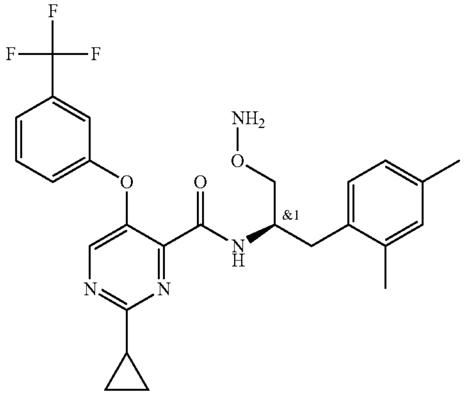 [SMILES: Cc1ccc(C[C@H](CON)NC(=O)c2nc(C3CC3)ncc2Oc2cccc(C(F)(F)F)c2)c(C)c1] | 4-01: $^1$H-NMR(500.1 MHz, CDCl3): δ = 8.4385 (6.9); 8.2182 (1.0); 8.2008 (1.0); 7.4464 (0.9); 7.4305 (2.2); 7.4144 (1.4); 7.3554 (2.0); 7.3399 (1.4); 7.2591 (15.2); 7.1665 (2.5); 7.1090 (1.4); 7.1044 (1.3); 7.0925 (1.2); 7.0880 (1.2); 7.0644 (2.4); 7.0489 (2.9); 6.9639 (3.0); 6.9246 (1.7); 6.9091 (1.4); 5.5142 (1.8); 5.2978 (6.8); 4.4775 (0.5); 4.4707 (0.5); 4.4656 (0.6); 4.4592 (0.8); 4.4530 (0.6); 4.4480 (0.6); 4.4411 (0.5); 3.7424 (1.2); 3.7354 (1.3); 3.7202 (1.9); 3.7132 (1.8); 3.6375 (1.8); 3.6255 (1.8); 3.6153 (1.2); 3.6033 (1.2); 2.8845 (4.2); 2.8700 (4.5); 2.8082 (0.7); 2.6180 (0.5); 2.3584 (0.4); 2.3439 (0.8); 2.3322 (1.9); 2.3248 (16.0); 2.3070 (0.5); 2.2923 (0.6); 2.2811 (0.6); 2.2698 (15.0); 1.5704 (1.0); 1.2544 (1.1); 1.1649 (0.5); 1.1524 (3.6); 1.1460 (2.6); 1.1370 (7.1); 1.1322 (2.4); 1.1269 (1.7); 1.1209 (1.2); 1.1136 (0.4); 0.0697 (11.0); 0.0062 (0.6); −0.0002 (20.7); −0.0064 (1.0) | 3.70[a] |
| 4-02 | 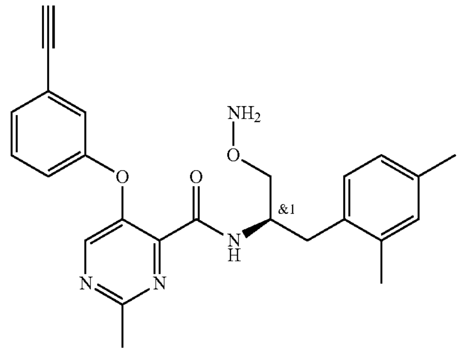 [SMILES: C#Cc1cccc(Oc2cnc(C)nc2C(=O)N[C@@H](CON)Cc2ccc(C)cc2C)c1] | 4-02: $^1$H-NMR(400.1 MHz, CDCl3): δ = 8.4616 (5.1); 8.1493 (1.5); 8.1269 (1.5); 7.8719 (0.4); 7.7502 (0.6); 7.3179 (1.0); 7.2982 (2.8); 7.2781 (2.7); 7.2604 (25.1); 7.0714 (2.5); 7.0525 (3.2); 7.0275 (3.7); 7.0133 (2.4); 6.9936 (2.0); 6.9637 (4.5); 6.9206 (2.7); 6.9030 (2.1); 5.5263 (4.6); 5.2989 (3.5); 4.5142 (1.3); 4.1450 (0.6); 3.7584 (1.3); 3.7514 (1.3); 3.7306 (2.1); 3.7243 (2.0); 3.6562 (1.9); 3.6396 (1.9); 3.6288 (1.4); 3.6134 (1.1); 3.0745 (4.9); 2.9561 (0.5); 2.9365 (0.4); 2.8970 (3.6); 2.8851 (3.3); 2.8410 (0.4); 2.8157 (1.2); 2.8034 (3.4); 2.7680 (16.0); 2.5652 (0.7); 2.4969 (0.7); 2.4492 (1.0); 2.3405 (15.7); 2.2691 (16.0); 2.2024 (0.5); 1.5568 (18.8); 1.3102 (0.6); 1.2546 (1.8); 0.8800 (0.4); 0.2172 (0.4); 0.0695 (7.8); −0.0002 (26.9); −0.0780 (0.6) | 2.53[a] |
| 4-03 | 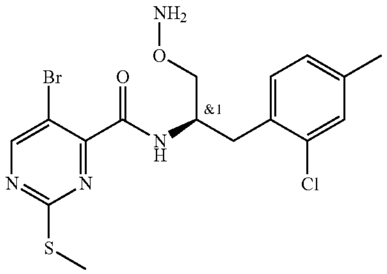 [SMILES: CSc1ncc(Br)c(C(=O)N[C@@H](CON)Cc2ccc(C)cc2Cl)n1] | 4-03: $^1$H-NMR(400.1 MHz, CDCl3): δ = 8.7373 (5.3); 8.0315 (0.6); 8.0100 (0.6); 7.2599 (11.6); 7.2090 (1.9); 7.1896 (2.3); 7.1697 (2.3); 7.0076 (1.3); 6.9883 (1.0); 5.2979 (1.2); 4.6728 (0.4); 4.6635 (0.4); 4.6570 (0.5); 4.6481 (0.6); 4.6413 (0.5); 4.6346 (0.5); 4.6254 (0.4); 3.8497 (0.9); 3.8404 (1.0); 3.8218 (1.5); 3.8126 (1.4); 3.7242 (1.4); 3.7084 (1.3); 3.6963 (0.9); 3.6806 (0.9); 3.0707 (3.4); 3.0525 (3.4); 2.8026 (1.4); 2.5571 (16.0); 2.2870 (10.4); 1.2553 (0.5); 0.0693 (2.3); −0.0002 (15.1); −0.0083 (0.9) | 2.58[a] |

Compounds of Formula (6a)
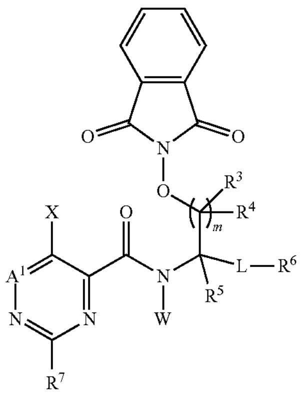
(6a)
TABLE 5
| Compounds according to formula (6a), their $^1$H-NMR data and LogP values | | | |
|---|---|---|---|
| Ex No | Structure | $^1$H-NMR Peak List | LogP |
| 6a-01 | 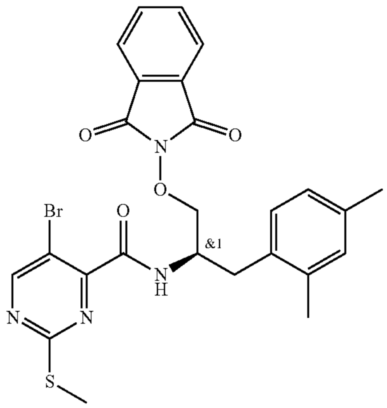 [SMILES: CSc1ncc(Br)c(C(=O)N[C@@H](CON2C(=O)c3ccccc3C2=O)Cc2ccc(C)cc2C)n1] | 6a-01: $^1$H-NMR(400.1 MHz, $d_6$-DMSO): δ = 8.9720 (1.3); 8.9509 (1.3); 8.8942 (4.4); 7.8660 (16.0); 7.1714 (1.6); 7.1523 (1.9); 6.9638 (2.5); 6.9176 (1.4); 6.9005 (1.3); 4.4427 (0.7); 4.4288 (0.8); 4.3345 (0.7); 4.3207 (0.6); 4.3103 (1.2); 4.2972 (1.0); 4.2545 (1.1); 4.2403 (1.1); 4.2301 (0.8); 4.2156 (0.6); 3.3269 (68.9); 3.2946 (0.8); 3.1224 (0.6); 3.1089 (0.7); 3.0872 (0.9); 3.0728 (0.9); 2.9211 (0.8); 2.8930 (1.5); 2.8651 (0.7); 2.7321 (1.0); 2.5488 (11.4); 2.5040 (23.4); 2.3248 (9.7); 2.2197 (9.3); −0.0002 (4.5) | 4.55[a] |
Compounds of Formula (6b)
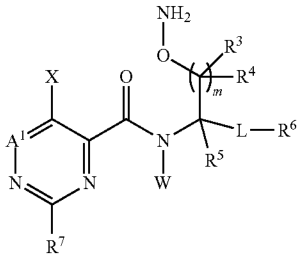
(6b)

TABLE 6
Compounds according to formula (6b), their $^{1}$H-NMR data and LogP values
| Ex No | Structure | $^{1}$H-NMR Peak List | LogP |
|---|---|---|---|
| 6b-01 | 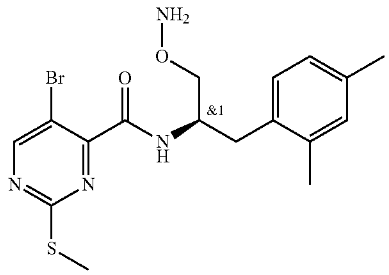 [SMILES: CSc1ncc(Br)c(C(=O)N[C@@H](CON)Cc2ccc(C)cc2C)n1] | 6b-01: $^{1}$H-NMR(400.1 MHz, CDCl3): δ = 8.7484 (5.2); 8.1656 (0.9); 8.1450 (0.9); 7.8626 (0.3); 7.8549 (0.4); 7.7493 (0.4); 7.7416 (0.4); 7.7360 (0.4); 7.2591 (6.9); 7.0963 (2.0); 7.0772 (2.5); 6.9820 (2.9); 6.9446 (1.8); 6.9249 (1.4); 5.5718 (1.3); 5.2963 (0.7); 4.5290 (0.6); 4.5219 (0.7); 4.5146 (0.8); 4.5081 (0.8); 4.5012 (0.7); 4.4934 (0.6); 4.1438 (0.4); 3.7873 (0.9); 3.7787 (1.0); 3.7594 (1.7); 3.7509 (1.6); 3.6915 (1.6); 3.6771 (1.6); 3.6637 (1.0); 3.6492 (1.0); 2.9869 (0.4); 2.9706 (0.4); 2.9522 (1.7); 2.9355 (3.2); 2.9144 (1.8); 2.9004 (0.6); 2.8798 (0.5); 2.8147 (0.4); 2.5506 (16.0); 2.3781 (12.9); 2.3476 (0.4); 2.2779 (12.6); 2.2523 (0.6); 1.5655 (2.0); 1.2555 (0.4); 0.0696 (2.4); −0.0002 (8.3) | 2.49[a] |
Compounds of Formula (7)
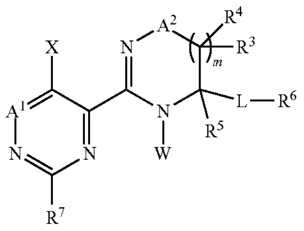
(7)
TABLE 7
Compounds according to formula (7), their $^{1}$H-NMR data and LogP values
| Ex No | Structure | $^{1}$H-NMR Peak List | LogP |
|---|---|---|---|
| 7-01 | 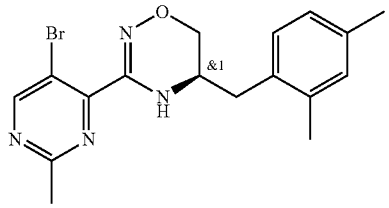 [SMILES: Cc1ccc(C[C@@H]2CON=C(c3nc(C)ncc3Br)N2)c(C)c1] | 7-01: $^{1}$H-NMR(400.1 MHz, CDCl3): δ = 8.8302 (4.9); 7.2597 (10.0); 7.0828 (2.1); 7.0638 (3.5); 7.0404 (3.9); 7.0138 (2.6); 6.9956 (1.8); 6.3403 (2.0); 5.2986 (6.3); 4.0988 (1.3); 4.0905 (1.5); 4.0719 (1.7); 4.0638 (1.8); 3.8397 (1.4); 3.7825 (1.9); 3.7688 (1.5); 3.7555 (1.7); 3.7417 (1.3); 2.9716 (0.9); 2.9559 (1.1); 2.9381 (1.8); 2.9217 (1.8); 2.8668 (1.7); 2.8468 (1.8); 2.8328 (1.3); 2.8132 (1.0); 2.7122 (0.6); 2.6709 (16.0); 2.3349 (14.7); 2.3179 (15.9); 1.5472 (9.4); 1.2865 (0.3); 1.2555 (0.6); 0.0692 (3.7); −0.0002 (13.7) | 3.05[a] |
| 7-02 | 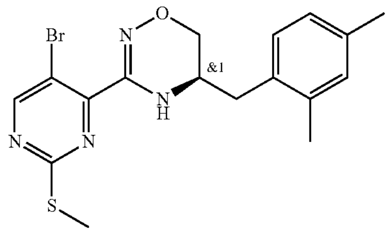 [SMILES: CSc1ncc(Br)c(C2=NOC[C@@H](Cc3ccc(C)cc3C)N2)n1] | 7-02: $^{1}$H-NMR(400.1 MHz, CDCl3): δ = 8.7370 (0.9); 8.7274 (0.4); 8.6958 (5.1); 7.2588 (10.5); 7.0696 (2.0); 7.0507 (3.2); 7.0315 (3.4); 7.0033 (2.6); 6.9851 (1.7); 6.9437 (0.4); 6.9366 (0.4); 6.1583 (1.8); 4.1475 (1.3); 4.1393 (1.4); 4.1204 (1.6); 4.1125 (1.8); 3.8584 (0.9); 3.8514 (1.0); 3.8442 (1.1); 3.8367 (1.0); 3.7928 (1.7); 3.7788 (1.2); 3.7663 (1.4); 3.7521 (1.0); 2.9699 (1.0); 2.9555 (1.1); 2.9354 (1.7); 2.9216 (1.5); 2.8192 (1.4); 2.7975 (1.4); 2.7850 (1.0); 2.7632 (0.9); 2.4986 (1.8); 2.4827 (1.0); 2.4788 (1.1); 2.4696 (0.9); 2.4300 (16.0); 2.4097 (1.6); 2.3932 (0.9); 2.3617 (2.0); 2.3447 (0.9); 2.3195 (15.4); 2.3105 (15.3); 2.2919 (2.3); 2.2808 (2.8); 2.0417 (0.8); 1.5489 (17.2); 1.2651 (1.9); 1.2402 (0.5); 0.8977 (0.7); 0.8817 (1.5); 0.8644 (0.7); 0.0694 (2.3); −0.0002 (12.8) | 4.05[a] |
| 7-03 | 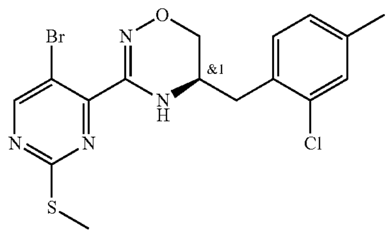 [SMILES: CSc1ncc(Br)c(C2=NOC[C@@H](Cc3ccc(C)cc3Cl)N2)n1] | 7-03: $^{1}$H-NMR(400.1 MHz, CDCl3): δ = 8.7364 (0.4); 8.7223 (0.6); 8.7060 (5.1); 7.6130 (0.3); 7.2602 (9.1); 7.2381 (2.8); 7.1851 (0.3); 7.1441 (1.9); 7.1249 (2.8); 7.0582 (1.7); 7.0390 (1.2); 6.1794 (1.3); 5.2984 (0.9); 4.0813 (1.0); 4.0730 (1.2); 4.0540 (1.2); 4.0458 (1.4); 3.9845 (0.7); 3.9770 (0.8); 3.9696 (0.8); 3.9635 (0.7); 3.9497 (0.4); 3.8467 (1.4); 3.8344 (1.2); 3.8195 (1.2); 3.8074 (1.0); 3.1701 (0.3); 3.1524 (0.3); 3.1049 (0.9); 3.0898 (0.9); 3.0712 (1.4); 3.0561 (1.3); 2.9715 (1.3); 2.9514 (1.3); 2.9378 (0.9); 2.9178 (0.8); 2.5656 (1.0); 2.4964 (1.4); 2.4710 (16.0); 2.3323 (12.1); 2.3192 (1.1); 2.2927 (1.4); 1.5516 (4.7); 1.2560 (0.6); 0.0695 (2.2); −0.0002 (11.4) | 4.08[a] |

Compounds According to Formula (9)
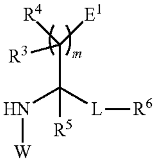
(9)
TABLE 8
Compounds according to formula (9), their $^1$H-NMR data and LogP values
| Ex No | Structure | $^1$H-NMR Peak List | LogP |
|---|---|---|---|
| 9-01 | 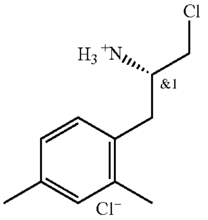 | 9-01: $^1$H-NMR(300.2 MHz, CDCl3): δ = 7.6438 (0.5); 7.3661 (0.6); 7.3167 (0.5); 7.2990 (107.3); 7.2639 (0.4); 7.2354 (0.5); 7.1375 (1.2); 7.1101 (1.9); 7.0359 (2.6); 7.0282 (2.3); 7.0171 (1.6); 6.9904 (1.0); 6.9484 (0.8); 4.5372 (0.5); 4.5099 (0.4); 4.2226 (0.4); 4.2061 (0.5); 4.0962 (0.4); 3.8770 (0.7); 3.8498 (0.8); 3.8306 (0.6); 3.8113 (0.5); 3.7436 (16.0); 3.7105 (1.5); 3.6820 (1.5); 3.2699 (0.5); 3.2302 (0.7); 3.1379 (0.5); 3.1032 (0.6); 3.0910 (0.7); 3.0610 (0.4); 2.9134 (0.4); 2.8926 (0.7); 2.8630 (0.4); 2.3783 (9.4); 2.3379 (3.1); 2.3211 (13.5); 2.0640 (0.3); 1.7885 (0.7); 1.7676 (0.8); 1.7013 (2.1); 1.6039 (3.8); 1.3928 (1.2); 1.3716 (2.1); 1.3493 (1.3); 1.3233 (0.6); 1.2923 (1.1); 1.2598 (2.2); 1.2395 (1.4); 0.2335 (0.6); 0.1071 (9.8); 0.0771 (0.4); 0.0551 (0.5); 0.0487 (3.2); 0.0380 (131.2); 0.0275 (5.8); −0.0108 (0.4); −0.0221 (0.5); −0.0306 (0.5); −0.1608 (0.5) | 1.13[a] |
| 9-02 | 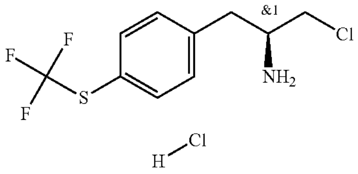 | 9-02: $^1$H-NMR(400.1 MHz, $d_6$-DMSO): δ = 8.5369 (10.2); 7.7228 (12.5); 7.7026 (15.7); 7.4889 (16.0); 7.4684 (14.2); 3.9139 (3.1); 3.9056 (4.5); 3.8763 (6.9); 3.8630 (3.3); 3.8515 (3.4); 3.6681 (3.8); 3.6575 (5.0); 3.6384 (4.5); 3.6282 (3.3); 3.5681 (0.5); 3.3321 (6.5); 3.1498 (2.5); 3.1352 (2.6); 3.1154 (3.7); 3.1006 (3.8); 3.0210 (4.4); 3.0005 (4.4); 2.9864 (2.8); 2.9660 (2.6); 2.5072 (13.7); 2.5027 (19.4); 2.4983 (15.0); 0.0080 (0.4); −0.0002 (10.5) | 1.68[a] |
| 9-03 | 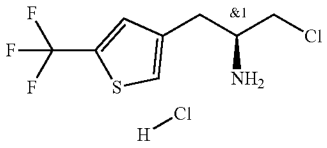 | 9-03: $^1$H-NMR(400.1 MHz, $d_6$-DMSO): δ = 8.4567 (16.0); 7.7978 (15.8); 7.7497 (0.3); 7.6970 (14.4); 3.9218 (5.5); 3.8926 (10.8); 3.7250 (4.9); 3.7143 (5.7); 3.6951 (4.8); 3.6857 (3.8); 3.5684 (2.3); 3.3192 (17.2); 3.0687 (1.7); 3.0356 (13.2); 3.0190 (8.1); 2.9814 (1.3); 2.5014 (28.9); 1.1062 (1.7); −0.0002 (16.4) | 1.29[a] |
| 9-04 | 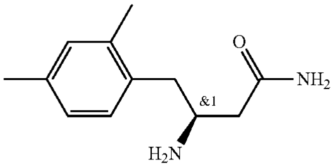 | 9-04: $^1$H-NMR(300.2 MHz, $d_6$-DMSO): δ = 7.5393 (0.9); 7.0418 (1.3); 7.0161 (3.2); 7.0024 (3.1); 6.9744 (1.6); 6.9489 (0.8); 3.4134 (0.4); 3.3897 (0.9); 3.3662 (1.1); 3.3473 (0.9); 3.3240 (0.5); 2.7093 (2.1); 2.7044 (2.6); 2.6803 (2.1); 2.5345 (1.6); 2.5286 (3.5); 2.5226 (4.9); 2.5166 (3.6); 2.5107 (1.8); 2.2552 (16.0); 2.2263 (2.8); 2.2095 (1.8); 2.2005 (1.6); 2.0094 (0.4); 0.0204 (6.1) | 0.69[a] |
| 9-05 | 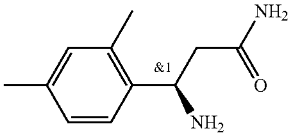 | 9-05: $^1$H-NMR(300.2 MHz, CDCl3): δ = 7.3292 (0.5); 7.2991 (1.7); 7.0887 (0.4); 7.0622 (0.4); 7.0162 (0.6); 4.5819 (0.5); 2.8373 (16.0); 2.5265 (1.0); 2.5033 (1.5); 2.3677 (3.6); 2.3333 (3.4); 1.8587 (1.5); 0.0347 (1.9) | 0.55[b] |
| 9-06 | 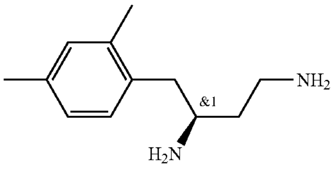 | 9-06: $^1$H-NMR(300.2 MHz, $d_6$-DMSO): δ = 7.0363 (1.8); 7.0110 (3.3); 6.9851 (3.0); 6.9558 (2.0); 6.9305 (1.1); 5.0883 (0.3); 4.9774 (0.4); 4.9157 (0.4); 4.8595 (0.4); 4.7461 (0.3); 3.0967 (2.8); 2.9721 (0.6); 2.9616 (0.8); 2.9408 (1.0); 2.9301 (0.7); 2.9184 (0.7); 2.9001 (0.9); 2.8765 (1.8); 2.8532 (1.7); 2.8320 (0.8); 2.8133 (0.4); 2.6178 (3.0); 2.5934 (2.2); 2.5340 (2.2); 2.5283 (4.4); 2.5224 (5.8); 2.5164 (4.3); 2.2549 (16.0); 2.2456 (14.8); 1.6161 (0.4); 1.6044 (0.4); 1.5929 (0.6); 1.5808 (0.6); 1.5715 (0.6); 1.5589 (0.6); 1.5475 (0.4); 1.4592 (0.7); 1.4289 (0.7); 1.4141 (0.5); 1.4054 (0.5); 1.3825 (0.4); 1.1264 (8.5); 0.0204 (5.2) | 0.23[a] |

Compounds of Formula (10)
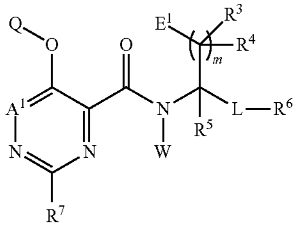
(10)
TABLE 9
Compounds according to formula (10), their $^{1}$H-NMR data and LogP values
| Ex No | Structure | $^{1}$H-NMR Peak List | LogP |
|---|---|---|---|
| 10-01 | 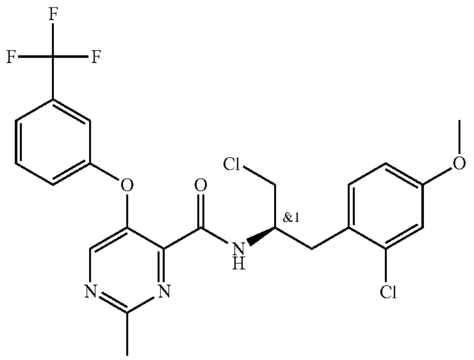 [SMILES: COc1ccc(C[C@H](CCl)NC(=O)c2nc(C)ncc2Oc2cccc(C(F)(F)F)c2)c(Cl)c1] | 10-01: $^{1}$H-NMR(400.1 MHz, CDCl3): δ = 8.5111 (4.9); 8.1701 (1.1); 8.1498 (1.1); 7.4709 (0.8); 7.4507 (2.0); 7.4306 (1.4); 7.3834 (2.2); 7.3644 (1.3); 7.2599 (10.4); 7.2226 (2.4); 7.2014 (2.6); 7.1735 (2.7); 7.1115 (1.5); 7.0915 (1.4); 6.9078 (2.6); 6.9018 (2.8); 6.7563 (1.5); 6.7502 (1.4); 6.7350 (1.4); 6.7290 (1.3); 5.2979 (0.4); 4.6235 (0.3); 4.6143 (0.6); 4.6050 (0.9); 4.5954 (0.9); 4.5855 (0.9); 4.5764 (0.6); 3.7693 (16.0); 3.7540 (1.5); 3.7359 (1.8); 3.7256 (1.6); 3.6385 (1.6); 3.6300 (1.6); 3.6101 (1.1); 3.6017 (1.0); 3.1707 (0.5); 3.1520 (0.5); 3.1358 (1.8); 3.1155 (2.5); 3.0943 (1.8); 3.0778 (0.6); 3.0597 (0.5); 2.8117 (15.2); 1.5520 (15.0); 1.3043 (1.1); 1.2652 (4.9); 0.8980 (2.0); 0.8820 (4.5); 0.8645 (2.2); 0.0695 (2.4); −0.0002 (13.6) | 4.47[a] |
| 10-02 | 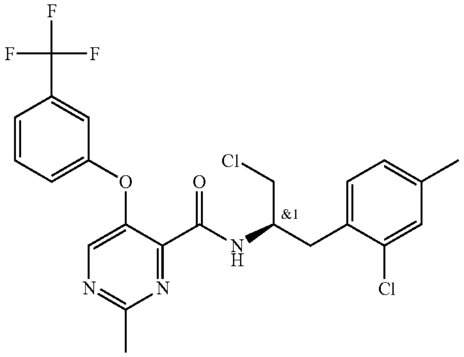 [SMILES: Cc1ccc(C[C@H](CCl)NC(=O)c2nc(C)ncc2Oc2cccc(C(F)(F)F)c2)c(Cl)c1] | 10-02: $^{1}$H-NMR(400.1 MHz, CDCl3): δ = 8.5085 (5.0); 8.1818 (1.1); 8.1621 (1.1); 7.4706 (0.8); 7.4510 (2.0); 7.4310 (1.5); 7.3838 (2.2); 7.3650 (1.4); 7.2599 (8.7); 7.1983 (2.3); 7.1763 (4.7); 7.1202 (1.6); 7.0996 (1.4); 6.9962 (1.9); 6.9777 (1.6); 5.2980 (0.7); 4.6416 (0.3); 4.6312 (0.6); 4.6219 (0.9); 4.6125 (1.0); 4.6027 (1.0); 4.5933 (0.7); 4.5843 (0.4); 3.7674 (1.0); 3.7567 (1.1); 3.7392 (1.6); 3.7286 (1.6); 3.6428 (1.6); 3.6342 (1.7); 3.6145 (1.1); 3.6059 (1.1); 3.2008 (0.5); 3.1824 (0.5); 3.1662 (1.7); 3.1470 (2.0); 3.1411 (2.1); 3.1223 (1.8); 3.1058 (0.6); 3.0873 (0.5); 2.8111 (16.0); 2.3203 (0.4); 2.3107 (0.4); 2.2868 (13.2); 1.5594 (3.4); 1.2549 (0.5); 0.0697 (2.7); −0.0002 (10.8) | 4.74[a] |
| 10-03 | 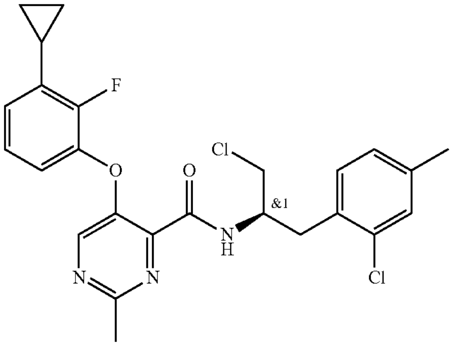 [SMILES: Cc1ccc(C[C@H](CCl)NC(=O)c2nc(C)ncc2Oc2cccc(C3CC3)c2F)c(Cl)c1] | 10-03: $^{1}$H-NMR(400.1 MHz, CDCl3): δ = 8.3394 (4.7); 8.1350 (1.3); 8.1152 (1.3); 7.2604 (11.7); 7.2288 (2.4); 7.2093 (2.8); 7.1727 (3.8); 7.0099 (1.1); 6.9932 (3.6); 6.9747 (2.5); 6.8463 (1.2); 6.8278 (2.0); 6.8088 (1.0); 6.7326 (1.2); 6.7152 (1.9); 6.6983 (1.0); 5.2985 (4.8); 4.7094 (0.7); 4.6998 (1.1); 4.6904 (1.1); 4.6809 (1.1); 4.6720 (0.8); 3.8283 (1.1); 3.8178 (1.2); 3.7999 (1.7); 3.7896 (1.7); 3.6881 (1.8); 3.6799 (1.8); 3.6594 (1.2); 3.6518 (1.2); 3.2302 (0.6); 3.2118 (0.6); 3.1957 (1.8); 3.1773 (1.9); 3.1654 (2.0); 3.1472 (1.8); 3.1306 (0.7); 3.1128 (0.6); 2.7554 (16.0); 2.3170 (0.4); 2.2857 (13.9); 2.1250 (0.4); 2.1117 (0.8); 2.1029 (0.9); 2.0907 (1.4); 2.0789 (1.0); 2.0703 (0.8); 2.0571 (0.4); 1.5625 (24.7); 1.2570 (0.8); 1.0381 (0.8); 1.0227 (3.0); 1.0049 (3.0); 0.7635 (1.0); 0.7508 (3.7); 0.7378 (3.6); 0.0695 (5.2); −0.0002 (14.2) | 4.93[a] |

TABLE 9-continued
| Ex No | Structure | $^1$H-NMR Peak List | LogP |
|---|---|---|---|
| Compounds according to formula (10), their $^1$H-NMR data and LogP values | | | |
| 10-04 | 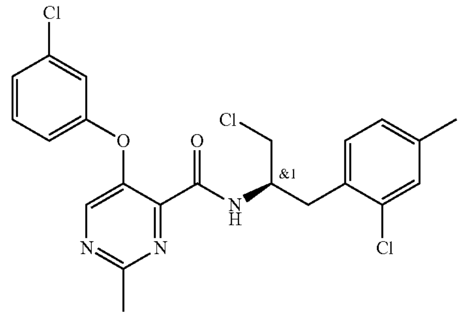 [SMILES: Cc1ccc(C[C@H](CCl)NC(=O)c2nc(C)ncc2Oc2cccc(Cl)c2)c(Cl)c1] | 10-04: $^1$H-NMR(400.1 MHz, CDCl3): δ = 8.4923 (5.1); 8.1528 (1.7); 8.1341 (1.7); 7.2580 (7.8); 7.2353 (2.0); 7.1986 (2.7); 7.1748 (6.2); 7.1091 (2.8); 7.0892 (2.2); 6.9972 (2.7); 6.9794 (2.3); 6.9107 (3.8); 6.8501 (2.4); 6.8303 (2.1); 5.2972 (0.8); 4.6252 (1.6); 4.6148 (1.6); 3.7689 (1.5); 3.7498 (2.0); 3.7406 (2.1); 3.6442 (2.4); 3.6162 (1.5); 3.2027 (0.7); 3.1683 (2.2); 3.1437 (3.2); 3.1251 (2.2); 3.0900 (0.6); 2.7956 (16.0); 2.2877 (14.9); 1.5600 (13.4); 1.2547 (0.4); 0.0698 (3.4); −0.0002 (6.8) | 4.61[a] |
| 10-05 | 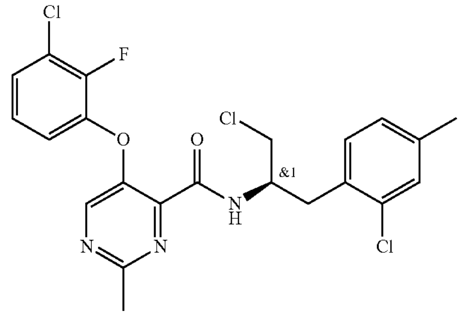 [SMILES: Cc1ccc(C[C@H](CCl)NC(=O)c2nc(C)ncc2Oc2cccc(Cl)c2F)c(Cl)c1] | 10-05: $^1$H-NMR(400.1 MHz, CDCl3): δ = 8.4158 (4.2); 8.1428 (0.8); 8.1219 (0.8); 7.2598 (17.8); 7.2139 (2.3); 7.2040 (1.2); 7.1997 (2.0); 7.1948 (3.2); 7.1788 (2.9); 7.0423 (0.8); 7.0378 (0.8); 7.0216 (1.6); 7.0171 (1.7); 7.0014 (2.0); 6.9968 (1.2); 6.9860 (1.2); 6.8723 (0.9); 6.8687 (0.9); 6.8513 (1.5); 6.8338 (0.7); 6.8301 (0.6); 5.2986 (8.8); 4.6656 (0.5); 4.6556 (0.7); 4.6460 (0.7); 4.6362 (0.7); 4.6262 (0.5); 3.7971 (1.0); 3.7865 (1.0); 3.7688 (1.5); 3.7583 (1.4); 3.6678 (1.6); 3.6591 (1.6); 3.6394 (1.0); 3.6307 (1.0); 3.2169 (0.5); 3.1982 (0.5); 3.1824 (1.5); 3.1636 (1.5); 3.1518 (1.5); 3.1336 (1.5); 3.1170 (0.5); 3.0990 (0.5); 2.8019 (0.5); 2.7791 (16.0); 2.3225 (0.4); 2.3104 (0.8); 2.2910 (11.6); 1.5528 (1.7); 1.2561 (0.4); 0.0692 (4.2); −0.0002 (24.1) | 4.70[a] |
| 10-06 | 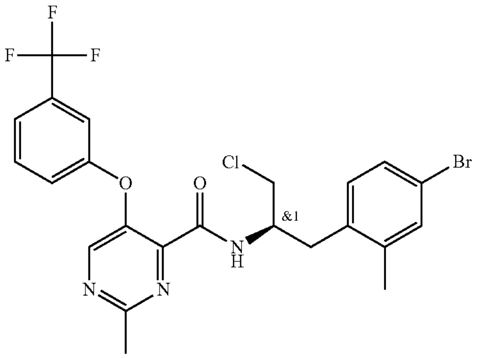 [SMILES: Cc1ncc(Oc2cccc(C(F)(F)F)c2)c(C(=O)N[C@@H](CCl)Cc2ccc(Br)cc2C)n1] | 10-06: $^1$H-NMR(400.1 MHz, CDCl3): δ = 8.5279 (5.2); 8.1633 (0.9); 8.1426 (0.9); 7.4875 (0.7); 7.4677 (1.8); 7.4476 (1.3); 7.3989 (1.8); 7.3797 (1.1); 7.3110 (2.5); 7.2589 (13.1); 7.2396 (1.6); 7.2351 (1.4); 7.1978 (2.2); 7.1260 (1.2); 7.0964 (3.0); 7.0758 (2.0); 5.2969 (0.6); 4.5188 (0.6); 4.5105 (0.7); 4.5026 (0.7); 4.4942 (0.5); 3.7174 (0.9); 3.7075 (0.9); 3.6890 (1.4); 3.6791 (1.4); 3.5951 (1.6); 3.5875 (1.6); 3.5666 (1.1); 3.5590 (1.0); 3.0431 (0.5); 3.0217 (0.4); 3.0083 (1.6); 2.9866 (2.1); 2.9662 (1.6); 2.9478 (0.5); 2.9316 (0.4); 2.8145 (16.0); 2.3646 (12.8); 1.5404 (14.6); 1.2578 (0.4); 0.0695 (2.4); −0.0002 (14.9) | 4.86[a] |
| 10-07 | 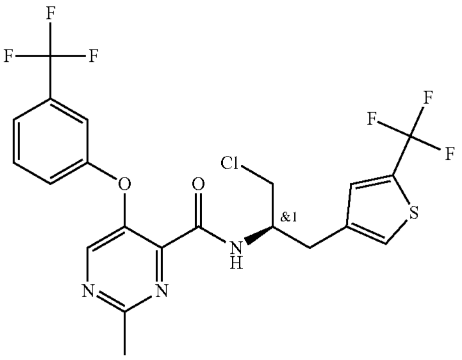 [SMILES: Cc1ncc(Oc2cccc(C(F)(F)F)c2)c(C(=O)N[C@@H](CCl)Cc2csc(C(F)(F)F)c2)n1] | 10-07: $^1$H-NMR(400.1 MHz, CDCl3): δ = 8.5549 (5.1); 8.1177 (0.8); 8.0958 (0.8); 7.4908 (0.7); 7.4711 (1.7); 7.4511 (1.2); 7.3993 (1.7); 7.3799 (1.1); 7.3614 (2.5); 7.2849 (2.8); 7.2599 (11.9); 7.1734 (2.0); 7.1303 (1.2); 7.1099 (1.0); 5.2987 (1.5); 4.5664 (0.5); 4.5563 (0.6); 4.5469 (0.6); 4.5361 (0.6); 4.5259 (0.4); 3.6904 (0.8); 3.6794 (0.9); 3.6619 (1.7); 3.6509 (1.6); 3.6086 (1.6); 3.6000 (1.7); 3.5800 (0.9); 3.5714 (0.8); 3.0768 (3.7); 3.0591 (3.6); 2.8123 (16.0); 1.5512 (1.2); 0.0695 (0.5); −0.0002 (16.6) | 4.55[a] |

TABLE 9-continued
| Compounds according to formula (10), their $^1$H-NMR data and LogP values | | | |
|---|---|---|---|
| Ex No | Structure | $^1$H-NMR Peak List | LogP |
| 10-08 | 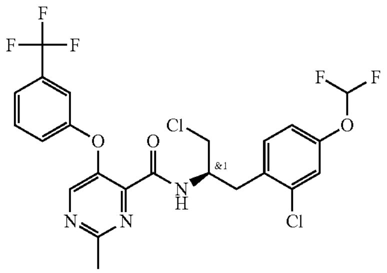 [SMILES: Cc1ncc(Oc2cccc(C(F)(F)F)c2)c(C(=O)N[C@@H](CCl)Cc2ccc(OC(F)F)cc2Cl)n1] | 10-08: $^1$H-NMR(400.1 MHz, CDCl3): δ = 8.5193 (5.2); 8.1960 (1.4); 8.1751 (1.3); 7.4774 (1.0); 7.4576 (2.2); 7.4378 (1.6); 7.3913 (2.5); 7.3725 (1.5); 7.3221 (2.5); 7.3008 (2.9); 7.2609 (12.4); 7.1674 (6.1); 7.1131 (1.8); 7.0927 (1.6); 6.9840 (1.8); 6.9638 (1.6); 6.6569 (1.3); 6.4740 (2.7); 6.2911 (1.3); 5.3001 (2.4); 4.6461 (1.1); 4.6367 (1.1); 4.6275 (1.1); 3.7748 (1.2); 3.7644 (1.2); 3.7464 (1.8); 3.7363 (1.7); 3.6491 (1.9); 3.6409 (1.9); 3.6206 (1.2); 3.6124 (1.2); 3.2229 (0.6); 3.2038 (0.7); 3.1878 (2.1); 3.1686 (3.8); 3.1503 (2.0); 3.1336 (0.6); 3.1151 (0.5); 2.8144 (16.0); 1.5518 (10.3); 1.2565 (0.7); 0.0695 (3.4); −0.0002 (17.2) | 4.51[a] |
| 10-09 | 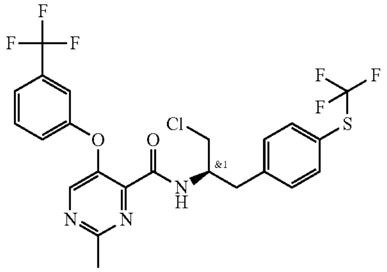 [SMILES: Cc1ncc(Oc2cccc(C(F)(F)F)c2)c(C(=O)N[C@@H](CCl)Cc2ccc(SC(F)(F)F)cc2)n1] | 10-09: $^1$H-NMR(400.1 MHz, CDCl3): δ = 8.5435 (5.2); 8.1562 (0.7); 8.1348 (0.8); 7.6048 (2.7); 7.5846 (3.4); 7.4882 (0.6); 7.4683 (1.5); 7.4483 (1.2); 7.3996 (1.5); 7.3802 (1.0); 7.3437 (3.6); 7.3232 (3.3); 7.2599 (8.5); 7.1763 (1.8); 7.1300 (1.1); 7.1246 (1.0); 7.1096 (1.0); 7.1043 (0.9); 5.2979 (1.2); 4.5818 (0.4); 4.5717 (0.6); 4.5632 (0.6); 4.5519 (0.6); 4.5434 (0.4); 3.6961 (0.9); 3.6857 (0.9); 3.6676 (1.4); 3.6571 (1.4); 3.5713 (1.4); 3.5630 (1.5); 3.5427 (1.0); 3.5345 (1.0); 3.0844 (2.9); 3.0686 (1.9); 3.0643 (2.1); 2.8091 (16.0); 1.5509 (3.6); 0.0699 (3.7); 0.0079 (0.4); −0.0002 (9.8); −0.0084 (0.7) | 4.92[a] |
| 10-10 | 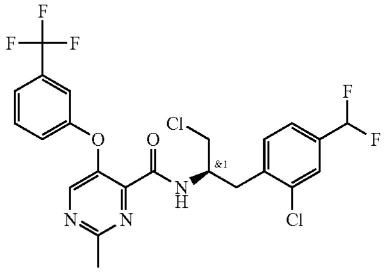 [SMILES: Cc1ncc(Oc2cccc(C(F)(F)F)c2)c(C(=O)N[C@@H](CCl)Cc2ccc(C(F)F)cc2Cl)n1] | 10-10: $^1$H-NMR(400.1 MHz, CDCl3): δ = 8.5158 (5.1); 8.2045 (0.7); 8.1839 (0.7); 7.5154 (2.0); 7.4727 (0.6); 7.4529 (1.5); 7.4328 (1.2); 7.4260 (1.4); 7.4062 (1.9); 7.3891 (1.6); 7.3697 (1.0); 7.3354 (1.4); 7.3157 (1.0); 7.2598 (12.4); 7.1632 (1.7); 7.1100 (1.0); 7.1048 (0.9); 7.0896 (0.9); 7.0844 (0.8); 6.7150 (1.0); 6.5745 (2.0); 6.4340 (1.0); 5.2982 (0.6); 4.6951 (0.4); 4.6855 (0.6); 4.6750 (0.6); 4.6648 (0.6); 4.6555 (0.5); 3.7810 (0.9); 3.7704 (0.9); 3.7525 (1.4); 3.7420 (1.4); 3.6566 (1.4); 3.6479 (1.5); 3.6281 (1.0); 3.6194 (1.0); 3.2545 (1.1); 3.2327 (1.7); 3.2136 (1.2); 3.1966 (0.4); 3.1786 (0.4); 2.8126 (16.0); 1.5452 (10.4); 0.0695 (2.2); 0.0080 (0.6); −0.0002 (15.2); −0.0084 (0.8) | 4.37[a] |
| 10-11 | 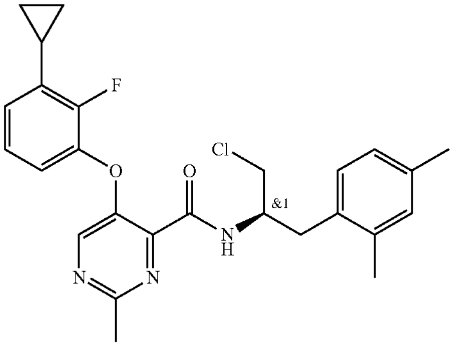 [SMILES: Cc1ccc(C[C@H](CCl)NC(=O)c2nc(C)ncc2Oc2cccc(C3CC3)c2F)c(C)c1] | 10-11: $^1$H-NMR(400.1 MHz, CDCl3): δ = 8.3512 (5.1); 8.1423 (2.0); 8.1230 (2.0); 7.2606 (8.8); 7.1404 (2.6); 7.1223 (3.2); 7.0203 (1.5); 6.9871 (6.1); 6.9462 (2.9); 6.9298 (2.6); 6.8742 (1.8); 6.8561 (2.7); 6.8375 (1.4); 6.7410 (1.7); 6.7244 (2.6); 6.7079 (1.5); 5.2979 (2.6); 4.5792 (1.7); 3.7599 (1.6); 3.7319 (2.4); 3.6498 (2.7); 3.6229 (1.8); 3.0414 (5.4); 3.0240 (5.5); 2.7601 (16.0); 2.3876 (15.7); 2.2796 (15.5); 2.0942 (1.9); 1.5606 (19.6); 1.2568 (0.5); 1.0252 (4.3); 1.0058 (4.4); 0.7519 (5.2); 0.7418 (5.4); 0.0703 (3.5); −0.0002 (10.0) | 4.86[a] |

Compounds of Formula (11)
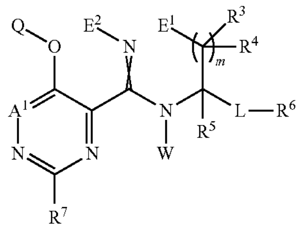
(11)
TABLE 10
Compounds according to formula (11), their $^1$H-NMR data and LogP values (mixture of stereoisomers)
| Ex No | Structure | $^1$H-NMR Peak List | LogP |
|---|---|---|---|
| 11-01 | 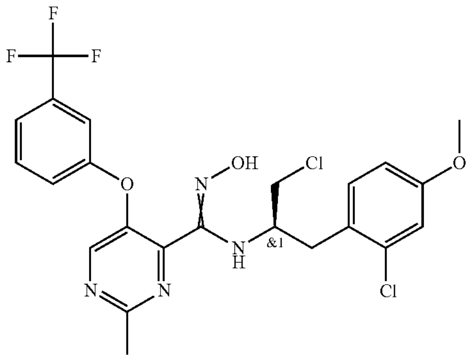 [SMILES: COc1ccc(C[C@H](CCl)NC(=NO)c2nc(C)ncc2Oc2cccc(C(F)(F)F)c2)c(Cl)c1] | 11-01: $^1$H-NMR(400.1 MHz, CDCl3): δ = 8.3528 (1.8); 7.4583 (0.9); 7.4385 (0.8); 7.4166 (1.0); 7.3981 (0.6); 7.3849 (0.4); 7.2618 (6.4); 7.1807 (1.6); 7.1597 (1.5); 6.8214 (1.0); 6.8156 (1.2); 6.7633 (0.7); 6.7575 (0.7); 6.7422 (0.6); 6.7359 (0.7); 3.7703 (1.3); 3.7557 (6.1); 3.7036 (16.0); 3.6728 (0.9); 3.6627 (0.8); 3.6381 (0.3); 3.6302 (0.3); 3.5413 (0.6); 3.5336 (0.6); 3.5132 (0.5); 3.5057 (0.5); 3.0027 (0.7); 2.9846 (1.2); 2.9681 (0.7); 2.8124 (1.0); 2.8033 (0.4); 2.7421 (5.4); 0.0697 (0.6); −0.0002 (7.2) | 4.01[a] |
| 11-02 | 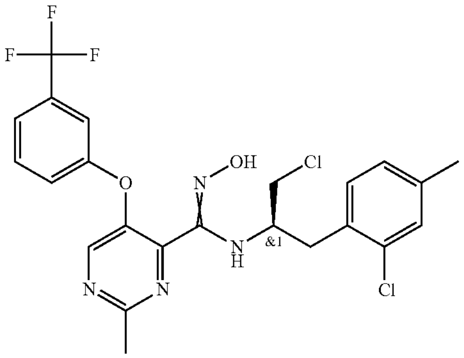 [SMILES: Cc1ccc(C[C@H](CCl)NC(=NO)c2nc(C)ncc2Oc2cccc(C(F)(F)F)c2)c(Cl)c1] | 11-02: $^1$H-NMR(400.1 MHz, CDCl3): δ = 8.3661 (2.4); 7.4516 (0.5); 7.4321 (1.1); 7.4126 (0.9); 7.3891 (1.4); 7.3709 (0.7); 7.2610 (6.0); 7.2164 (1.5); 7.1581 (1.3); 7.1387 (1.4); 7.0919 (2.5); 7.0013 (1.1); 6.9823 (0.9); 5.8182 (0.7); 5.7921 (0.7); 5.2993 (0.6); 4.0953 (0.4); 4.0873 (0.4); 3.7030 (16.0); 3.6735 (0.7); 3.6641 (0.6); 3.6456 (0.8); 3.6357 (0.8); 3.5019 (0.8); 3.4948 (0.8); 3.4740 (0.6); 3.4670 (0.6); 3.0090 (1.0); 2.9968 (1.3); 2.9903 (1.3); 2.9806 (1.1); 2.8106 (0.7); 2.7516 (7.3); 2.3093 (0.3); 2.2777 (6.5); 1.6333 (0.3); 1.2580 (0.4); 0.0696 (2.2); −0.0002 (7.5) | 4.31[a] |
| 11-03 | 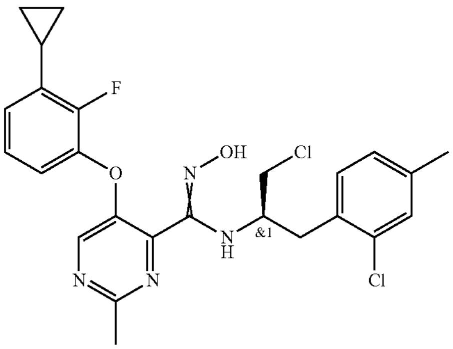 [SMILES: Cc1ccc(C[C@H](CCl)NC(=NO)c2nc(C)ncc2Oc2cccc(C3CC3)c2F)c(Cl)c1] | 11-03: $^1$H-NMR(400.1 MHz, CDCl3): δ = 8.3398 (0.5); 8.1908 (1.7); 7.3823 (0.7); 7.3635 (0.5); 7.2604 (6.2); 7.1619 (1.0); 7.1423 (1.1); 7.0714 (1.6); 6.9878 (1.7); 6.9706 (1.2); 6.8526 (0.6); 6.8346 (0.9); 6.8165 (0.4); 6.7077 (0.9); 6.6891 (0.4); 5.8864 (0.5); 5.8614 (0.5); 5.2978 (0.8); 4.5949 (1.0); 4.0262 (0.4); 3.7589 (0.5); 3.7500 (0.5); 3.7305 (0.7); 3.7031 (16.0); 3.5282 (0.7); 3.4995 (0.6); 3.0258 (1.6); 3.0080 (1.6); 2.7547 (1.6); 2.6990 (5.5); 2.3095 (0.4); 2.2841 (1.7); 2.2707 (5.3); 2.2409 (0.4); 2.0680 (1.0); 1.7214 (0.3); 1.6696 (0.3); 1.2569 (0.4); 1.0227 (1.6); 1.0029 (1.6); 0.7424 (1.9); 0.7309 (1.7); 0.0693 (2.6); −0.0002 (7.4) | 4.62[a] |

TABLE 10-continued
Compounds according to formula (11), their $^1$H-NMR data and LogP values (mixture of stereoisomers)
| Ex No | Structure | $^1$H-NMR Peak List | LogP |
|---|---|---|---|
| 11-04 | 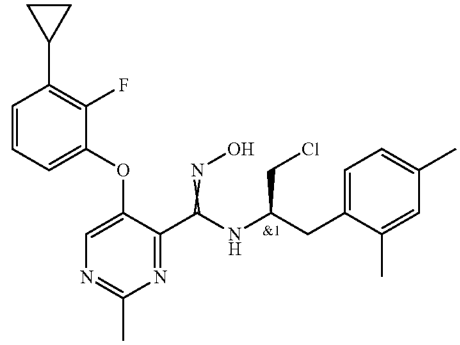 [SMILES: Cc1ccc(C[C@H](CCl)NC(=NO)c2nc(C)ncc2Oc2cccc(C3CC3)c2F)c(C)c1] | 11-04: $^1$H-NMR(400.1 MHz, CDCl3): δ = 8.3510 (0.9); 8.2035 (2.8); 8.1386 (0.3); 8.1201 (0.4); 7.3830 (0.5); 7.3608 (0.4); 7.2594 (7.8); 7.1406 (0.6); 7.1213 (0.8); 7.0830 (0.4); 7.0203 (1.7); 7.0012 (3.1); 6.9844 (2.8); 6.9649 (1.3); 6.9477 (0.9); 6.9122 (4.2); 6.8575 (1.3); 6.8409 (1.6); 6.7241 (1.4); 6.7070 (1.8); 5.8690 (1.0); 5.8584 (0.7); 5.8440 (1.0); 5.2973 (5.7); 4.5938 (0.8); 3.8621 (0.8); 3.7571 (0.4); 3.7024 (16.0); 3.6743 (1.1); 3.6646 (1.1); 3.6467 (1.7); 3.5189 (1.4); 3.4921 (1.0); 3.0405 (1.0); 3.0226 (1.2); 2.9779 (1.2); 2.9563 (1.1); 2.9258 (1.1); 2.9131 (1.3); 2.8927 (0.6); 2.8792 (0.6); 2.7595 (3.2); 2.7135 (8.9); 2.3866 (2.9); 2.3336 (0.5); 2.3078 (0.8); 2.2784 (3.4); 2.2552 (8.8); 2.0839 (9.1); 2.0553 (1.6); 1.9914 (0.4); 1.9559 (0.3); 1.9259 (0.4); 1.2574 (0.7); 1.0148 (3.0); 0.9964 (2.8); 0.7360 (3.6); 0.7248 (3.2); 0.0696 (5.2); −0.0002 (8.6) | 4.51[a] |
| 11-05 | 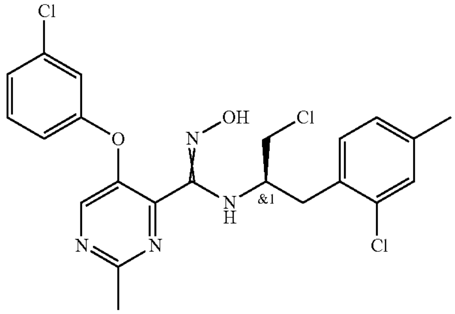 [SMILES: Cc1ccc(C[C@H](CCl)NC(=NO)c2nc(C)ncc2Oc2cccc(Cl)c2)c(Cl)c1] | 11-05: $^1$H-NMR(400.1 MHz, CDCl3): δ = 8.4915 (1.3); 8.3554 (4.6); 8.1542 (0.5); 8.1345 (0.5); 7.2596 (13.3); 7.2351 (3.4); 7.2147 (1.9); 7.1991 (1.3); 7.1758 (2.4); 7.1603 (3.0); 7.1398 (3.4); 7.1137 (3.8); 7.0932 (6.7); 6.9989 (3.5); 6.9822 (2.8); 6.9455 (3.8); 6.9118 (1.3); 6.8501 (0.8); 6.8267 (2.7); 6.8058 (2.1); 5.8251 (1.7); 5.8012 (1.7); 5.2972 (1.4); 4.6242 (0.4); 4.0730 (1.3); 3.9405 (0.3); 3.7671 (0.5); 3.7415 (0.8); 3.7019 (12.0); 3.6448 (2.6); 3.5060 (2.3); 3.4777 (1.6); 3.1687 (0.6); 3.1453 (0.9); 3.1247 (0.6); 3.0510 (0.6); 3.0148 (2.4); 2.9995 (4.0); 2.9866 (2.6); 2.9492 (0.6); 2.7945 (4.5); 2.7380 (14.4); 2.2811 (16.0); 2.2411 (0.8); 2.2203 (0.4); 2.2009 (0.4); 2.1761 (0.4); 2.1266 (0.4); 2.0659 (1.6); 2.0302 (0.4); 1.9876 (0.4); 1.8801 (0.5); 1.8339 (0.5); 1.7930 (0.5); 1.7638 (0.5); 1.7383 (0.5); 1.6228 (0.4); 1.6039 (0.4); 1.5819 (0.4); 1.5596 (0.4); 1.2559 (0.7); 0.0692 (3.5); −0.0002 (15.2) | 4.28[a] |
| 11-06 | 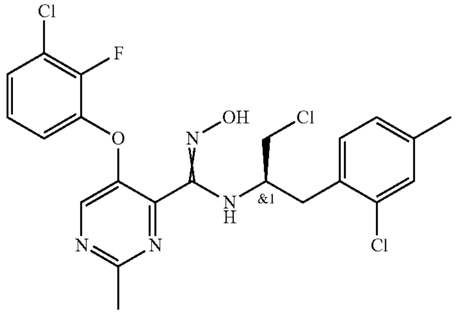 [SMILES: Cc1ccc(C[C@H](CCl)NC(=NO)c2nc(C)ncc2Oc2cccc(Cl)c2F)c(Cl)c1] | 11-06: $^1$H-NMR(400.1 MHz, CDCl3): δ = 8.2592 (4.1); 7.2600 (16.2); 7.2313 (0.8); 7.2276 (0.8); 7.2153 (1.0); 7.2113 (1.5); 7.2072 (1.0); 7.1950 (1.0); 7.1914 (0.9); 7.1556 (2.1); 7.1362 (2.6); 7.0754 (2.7); 7.0486 (0.9); 7.0443 (0.9); 7.0279 (1.7); 7.0237 (1.7); 7.0073 (1.0); 7.0029 (1.2); 6.9962 (1.7); 6.9769 (1.3); 6.9152 (1.0); 6.9115 (0.9); 6.8941 (1.6); 6.8767 (0.7); 6.8730 (0.7); 5.8627 (1.0); 5.8367 (1.1); 5.2986 (6.8); 4.1306 (0.5); 4.1128 (0.5); 4.0952 (0.4); 4.0883 (0.4); 4.0802 (0.6); 4.0709 (0.6); 4.0624 (0.6); 4.0535 (0.6); 4.0458 (0.4); 3.7398 (1.1); 3.7300 (1.1); 3.7119 (1.5); 3.7021 (1.3); 3.5339 (1.5); 3.5267 (1.5); 3.5061 (1.2); 3.4987 (1.1); 3.0131 (3.0); 2.9947 (3.2); 2.7525 (0.5); 2.7424 (0.6); 2.7250 (16.0); 2.2741 (11.9); 2.0438 (2.1); 1.2765 (0.8); 1.2587 (1.6); 1.2409 (0.7); 0.0692 (4.7); −0.0002 (21.8); −0.0081 (1.4) | 4.16[a] |
| 11-07 | 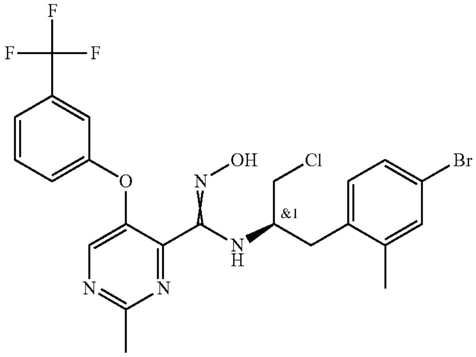 [SMILES: Cc1ncc(Oc2cccc(C(F)(F)F)c2)c(C(=NO)N[C@@H](CCl)Cc2ccc(Br)cc2C)n1] | 11-07: $^1$H-NMR(400.1 MHz, CDCl3): δ = 8.3677 (2.4); 7.4472 (0.4); 7.4275 (0.8); 7.4076 (0.8); 7.3873 (1.1); 7.3681 (0.5); 7.2594 (7.2); 7.2329 (0.6); 7.2281 (0.5); 7.2124 (0.7); 7.2073 (0.6); 7.1953 (1.0); 7.0478 (0.5); 7.0276 (0.4); 7.0062 (1.1); 6.9859 (0.9); 5.7770 (0.4); 5.7515 (0.5); 4.5946 (0.4); 3.7006 (16.0); 3.6217 (0.4); 3.6098 (0.4); 3.5938 (0.7); 3.5822 (0.6); 3.5334 (0.7); 3.5255 (0.7); 3.5057 (0.4); 3.4978 (0.4); 2.9948 (0.3); 2.9759 (0.3); 2.9598 (0.6); 2.9411 (0.6); 2.8761 (0.5); 2.8597 (0.5); 2.8413 (0.3); 2.8128 (0.4); 2.7541 (7.1); 2.1743 (5.4); 0.0694 (2.2); −0.0002 (7.5) | |

TABLE 10-continued
Compounds according to formula (11), their $^1$H-NMR data and LogP values (mixture of stereoisomers)
| Ex No | Structure | $^1$H-NMR Peak List | LogP |
| --- | --- | --- | --- |
| 11-08 | 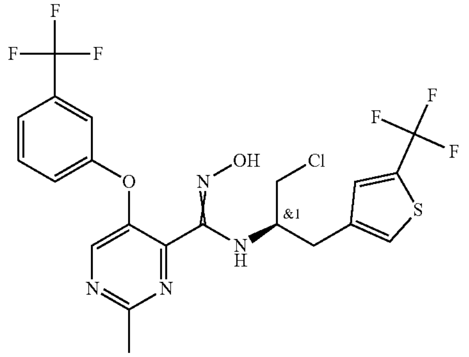 [SMILES: Cc1ncc(Oc2cccc(C(F)(F)F)c2)c(C(=NO)N[C@@H](CCl)Cc2csc(C(F)(F)F)c2)n1] | 11-08: $^1$H-NMR(400.1 MHz, CDCl3): δ = 8.3983 (5.4); 7.4671 (0.8); 7.4473 (1.9); 7.4274 (1.6); 7.4048 (2.1); 7.3854 (1.2); 7.2700 (6.1); 7.2597 (17.6); 7.2140 (2.2); 7.1027 (1.2); 7.0819 (1.0); 5.8016 (0.8); 5.7756 (0.8); 5.2984 (3.9); 4.5953 (0.5); 4.0884 (0.6); 4.0761 (0.6); 4.0635 (0.5); 3.7016 (8.5); 3.5831 (0.4); 3.5646 (2.8); 3.5602 (2.9); 3.5554 (2.5); 3.5472 (2.2); 3.5194 (0.3); 3.0131 (3.8); 2.9970 (3.7); 2.8259 (0.4); 2.8099 (0.6); 2.7791 (0.8); 2.7675 (16.0); 2.7472 (0.4); 1.2563 (0.4); 0.0694 (1.1); −0.0002 (24.1) | 4.12[a] |
| 11-09 | 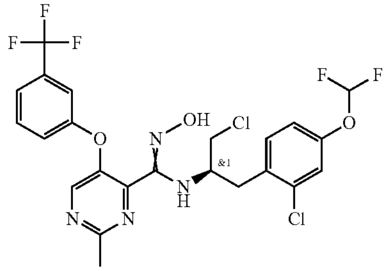 [SMILES: Cc1ncc(Oc2cccc(C(F)(F)F)c2)c(C(=NO)N[C@@H](CCl)Cc2ccc(OC(F)F)cc2Cl)n1] | 11-09: $^1$H-NMR(400.1 MHz, CDCl3): δ = 8.3665 (2.0); 7.4596 (0.6); 7.4402 (1.0); 7.4209 (0.9); 7.3968 (1.3); 7.3771 (0.7); 7.2934 (1.2); 7.2611 (5.5); 7.2098 (1.4); 7.1672 (0.5); 7.0878 (2.2); 7.0691 (0.7); 6.9926 (0.8); 6.9705 (0.7); 6.6515 (0.5); 6.4687 (1.1); 6.2859 (0.5); 5.8253 (0.6); 5.7994 (0.6); 4.1513 (0.5); 3.7032 (16.0); 3.6722 (0.7); 3.6627 (0.6); 3.5256 (0.8); 3.5192 (0.8); 3.4971 (0.5); 3.4901 (0.5); 3.0890 (0.3); 3.0696 (0.4); 3.0543 (0.7); 3.0363 (0.7); 3.0107 (0.7); 2.9925 (0.6); 2.8121 (0.8); 2.7472 (6.0); 2.0539 (0.4); 1.2589 (0.5); 0.0697 (2.1); −0.0002 (7.2) | 4.08[a] |
| 11-10 | 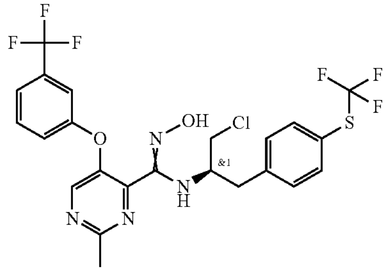 [SMILES: Cc1ncc(Oc2cccc(C(F)(F)F)c2)c(C(=NO)N[C@@H](CCl)Cc2ccc(SC(F)(F)F)cc2)n1] | 11-10: $^1$H-NMR(400.1 MHz, CDCl3): δ = 8.3908 (1.6); 7.5792 (0.9); 7.5590 (1.0); 7.4258 (0.5); 7.4060 (0.5); 7.3881 (0.6); 7.2600 (3.2); 7.2475 (1.2); 7.2270 (1.0); 7.1966 (0.7); 7.0764 (0.3); 5.2979 (0.4); 3.7009 (16.0); 3.5476 (0.5); 3.5351 (0.5); 3.5163 (0.5); 3.5077 (0.6); 3.0218 (0.7); 3.0077 (0.6); 3.0031 (0.6); 2.7671 (4.6); 0.0696 (2.2); −0.0002 (3.2) | 4.66[a] |
| 11-11 | 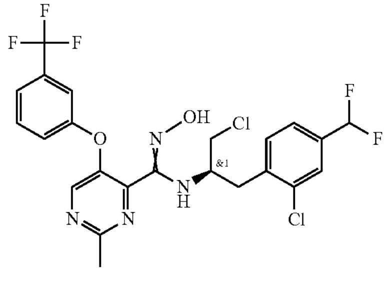 [SMILES: Cc1ncc(Oc2cccc(C(F)(F)F)c2)c(C(=NO)N[C@@H](CCl)Cc2ccc(C(F)F)cc2Cl)n1] | 11-11: $^1$H-NMR(400.1 MHz, CDCl3): δ = 8.3649 (2.2); 7.4425 (0.9); 7.4301 (0.7); 7.4101 (0.6); 7.4038 (0.6); 7.3843 (1.4); 7.3683 (0.4); 7.3454 (0.6); 7.3267 (0.4); 7.2596 (8.8); 7.1913 (0.8); 7.0662 (0.4); 7.0460 (0.4); 6.7099 (0.4); 6.5694 (0.9); 6.4290 (0.4); 5.8179 (0.4); 5.7918 (0.4); 5.2984 (1.9); 3.7019 (16.0); 3.6935 (0.9); 3.6756 (0.6); 3.6650 (0.6); 3.5250 (0.6); 3.5172 (0.6); 3.4969 (0.4); 3.4892 (0.4); 3.1182 (0.4); 3.1003 (0.4); 3.0722 (0.4); 3.0540 (0.4); 2.7420 (6.7); 0.0691 (1.9); 0.0080 (0.4); −0.0002 (13.9); −0.0085 (0.8) | 4.02[a] |

Compounds According to Formula (12)
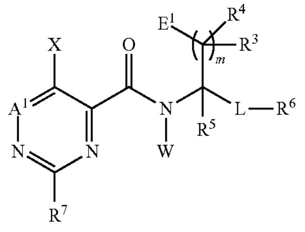
(12)
TABLE 11
| Compounds according to formula (11), their $^1$H-NMR data and LogP values | | | |
|---|---|---|---|
| Ex No | Structure | $^1$H-NMR Peak List | LogP |
| 12-01 | 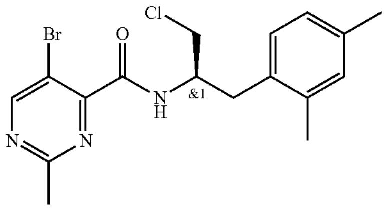 [SMILES: Cc1ccc(C[C@H](CCl)NC(=O)c2nc(C)ncc2Br)c(C)c1] | 12-01: $^1$H-NMR(500.1 MHz, CDCl3): δ = 8.9031 (4.9); 8.2428 (0.8); 8.2264 (0.8); 7.2594 (7.2); 7.1474 (2.1); 7.1321 (2.5); 7.0069 (2.9); 6.9709 (1.6); 6.9555 (1.4); 5.2980 (3.4); 4.5750 (0.5); 4.5672 (0.7); 4.5596 (0.7); 4.5524 (0.8); 4.5447 (0.5); 4.5363 (0.3); 3.7640 (1.0); 3.7560 (1.0); 3.7414 (1.6); 3.7334 (1.5); 3.6595 (1.6); 3.6534 (1.6); 3.6369 (1.1); 3.6307 (1.0); 3.0474 (2.4); 3.0432 (2.3); 3.0306 (3.7); 2.7486 (16.0); 2.4014 (14.0); 2.2908 (13.2); 1.5485 (9.8); 1.2543 (0.3); 0.0695 (2.8); −0.0002 (9.0) | 3.66[a] |
Compounds According to Formula (13)
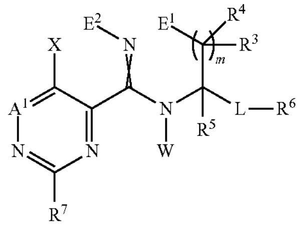
(13)
TABLE 12
| Compounds according to formula (13), their $^1$H-NMR data and LogP values (mixture of stereoisomers) | | | |
|---|---|---|---|
| Ex No | Structure | $^1$H-NMR Peak List | LogP |
| 13-01 | 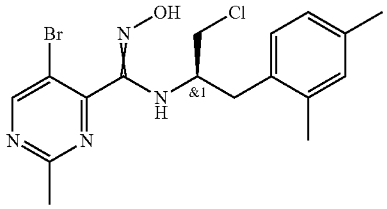 [SMILES: Cc1ccc(C[C@H](CCl)NC(=NO)c2nc(C)ncc2Br)c(C)c1] | 13-01: $^1$H-NMR(400.1 MHz, CDCl3): δ = 8.7981 (5.0); 7.2581 (9.2); 6.9720 (1.8); 6.9523 (3.5); 6.9113 (5.8); 6.8594 (0.6); 5.7311 (1.6); 5.7063 (1.6); 5.2966 (4.7); 3.6154 (1.4); 3.5980 (1.9); 3.5894 (1.8); 3.4844 (3.8); 3.4590 (2.1); 3.0043 (0.8); 2.9704 (1.7); 2.9493 (1.6); 2.8938 (1.7); 2.8812 (1.8); 2.8598 (1.0); 2.8463 (0.9); 2.7348 (0.6); 2.7110 (16.0); 2.3641 (0.4); 2.2935 (0.5); 2.2574 (14.6); 2.0538 (14.9); 1.5667 (1.4); 1.2589 (0.7); 0.0689 (0.6); −0.0002 (12.7); −0.0024 (11.8) | 3.26[a] |

Compounds of Formula (16)
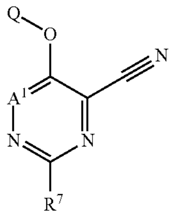
(16)
TABLE 13
| Compounds according to formula (16), their $^1$H-NMR data and LogP values | | | |
|---|---|---|---|
| Ex No | Structure | $^1$H-NMR Peak List | LogP |
| 16-01 | 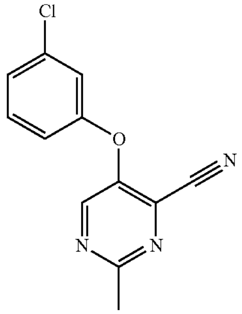 [SMILES: Cc1ncc(Oc2cccc(Cl)c2)c(C#N)n1] | 16-01: $^1$H-NMR(400.1 MHz, CDCl3): δ = 8.4682 (4.4); 7.4002 (1.1); 7.3800 (2.4); 7.3595 (1.6); 7.2830 (1.3); 7.2807 (1.5); 7.2783 (1.4); 7.2760 (1.4); 7.2603 (7.5); 7.2559 (1.3); 7.1139 (1.6); 7.1086 (2.3); 7.1033 (1.4); 7.0024 (1.2); 7.0001 (1.2); 6.9964 (1.1); 6.9941 (1.0); 6.9819 (1.0); 6.9795 (1.0); 6.9758 (1.0); 6.9735 (0.8); 2.8214 (0.4); 2.7713 (16.0); 2.7216 (0.4); 1.6387 (0.6); 1.2550 (0.3); 0.0694 (3.6); 0.0077 (0.8); −0.0002 (9.8); −0.0084 (0.7) | 3.07[a] |
Compounds of Formula (17)
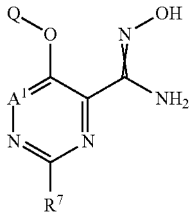
(17)
TABLE 14
| Compounds according to formula (17), their $^1$H-NMR data and LogP values (mixture of stereoisomers) | | | |
|---|---|---|---|
| Ex No | Structure | $^1$H-NMR Peak List | LogP |
| 17-01 | 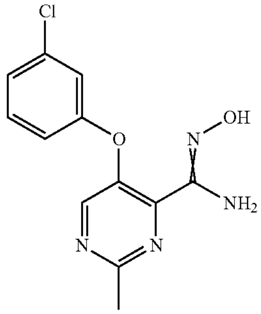 [SMILES: Cc1ncc(Oc2cccc(Cl)c2)c(C(N)=NO)n1] | 17-01: $^1$H-NMR(400.1 MHz, CDCl3): δ = 8.8771 (0.4); 8.4668 (0.4); 8.3376 (5.2); 7.2734 (1.4); 7.2599 (8.1); 7.2532 (3.6); 7.2326 (1.8); 7.1216 (1.6); 7.1193 (1.7); 7.1171 (1.7); 7.1017 (1.4); 7.0993 (1.4); 7.0972 (1.3); 6.9862 (1.5); 6.9810 (2.9); 6.9762 (1.9); 6.8672 (1.5); 6.8614 (1.5); 6.8466 (1.3); 6.8408 (1.3); 5.6095 (2.6); 2.7822 (1.1); 2.7697 (1.6); 2.7529 (16.0); 2.7092 (0.4); 1.5592 (0.9); 1.2540 (0.7); 0.0692 (2.0); −0.0002 (11.6) | 1.66[a] |

Compounds of Formula (19)
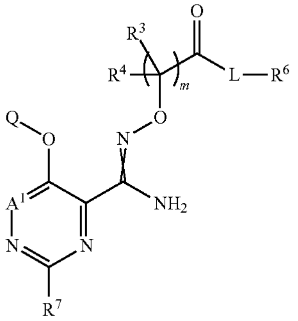
(19)
TABLE 15
Compounds according to formula (19), their $^1$H-NMR data and LogP values (mixture of stereoisomers)
| Ex No | Structure | $^1$H-NMR Peak List | LogP |
|---|---|---|---|
| 19-01 | 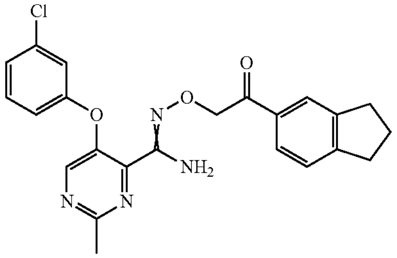 [SMILES: Cc1ncc(Oc2cccc(Cl)c2)c(C(N)=NOCC(=O)c2ccc3c(c2)CCC3)n1] | 19-01: $^1$H-NMR(400.1 MHz, CDCl3): δ = 8.5224 (0.6); 8.4525 (5.0); 8.3724 (1.6); 7.8415 (0.9); 7.8164 (0.5); 7.7883 (0.6); 7.7686 (0.7); 7.7563 (0.4); 7.7366 (0.4); 7.6634 (2.1); 7.6077 (1.2); 7.5883 (1.2); 7.3310 (1.1); 7.3106 (1.4); 7.2939 (0.6); 7.2742 (2.1); 7.2599 (33.7); 7.2423 (1.3); 7.2219 (0.9); 7.2101 (0.6); 7.2051 (0.4); 7.1950 (0.4); 7.1753 (0.3); 7.1617 (0.4); 7.1510 (0.4); 7.1412 (0.5); 7.1276 (0.4); 7.1230 (0.4); 7.1029 (0.6); 7.1005 (0.6); 7.0980 (0.6); 7.0958 (0.6); 7.0826 (0.4); 7.0804 (0.5); 7.0781 (0.5); 7.0758 (0.5); 7.0639 (1.3); 7.0435 (2.6); 7.0231 (1.7); 6.9959 (0.4); 6.9548 (0.4); 6.9493 (0.5); 6.9437 (0.4); 6.9387 (0.7); 6.9335 (0.9); 6.9282 (0.5); 6.8867 (0.4); 6.8680 (0.5); 6.8577 (1.3); 6.8555 (1.3); 6.8530 (1.4); 6.8509 (1.2); 6.8377 (1.0); 6.8356 (1.1); 6.8330 (1.3); 6.8308 (1.3); 6.8248 (0.6); 6.8098 (0.5); 6.8040 (0.4); 6.7588 (1.5); 6.7534 (2.3); 6.7480 (1.5); 6.6053 (1.0); 6.6032 (1.0); 6.5991 (1.0); 6.5972 (1.0); 6.5845 (1.0); 6.5824 (0.9); 6.5784 (1.0); 6.5763 (0.8); 5.6614 (1.4); 5.5875 (0.8); 5.5327 (0.5); 5.2983 (7.4); 5.2540 (0.7); 5.0328 (10.2); 4.6917 (2.5); 4.4376 (4.7); 4.1305 (0.3); 4.1126 (0.4); 3.0020 (0.5); 2.9867 (2.3); 2.9686 (5.6); 2.9513 (6.3); 2.9333 (3.2); 2.9199 (1.3); 2.9021 (0.7); 2.8846 (0.9); 2.8661 (0.5); 2.8603 (0.6); 2.8534 (0.6); 2.8488 (0.6); 2.8329 (1.3); 2.8207 (0.6); 2.8076 (1.6); 2.7957 (0.6); 2.7852 (3.0); 2.7785 (16.0); 2.7665 (5.8); 2.7468 (1.0); 2.7289 (0.5); 2.6904 (0.6); 2.6719 (0.6); 2.4845 (0.5); 2.1674 (0.5); 2.1576 (0.8); 2.1485 (1.6); 2.1387 (2.4); 2.1298 (2.4); 2.1200 (3.4); 2.1113 (1.9); 2.1015 (2.5); 2.0923 (0.9); 2.0829 (1.0); 2.0629 (0.4); 2.0437 (1.8); 2.0050 (0.4); 1.5685 (2.2); 1.4433 (1.8); 1.4411 (1.8); 1.3100 (0.4); 1.3006 (0.4); 1.2835 (0.5); 1.2765 (0.9); 1.2586 (1.9); 1.2436 (0.5); 1.2408 (0.6); 1.2271 (0.5); 1.2093 (0.9); 1.1913 (0.5); 0.8805 (0.4); 0.0782 (0.4); 0.0693 (13.6); 0.0600 (0.7); 0.0499 (0.8); 0.0080 (1.4); −0.0002 (48.6); −0.0084 (2.4); −0.0389 (0.3); −0.0501 (0.8) | 4.15[a] |
| 19-02 | 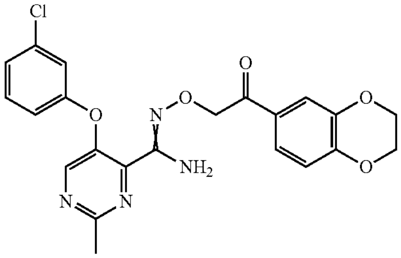 [SMILES: Cc1ncc(Oc2cccc(Cl)c2)c(C(N)=NOCC(=O)c2ccc3c(c2)OCCO3)n1] | 19-02: $^1$H-NMR(400.1 MHz, CDCl3): δ = 8.4521 (5.1); 7.5351 (0.4); 7.5074 (2.0); 7.4870 (0.8); 7.4816 (0.5); 7.4649 (0.3); 7.3732 (2.4); 7.3682 (3.3); 7.3554 (2.0); 7.3502 (1.2); 7.3344 (1.8); 7.3292 (1.5); 7.3115 (0.4); 7.2738 (0.4); 7.2612 (18.1); 7.0861 (1.3); 7.0658 (2.7); 7.0454 (1.7); 6.9454 (0.9); 6.9354 (0.4); 6.9243 (0.8); 6.9176 (0.5); 6.8888 (3.0); 6.8799 (1.4); 6.8780 (1.5); 6.8754 (1.5); 6.8734 (1.4); 6.8678 (2.9); 6.8601 (1.1); 6.8580 (1.2); 6.8555 (1.2); 6.7353 (1.5); 6.7299 (2.4); 6.7245 (1.5); 6.6129 (1.1); 6.6111 (1.1); 6.6068 (1.0); 6.5922 (1.0); 6.5903 (1.0); 6.5861 (1.0); 5.6511 (1.5); 5.2989 (4.6); 4.9713 (10.3); 4.6238 (4.1); 4.3809 (0.4); 4.3718 (0.5); 4.3444 (0.8); 4.3384 (2.1); 4.3354 (2.0); 4.3301 (3.5); 4.3262 (3.2); 4.3214 (3.0); 4.3170 (3.7); 4.2970 (4.5); 4.2920 (3.7); 4.2874 (3.0); 4.2834 (4.2); 4.2782 (2.1); 4.2567 (0.5); 4.1304 (0.4); 4.1125 (0.4); 3.2881 (0.5); 3.2824 (0.6); 3.2704 (1.6); 3.2641 (0.6); 3.2607 (0.6); 3.2526 (1.9); 3.2423 (1.7); 3.2349 (0.9); 3.2246 (1.7); 3.2069 (0.9); 3.1989 (0.5); 3.1880 (0.5); 2.8284 (0.4); 2.8095 (6.2); | 3.12[a] |

TABLE 15-continued

Compounds according to formula (19), their $^{1}$H-NMR data and LogP values (mixture of stereoisomers)

| Ex No | Structure | $^{1}$H-NMR Peak List | LogP |
|---|---|---|---|
| | | 2.7841 (6.9); 2.7778 (16.0); 2.7536 (1.0); 2.7295 (0.4); 2.5295 (0.9); 2.0437 (1.5); 1.5761 (7.5); 1.4950 (0.3); 1.4445 (11.7); 1.4427 (11.2); 1.2765 (0.6); 1.2587 (1.2); 1.2409 (0.5); 1.2280 (2.6); 1.2102 (5.3); 1.1923 (2.6); 0.0692 (2.0); 0.0502 (0.4); 0.0078 (0.8); −0.0002 (27.2); −0.0084 (1.6); −0.0497 (0.5) | |
| 19-03 | 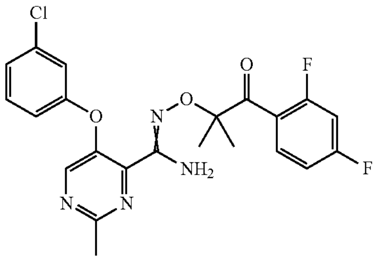 [SMILES: Cc1ncc(Oc2cccc(Cl)c2)c(C(N)=NOC(C)(C)C(=O)c2ccc(F)cc2F)n1] | | 3.41& 4.35[a] |
| 19-04 | 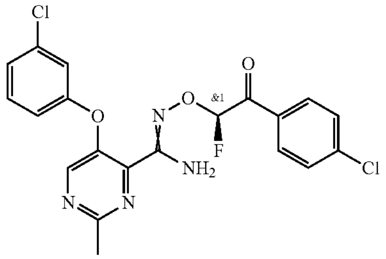 [SMILES: Cc1ncc(Oc2cccc(Cl)c2)c(C(N)=NO[C@H](F)C(=O)c2ccc(Cl)cc2)n1] | | 3.40& 4.01[a] |

Compounds of Formula (20)

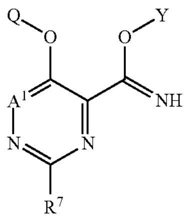

(20)

TABLE 16

Compounds according to formula (20), their LogP values

| Ex No | Structure | LogP |
|---|---|---|
| 20-01 | 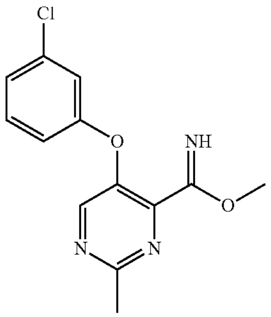 [SMILES: COC(=N)c1nc(C)ncc1Oc1cccc(Cl)c1] | 2.19[a] |

B. Biological Examples

B-1. *Alternaria alternata* In Vitro Cell Test

Solvent: DMSO

Culture medium: 14.6 g anhydrous D-glucose (VWR), 7.1 g Mycological Peptone (Oxoid), 1.4 g granulated Yeast Extract (Merck), QSP 1 liter Inoculum: spore suspension Fungicides were solubilized in DMSO and the solution used to prepare the required range of concentrations. The final concentration of DMSO used in the assay was ≤1%.

A spore suspension of *A. alternata* was prepared and diluted to the desired spore density.

Fungicides were evaluated for their ability to inhibit spore germination and mycelium growth in liquid culture assay. The compounds were added in the desired concentration to the culture medium with spores. After 5 days incubation, fungi-toxicity of compounds was determined by spectrometric measurement of mycelium growth. Inhibition of fungal growth was determined by comparing the absorbance values in wells containing the fungicides with the absorbance in control wells without fungicides.

In this test the following compounds according to the invention showed efficacy between 70% and 79% at a concentration of 20 ppm of active ingredient: I-007; I-015; I-017

In this test the following compounds according to the invention showed efficacy between 80% and 89% at a concentration of 20 ppm of active ingredient: I-030

In this test the following compounds according to the invention showed efficacy between 90% and 100% at a concentration of 20 ppm of active ingredient: I-001; I-002;

I-003; I-004; I-005; I-006; I-008; 1-009; I-013; I-014; I-016; I-018; I-019; I-021; I-023; I-024; I-025; I-026; I-027; I-028; I-029; I-031; I-032; I-033; I-034

B-2. *Pyricularia oryzae* In Vitro Cell Test

Solvent: DMSO

Culture medium: 14.6 g anhydrous D-glucose (VWR), 7.1 g Mycological Peptone (Oxoid), 1.4 g granulated Yeast Extract (Merck), QSP 1 liter Inoculum: spore suspension Fungicides were solubilized in DMSO and the solution used to prepare the required range of concentrations. The final concentration of DMSO used in the assay was ≤1%.

A spore suspension of *P. oryzae* was prepared and diluted to the desired spore density.

Fungicides were evaluated for their ability to inhibit spore germination and mycelium growth in liquid culture assay. The compounds were added in the desired concentration to the culture medium with spores. After 5 days incubation, fungi-toxicity of compounds was determined by spectrometric measurement of mycelium growth. Inhibition of fungal growth was determined by comparing the absorbance values in wells containing the fungicides with the absorbance in control wells without fungicides.

In this test the following compounds according to the invention showed efficacy between 70% and 79% at a concentration of 20 ppm of active ingredient: I-006; I-033

In this test the following compounds according to the invention showed efficacy between 80% and 89% at a concentration of 20 ppm of active ingredient: I-001; I-005; I-032

In this test the following compounds according to the invention showed efficacy between 90% and 100% at a concentration of 20 ppm of active ingredient: I-002; I-003; I-004; I-008; I-009; I-014; I-016; I-018; I-019; I-021; I-023; I-024; I-025; I-026; I-028; I-029; I-031

B-3. *Colletotrichum lindemuthianum* In Vitro Cell Test

Solvent: DMSO

Culture medium: 14.6 g anhydrous D-glucose (VWR), 7.1 g Mycological Peptone (Oxoid), 1.4 g granulated Yeast Extract (Merck), QSP 1 liter Inoculum: spore suspension Fungicides were solubilized in DMSO and the solution used to prepare the required range of concentrations. The final concentration of DMSO used in the assay was ≤1%.

A spore suspension of *C. lindemuthianum* was prepared and diluted to the desired spore density.

Fungicides were evaluated for their ability to inhibit spores germination and mycelium growth in liquid culture assay. The compounds were added in the desired concentration to the culture medium with spores. After 6 days incubation, fungi-toxicity of compounds was determined by spectrometric measurement of mycelium growth. Inhibition of fungal growth was determined by comparing the absorbance values in wells containing the fungicides with the absorbance in control wells without fungicides.

In this test the following compounds according to the invention showed efficacy between 70% and 79% at a concentration of 20 ppm of active ingredient: I-034

In this test the following compounds according to the invention showed efficacy between 90% and 100% at a concentration of 20 ppm of active ingredient: I-001; I-002; I-003; I-004; I-005; I-006; I-007; 1-008; I-009; I-013; I-014; I-015; I-016; I-017; I-018; I-019; I-020; I-021; I-023; I-024; I-025; I-026; I-029; I-030; I-031; I-032; I-033

B-4. *Pyrenophora teres* In Vitro Cell Test

Solvent: DMSO

Culture medium: 14.6 g anhydrous D-glucose (VWR), 7.1 g Mycological Peptone (Oxoid), 1.4 g granulated Yeast Extract (Merck), QSP 1 liter Inoculum: spore suspension Fungicides were solubilized in DMSO and the solution used to prepare the required range of concentrations. The final concentration of DMSO used in the assay was ≤□1%.

A spore suspension of *P. teres* was prepared and diluted to the desired spore density.

Fungicides were evaluated for their ability to inhibit spore germination and mycelium growth in liquid culture assay. The compounds were added in the desired concentration to the culture medium with spores. After 6 days incubation, fungi-toxicity of compounds was determined by spectrometric measurement of mycelium growth. Inhibition of fungal growth was determined by comparing the absorbance values in wells containing the fungicides with the absorbance in control wells without fungicides.

In this test the following compounds according to the invention showed efficacy between 90% and 100% at a concentration of 20 ppm of active ingredient: I-001; I-002; I-003; I-004; I-005; I-006; I-007; 1-008; I-009; I-012; I-013; I-014; I-015; I-016; I-017; I-018; I-019; I-020; I-021; I-023; I-024; I-025; I-026; I-027; I-028; I-029; I-030; I-031; I-032; I-033; I-034

B-5. *Botrytis cinerea* In Vitro Cell Test

Solvent: DMSO

Culture medium: 1 g $KH_2PO_4$ (VWR), 1 g $K_2HPO_4$ (VWR), 0.5 g Urea (VWR), 3 g $KNO_3$ (Prolabo), 10 g saccharose (VWR), 0.5 g $MgSO_4$, $7H_2O$ (Sigma), 0.07 g $CaCl_2$, $2H_2O$ (Prolabo), 0.2 mg $MnSO_4$, $H_2O$ (Sigma), 0.6 mg $CuSO_4$, $5H_2O$ (Sigma), 7.9 mg $ZnSO_4$, $7H_2O$ (Sigma), 0.1 mg $H_3BO_3$ (Merck), 0.14 mg $NaMoO_4$, $2H_2O$ (Sigma), 2 mg thiamine (Sigma), 0.1 mg biotine (VWR), 4 mg $FeSO_4$, $7H_2O$ (Sigma), QSP 1 liter Inoculum: spore suspension Fungicides were solubilized in DMSO and the solution used to prepare the required range of concentrations. The final concentration of DMSO used in the assay was ≤1%.

A spore suspension of *B. cinerea* was prepared and diluted to the desired spore density.

Fungicides were evaluated for their ability to inhibit spore germination and mycelium growth in liquid culture assay. The compounds were added in the desired concentration to the culture medium with spores. After 6 days incubation, fungi-toxicity of compounds was determined by spectrometric measurement of mycelium growth. Inhibition of fungal growth was determined by comparing the absorbance values in wells containing the fungicides with the absorbance in control wells without fungicides.

In this test the following compounds according to the invention showed efficacy between 90% and 100% at a concentration of 20 ppm of active ingredient: I-001; I-002; I-003; I-004; I-005; I-006; I-007; 1-008; I-009; I-012; I-013; I-014; I-015; I-016; I-017; I-018; I-019; I-020; I-021; I-023; I-024; I-025; I-026; I-027; I-028; I-029; I-030; I-031; I-032; I-033; I-034

B-6. *Septoria tritici* In Vitro Cell Test

Solvent: DMSO

Culture medium: 1 g $KH_2PO_4$ (VWR), 1 g $K_2HPO_4$ (VWR), 0.5 g Urea (VWR), 3 g $KNO_3$ (Prolabo), 10 g saccharose (VWR), 0.5 g $MgSO_4$, $7H_2O$ (Sigma), 0.07 g $CaCl_2$, $2H_2O$ (Prolabo), 0.2 mg $MnSO_4$, $H_2O$ (Sigma), 0.6 mg $CuSO_4$, $5H_2O$ (Sigma), 7.9 mg $ZnSO_4$, $7H_2O$ (Sigma), 0.1 mg $H_3BO_3$ (Merck), 0.14 mg $NaMoO_4$, $2H_2O$ (Sigma), 2 mg thiamine (Sigma), 0.1 mg biotine (VWR), 4 mg $FeSO_4$, $7H_2O$ (Sigma), QSP 1 liter Inoculum: spore suspension Fungicides were solubilized in DMSO and the solution used to prepare the required range of concentrations. The final concentration of DMSO used in the assay was ≤1%.

A spore suspension of *S. tritici* was prepared and diluted to the desired spore density.

Fungicides were evaluated for their ability to inhibit spore germination and mycelium growth in liquid culture assay. The compounds were added in the desired concentration to the culture medium with spores. After 7 days incubation, fungi-toxicity of compounds was determined by spectrometric measurement of mycelium growth. Inhibition of fungal growth was determined by comparing the absorbance values in wells containing the fungicides with the absorbance in control wells without fungicides.

In this test the following compounds according to the invention showed efficacy between 70% and 79% at a concentration of 20 ppm of active ingredient: I-017; I-020; I-030

In this test the following compounds according to the invention showed efficacy between 80% and 89% at a concentration of 20 ppm of active ingredient: I-023 In this test the following compounds according to the invention showed efficacy between 90% and 100% at a concentration of 20 ppm of active ingredient: I-001; I-002; I-003; I-004; I-005; I-006; I-008; 1-009; I-013; I-014; 1-016; I-018; 1-019; I-021; 1-024; I-025; 1-026; I-027; 1-028; I-029; I-032; 1-033

B-7. In Vivo Preventive Test on *Alternaria brassicae* (Leaf Spot on Radish or Cabbage)

Solvent: 5% by volume of Dimethyl sulfoxide
10% by volume of Acetone

Emulsifier: 1 µl of Tween® 80 per mg of active ingredient

The active ingredients were made soluble and homogenized in a mixture of Dimethyl sulfoxide/Acetone// Tween®80 and then diluted in water to the desired concentration.

The young plants of radish or cabbage were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Alternaria brassicae* spores. The contaminated radish or cabbage plants were incubated for 3 to 4 days at 20° C. and at 100% relative humidity.

The test was evaluated 6 days after the inoculation. 0% means an efficacy which corresponds to that of the control plants while an efficacy of 100% means that no disease was observed.

In this test the following compounds according to the invention showed efficacy between 80% and 89% at a concentration of 500 ppm of active ingredient: I-015; I-030

In this test the following compounds according to the invention showed efficacy between 90% and 100% at a concentration of 500 ppm of active ingredient: I-001; I-002; I-003; I-004; I-005; I-006; I-007; I-008; I-009; I-012; I-013; I-014; I-016; I-017; I-018; I-019; I-020; I-021; I-023; I-024; I-025; I-026; I-027; I-029; I-032; I-033

B-8. In Vivo Preventive Test on *Botrytis cinerea* (Grey Mould)

Solvent: 5% by volume of Dimethyl sulfoxide
10% by volume of Acetone

Emulsifier: 1 µl of Tween® 80 per mg of active ingredient

The active ingredients were made soluble and homogenized in a mixture of Dimethyl sulfoxide/Acetone// Tween®80 and then diluted in water to the desired concentration.

The young plants of gherkin or cabbage were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Botrytis cinerea* spores. The contaminated gherkin plants were incubated for 4 to 5 days at 17° C. and at 90% relative humidity. The contaminated cabbage plants were incubated for 4 to 5 days at 20° C. and at 100% relative humidity.

The test was evaluated 4 to 5 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: I-015

In this test the following compounds according to the invention showed efficacy between 80% and 89% at a concentration of 500 ppm of active ingredient: I-006

In this test the following compounds according to the invention showed efficacy between 90% and 100% at a concentration of 500 ppm of active ingredient: I-001; I-002; I-003; I-004; I-005; I-007; I-008; I-009; I-012; I-013; I-014; I-016; I-017; I-018; I-019; I-020; I-021; I-023; I-024; I-025; I-026; I-027; I-029; I-030; I-032; I-033

B-9. In Vivo Preventive Test on *Sphaerotheca fuliginea* (Powdery Mildew on Cucurbits)

Solvent: 5% by volume of Dimethyl sulfoxide
10% by volume of Acetone

Emulsifier: 1 µl of Tween® 80 per mg of active ingredient

The active ingredients were made soluble and homogenized in a mixture of Dimethyl sulfoxide/Acetone// Tween®80 and then diluted in water to the desired concentration.

The young plants of gherkin were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Sphaerotheca fuliginea* spores. The contaminated gherkin plants were incubated for 8 days at 20° C. and at 70-80% relative humidity.

The test was evaluated 8 days after the inoculation. 0% means an efficacy which corresponds to that of the control plants while an efficacy of 100% means that no disease was observed.

In this test the following compounds according to the invention showed efficacy between 80% and 89% at a concentration of 500 ppm of active ingredient: I-003; I-015; I-019

In this test the following compounds according to the invention showed efficacy between 90% and 100% at a concentration of 500 ppm of active ingredient: I-001; I-002; I-004; I-005; I-006; I-007; I-008; I-009; I-012; I-013; I-014; I-016; I-017; I-018; I-020; I-021; I-023; I-024; I-025; I-026; I-027; I-029; I-030; I-032; I-033

B-10. In Vivo Preventive Test on *Colletotrichum lindemuthianum* (Leaf Spot on Bean)

Solvent: 5% by volume of Dimethyl sulfoxide
10% by volume of Acetone

Emulsifier: 1 μl of Tween® 80 per mg of active ingredient

The active ingredients were made soluble and homogenized in a mixture of Dimethyl sulfoxide/Acetone// Tween®80 and then diluted in water to the desired concentration.

The young plants of bean were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Colletotrichum lindemuthianum* spores. The contaminated bean plants were incubated for 24 hours at 20° C. and at 100% relative humidity and then for 6 days at 20° C. and at 90% relative humidity.

The test was evaluated 7 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: I-030

In this test the following compounds according to the invention showed efficacy between 80% and 89% at a concentration of 500 ppm of active ingredient: I-017; I-033

In this test the following compounds according to the invention showed efficacy between 90% and 100% at a concentration of 500 ppm of active ingredient: I-001; I-002; I-004; I-005; I-006; I-007; I-008; I-009; I-012; I-013; I-015; I-016; I-018; I-019; I-021; I-023; I-024; I-025; I-026; I-027; I-029; I-032

The invention claimed is:

1. A compound of formula (I):

(I)

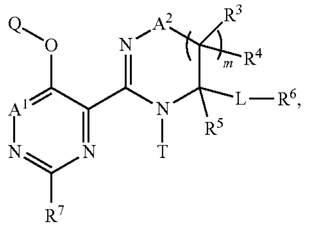

wherein $A^1$ is N or $CR^8$, wherein $R^8$ is hydrogen, halogen, cyano or $C_1$-$C_4$-alkyl, $A^2$ is O, S, C(═O), S(═O), $S(═O)_2$, $NR^1$ or $CR^{2A}R^{R2B}$, wherein $R^1$ is hydrogen, formyl, $C_1$-$C_6$-alkyl or $C_3$-$C_8$-cycloalkyl, wherein $C_1$-$C_6$-alkyl is optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, $R^{2A}$ and $R^{2B}$ are independently hydrogen, $C_1$-$C_6$-alkyl or $C_3$-$C_8$-cycloalkyl, wherein $C_1$-$C_6$-alkyl is optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_5$-cycloalkyl, $C_3$-$C_8$-halocycloalkyl, —O—Si($C_1$-$C_6$-alkyl)$_3$ and 3- to 7-membered heterocyclyl, or $R^{2A}$ and $R^{2B}$ form together with the carbon atom to which they are attached to a $C_3$-$C_8$-cycloalkyl-ring or a 3- to 7-membered heterocyclyl-ring, m is 0, 1 or 2, T is hydrogen, hydroxyl, $C_1$-$C_6$-alkyl, —C(═O)$R^{11}$, —C(═O)($OR^{12}$), —C(═O)N($R^{13}$)$_2$, —S(═O)$R^{14}$, —S(═O)$_2R^{14}$ or —S(═O)$_2$N($R^{14}$)$_2$, wherein $R^{11}$ and $R^{12}$ are independently $C_1$-$C_6$-alkyl, $C_1$-$C_6$-haloalkyl, $C_3$-$C_8$-cycloalkyl or $C_2$-$C_6$-alkenyl, $R^{13}$ and $R^{14}$ are independently hydrogen, $C_1$-$C_6$-alkyl, $C_1$-$C_6$-haloalkyl, $C_3$-$C_8$-cycloalkyl or $C_2$-$C_6$-alkenyl, $R^3$ and $R^4$ are independently hydrogen, halogen, cyano, hydroxyl, formyl, carboxyl, $C_1$-$C_6$-alkyl, $C_1$-$C_6$-alkoxy, $C_1$-$C_6$-alkylcarbonyl, $C_1$-$C_6$-alkylcarbonyloxy, $C_1$-$C_6$-alkoxycarbonyl, $C_2$-$C_6$-alkenyl, $C_2$-$C_6$-alkynyl, $C_3$-$C_8$-cycloalkyl, $C_6$-$C_{14}$-aryl, 5- to 14-membered heteroaryl, 3- to 14-membered heterocyclyl or —O—Si($C_1$-$C_6$-alkyl)$_3$, wherein $C_1$-$C_6$-alkyl, $C_1$-$C_6$-alkoxy, $C_1$-$C_6$-alkylcarbonyl, $C_1$-$C_6$-alkyl-carbonyloxy, $C_1$-$C_6$-alkoxycarbonyl, $C_2$-$C_6$-alkenyl, $C_2$-$C_6$-alkynyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$- haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl, $C_6$-$C_{14}$-aryl, 5- to 14-membered heteroaryl and 3- to 14-membered heterocyclyl are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^4$ form together with the carbon atom to which they are attached to a carbonyl, a methylidene, a $C_3$-$C_8$-cycloalkyl-ring or a 3- to 7-membered heterocyclyl-ring, wherein $C_3$-$C_8$-cycloalkyl-ring and 3- to 7-membered heterocyclyl-ring are optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-halo-alkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, $R^5$ is hydrogen, hydroxyl, $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl, $C_3$-$C_8$-cycloalkyl or —O—Si($C_1$-$C_6$-alkyl)$_3$, wherein $C_1$-$C_6$-alkyl, $C_1$-$C_6$-alkoxy, $C_1$-$C_6$-alkylcarbonyloxy, $C_1$-$C_6$-alkylsulfanyl, $C_1$-$C_6$-alkylsulfinyl, $C_1$-$C_6$-alkylsulfonyl and —O—Si($C_1$-$C_6$-alkyl)$_3$ are optionally substituted with one to three substituents independently selected from the group consisting of halogen, cyano, amino, nitro, hydroxyl, formyl, carboxyl, $C_1$-$C_6$-alkoxy, $C_1$-$C_6$-haloalkoxy, $C_1$-$C_6$-alkoxycarbonyl, $C_3$-$C_8$-cycloalkyl, $C_3$-$C_8$-halocycloalkyl, —O—Si($C_1$-$C_6$-alkyl)$_3$ and 3- to 7-membered heterocyclyl, and wherein $C_3$-$C_8$-cycloalkyl is optionally substituted with one to three substituents independently selected from the group consisting of halogen, cyano, nitro, hydroxyl, formyl, oxo, methylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ and 3- to 7-membered heterocyclyl, or $R^3$ and $R^5$ or $R^4$ and $R^5$ form together with the carbon atom to which they are attached to a $C_3$-$C_8$-cycloalkyl-ring, L is a direct bond, carbonyl, $C_1$-$C_6$-alkylene, $C_2$-$C_6$-alkenylene, $C_2$-$C_6$-alkynylene, —C(═O)—$C_1$-$C_6$-alkylene-, —$C_1$-$C_6$-alkylene-C(═O)—, —$NR^{L1}$—, —$NR^{L2}$(C═O)—, —C(═O)$NR^{L3}$—, —$NR^{L4}$S(═O)$_2$—, —S(═O)$_2$$NR^{L5}$—, —C(═$NOR^{L6}$)—, —C(═N—N($R^{L7}$)$_2$)—, —C(═$NR^{L8}$)— or a group of formula

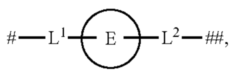

wherein said $C_1$-$C_6$-alkylene, $C_2$-$C_6$-alkenylene, $C_2$-$C_6$-alkynylene, —C(═O)—$C_1$-$C_6$-alkylene- and —$C_1$-$C_6$-alkylene-C(═O)— are optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl, $C_3$-$C_8$-cycloalkenyl or 3- to 7-membered heterocyclyl, wherein said $C_3$-$C_8$-cycloalkyl, $C_3$-$C_8$-cycloalkenyl and 3- to 7-membered heterocyclyl in turn are optionally substituted with one to three substituents $L^{SC}$, $R^{L1}$, $R^{L2}$, $R^{L3}$ and $R^{L4}$ are independently hydrogen or $C_1$-$C_6$-alkyl, $R^{L5}$, $R^{L6}$, $R^{L7}$ and $R^{L8}$ are independently hydrogen, $C_1$-$C_6$-alkyl, $C_1$-$C_6$-haloalkyl, $C_3$-$C_8$-cycloalkyl or $C_2$-$C_6$-alkenyl, wherein $L^{SA}$ is independently halogen, cyano, hydroxyl, carboxyl, methylidene, halomethylidene, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$ or 3- to 7-membered heterocyclyl, and/or two substituents $L^{SA}$ that are bound to the same carbon atom form together with the carbon atom which they are attached to a $C_3$-$C_8$-cycloalkyl-ring or a 3- to 7-membered heterocyclyl-ring, $L^{SC}$ is independently halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, and/or two $L^{SC}$ substituents form together with the carbon atom to which they are attached to a $C_3$-$C_8$-cycloalkyl-ring, $R^6$ is $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl, 3- to 14-membered heterocyclylsulfonyl, $C_1$-$C_3$-alkoxy, $C_1$-$C_3$-haloalkoxy, $C_1$-$C_3$-alkylsulfanyl, $C_1$-$C_3$-alkylsulfinyl or $C_1$-$C_3$-alkylsulfonyl, wherein $C_1$-$C_3$-alkoxy, $C_1$-$C_3$-haloalkoxy, $C_1$-$C_3$-alkylsulfanyl, $C_1$-$C_3$-alkylsulfinyl and $C_1$-$C_3$-alkylsulfonyl are substituted with one substituent selected from the group consisting of $C_3$-$C_{12}$-carbocyclyl, $C_6$-$C_{14}$-aryl, 3- to 14-membered heterocyclyl and 5- to 14-membered heteroaryl, wherein said $C_3$-$C_{12}$-carbocyclyl, $C_6$-$C_{14}$-aryl, 3- to 14-membered heterocyclyl and 5- to 14-membered heteroaryl in turn are optionally substituted with one to four $R^{6S}$ substituents, wherein $C_3$-$C_{12}$-carbocyclyl, $C_6$-$C_{14}$-aryl, 3- to 14-membered heterocyclyl, 5- to 14-membered heteroaryl, $C_3$-$C_{12}$-carbocyclyloxy, $C_6$-$C_{14}$-aryloxy, 5- to 14-membered heteroaryloxy, 3- to 14-membered heterocyclyloxy, $C_3$-$C_{12}$-carbocyclylsulfanyl, $C_6$-$C_{14}$-arylsulfanyl, 5- to 14-membered heteroarylsulfanyl, 3- to 14-membered heterocyclylsulfanyl, $C_3$-$C_{12}$-carbocyclylsulfinyl, $C_6$-$C_{14}$-arylsulfinyl, 5- to 14-membered heteroarylsulfinyl, 3- to 14-membered heterocyclylsulfinyl, $C_3$-$C_{12}$-carbocyclylsulfonyl, $C_6$-$C_{14}$-arylsulfonyl, 5- to 14-membered heteroarylsulfonyl and 3- to 14-membered heterocyclylsulfonyl are optionally substituted with one to four $R^{6S}$ substituents, wherein $R^{6S}$ is independently selected from the group consisting of halogen, cyano, isocyano, nitro, hydroxyl, mercapto, pentafluorosulfanyl, oxo, methylidene, halomethylidene, formyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_3$-$C_8$-cycloalkylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl, 3- to 7-membered heterocyclyl, —$N(R^{15})_2$, —O(C═O)$R^{16}$, —C(═O)$R^{16}$, —C(═O)($OR^{17}$), —C(═O)$N(R^{18})_2$, —S(═O)$_2$N$(R^{19})_2$, —O—Si($C_1$-$C_6$-alkyl)$_3$ and —Si($C_1$-$C_6$-alkyl)$_3$, wherein $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkylnyloxy, $C_2$-$C_6$-haloalkylnyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are furthermore optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halo-cycloalkyl and 3- to 7-membered heterocyclyl, or two substituents $C_1$-$C_6$-alkyl attached to the same carbon atom from a $C_3$-$C_8$-cycloalkyl-ring, and wherein $C_3$-$C_8$-cycloalkylsulfanyl, $C_3$-$C_8$-cycloalkylsulfinyl, $C_3$-$C_8$-cycloalkylsulfonyl, $C_3$-$C_8$-cycloalkyl, $C_3$-$C_8$-cycloalkyloxy, $C_3$-$C_8$-cycloalkenyl, $C_6$-$C_{14}$-aryl, 5- or 6-membered heteroaryl and 3- to 7-membered heterocyclyl are furthermore optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-halo-alkoxycarbonyl, $C_2$-$C_6$-alkenyl, $C_3$-$C_8$-cycloalkyl and $C_3$-$C_8$-halo-cycloalkyl, and wherein $R^{15}$ is independently hydrogen, $C_1$-$C_6$-alkyl or $C_3$-$C_8$-cycloalkyl, wherein said $C_1$-$C_6$-alkyl in turn is optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocycloalkyl and 3- to 7-membered heterocyclyl, and wherein said $C_3$-$C_8$-cycloalkyl in turn is optionally substituted with one to four substituents independently selected from the group consisting of halogen, cyano, nitro, hydroxyl, formyl, carboxyl, oxo, methylidene, halomethylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_3$-$C_8$-cycloalkyl and $C_3$-$C_8$-halo-cycloalkyl, $R^{16}$, $R^{17}$, $R^{18}$ and $R^{19}$ are independently hydrogen, $C_1$-$C_6$-alkyl or $C_1$-$C_6$-haloalkyl, wherein said $C_1$-$C_6$-alkyl and $C_1$-$C_6$-haloalkyl in turn are optionally substituted with one to three substituents independently selected from the group consisting of halogen, cyano, hydroxyl, $C_1$-$C_6$-alkoxy, $C_1$-$C_6$-haloalkoxy, —O—Si($C_1$-$C_6$-alkyl)$_3$, —Si($C_1$-$C_6$-alkyl)$_3$, $C_3$-$C_8$-cycloalkyl, $C_3$-$C_8$-halocyclo-alkyl and 3- to 7-membered heterocyclyl, $R^7$ is hydrogen, halogen, cyano, isocyano, hydroxyl, mercapto, nitro, amino, formyl, $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_3$-$C_8$-cyclo-alkylsulfanyl, $C_2$-$C_6$-alkenylsulfanyl, $C_2$-$C_6$-alkynylsulfanyl, $C_1$-$C_6$-alkylsulfinyl, $C_1$-$C_6$-haloalkylsulfinyl, $C_3$-$C_8$-cycloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered hetero-aryloxy, 3- to 7-membered heterocyclyloxy, —O—Si($C_1$-$C_6$-alkyl)$_3$, —Si($C_1$-$C_6$-alkyl)$_3$, —$N(R^{20})_2$, —C(═$NR^{21}$)$R^{22}$, —$NR^{23}$C(═O)$R^{24}$, —C(═O)($OR^{25}$), —C(═O)$N(R^{26})_2$, —S(═O)$_2$N$(R^{27})_2$ or —S(═O)(═$NR^{28}$)$R^{29}$, wherein $C_1$-$C_6$-alkyl, $C_1$-$C_6$-haloalkyl, $C_1$-$C_6$-hydroxyalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkylsulfanyl, $C_1$-$C_6$-haloalkylsulfanyl, $C_2$-$C_6$-alkenyl-sulfanyl, $C_2$-$C_6$-alkynylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ are optionally substituted with one to three $R^{7Sa}$ substituents, wherein $C_3$-$C_8$-cycloalkylsulfanyl, $C_3$-$C_8$-cycloalkylsulfinyl, $C_3$-$C_8$-cycloalkyl-sulfonyl, $C_3$-$C_8$-cycloalkyl, $C_3$-$C_6$-cycloalkenyl, $C_6$-$C_{14}$-aryl, 5- or 6-membered heteroaryl, 3- to 7-membered heterocyclyl, $C_3$-$C_8$-cycloalkyloxy, $C_6$-$C_{14}$-aryloxy, 5- or 6-membered heteroaryloxy, 3- to 7-membered heterocyclyloxy are optionally substituted with one to three $R^{7Sc}$ substituents, and wherein $R^{20}$ is independently hydrogen, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_6$-$C_{14}$-aryl, 5- or 6-membered heteroaryl or 3- to 7-membered heterocyclyl, wherein $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl, $C_2$-$C_6$-alkynyl and $C_2$-$C_6$-haloalkynyl in turn are optionally substituted with one to three substituents $R^{7Sa}$, and wherein $C_3$-$C_8$-cycloalkyl, $C_3$-$C_8$-halocycloalkyl, $C_6$-$C_{14}$-aryl, 5- or 6-membered heteroaryl and 3- to 7-membered heterocyclyl in turn are optionally substituted with one to three substituents $R^{7Sc}$, $R^{21}$ and $R^{22}$ are independently hydroxyl, amino, cyano, $C_1$-$C_6$-alkyl, $C_1$-$C_6$-halo-alkyl, $C_1$-$C_6$-alkoxy, mono-($C_1$-$C_6$-alkyl)amino or di-($C_1$-$C_6$-alkyl) amino, wherein $C_1$-$C_6$-alkyl, $C_1$-$C_6$-haloalkyl, $C_1$-$C_6$-alkoxy, mono-($C_1$-$C_6$-alkyl)amino and di-($C_1$-$C_6$-alkyl)amino in turn are optionally substituted with one to three $R^{7Sa}$ substituents, $R^{23}$, $R^{24}$, $R^{25}$, $R^{26}$, $R^{27}$, $R^{28}$ and $R^{29}$ are independently hydrogen, $C_1$-$C_6$-alkyl, $C_1$-$C_6$-haloalkyl and $C_3$-$C_8$-cycloalkyl, wherein $C_1$-$C_6$-alkyl and $C_1$-$C_6$-haloalkyl in turn are optionally substituted with one to three $R^{7Sa}$ substituents, and wherein $C_3$-$C_8$-cycloalkyl in turn is optionally substituted with one to three $R^{7Sc}$ substituents, wherein $R^{7Sa}$ is independently cyano, hydroxyl, carboxyl, $C_1$-$C_6$-alkoxy, $C_1$-$C_6$-haloalkoxy, $C_3$-$C_8$-cycloalkyl, $C_3$-$C_8$-halocycloalkyl, $C_1$-$C_6$-alkoxycarbonyl, —O—Si($C_1$-$C_6$-alkyl)$_3$, —Si($C_1$-$C_6$-alkyl)$_3$, $C_6$-$C_{14}$-aryl or 3- to 7-membered heterocyclyl, $R^{7Sc}$ is independently halogen, cyano, nitro, hydroxyl, formyl, oxo, methylidene, halomethylidene, $C_1$-$C_6$-alkyl, $C_1$-$C_6$-haloalkyl $C_1$-$C_6$-alkoxy, $C_1$-$C_6$-haloalkoxy, $C_2$-$C_6$-alkenyl, $C_3$-$C_8$-cycloalkyl, $C_3$-$C_8$-halocycloalkyl, —O—Si($C_1$-$C_6$-alkyl)$_3$ or 3- to 7-membered heterocyclyl, or two $R^{7Sc}$ substituents $C_1$-$C_6$-alkyl that are bound to the same carbon atom form together a $C_3$-$C_8$-cycloalkyl-ring, Q is $C_6$-$C_{14}$-aryl, $C_3$-$C_{12}$-carbocyclyl, 3- to 14-membered heterocyclyl or 5- to 14-membered heteroaryl, wherein $C_6$-$C_{14}$-aryl, $C_3$-$C_{12}$-carbocyclyl, 3- to 14-membered heterocyclyl or 5- to 14-membered heteroaryl are optionally substituted with one to five substituents $Q^S$ wherein $Q^S$ is independently selected from the group consisting of halogen, cyano, isocyano, nitro, hydroxyl, mercapto, formyl, carboxyl, $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyloxy, $C_3$-$C_6$-cycloalkenyl, 3- to 7-membered heterocyclyl, $C_6$-$C_{14}$-aryl, 5- to 14-membered heteroaryl, —O—Si($C_1$-$C_6$-alkyl)$_3$, —Si($C_1$-$C_6$-alkyl)$_3$, —O—C(═O)$R^{33}$, —N$R^{34}$C(═O)$R^{35}$, —C(═O)N($R^{36}$)$_2$, —C(═S)$R^{37}$, —C(═S)N($R^{38}$)$_2$, —C(═N$R^{39}$)$R^{40}$, —C(═NO$R^{41}$)$R^{42}$ and —N($R^{43}$)$_2$, wherein said $C_1$-$C_6$-alkyl, $C_1$-$C_6$-haloalkyl, $C_1$-$C_6$-alkylcarbonyl, $C_1$-$C_6$-halo-alkylcarbonyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxycarbonyl, $C_1$-$C_6$-haloalkoxycarbonyl, $C_2$-$C_6$-alkenyl, $C_2$-$C_6$-haloalkenyl, $C_2$-$C_6$-alkynyl, $C_2$-$C_6$-haloalkynyl, $C_2$-$C_6$-alkenyloxy, $C_2$-$C_6$-haloalkenyloxy, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —O—Si($C_1$-$C_6$-alkyl)$_3$ and —Si($C_1$-$C_6$-alkyl)$_3$ in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, said $C_3$-$C_8$-cycloalkyl, $C_3$-$C_8$-cycloalkoxy, $C_3$-$C_6$-cycloalkenyl, 3- to 7-membered heterocyclyl and 5- to 14-membered heteroaryl in turn are optionally substituted with one to three substituents independently selected from the group consisting of halogen, cyano, amino, nitro, hydroxyl, formyl, carboxyl, oxo, methylidene, halo-methylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl, and wherein $R^{33}$ is hydrogen, $C_1$-$C_6$-alkyl, $C_1$-$C_6$-haloalkyl and $C_1$-$C_6$-alkoxy, $R^{34}$, $R^{35}$, $R^{36}$ $R^{37}$ $R^{38}$ $R^{39}$ $R^{40}$ $R^{41}$ and $R^{42}$ are independently hydrogen, $C_1$-$C_6$-alkyl, $C_1$-$C_6$-haloalkyl or $C_1$-$C_6$-alkoxy, wherein said $C_1$-$C_6$-alkyl, $C_1$-$C_6$-haloalkyl and $C_1$-$C_6$-alkoxy in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxycarbonyl, $C_1$-$C_6$-haloalkoxycarbonyl, $C_3$-$C_8$-cycloalkyl, $C_3$-$C_8$-halocyclo-alkyl, —Si($C_1$-$C_6$-alkyl)$_3$ and 3- to 7-membered heterocyclyl, and wherein $R^{43}$ is hydrogen, hydroxyl, $C_1$-$C_6$-alkyl, $C_1$-$C_6$-haloalkyl, $C_1$-$C_6$-alkoxy, $C_2$-$C_6$-alkenyl, $C_2$-$C_6$-haloalkenyl or $C_3$-$C_8$-cycloalkyl, wherein said $C_1$-$C_6$-alkyl, $C_1$-$C_6$-haloalkyl, $C_1$-$C_6$-alkoxy, $C_2$-$C_6$-alkenyl and $C_2$-$C_6$-haloalkenyl in turn are optionally substituted with one to three substituents independently selected from the group consisting of cyano, amino, nitro, hydroxyl, $C_1$-$C_6$-alkoxy, $C_1$-$C_6$-haloalkoxy, $C_1$-$C_6$-alkoxy-carbonyl, $C_1$-$C_6$-haloalkoxycarbonyl, $C_3$-$C_8$-cycloalkyl, $C_3$-$C_8$-halocycloalkyl, —Si($C_1$-$C_6$-alkyl)$_3$ and 3- to 7-membered heterocyclyl, wherein said $C_3$-$C_8$-cycloalkyl in turn is optionally substituted with one to three substituents independently selected from the group consisting of halogen, cyano, amino, nitro, hydroxyl, formyl, carboxyl, oxo, methylidene, halo-methylidene, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, $C_1$-$C_6$-halo-alkoxycarbonyl, $C_3$-$C_8$-cycloalkyl, $C_3$-$C_8$-halocycloalkyl, $C_2$-$C_6$-alkenyl and 3- to 7-membered heterocyclyl, wherein said $C_3$-$C_8$-cycloalkyl, $C_3$-$C_8$-halocycloalkyl and 3- to 7-membered heterocyclyl furthermore are optionally substituted with two substituents forming together with the carbon atom to which they are attached to a $C_3$-$C_8$-cycloalkyl, as well as N-oxides, salts, hydrates and hydrates of the salts and N-oxides thereof.

2. The compound of formula (I) according to claim 1, wherein $A^1$ is $CR^8$, wherein $R^8$ is hydrogen, fluoro, chloro or methyl $A^2$ is O, C(═O), $NR^1$ or $CR^{2A}R^{R2B}$, wherein $R^1$ is hydrogen, formyl, $C_1$-$C_4$-alkyl or $C_3$-$C_6$-cycloalkyl, $R^{2A}$ and $R^{2B}$ are independently hydrogen or $C_1$-$C_4$-alkyl, m is 0, 1 or 2, T is hydrogen or $C_1$-$C_4$-alkyl $R^3$ and $R^4$ are independently hydrogen, fluoro, chloro, $C_1$-$C_4$-alkyl $C_1$-$C_4$-alkylcarbonyl, $C_1$-$C_4$-alkylcarbonyloxy, $C_2$-$C_4$-alkenyl, $C_2$-$C_4$-alkynyl or $C_3$-$C_6$-cycloalkyl, $R^5$ is hydrogen or $C_1$-$C_4$-alkyl, L is a direct bond, $C_1$-$C_4$-alkylene or a group of formula

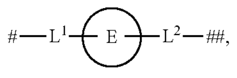

wherein said $C_1$-$C_4$-alkylene is optionally substituted with one to three substituents $L^{SA}$, # is the point of attachment to the heterocyclyl-moiety, ## is the point of attachment to $R^6$, $L^1$ is a direct bond or $C_1$-$C_6$-alkylene, $L^2$ is a direct bond or $C_1$-$C_6$-alkylene, E is $C_3$-$C_8$-cycloalkyl or 3- to 7-membered heterocyclyl, wherein said $C_3$-$C_8$-cycloalkyl and 3- to 7-membered heterocyclyl in turn are optionally substituted with one to three substituents $L^{SC}$ wherein $L^{SA}$ is independently fluoro, chloro or hydroxyl, or two substituents $L^{SA}$ that are bound to the same carbon atom form together with the carbon atom which they are attached to a $C_3$-$C_6$-cycloalkyl-ring or a 4- to 7-membered heterocyclyl-ring, $L^{SC}$ is independently fluoro, chloro hydroxyl, oxo, $C_1$-$C_4$-alkyl, $C_1$-$C_4$-haloalkyl, $C_1$-$C_4$-alkoxy or $C_1$-$C_4$-haloalkoxy, $R^6$ is $C_5$-$C_{10}$-carbocyclyl, phenyl, naphthyl, 5- to 10-membered heterocyclyl or 5- to 10-membered heteroaryl, $C_5$-$C_{10}$-carbocyclyloxy, phenoxy, naphthyloxy, 5- to 10-membered heteroaryloxy, 5- to 10-membered heterocyclyloxy, $C_5$-$C_{10}$-carbocyclylsulfanyl, phenylsulfanyl, naphthylsulfanyl, 5- to 10-membered heteroarylsulfanyl, 5- to 10-membered heterocyclylsulfanyl, $C_1$-$C_3$-alkoxy or $C_1$-$C_3$-haloalkoxy, wherein $C_1$-$C_3$-alkoxy and $C_1$-$C_3$-haloalkoxy are substituted with one substituent selected from the group consisting of $C_5$-$C_{10}$-carbocyclyl, phenyl, naphthyl, 5- to 10-membered heterocyclyl and 5- to 10-membered heteroaryl, wherein said $C_5$-$C_{10}$-carbocyclyl, phenyl, naphthyl, 5- to 10-membered heterocyclyl and 5- to 10-membered heteroaryl in turn are optionally substituted with one to three $R^{6S}$ substituents, wherein $C_5$-$C_{10}$-carbocyclyl, phenyl, naphthyl, 5- to 10-membered heterocyclyl or 5- to 10-membered heteroaryl, $C_5$-$C_{10}$-carbocyclyloxy, phenoxy, naphthyloxy, 5- to 10-membered heteroaryloxy, 5- to 10-membered heterocyclyloxy, $C_5$-$C_{10}$-carbocyclylsulfanyl, phenylsulfanyl, naphthylsulfanyl, 5- to 10-membered heteroarylsulfanyl and 5- to 10-membered heterocyclylsulfanyl are optionally substituted with one to three $R^{6S}$ substituents, wherein $R^{6S}$ is independently selected from the group consisting of halogen, cyano, hydroxyl, mercapto, pentafluorosulfanyl, oxo, methylidene, halomethylidene, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylsulfanyl, $C_1$-$C_4$-haloalkylsulfanyl, $C_3$-$C_6$-cyclo-alkylsulfanyl, $C_3$-$C_6$-cycloalkyl, $C_3$-$C_6$-cycloalkyloxy, 5- or 6-membered heteroaryl, 3- to 7-membered heterocyclyl, —C(═O)$R^{16}$, —C(═O)($OR^{17}$) or —C(═O)N($R^{18}$)$_2$, wherein $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylsulfanyl and $C_1$-$C_4$-haloalkylsulfanyl are furthermore optionally substituted with one to three substituents independently selected from the group consisting of halogen, hydroxyl, $C_1$-$C_4$-alkoxy, $C_1$-$C_4$-haloalkoxy, —Si($C_1$-$C_4$-alkyl)$_3$, $C_3$-$C_6$-cycloalkyl and $C_3$-$C_6$-halocycloalkyl, and wherein $C_3$-$C_6$-cycloalkylsulfanyl, $C_3$-$C_6$-cycloalkyl, $C_3$-$C_6$-cyclo-alkyloxy, phenyl, naphthyl, 5- or 6-membered heteroaryl and 3- to 7-membered heterocyclyl are furthermore optionally substituted with one to three substituents independently selected from the group consisting of fluoro, chloro, $C_1$-$C_4$-alkyl, $C_1$-$C_4$-haloalkyl, $C_1$-$C_4$-alkoxy and $C_1$-$C_4$-haloalkoxy, and wherein $R^{16}$, $R^{17}$ and $R^{18}$ are independently hydrogen, $C_1$-$C_4$-alkyl or $C_1$-$C_4$-haloalkyl, wherein said $C_1$-$C_4$-alkyl and $C_1$-$C_4$-haloalkyl in turn are optionally substituted with one to three substituents independently selected from the group consisting of halogen, hydroxyl, $C_1$-$C_4$-alkoxy, $C_1$-$C_4$-haloalkoxy, $C_3$-$C_6$-cycloalkyl and $C_3$-$C_6$-halo-cycloalkyl, $R^7$ is hydrogen, halogen, cyano, hydroxyl, mercapto, $C_1$-$C_4$-alkyl, $C_1$-$C_4$-haloalkyl, $C_1$-$C_4$-hydroxyalkyl, $C_1$-$C_4$-alkoxy, $C_1$-$C_4$-haloalkoxy, $C_1$-$C_4$-alkylcarbonyl, $C_1$-$C_4$-haloalkylcarbonyl, $C_2$-$C_4$-alkenyl, $C_2$-$C_4$-haloalkenyl, $C_2$-$C_4$-alkynyl, $C_2$-$C_4$-halo-alkynyl, $C_1$-$C_4$-alkylsulfanyl, $C_1$-$C_4$-haloalkylsulfanyl, $C_3$-$C_6$-cycloalkylsulfanyl, $C_1$-$C_4$-alkylsulfinyl, $C_1$-$C_4$-haloalkylsulfinyl, $C_3$-$C_6$-cycloalkylsulfinyl, $C_1$-$C_4$-alkylsulfonyl, $C_1$-$C_4$-haloalkylsulfonyl, $C_3$-$C_6$-cycloalkylsulfonyl, $C_3$-$C_6$-cyclo-alkyl, $C_3$-$C_6$-cycloalkenyl, phenyl, 5- or 6-membered heteroaryl, 3- to 7-membered heterocyclyl, $C_3$-$C_6$-cycloalkyloxy, phenoxy, 5- or 6-membered heteroaryloxy, 3- to 7-membered heterocyclyloxy, $—N(R^{20})_2$, $—C(=NR^{21})R^{22}$, $—NR^{23}C(=O)R^{24}$, $—C(=O)(OR^{25})$, $—C(=O)N(R^{26})_2$, $—S(=O)_2N(R^{27})_2$ or $—S(=O)(=NR^{28})R^{29}$, wherein $C_1$-$C_4$-alkyl, $C_1$-$C_4$-haloalkyl, $C_1$-$C_4$-hydroxyalkyl, $C_1$-$C_4$-alkoxy, $C_1$-$C_4$-haloalkoxy, $C_1$-$C_4$-alkylcarbonyl, $C_1$-$C_4$-haloalkylcarbonyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylsulfanyl, $C_1$-$C_4$-halo-alkylsulfanyl, $C_1$-$C_4$-alkylsulfinyl, $C_1$-$C_4$-haloalkylsulfinyl, $C_1$-$C_4$-alkylsulfonyl and $C_1$-$C_4$-haloalkylsulfonyl are optionally substituted with one to three $R^{7Sa}$ substituents, wherein $C_3$-$C_6$-cycloalkylsulfanyl, $C_1$-$C_4$-alkylsulfinyl, $C_1$-$C_4$-haloalkylsulfinyl, $C_3$-$C_6$-cycloalkylsulfinyl, $C_1$-$C_4$-alkylsulfonyl, $C_1$-$C_4$-haloalkylsulfonyl, $C_3$-$C_6$-cycloalkylsulfonyl, $C_3$-$C_6$-cycloalkyl, $C_3$-$C_6$-cycloalkenyl, phenyl, 5- or 6-membered heteroaryl, 3- to 7-membered heterocyclyl, $C_3$-$C_6$-cycloalkyloxy, phenoxy, 5- or 6-membered heteroaryloxy and 3- to 7-membered heterocyclyloxy are optionally substituted with one to three $R^{7Sc}$ substituents, and wherein $R^{20}$ is independently hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl or $C_3$-$C_6$-cycloalkyl, $R^{21}$ and $R^{22}$ are independently hydroxyl, $C_1$-$C_4$-alkyl, $C_1$-$C_4$-haloalkyl or $C_1$-$C_4$-alkoxy, $R^{23}$, $R^{24}$, $R^{25}$, $R^{26}$, $R^{27}$, $R^{28}$ and $R^{29}$ are independently hydrogen, $C_1$-$C_4$-alkyl, $C_1$-$C_4$-haloalkyl and $C_3$-$C_6$-cycloalkyl, wherein $R^{7Sa}$ is independently hydroxyl, $C_1$-$C_4$-alkoxy, $C_1$-$C_4$-haloalkoxy, $C_3$-$C_6$-cyclo-alkyl or $—Si(C_1$-$C_4$-alkyl$)_3$, $R^{7Sc}$ is independently fluoro, chloro, hydroxyl, oxo, $C_1$-$C_4$-alkyl, $C_1$-$C_4$-haloalkyl, $C_1$-$C_4$-alkoxy, $C_1$-$C_4$-haloalkoxy or $C_3$-$C_8$-cycloalkyl, Q is phenyl, naphthyl, $C_5$-$C_{10}$-carbocyclyl, 5- to 10-membered heterocyclyl or 5- to 10-membered heteroaryl, wherein phenyl, naphthyl, $C_5$-$C_{10}$-carbocyclyl, 5- to 10-membered heterocyclyl and 5- to 10-membered heteroaryl are optionally substituted with one to three substituents $Q^S$ wherein $Q^S$ is independently selected from the group consisting of halogen, cyano, nitro, formyl, $C_1$-$C_4$-alkyl, $C_1$-$C_4$-haloalkyl, $C_1$-$C_4$-alkylcarbonyl, $C_1$-$C_4$-haloalkylcarbonyl, $C_1$-$C_4$-alkoxy, $C_1$-$C_4$-haloalkoxy, $C_1$-$C_4$-alkoxycarbonyl, $C_1$-$C_4$-haloalkoxycarbonyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylsulfanyl, $C_1$-$C_4$-haloalkylsulfanyl, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, 3- to 7-membered heterocyclyl, phenyl, 5- or 6-membered heteroaryl, $—O—C(=O)R^{33}$, and $—N(R^{43})_2$, wherein said $C_1$-$C_4$-alkyl, $C_1$-$C_4$-haloalkyl, $C_1$-$C_4$-alkylcarbonyl, $C_1$-$C_4$-halo-alkylcarbonyl, $C_1$-$C_4$-alkoxy, $C_1$-$C_4$-haloalkoxy, $C_1$-$C_4$-alkoxycarbonyl, $C_1$-$C_4$-haloalkoxycarbonyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylsulfanyl, $C_1$-$C_4$-haloalkylsulfanyl, $C_1$-$C_4$-alkylsulfinyl, $C_1$-$C_4$-haloalkyl-sulfinyl, $C_1$-$C_4$-alkylsulfonyl and $C_1$-$C_4$-haloalkylsulfonyl in turn are optionally substituted with one to three substituents independently selected from the group consisting of cyano, amino, nitro, hydroxyl, $C_1$-$C_4$-alkoxy, $C_1$-$C_4$-haloalkoxy, $C_1$-$C_4$-alkoxycarbonyl, $C_1$-$C_4$-haloalkoxycarbonyl, $C_3$-$C_6$-cycloalkyl, $C_3$-$C_6$-halocycloalkyl and 3- to 7-membered heterocyclyl, said $C_3$-$C_6$-cycloalkyl, 3- to 7-membered heterocyclyl and 5- or 6-membered heteroaryl in turn are optionally substituted with one to three substituents independently selected from the group consisting of halogen, $C_1$-$C_4$-alkyl, $C_1$-$C_4$-haloalkyl, $C_1$-$C_4$-alkoxy, $C_1$-$C_4$-halo-alkoxy, $C_1$-$C_4$-alkoxycarbonyl, $C_1$-$C_4$-haloalkoxycarbonyl and $C_3$-$C_6$-cycloalkyl, $R^{33}$ is $C_1$-$C_4$-alkyl or $C_1$-$C_6$-haloalkyl, $R^{43}$ is independently hydrogen, $C_1$-$C_4$-alkyl, $C_1$-$C_4$-haloalkyl or $C_3$-$C_6$-cycloalkyl, as well as salts, hydrates and hydrates of the salts thereof.

3. The compound of formula (I) according to claim 1, wherein $A^1$ is $CR^8$, wherein $R^8$ is hydrogen, $A^2$ is O, C(=O) or $CR^{2A}R^{R2B}$, wherein $R^{2A}$ and $R^{2B}$ are independently hydrogen, m is 1, T is hydrogen, $R^3$ and $R^4$ are independently hydrogen, fluoro, chloro, $C_1$-$C_4$-alkyl, $C_1$-$C_4$-alkylcarbonyl, $C_1$-$C_4$-alkoxycarbonyl, $C_1$-$C_4$-alkylcarbonyloxy, $C_2$-$C_4$-alkenyl, $C_2$-$C_4$-alkynyl or $C_3$-$C_6$-cycloalkyl, $R^5$ is hydrogen, L is a direct bond, methylene or ethylene, wherein said methylene and ethylene are optionally substituted with one or two substituents $L^{SA}$, wherein $L^{SA}$ is independently fluoro, or two substituents $L^{SA}$ that are bound to the same carbon atom form together with the carbon atom which they are attached to a cyclopropyl- or a cyclobutyl-ring, $R^6$ is indanyl, tetrahydronaphthalenyl, phenyl, naphthyl, 1,3-benzodioxolyl, 1,2,3,4-tetrahydroquinolinyl, chromanyl, isochromanyl, thiochromanyl, 2,3-dihydro-1,4-benzodioxinyl, tetrahydroquinolinyl, furanyl, thienyl, pyrazolyl, pyridinyl or pyrimidinyl, wherein indanyl, tetrahydronaphthalenyl, phenyl, naphthyl, 1,3-benzodioxolyl, 1,2,3,4-tetrahydroquinolinyl, chromanyl, isochromanyl, thiochromanyl, 2,3-dihydro-1,4-benzodioxinyl, tetrahydroquinolinyl, furanyl, thienyl, pyrazolyl, pyridinyl and pyrimidinyl are optionally substituted with one to three $R^{6S}$ substituents, wherein $R^{6S}$ is independently selected from the group consisting of halogen, cyano, oxo, $C_1$-$C_4$-alkyl, difluoromethyl, trifluoromethyl, $C_1$-$C_4$-alkoxy, difluoromethoxy, trifluoromethoxy, $C_2$-$C_4$-alkenyl, $C_2$-$C_4$-alkynyl, $C_1$-$C_4$-alkylsulfanyl, difluoromethylsulfanyl, trifluoromethylsulfanyl, $C_3$-$C_6$-cycloalkyl, furanyl, thienyl, pyrazolyl, imidazolyl, triazolyl, oxazolyl, thiazolyl, pyridinyl, pyridazinyl, pyrimidinyl, oxetanyl, tetrahydrofuranyl or —C(═O)$R^{16}$, wherein $C_1$-$C_4$-alkyl, $C_1$-$C_4$-alkoxy, $C_2$-$C_4$-alkenyl, $C_2$-$C_4$-alkynyl and $C_1$-$C_4$-alkylsulfanyl are furthermore optionally substituted with one or two substituents independently selected from the group consisting of hydroxyl, $C_1$-$C_4$-alkoxy, $C_1$-$C_4$-haloalkoxy, —Si($C_1$-$C_4$-alkyl)$_3$ and $C_3$-$C_6$-cycloalkyl and wherein $R^{16}$ is $C_1$-$C_4$-alkyl, $R^7$ is hydrogen, $C_1$-$C_4$-alkyl, difluoromethyl, trifluoromethyl, $C_1$-$C_4$-alkoxy, difluoro-methoxy, trifluoromethoxy, $C_1$-$C_4$-alkylsulfanyl or $C_3$-$C_6$-cycloalkyl, Q is phenyl, naphthyl, 3-bicyclo[4.2.0]octa-1,3,5-trienyl, indanyl, tetrahydronaphthalenyl, dihydrobenzofuranyl, indenyl, dihydronaphthalenyl, indolinyl, 1,3-benzodioxolyl, chromanyl, dihydro-1,4-benzodioxinyl, [1,3]dioxolo[4,5-b]pyridinyl, tetrahydroquinolinyl, 6,7-dihydro-5H-cyclo-penta[b]pyridinyl, pyrrolyl, furanyl, thienyl, imidazolyl, oxazolyl, thiazolyl, pyridinyl, pyrimidinyl, indolyl, benzimidazolyl, indazolyl, benzofuranyl, benzothiophenyl, benzothiazolyl, benzoxazolyl or quinolinyl, wherein phenyl, naphthyl, 3-bicyclo[4.2.0]octa-1,3,5-trienyl, indanyl, tetrahydro-naphthalenyl, dihydrobenzofuranyl, indenyl, dihydronaphthalenyl, indolinyl, 1,3-benzodioxolyl, chromanyl, dihydro-1,4-benzodioxinyl, [1,3]dioxolo[4,5-b]pyridinyl, tetrahydroquinolinyl, 6,7-dihydro-5H-cyclopenta[b]pyridinyl, pyrrolyl, furanyl, thienyl, imidazolyl, oxazolyl, thiazolyl, pyridinyl, pyrimidinyl, indolyl, benzimidazolyl, indazolyl, benzofuranyl, benzothiophenyl, benzothiazolyl, benzoxazolyl and quinolinyl, are optionally substituted with one to three substituents $Q^S$ wherein $Q^S$ is independently selected from the group consisting of halogen, cyano, nitro, formyl, $C_1$-$C_4$-alkyl, difluoromethyl, trifluoromethyl, $C_1$-$C_4$-alkylcarbonyl, $C_1$-$C_4$-alkoxy, difluoromethoxy, trifluoromethoxy, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylsulfanyl, $C_3$-$C_6$-cycloalkyl oxetanyl, pyrrolidinyl, tetrahydrofuranyl, phenyl, thienyl, furanyl, pyrrolyl, pyridyl, —O(C═O)$R^{33}$ and —N($R^{43}$)$_2$, wherein said $C_1$-$C_4$-alkyl, $C_1$-$C_4$-alkylcarbonyl, $C_1$-$C_4$-alkoxy, $C_2$-$C_4$-alkenyl, $C_2$-$C_4$-haloalkenyl, $C_2$-$C_4$-alkynyl, $C_2$-$C_4$-haloalkynyl and $C_1$-$C_4$-alkylsulfanyl in turn are optionally substituted with one or two substituents independently selected from the group consisting of hydroxyl, $C_1$-$C_4$-alkoxy and $C_1$-$C_4$-alkoxycarbonyl $R^{33}$ is $C_1$-$C_4$-alkyl, $R^{43}$ is independently hydrogen or $C_1$-$C_4$-alkyl, as well as salts, hydrates and hydrates of the salts thereof.

4. The compound of formula (I) according to claim 1, wherein

Q is phenyl, wherein phenyl is substituted with one or two substituents $Q^S$ independently selected from the group consisting of halogen, nitro, $C_1$-$C_4$-alkyl, difluoromethyl, trifluoromethyl, $C_1$-$C_4$-alkoxy, difluoromethoxy, trifluoromethoxy, $C_2$-$C_4$-alkynyl, cyclopropyl and cyclobutyl.

5. The compound of formula (I) according to claim 1, wherein $R^6$ is indanyl, phenyl, dihydrobenzodioxinyl or thienyl, wherein indanyl, phenyl, di-hydrobenzodioxinyl and thienyl are optionally substituted with one or two $R^{6S}$ substituents, wherein $R^{6S}$ is independently selected from the group consisting of fluoro, chloro, $C_1$-$C_4$-alkyl, difluoromethyl, trifluoromethyl, $C_1$-$C_4$-alkoxy, difluoromethoxy, trifluoromethoxy, $C_2$-$C_4$-alkenyl, $C_2$-$C_4$-alkynyl, cyclopropyl and cyclobutyl, wherein said $C_2$-$C_4$-alkynyl is optionally substituted with one substituent —Si($CH_3$)$_3$.

6. The compound of formula (I) according to claim 1, wherein $R^7$ is methyl, methylsulfanyl or cyclopropyl, and $R^8$ is hydrogen.

7. A composition comprising at least one compound of formula (I) according to claim 1 and at least one carrier and/or surfactant.

8. A method for controlling harmful microorganisms in crop protection and in the protection of materials, comprising applying at least one compound of formula (I) according to claim 1;

and/or a composition comprising at least one compound of formula (I) according to claim 1 and at least one carrier and/or surfactant to the harmful microorganisms and/or their habitat.

9. The method of claim 8, wherein the harmful microorganisms comprise phytopathogenic harmful fungi.

* * * * *